US010953083B2

(12) United States Patent
Collins et al.

(10) Patent No.: US 10,953,083 B2
(45) Date of Patent: Mar. 23, 2021

(54) RECOMBINANT RESPIRATORY SYNCYTIAL VIRUS STRAINS COMPRISING NS1 AND NS2 GENE SHIFTS

(71) Applicant: The United States of America, as represented by the Secretary, Department of Health and Human Services, Bethesda, MD (US)

(72) Inventors: Peter L. Collins, Silver Spring, MD (US); Thomas Charles McCarty, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/061,316

(22) PCT Filed: Dec. 12, 2016

(86) PCT No.: PCT/US2016/066142

§ 371 (c)(1),
(2) Date: Jun. 11, 2018

(87) PCT Pub. No.: WO2017/100756

PCT Pub. Date: Jun. 15, 2017

(65) Prior Publication Data

US 2019/0184000 A1 Jun. 20, 2019

Related U.S. Application Data

(60) Provisional application No. 62/266,206, filed on Dec. 11, 2015.

(51) Int. Cl.

| | |
|---|---|
| ***A61K 39/12*** | (2006.01) |
| ***C12N 7/04*** | (2006.01) |
| ***C12N 7/00*** | (2006.01) |
| *A61K 39/00* | (2006.01) |

(52) U.S. Cl.

CPC ................ *A61K 39/12* (2013.01); *C12N 7/00* (2013.01); *C12N 7/04* (2013.01); *A61K 2039/5254* (2013.01); *A61K 2039/55* (2013.01); *C12N 2760/18521* (2013.01); *C12N 2760/18534* (2013.01); *C12N 2760/18551* (2013.01)

(58) Field of Classification Search

None

See application file for complete search history.

(56) References Cited

U.S. PATENT DOCUMENTS

2005/0158338 A1 7/2005 Buchholz et al.

FOREIGN PATENT DOCUMENTS

| | | |
|---|---|---|
| JP | 11-512609 | 11/1999 |
| JP | 2004-501639 A | 1/2004 |
| WO | WO 97/12032 | 4/1997 |
| WO | WO 02/00868 A1 | 1/2002 |
| WO | WO 2002/00693 * | 1/2002 |

OTHER PUBLICATIONS

Anderson. "Respiratory syncytial virus vaccine development." In *Seminars in Immunology*, vol. 25, No. 2, pp. 160-171. Academic Press, 2013.

Bitko, et al. "Nonstructural proteins of respiratory syncytial virus suppress premature apoptosis by an NF-κB-dependent, interferon-independent mechanism and facilitate virus growth." *Journal of Virology* 81, No. 4 (2007): 1786-1795.

Bukreyev, et al. "Granulocyte-macrophage colony-stimulating factor expressed by recombinant respiratory syncytial virus attenuates viral replication and increases the level of pulmonary antigen-presenting cells." *Journal of Virology* 75, No. 24 (2001): 12128-12140.

Chirkova, et al. "Respiratory syncytial virus G protein CX3C motif impairs human airway epithelial and immune cell responses." *Journal of Virology* 87, No. 24 (2013): 13466-13479.

Collins, et al. "Production of infectious human respiratory syncytial virus from cloned cDNA confirms an essential role for the transcription elongation factor from the 5'proximal open reading frame of the M2 mRNA in gene expression and provides a capability for vaccine development," *Proceedings of the National Academy of Sciences* 92, No. 25 (1995): 11563-11567.

Collins, et al. "Rational design of live-attenuated recombinant vaccine virus for human respiratory syncytial virus by reverse genetics." In *Advances in Virus Research*, vol. 54, pp. 423-451. Academic Press, 1999.

Connors, et a "A cold-passaged, attenuated strain of human respiratory syncytial virus contains mutations in the F and L genes." *Virology* 208, No. 2 (1995): 478-484.

Firestone, et al. "Nucleotide sequence analysis of the respiratory syncytial virus subgroup a cold-passaged (cp) temperature sensitive (ts) cpts-248/404 live attenuated virus vaccine candidate." *Virology* 225, No. 2 (1996): 419-422.

Ilyushina, et al. "Comparative study of influenza virus replication in MDCK cells and in primary cells derived from adenoids and airway epithelium." *Journal of Virology* 86, No. 21 (2012): 11725-11734.

Jin, et al. "Evaluation of recombinant respiratory syncytial virus gene deletion mutants in African green monkeys for their potential as live attenuated vaccine candidates." *Vaccine* 21, No. 25-26 (2003): 3647-3652.

(Continued)

*Primary Examiner* — Nicole Kinsey White

(74) *Attorney, Agent, or Firm* — Klarquist Sparkman, LLP

(57) ABSTRACT

Reported herein are novel recombinant respiratory syncytial viruses (RSV) having an attenuated phenotype in which the native positions of the NS1 and/or NS2 genes in the RSV genome are shifted to a higher position, that is at positions that are more distal to the promoter. The changes in the gene positions may be present in combination with mutations at other loci to achieve desired levels of attenuation and immunogenicity. The recombinant RSV strains described here are suitable for use as live-attenuated RSV vaccines. Also provided are polynucleotide sequences capable of encoding the described viruses, as well as methods for producing and using the viruses.

22 Claims, 10 Drawing Sheets

Specification includes a Sequence Listing.

(56) References Cited

OTHER PUBLICATIONS

Juhasz, et al. "The two anuno acid substitutions in the L protein of cpts530/1009, a live-attenuated respiratory syncytial virus candidate vaccine, are independent temperature-sensitive and attenuation mutations." *Vaccine* 17, No. 11-12 (1999): 1416-4424.

Karron, et al. "Identification of a recombinant live attenuated respiratory syncytial virus vaccine candidate that is highly attenuated in infants." *The Journal of Infectious Diseases* 191, No. 7 (2005): 1093-1104.

Karron, et al. "Live-attenuated respiratory syncytial virus vaccines" In *Challenges and Opportunities for Respiratory Syncytial Virus Vaccines*, pp. 259-284. Springer, Berlin, Heidelberg, 2013.

Karron, et al. "A gene deletion that up-regulates viral gene expression yields an attenuated RSV vaccine with improved antibody responses in children." *Science Translational Medicine* 7, No. 312 (2015): 312ra175-312ra175.

Kwilas, et al. "Respiratory syncytial virus engineered to express the cystic fibrosis transmembrane conductance regulator corrects the bioelearic phenotype of human cystic fibrosis airway epithelium in vitro." *Journal of Virology* 84, No. 15 (2010): 7770-7781.

Liang, et at "Enhanced neutralizing antibody response induced by respiratory syncytial virus prefusion F protein expressed by a vaccine candidate." *Journal of Virology* 89, No. 18 (2015): 9499-9510.

Liang, et al. "Chimeric bovine/human parainfluenza virus type 3 expressing respiratory syncytial virus (RSV) F glycoprotein: effect of insert position on expression, replication, immunogenicity, stability, and protection against RSV infection." *Journal of Virology* 88, No. 8 (2014): 4237-4250.

Le Nouën, et al. "Attenuation of human respiratory syncytial virus by genome-scale codon-pair deoptimization." *Proceedings of the National Academy of Sciences* 111, No. 36 (2014): 13169-13174.

Luongo, et al. "Codon stabilization analysis of the "248" temperature sensitive mutation for increased phenotypic stability of respiratory syncytial virus vaccine candidates." *Vaccine* 27, No. 41 (2009): 5667-5676.

Luongo, et al. "Increased genetic and phenotypic stability of a promising live-attenuated respiratory syncytial virus vaccine candidate by reverse genetics." *Journal of Virology* 86, No. 19 (2012): 10792-10804.

Luongo, et al. "Respiratory syncytial virus modified by deletions of the NS2 gene and amino acid S1313 of the L polymerase protein is a temperature-sensitive, live-attenuated vaccine candidate that is phenotypically stable at physiological temperature." *Journal of Virology* 87, No. 4 (2013): 1985-1996.

Meng, et al. "Refining the balance of attenuation and Immunogenicity of respiratory syncytial virus by targeted codon deoptimization of virulence genes." *MBio* 5, No. 5 (2014): e01704-14.

McLellan, et al. "Structure of RSV fusion glycoprotein trimer bound to a prefusion-specific neutralizing antibody." *Science* 340, No. 6136 (2013): 1113-1117.

McLellan, et al. "Structure-based design of a fusion glycoprotein vaccine for respiratory syncytial virus." *Science* 342, No. 6158 (2013): 592-598.

Munir, et al. "Nonstructural proteins 1 and 2 of respiratory syncytial virus suppress maturation of human dendritic cells." *Journal of Virology* 82, No. 17 (2008): 8780-8796.

Pulmanausahakul, et al. "Overexpression of cytochrome C by a recombinant rabies virus attenuates pathogenicity and enhances antiviral immunity." *Journal of virology* 75, No. 22 (2001): 10800-10807.

Schaap-Nutt et al. "Growth restriction of an experimental live attenuated human parainfluenza virus type 2 vaccine in human ciliated airway epithelium in vitro parallels attenuation in African green monkeys." *Vaccine* 28, No. 15 (2010): 2788-2798.

Valarcher, et al. "Role of alpha/beta interferons in the attenuation and immunogenicity of recombinant bovine respiratory syncytial viruses lacking NS proteins." *Journal of Virology* 77. No. 15 (2003): 8426-8439.

Whitehead, et al. "Recombinant respiratory syncytial virus (RSV) bearing a set of mutations from cold-passaged RSV is attenuated in chimpanzees." *Journal of Virology* 72, No. 5 (1998): 4467-4471.

Whitehead, et al. "Addition of a missense mutation present in the L gene of respiratory syncytial virus (RSV) cpts530/1030 to RSV vaccine candidate cpts248/404 increases its attenuation and temperature sensitivity." *Journal of Virology* 73, No. 2 (1999): 871-877.

Whitehead, et al. "Recombinant respiratory syncytial virus bearing a deletion of either the NS2 or SH gene is attenuated in chimpanzees." *Journal of Virology* 73, No. 4 (1999): 3438-3442.

Whitehead, et al. "Replacement of the F and G proteins of respiratory syncytial virus (RSV) subgroup a with those of subgroup B generates chimeric live attenuated RSV subgroup B vaccine candidates," *Journal of Virology* 73, No. 12 (1999): 9773-9780.

Whitehead, et al. "A Single Nucleotide Substitution in the Transcription Start Signal of the M2 Gene of Respiratory Syncytial Virus Vaccine Candidate cpts248/404 is the Major Determinant of the Temperature-Sensitive and Attenuation Phenotypes." *Virology* 247, No. 2 (1998): 232-239.

Zhang, et al. "Respiratory syncytial virus infection of human airway epithelial cells is polarized, specific to ciliated cells, and without obvious cytopathology." *Journal of Virology* 76, No. 11 (2002): 5654-5666.

* cited by examiner

Generation of the RSV 6120/NS12FM2/GFP virus, in which the NS1 and NS2 genes are shifted from their native positions 1 and 2 in the genome to positions 7 and 8

Creation of the RSV 6120/NS12Ltr/GFP virus, in which the NS1 and NS2 genes are shifted from their native positions 1 and 2 in the genome to positions 9 and 10

Multicycle replication in Vero cells of RSV with NS1-NS2 between F-M2

1 — RSV 6120/NS12FM2/GFP (01)
2 — RSV 6120/NS12FM2/GFP (02)
3 — RSV wt/GFP (01)
4 — RSV wt/GFP (02)
5 — RSV ΔNS1/ΔNS2/GFP (01)
6 — RSV ΔNS1/ΔNS2/GFP (02)

Multicycle replication in A549 cells of RSV with NS1-NS2 between F-M2

1 — RSV 6120/NS12FM2/GFP (01)
2 — RSV 6120/NS12FM2/GFP (02)
3 — RSV wt/GFP (01)
4 — RSV wt/GFP (02)
5 — RSV ΔNS1/ΔNS2/GFP (01)
6 — RSV ΔNS1/ΔNS2/GFP (02)

Multicycle replication in Vero cells of RSV with NS1-NS2 between L-trailer

1 — RSV 6120/NS12Ltr/GFP (01)
2 — RSV 6120/NS12Ltr/GFP (02)
3 — RSV wt/GFP (01)
4 — RSV wt/GFP (02)
5 — RSV ΔNS1/ΔNS2/GFP (01)
6 — RSV ΔNS1/ΔNS2/GFP (02)

Deletion of the NS2 gene from RSV 6120/NS12FM2/GFP to create RSV 6120/NS12FM2/ΔNS2/GFP

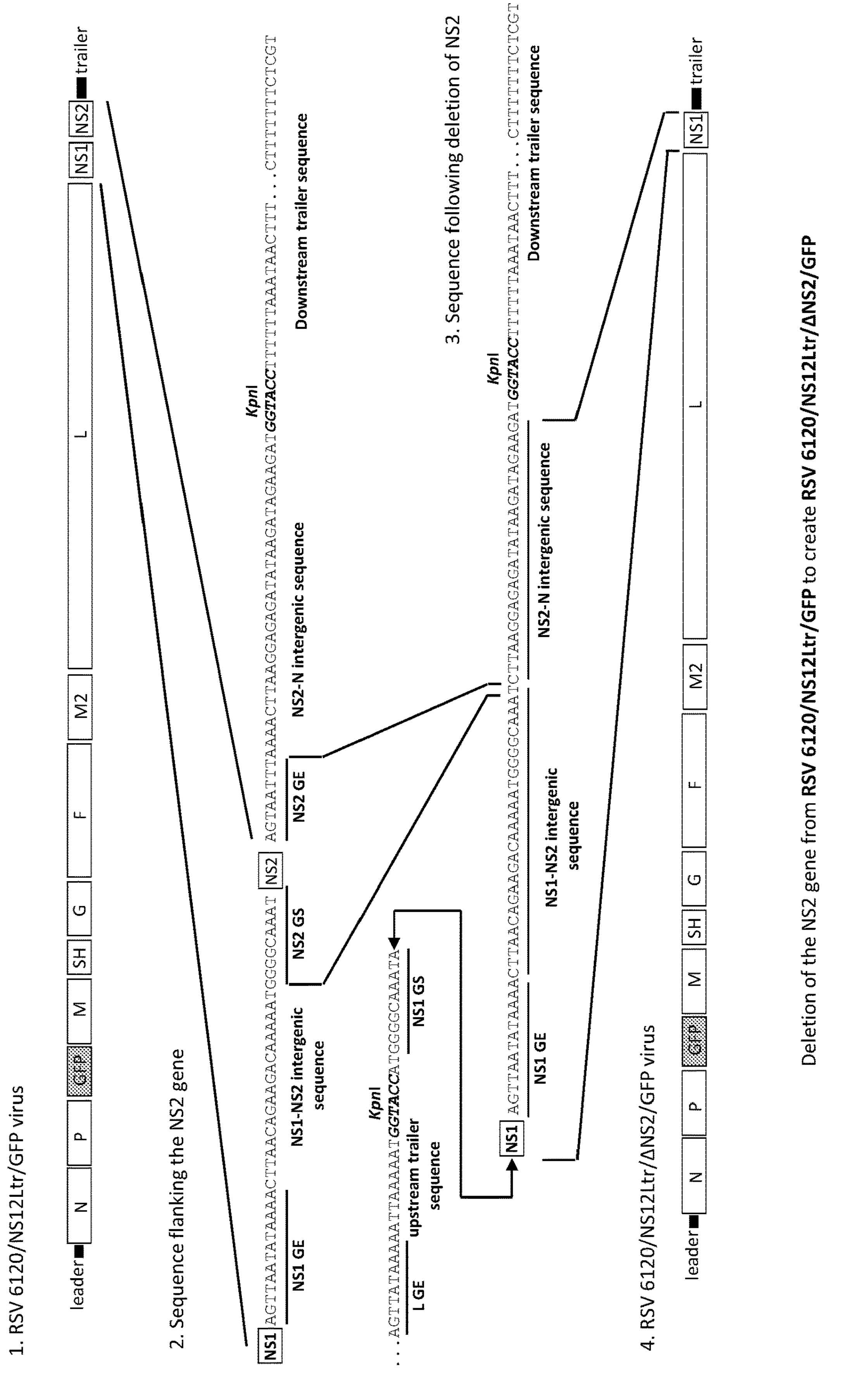

FIG. 8

1. RSV 6120/NS12Ltr/GFP virus leader—[N][P][GFP][M][SH][G][F][M2][L][NS1][NS2]—trailer 2. Sequence flanking the NS2 gene

[NS1] AGTTAATATAAAACTTAAACAGAAGACAAAAATGGGGCAAAT [NS2] AGTAATTAAAACTTAAGGAGAGATATAAGAGATAGAAGATGGTACCTTTTTAATAACTTT...CTTTTTTTCTCGT

NS1 GE | NS1-NS2 intergenic sequence | NS2 GS     NS2 GE | NS2-N intergenic sequence    *Kpnl*   *GGTACC*   Downstream trailer sequence

*Kpnl*

...AGTTAATATAAAAATTAAAAAT*GGTACC*ATGGGCAAATA

L GE | upstream trailer sequence | NS1 GS

3. Sequence following deletion of NS2

[NS1] AGTTAATATAAAACTTAAACAGAAGACAAAAATGGGGCAAATCTTAAGGAGAGATATAAGAGATAGAAGATGGTACCTTTTTAATAACTTT...CTTTTTTTCTCGT

NS1 GE | NS1-NS2 intergenic sequence | NS2-N intergenic sequence   *Kpnl GGTACC*   Downstream trailer sequence 4. RSV 6120/NS12Ltr/ΔNS2/GFP virus leader—[N][P][GFP][M][SH][G][F][M2][L][NS1]—trailer Deletion of the NS2 gene from RSV 6120/NS12Ltr/GFP to create RSV 6120/NS12Ltr/ΔNS2/GFP

Multicycle replication of RSV 6120/NS12FM2/ΔNS2 in Vero cells

1. RSV wt/GFP
2. RSV ΔNS1/ΔNS2/GFP
3. RSV 6120/NS12FM2/GFP
4. RSV 6120/NS12FM2/ΔNS2GFF

RECOMBINANT RESPIRATORY SYNCYTIAL VIRUS STRAINS COMPRISING NS1 AND NS2 GENE SHIFTS

CROSS REFERENCE TO RELATED APPLICATIONS

This is the U.S. National Stage of International Application No. PCT/US2016/066142, filed Dec. 12, 2016, which was published in English under PCT Article 21(2), which in turn claims the benefit of U.S. Provisional Application No. 62/266,206, filed Dec. 11, 2015. The provisional application is incorporated by reference herein in its entirety.

FIELD

The subject matter disclosed herein relates to respiratory syncytial virus (RSV) and attenuated, mutant strains thereof suitable for use as vaccines.

BACKGROUND

Human respiratory syncytial virus (RSV) infects nearly everyone worldwide early in life and is responsible for considerable mortality and morbidity. In the United States alone, RSV is responsible for 75,000-125,000 hospitalizations yearly, and conservative estimates indicate that RSV is responsible worldwide for 64 million pediatric infections and 160,000 or more pediatric deaths each year. Another notable feature of RSV is that severe infection in infancy frequently is followed by lingering airway dysfunction, including a predisposition to airway reactivity, that in some individuals lasts for years and can extend into adolescence and beyond. RSV infection exacerbates asthma and may be involved in initiating asthma.

RSV is a member of the Paramyxoviridae family and, as such, is an enveloped virus that replicates in the cytoplasm and matures by budding at the host cell plasma membrane. The genome of RSV is a single, negative-sense strand of RNA of 15.2 kilobases that is transcribed by the viral polymerase into 10 mRNAs by a sequential stop-start mechanism that initiates at a single viral promoter at the 3' end of the genome. Each mRNA encodes a single major protein, with the exception of the M2 mRNA that has two overlapping open reading frames (ORFs) encoding two separate proteins M2-1 and M2-2. The 11 RSV proteins are: the RNA-binding nucleoprotein (N), the phosphoprotein (P), the large polymerase protein (L), the attachment glycoprotein (G), the fusion protein (F), the small hydrophobic (SH) surface glycoprotein, the internal matrix protein (M), the two nonstructural proteins NS1 and NS2, and the M2-1 and M2-2 proteins. The RSV gene order is: 3'-NS1-NS2-N-P-M-SH-G-F-M2-L. Each gene is flanked by short conserved transcription signals called the gene-start (GS) signal, present on the upstream end of each gene and involved in initiating transcription of the respective gene, and the gene-end (GE) signal, present at the downstream end of each gene and involved in directing synthesis of a polyA tail followed by release of the mRNA. Transcription initiates at a single promoter at the 3' end and proceeds sequentially.

The development of RSV vaccines has been in progress since the 1960's but has been complicated by a number of factors. For example, immunization of RSV-naïve infants with inactivated RSV has been shown to prime for enhanced disease upon subsequent natural RSV infection, and studies in experimental animals indicate that disease enhancement also is associated with purified RSV subunit vaccines.

Another obstacle to immune protection is that RSV replicates and causes disease in the superficial cells of the respiratory airway lumen, where immune protection has reduced effectiveness. Thus, immune control of RSV infection is inefficient and often incomplete, and it is important for an RSV vaccine to be as immunogenic as possible. Another obstacle to RSV vaccines is that the magnitude of the protective immune response is roughly proportional to the extent of virus replication (and antigen production). Thus, the attenuation of RSV necessary to make a live vaccine typically is accompanied by a reduction in replication and antigen synthesis, and a concomitant reduction in immunogenicity, and therefore it is beneficial to identify a level of replication that is well tolerated yet satisfactorily immunogenic.

Another obstacle is that RSV grows only to moderate titers in cell culture and is often present in long filaments that are difficult to purify. RSV can readily lose infectivity during handling. Another obstacle is the difficulty in identifying and developing attenuating mutations. Appropriate mutations must be attenuating in vivo, but should be minimally restrictive to replication in vitro, since this is preferred for efficient vaccine manufacture. Another obstacle is genetic instability that is characteristic of RNA viruses, whereby attenuating mutations can revert to the wild-type (wt) assignment or to an alternative assignment that confers a non-attenuated phenotype. Instability and de-attenuation are particularly problematic for point mutations.

Taking these factors together, there is a need for live attenuated RSV strains that replicate efficiently in vitro, are maximally immunogenic, are satisfactorily attenuated, and are refractory to de-attenuation.

SUMMARY

Reported herein are novel recombinant RSV having an attenuated phenotype in which the position of the NS1 and/or NS2 gene in the RSV genome or antigenome is shifted to a position that is more distal to the promoter. The changes in the gene positions may be present in combination with mutations at other loci to achieve desired levels of attenuation and immunogenicity. The recombinant RSV strains described here are suitable for use as live-attenuated RSV vaccines.

In some embodiments, a recombinant RSV is provided that is attenuated by one or more modifications to the genome of the RSV. In some embodiments, the one or more modifications comprise a shift of the NS1 gene and the NS2 gene from gene positions 1 and 2 to gene positions 7 and 8 of the RSV genome, respectively. In some embodiments, the one or more modifications comprise a shift of the NS1 and NS2 genes from gene positions 1 and 2 (of a native RSV genome) to gene positions 9 and 10 of the genome of the recombinant RSV, respectively. In some embodiments, the one or more modifications comprise a shift of the NS1 gene to a gene position higher than position 1 (for example, to gene position 7 or 9). In some embodiments, the one or more modifications comprise a shift of the NS2 gene to a gene position higher than position 2. In some embodiments, the one or more modifications comprise a shift of the NS1 gene to a gene position higher than position 1, and the NS2 gene to a gene position higher than position 2.

In addition to the modification that shifts the gene position of the NS1 gene and/or the NS2 gene, the genome of the recombinant RSV can comprise further modifications to increase or decrease viral attenuation, or other properties of the recombinant virus, such as deletion of all or part of the NS1, the NS2 gene, and/or the M2-2 gene.

In some embodiments, the RSV genome comprises the one or more modifications as discussed above, and comprises a nucleotide sequence corresponding to a positive-sense sequence at least 90%, at least 95%, and/or at least 99% identical to SEQ ID NO: 2 (6120/NS12FM2), SEQ ID NO: 4 (6120/NS12Ltr), SEQ ID NO: 6 (6120/NS12FM2/ΔNS2), or SEQ ID NO: 8 (6120/NS12Ltr/ΔNS2). For example, the RSV genome can comprise or consist of a nucleotide sequence corresponding to a positive-sense sequence denoted by SEQ ID NO: 2 (6120/NS12FM2), SEQ ID NO: 4 (6120/NS12Ltr), SEQ ID NO: 6 (6120/NS12FM2/ΔNS2), or SEQ ID NO: 8 (6120/NS12Ltr/ΔNS2).

In some embodiments, the RSV genome further comprises a reporter gene, such as gene encoding Green Fluorescent Protein (GFP). In some embodiments, the RSV genome comprises the one or more modifications as discussed above and the reporter gene, and comprises a nucleotide sequence corresponding to a positive-sense sequence to SEQ ID NO: 1, SEQ ID NO: 3, SEQ ID NO: 5, or SEQ ID NO: 7, or a nucleotide sequence corresponding to a positive-sense sequence at least 90%, at least 95%, and/or at least 99% identical to SEQ ID NO: 1, SEQ ID NO: 3, SEQ ID NO: 5, or SEQ ID NO: 7.

In some embodiments, the recombinant RSV exhibits one or more of (a) reduced expression of the NS1 gene and/or NS2 gene compared to an RSV having the NS1 gene in gene position 1 and the NS2 gene in gene position 2, (b) reduced transcription of the NS1 gene and/or NS2 gene compared to an RSV having the NS1 gene in gene position 1 and the NS2 gene in gene position 2; and/or (c) reduced inhibition of host interferon response compared to an RSV having the NS1 gene in gene position 1 and the NS2 gene in gene position 2. In some embodiments, the recombinant RSV is increasingly susceptible to restriction in cultured cells that can produce interferons in response to viral infection. In some embodiments, the recombinant RSV retains replication efficiency in cultured cells that cannot produce interferons in response to viral infection.

The embodiments of recombinant RSV disclosed herein can be subtype A RSV or a subtype B RSV. The embodiments of recombinant RSV disclosed herein are infectious, attenuated, and self-replicating.

Also provided herein are methods and compositions related to the expression of the disclosed viruses. For example, isolated polynucleotide molecules that include a nucleic acid sequence encoding the genome or antigenome of the described viruses are disclosed.

Pharmaceutical compositions including the recombinant RSV are also provided. The compositions can further include an adjuvant. Methods of eliciting an immune response in a subject by administering an immunogenically effective amount of a disclosed recombinant RSV to the subject are also disclosed. In some embodiments, the subject is a human subject, for example, a human subject between 1 and 6 months of age, or between 1 and 12 months of age, or between 1 and 18 months of age, or older.

The foregoing and other features and advantages of this disclosure will become more apparent from the following detailed description of several embodiments which proceeds with reference to the accompanying drawings.

BRIEF DESCRIPTION OF THE DRAWINGS

FIG. 8 shows schematic diagrams illustrating the deletion of the NS2 gene from RSV 6120/NS12Ltr/GFP. The upper sequence line shows SEQ ID NOs: 18 and 22. The lower sequence line shows SEQ ID NOs: 23 and 24.

SEQUENCE LISTING

Figure 1:
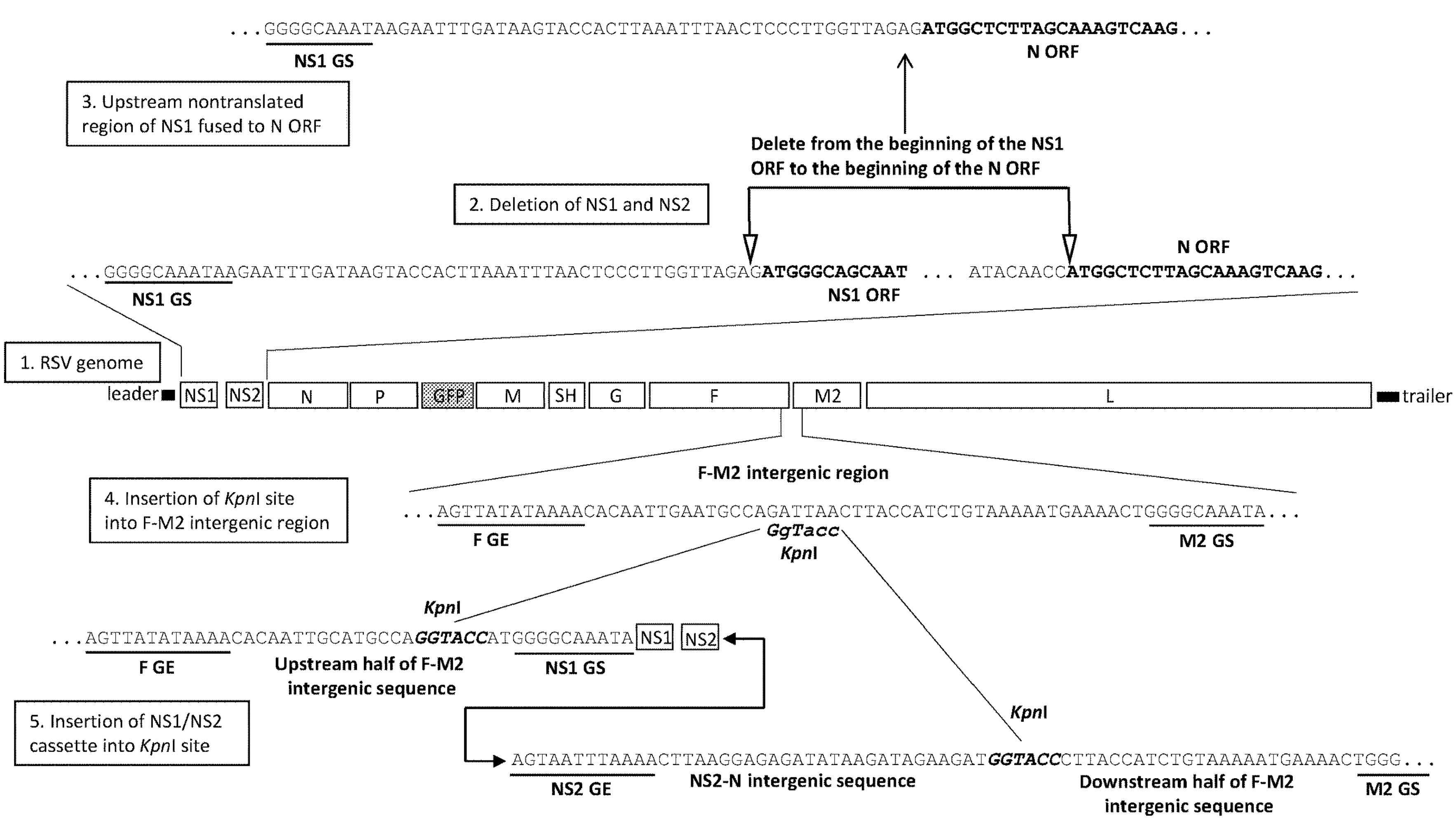
FIG. 1 shows schematic diagrams illustrating the creation of the recombinant RSV 6120/NS12FM2/GFP in which NS1 and NS2 genes were shifted to gene positions 7 and 8. Note that the GFP gene is not included in the gene position numbering. The sequences shown (from top to bottom) are SEQ ID NO: 9, SEQ ID NOs: 10 and 11, SEQ ID NO: 12, and SEQ ID NOs: 13 and 14, respectively.

The nucleic and amino acid sequences listed in the accompanying sequence listing are shown using standard letter abbreviations for nucleotide bases, and three letter code for amino acids, as defined in 37 C.F.R. 1.822. The Sequence Listing is submitted as an ASCII text file in the form of the file named "Sequence.txt" (~164 kb), which was created on May 25, 2018 which is incorporated by reference herein. In the accompanying sequence listing:

SEQ ID NO: 1 is the antigenomic cDNA sequence for recombinant RSV strain 6120/NS12FM2GFP.

SEQ ID NO: 2 is the antigenomic cDNA sequence for recombinant RSV strain 6120/NS12FM2.

SEQ ID NO: 3 is the antigenomic cDNA sequence for recombinant RSV strain 6120/NS12LtrGFP.

SEQ ID NO: 4 is the antigenomic cDNA sequence for recombinant RSV strain 6120/NS12Ltr.

SEQ ID NO: 5 is the antigenomic cDNA sequence for recombinant RSV strain 6120/NS12FM2/ΔNS2/GFP.

SEQ ID NO: 6 is the antigenomic cDNA sequence for recombinant RSV strain 6120/NS12FM2/ΔNS2.

SEQ ID NO: 7 is the antigenomic cDNA sequence for recombinant RSV strain 6120/NS12Ltr/ΔNS2/GFP.

SEQ ID NO: 8 is the antigenomic cDNA sequence for recombinant RSV strain 6120/NS12Ltr/ΔNS2.

SEQ ID NOs: 9-24 are fragments of recombinant RSV antigenomic cDNA sequences shown in FIGS. 1-2 and 7-8.

SEQ ID NOs: 25 and 26 are the nucleotide sequences of gene-start transcription signals.

DETAILED DESCRIPTION

Disclosed herein are mutations that are useful in producing recombinant strains of human RSV exhibiting a range of attenuation phenotypes. The mutations of the present invention are based on shifting of the NS1 and/or NS2 genes from their native positions in the RSV genome or antigenome to a higher position i.e. a position that is more distal to the promoter. Also disclosed herein are recombinant RSV strains that include such mutations and are suitable for use as attenuated, live vaccines. Further disclosed herein are methods and compositions related to the expression of the disclosed viruses. For example, isolated polynucleotide molecules that include a nucleic acid sequence encoding the genome or antigenome of the described viruses are disclosed.

The recombinant RSV strains of the present invention comprise a wt RSV genome or antigenome containing modifications or mutations as described in detail below. The wt RSV genome or antigenome encodes the following 11 proteins: the RNA-binding nucleoprotein (N), the phosphoprotein (P), the large polymerase protein (L), the attachment surface glycoprotein (G), the fusion surface glycoprotein (F), the small hydrophobic surface glycoprotein (SH), the internal matrix protein (M), the two nonstructural proteins NS1 and NS2, and the M2-1 and M2-2 proteins. The complete amino acid sequences of these proteins are known in the art. The genome of RSV is a single strand of negative sense RNA of 15.2 kb comprising 10 genes encoding 10 mRNAs. Each mRNA encodes a single protein, except for the M2 mRNA which encodes two separate proteins M2-1 and M2-2. The RSV gene order is: 3'-NS1-NS2-N-P-M-SH-G-F-M2-L with a single viral promoter located at the 3' end. Thus, in the native RSV genome NS1 is at position 1, NS2 at position 2, N at position 3, P at position 4, M at position 5, SH at position 6, G at position 7, F at position 8, M2 at position 9 and L at position 10. This organization is shown schematically in FIG. 1, top panel.

As reported herein, moving NS1 and/or NS2 from their native positions as promoter-proximal genes to a higher gene position, that is a position further distal to the promoter, results in their decreased transcription and expression. For nonsegmented negative strand RNA viruses, the transcription gradient is an important factor in regulating viral gene expression. One recent study showed that expression of a foreign gene was four-fold higher when it was placed between the F and M2 genes in the RSV genome compared to between the L gene and trailer, a difference of two gene positions (Kwilas AR et al 2010 J Virol 84:7770-7781). Another recent study with the related parainfluenza virus type 3 revealed that expression of a foreign gene from gene position 1, 2, or 3 was 30-69-fold, 15-29-fold, and 5-6-fold higher compared to gene position 6 (Liang et al 2014 J Virol 88:4237-4250). This illustrates that moving one or more genes to positions that are progressively more distal to the promoter can provide incremental reductions in gene expression that, when over a range of multiple gene positions, can be substantial.

The NS1 and NS2 proteins antagonize host innate responses including interferon and apoptosis. This antagonistic effect is particularly prominent for NS1. Recombinant RSV in which NS1 and/or NS2 are deleted, in particular NS1 deletion mutant, show reduced virus replication in vitro due to increased apoptosis, an effect that also is observed in Vero cells used in the manufacture of live RSV vaccines (Bitko et al, 2007 J Virol 81:1786-1795). For example, efforts to manufacture an RSV ΔNS2 virus as a live vaccine have been unsuccessful due to unsatisfactorily low yields (unpublished results). A ΔNS2/ΔNS2 virus also appears to be over-attenuated in African green monkeys (Jin et al 2003 Vaccine 21:3647-3652). In contrast, the RSV recombinant viruses of the present invention comprising NS1 and/or NS2 gene shift mutations did not exhibit growth restriction in Vero cells. This indicates that the levels of NS1 and NS2 that are produced by either mutant control apoptosis sufficiently to obtain efficient viral replication, a surprising result that could not have been predicted. However, these viruses were attenuated in interferon competent cells, indicating that the expected decreased expression of NS1 and/or NS2 indeed rendered the virus increasingly susceptible to restriction.

Thus, NS1 and/or NS2 gene-shift provides a novel means to avoid the over-attenuation associated with gene-deletion. The ability to place the genes in incrementally distal locations relative to the promoter provides a means to incrementally change the magnitude of attenuation. Gene-shift can be combined with other previously described attenuating mutations. Additionally, since NS1 (in particular) and NS2 inhibit the host interferon response, reducing their expression may increase viral immunogenicity due to the adjuvant effects of increased interferon expression. For example, in the bovine model, bovine RSV mutants with NS deletions were shown to have increased immunogenicity in the natural host (Valarcher et al 2003 J Virol 77:8426-8439). Increased apoptosis, as would result from decreased expression of the RSV NS1 and/or NS2 proteins, also has the potential to increase immunogenicity (Pulmanausahakul et al 2001 J Virol 75:10800-10807).

Since there are 8 other RSV genes, NS1 and/or NS2 may be moved to a number of different higher gene positions in different combinations to provide different levels of transcription and expression. The NS1 and/or NS2 genes may be moved to an intergenic region between other genes, or into other non-coding regions.

In some embodiments, the NS1 and NS2 genes may be moved in tandem to higher gene positions or progressively more distal gene positions to provide a graded set of increasing attenuated phenotypes. Thus, in some embodiments, NS1 and NS2 may be at gene positions 2 and 3, 3 and 4, 4 and 5, 5 and 6, 6 and 7, 7 and 8, 8 and 9, or 9 and 10 respectively. In some embodiments, the NS1 and NS2 genes may be moved in tandem from gene positions 1 and 2, respectively, to gene positions 7 and 8, respectively. In some embodiments, the NS1 and NS2 genes may be moved in tandem from gene positions 1 and 2, respectively, to gene positions 9 and 10, respectively. The gene position numbers of genes prior to shift refer to their positions in the native RSV genome before the shift, and the gene position numbers of the genes post-shift refer to their positions in the modified RSV genome.

Alternatively, the NS1 and NS2 may be moved singly or independently of each other. For example, only one of the NS1 or NS2 gene may be moved to a higher gene position. Thus, in some embodiments. NS1 gene may be at gene position 1 and NS2 may be at position 3, 4, 5, 6, 7, 8, 9 or 10. In some embodiments, NS2 gene may be at gene position 2 and NS1 may be at position 3, 4, 5, 6, 7, 8, 9 or 10. In some embodiments each NS1 and NS2 may be moved to a different higher position independently. For example, NS1 may be at any one of positions 2, 3, 4, 5, 6, 7, 8, 9 or 10 and NS2 may be at any one of positions 3, 4, 5, 6, 7, 8, 9 or 10.

In one exemplary embodiment described in Example 1 and shown in FIG. 1, the NS1 and NS2 genes were moved to positions 7 and 8 in the intergenic region between the F and M2 genes so that the gene order in the recombinant virus construct was 3' N-P-M-SH-G-F-NS1-NS2-M2-L. This recombinant construct is named RSV 6120/NS12FM2. The polynucleotide sequence of this construct is shown in SEQ ID NO:2. Some embodiments comprise a polynucleotide sequence that is at least 70%, 75%, 80%, 85%, 90%, 91%, 92%, 93%, 94%, 95%, 96%, 97%, 98%, 99% and 100%, and any number in between, identical to SEQ ID NO: 2.

In some embodiments, the recombinant RSV comprises a RSV genome comprising the 6120 and NS12FM2 mutations as described herein, and a positive-sense sequence denoted by a sequence that is at least 90%, at least 95%, and/or at least 99% identical to SEQ ID NO: 2 (6120/NS12FM2).

Figure 2:
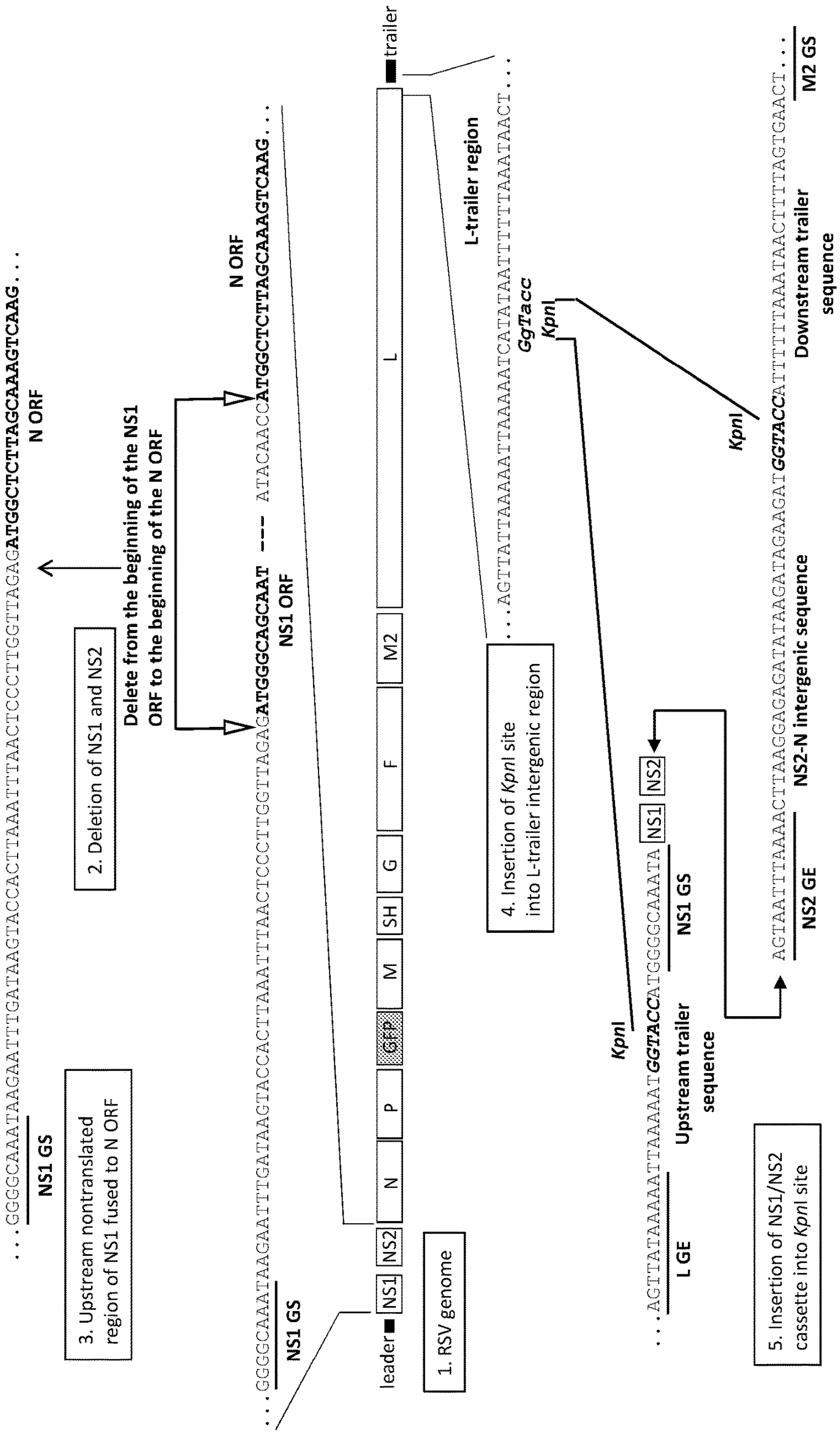
FIG. 2 shows schematic diagrams illustrating the creation of the recombinant RSV 6120/NS12Ltr/GFP virus in which the NS1 and NS2 genes were shifted to positions 9 and 10. The sequences shown (from top to bottom) are SEQ ID NO: 9, SEQ ID NOs: 10 and 11, SEQ ID NO: 15, and SEQ ID NOs: 16 and 17, respectively.

In another exemplary embodiment described in Example 2 and shown in FIG. 2, the NS1 and NS2 genes were moved to positions 9 and 10 so that the gene order in the recombinant virus construct was 3' N-P-M-SH-G-F-M2-L-NS1-NS2. This recombinant construct is named RSV 6120/NS12LTr. The polynucleotide sequence of this construct is shown in SEQ ID NO: 4. Some embodiments comprise a polynucleotide sequence that is at least 70%, 75%, 80%, 85%, 90%, 91%, 92%, 93%, 94%, 95%, 96%, 97%, 98%, 99% and 100%, and any number in between, identical to SEQ ID NO: 4.

In some embodiments, the recombinant RSV comprises a RSV genome comprising the 6120 and NS12Ltr mutations as described herein, and a positive-sense sequence denoted by a sequence that is at least 90%, at least 95%, and/or at least 99% identical to SEQ ID NO: 4 (6120/NS12Ltr).

In some embodiments, the RSV genome or antigenome comprises one or more mutations in the NS1 and/or NS2 gene, in addition to the shift in the position of the NS1/NS2 genes (for example to positions 7 and 8, or 9 and 10, respectively). The mutation may be a point mutation, a substitution or a deletion. The deletion may be partial or complete. Some exemplary embodiments are described in Examples 5 and 6 and shown in FIGS. 7 and 8. These include the constructs 6120/NS12M2F/ΔNS2 (SEQ ID NO: 6) and 6120/NS12Ltr/ΔNS2 (SEQ ID NO: 8). Design and construction of these constructs is described in Examples 5 and 6.

In some embodiments, the recombinant RSV comprises a RSV genome comprising the 6120, NS12FM2, and ΔNS2 mutations as described herein, and a positive-sense sequence denoted by a sequence that is at least 90%, at least 95%, and/or at least 99% identical to SEQ ID NO: 6 (6120/NS12FM2/ΔNS2).

In some embodiments, the recombinant RSV comprises a RSV genome comprising the 6120, NS12Ltr, and ΔNS2 mutations as described herein, and a positive-sense sequence denoted by a sequence that is at least 90%, at least 95%, and/or at least 99% identical to SEQ ID NO: 8 (6120/NS12Ltr/ΔNS2).

In several embodiments, the genome of the recombinant RSV comprises the one or more mutations as discussed herein, and any remaining sequence difference of the genome of the recombinant RSV compared to the genomic sequence of D46 RSV (GenBank accession number KT992094, which is incorporated by reference herein) is biologically insignificant (for example, the remaining sequence differences do not include changes to the wild-type genomic sequence that modify a known cis-acting signal or change amino acid coding, or measurably affect in vitro replication or plaque size of the virus).

In another exemplary embodiment, the antigenome cDNA may be modified to contain a reporter gene, for instance a gene encoding enhanced green fluorescent protein (GFP). The GFP gene could be inserted between the RSV P and M genes (Munir et al 2008 J Virol 82:8780-8796), or as the first gene in the genome (Zhang et al 2002 J Virol 76:5654-5666), or between any pair of genes. The insertion of a GFP gene in the first gene position had little or no effect on RSV replication or pathogenesis in cell lines and in an in vitro human airway epithelium (HAE) culture (Zhang et al 2002 J Virol 76:5654-5666), and the same appeared to be the case for GFP inserted between the P and M genes (Munir et al 2008 J Virol 82:8780-8796). One purpose of expressing GFP from the viral genome is to facilitate monitoring infection in initial experiments, because it allows visualization of infections in live cells without interfering with the infection. GFP is often used in this fashion in initial experiments. Note that, when used, GFP is not included in the gene position numbering in this disclosure. While GFP expression can be helpful in initial pre-clinical studies, it typically would not be included in products for human use. Some exemplary embodiments are described herein. These are RSV 6120/NS12FM2/GFP (SEQ ID NO: 1), 6120/NS12Ltr/GFP (SEQ ID NO: 3), 6120/NS12M2F/ΔNS2/GFP (SEQ ID NO: 5) and 6120/NS12Ltr/ΔNS2/GFP (SEQ ID NO: 7). Design and construction of these constructs is described in Examples 1, 2, 5 and 6 and shown in FIGS. 1, 2, 7 and 8.

Additional mutations may be introduced to construct additional viral strains with desired characteristics. For example, the added mutations may specify different magnitudes of attenuation, and thus give incremental increases in attenuation. Thus, candidate vaccine strains may be further attenuated by incorporation of at least one, and preferably two or more different attenuating mutations, for example mutations identified from a panel of known, biologically derived mutant RSV strains. A number of such mutations are discussed here as examples. From this exemplary panel a large "menu" of attenuating mutations can be created, in which the NS1 and/or NS2 gene shift mutation may be combined with any other mutation(s) within the panel for calibrating the level of attenuation and other desirable phenotypes. Additional attenuating mutations may be identified in non-RSV negative stranded RNA viruses and incorporated in RSV mutants of the invention by mapping the mutation to a corresponding, homologous site in the recipient RSV genome or antigenome and mutating the existing sequence in the recipient to the mutant genotype (either by an identical or conservative mutation). Additional useful mutations can be determined empirically by mutational analysis using recombinant minigenome systems and infectious virus as described in the references incorporated herein. Attenuation also can be achieved by codon-pair-deoptimization, which does not depend on identification of specific attenuating lesions, but rather alters gene expression by general mechanisms such reducing the efficiency of mRNA translation, among other effects (Le Nouen et al 2014 Proc Natl Acad Sci USA 111:13169-13174). A number of exemplary additional mutations are described below. These are for exemplary purposes only and are not meant to limit the scope of the present invention.

The recombinant RSV constructs of the present invention comprising the NS1 and/or NS2 gene shift exhibit reduced expression of the NS1 and/or NS2 gene as compared to an RSV having the NS1 and NS2 genes in their native positions 1 and 2. The term "expression" as used herein refers to is intended to encompass the entire process of protein production, including transcription, translation, post-translational modification, and physical stability required to form and accumulate a functional protein.

The recombinant RSV constructs exhibit reduced inhibition of host interferon response i.e., the cells carrying such viruses exhibit increased expression of host interferon mRNAs and/or proteins, and/or decreased viral inhibition of interferon-mediated effects. In interferon competent cells i.e. cultured cells that can produce interferons in response to viral infection, e.g., human airway epithelial A549 cells, ATCC CCL-185, the recombinant RSV constructs of the present invention are increasingly susceptible to restriction. On the other hand, in interferon incompetent cells i.e. cultured cells that cannot produce interferons in response to viral infection, e.g., African green monkey Vero cells, ATCC CCL-81, the recombinant RSV constructs of the present invention retains replication efficiency.

The ability of a live RSV vaccine candidate to replicate efficiently in Vero cells is beneficial because this is a cell substrate often used for vaccine manufacture. This is relevant in the case of the NS1 and NS2 genes because deletion of either or both from RSV results in more rapid and more extensive apoptosis when cells are infected with the NS-deletion viruses, compared to wild type RSV (Bitko, et al. 2007. J Virol 81:1786-1795). Embodiments of the disclosed recombinant RSV provide the ability to reduce the expression (and interferon antagonism) of NS1 and/or NS2 without completely losing expression, and this provides the advantage of unrestricted growth in Vero cells. In addition, shifting of the NS1 and NS2 genes to higher gen positions in the RSV genome provides a means to derive a range of incrementally-increasing attenuation phenotypes.

Additional Mutations

In some embodiments, RSV genome or antigenome comprises one or more mutations in one or more of the N, P, M, SH, G, F, M2 (M2-1 ORF or M2-2 ORF) and L genes, in addition to the shift in the position of the NS1/NS2 genes (for example to positions 7 and 8, or 9 and 10, respectively). For example, the RSV genome or antigenome may comprise a mutation in the M2-2 ORF of the M2 gene which ablates or reduces the expression of the M2-2 protein, in addition to the shift in the position of the NS1/NS2 genes (for example to positions 7 and 8, or 9 and 10, respectively). Such mutation may comprise one or more point mutations, a partial deletion of the M2-2 ORF, or a complete deletion of the M2-2 protein.

In some embodiments, the recombinant RSV strains of the present invention comprises a deletion of the non-translated sequences in genes, in the intergenic regions, and in the trailer region, in addition to the shift in the position of the NS1/NS2 genes (for example to positions 7 and 8, or 9 and 10, respectively). In one embodiment, such deletion occurs in the downstream end of the SH gene, resulting in a mutation called the "6120 Mutation" herein. It involves deletion of 112 nucleotides of the downstream non-translated region of the SH gene and the introduction of five translationally-silent point mutations in the last three codons and the termination codon of the SH gene (Bukreyev, et al. 2001. J Virol 75:12128-12140). The 6120 mutation stabilizes the antigenomic cDNA in bacteria so that it can be more easily manipulated and prepared. In wt RSV, this mutation was previously found to confer a 5-fold increase in replication efficiency in vitro (Bukreyev, et al. 2001. J Virol 75:12128-12140), whereas it was not thought to increase replication efficiency in vivo.

In some embodiments the recombinant RSV strains may comprise the "cp" mutation, in addition to the shift in the position of the NS1/NS2 genes (for example to positions 7 and 8, or 9 and 10, respectively). This mutation refers to a set of five amino acid substitutions in three proteins (N (V2671), F (E218A and T5231), and L (C319Y and H1690Y)) that together (on their own) confer an approximate 10-fold reduction in replication in seronegative chimpanzees, and a reduction in illness (Whitehead, et al. 1998. J Virol 72:4467-4471). The cp mutation was previously shown to be associated with a moderate attenuation phenotype (Whitehead, 1999. J Virol 72:4467-4471).

In addition, previous analysis of 6 biological viruses that had been derived by chemical mutagenesis of cpRSV and selected for the temperature-sensitive (ts) phenoptype yielded a total of 6 independent mutations that each conferred a ts attenuation phenotype and could be introduced in the recombinant viruses of the present invention, in addition to the shift in the position of the NS1/NS2 genes (for example to positions 7 and 8, or 9 and 10, respectively). Five of these were amino acid substitutions in the L protein, which were named based on virus number rather than sequence position: "955" (N43I), "530" (F521L), "248" (Q831L), "1009" (M1169V), and "1030" (Y1321N) (Juhasz, et al. 1999. Vaccine 17:1416-1424; Collins, et al. 1999. Adv Virus Res 54:423-451; Firestone, et al. 1996. Virology 225:419-422; Whitehead, et al. 1999. J Virol 73:871-877). The sixth mutation (called "404") was a single nucleotide change in the gene-start transcription signal of the M2 gene (GGGGCAAATA, SEQ ID NO: 25 to GGGGCAAACA, SEQ ID NO: 26, mRNA-sense) (Whitehead, et al. 1998. Virology 247:232-239). Reverse genetics was recently used to increase the genetic stability of the 248 and 1030 mutations (Luongo, et al. 2009. Vaccine 27:5667-5676; Luongo, et al. 2012. J Virol 86:10792-10804). Another attenuating mutation comprises a deletion of codon 1313 in the L protein and combining it with an I1314L substitution to confer increased genetic stability (Luongo, et al. 2013. J Virol 87:1985-1996).

In some embodiments, the recombinant RSV strains may comprise one or more changes in the F protein, e.g. the "HEK" mutation, which comprises two amino acid substitutions in the F protein namely K66E and Q101P (described in Connors, et al. 1995. Virology 208:478-484; Whitehead, et al. 1998. J Virol 72:4467-4471), in addition to the shift in the position of the NS1/NS2 genes (for example to positions 7 and 8, or 9 and 10, respectively). The introduction of the HEK amino acid assignments into the strain A2 F sequence of this disclosure results in an F protein amino acid sequence that is identical to that of an early-passage (human embryonic kidney cell passage 7, HEK-7) of the original clinical isolate of strain A2 (Connors, et al. 1995. Virology 208:478-484; Whitehead, et al. 1998. J Virol 72:4467-4471). It results in an F protein that is much less fusogenic and is thought to represent the phenotype of the original A2 strain clinical isolate (Liang et al. J Virol 2015 89:9499-9510). The HEK F protein also forms a more stable trimer (Liang et al. J Virol 2015 89:9499-9510). This may provide a more authentic and immunogenic form of the RSV F protein, possibly enriched for the highly immunogenic pre-fusion conformation (McLellan et al. Science 2013 340(6136):1113-7; Science 2013 342(6158):592-8.). Thus, mutations can be introduced with effects additional to effects on the magnitude of virus replication.

In some embodiments the recombinant strains may comprise one or more changes in the L protein, e.g. the stabilized 1030 or the "1030s" mutation which comprises 1321K (AAA)/51313(TCA) (Luongo, et al. 2012. J Virol 86:10792-

10804), in addition to the shift in the position of the NS1/NS2 genes (for example to positions 7 and 8, or 9 and 10, respectively).

In some embodiments the recombinant strains may comprise one or more changes in the N protein, e.g. an amino substitution such as T24A, or in the NS protein, e.g. an amino acid substitution such as K51R, in addition to the shift in the position of the NS1/NS2 genes (for example to positions 7 and 8, or 9 and 10, respectively).

In some embodiments, the viral strains comprise a deletion in the SH gene, in addition to the shift in the position of the NS1/NS2 genes (for example to positions 7 and 8, or 9 and 10, respectively). For example, in some embodiments, the viral strains comprise a 419 nucleotide deletion at position 4197-4615 (4198-4616 of SEQ ID NO: 1), denoted herein as the "ΔSH" mutation. This deletion results in the deletion of M gene-end, M/SH intergenic region, and deletion of the SH ORF.

The F and/or G protein amino acid sequences of the disclosed recombinant RSV strains can be modified to represent currently-circulating strains (in addition to the shift in the position of the NS1/NS2 genes, for example to positions 7 and 8, or 9 and 10, respectively), which can be particularly relevant in the case of the divergent G protein, or to represent early-passage clinical isolates. Deletions or substitutions may be introduced into the G protein to obtain improved immunogenicity or other desired properties. For example, the CX3C fractalkine motif in the G protein might be ablated to improve immunogenicity (Chirkova et al. J Virol 2013 87:13466-13479). In some embodiments, the nucleotide sequence encoding the G protein of the RSV may be replaced with nucleotide sequence G001 from the clinical isolate A/Maryland/001/11 ("G001"). In some embodiments, the nucleotide sequence encoding the F protein of the RSV may be replaced with the nucleotide sequence F001 from the clinical isolate A/Maryland/001/11 ("F001").

In some embodiments, a native or naturally occurring nucleotide sequence encoding a protein of the RSV may be replaced with a codon optimized sequence designed for increased expression in a selected host, in particular the human, in addition to the shift in the position of the NS1/NS2 genes (for example to positions 7 and 8, or 9 and 10, respectively). Alternatively, a sequence can be designed to be suboptimal on the codon or codon-pair level.

In addition to the above described mutations, recombinant RSV according to the invention can incorporate heterologous, coding or non-coding nucleotide sequences from any RSV or RSV-like virus, e.g., human, bovine, ovine, murine (pneumonia virus of mice), or avian (turkey rhinotracheitis virus) pneumovirus, or from another enveloped virus, e.g., parainfluenza virus (PIV). Exemplary heterologous sequences include RSV sequences from one human RSV strain combined with sequences from a different human RSV strain. In yet additional aspects, one or more human RSV coding or non-coding polynucleotides are substituted with a counterpart sequence from a heterologous RSV or non-RSV virus to yield novel attenuated vaccine strains. Alternatively, the recombinant RSV may incorporate sequences from two or more, wild-type or mutant human RSV subgroups, for example a combination of human RSV subgroup A and subgroup B sequences. RSV exists as two antigenic subgroups, A and B, which have substantial sequence and antigenic differences, in particular for the G protein. It is common for A and B strains to alternate predominance in 1- to 2-year cycles, suggesting that the antigenic differences are sufficient to facilitate re-infection by a heterologous subgroup strain (Hall et al 1990 J Infect 162:1283-1290; Wattis 1991 J Infect Dis 163:464-469; Peret et al 1998 J Gen Virol 79:2221-2229). Therefore, the recombinant RSV may incorporate sequences from the heterologous subgroup in order to increase the breadth of protection. For example, the F and/or G proteins of an attenuated RSV of one subgroup might be swapped with those of the second subgroup in order to make a new vaccine matched to the heterologous subgroup (Whitehead et al 1999 J Virol 73:9773-9780). As another example, the G protein of the heterologous subgroup can be expressed as an additional gene. In this way, an RSV vaccine could be designed with one or more components that represent both antigenic subgroups.

In addition to the recombinant RSVs having the particular mutations described herein, the disclosed viruses may be modified further as would be appreciated by those skilled in the art. For example, the recombinant RSVs may have one or more of its proteins deleted or otherwise mutated or a heterologous gene from a different organism may be added to the genome or antigenome so that the recombinant RSV expresses or incorporates that protein upon infecting a cell and replicating. Furthermore, those skilled in the art will appreciate that other previously defined mutations known to have an effect on RSV may be combined with one or more of any of the mutations described herein to produce a recombinant RSV with desirable attenuation or stability characteristics.

In some embodiments, the disclosed recombinant RSV vaccine strains can be produced using a recombinant DNA-based technique called reverse genetics (Collins, et al. 1995. Proc Natl Acad Sci USA 92:11563-11567). This system allows de novo recovery of infectious virus entirely from cDNA in a qualified cell substrate under defined conditions. Reverse genetics provides a means to introduce predetermined mutations into the RSV genome via the cDNA intermediate. Specific attenuating mutations were characterized in preclinical studies and combined to achieve the desired level of attenuation. Derivation of vaccine viruses from cDNA minimizes the risk of contamination with adventitious agents and helps to keep the passage history brief and well documented. Once recovered, the engineered virus strains propagate in the same manner as a biologically derived virus. As a result of passage and amplification, the vaccine viruses do not contain recombinant DNA from the original recovery.

The Examples in the present disclosure utilized RSV strain A2 of antigenic subgroup A, which is the most widely used experimental strain and also is the parent of numerous live attenuated RSV vaccine candidates that have been evaluated in clinical studies. Given that a variety of additional RSV strains exist (e.g., RSV B1, RSV Long, RSV Line 19), those skilled in the art will appreciate that certain strains of RSV may have nucleotide or amino acid insertions or deletions that alter the position of a given residue. For example, if a protein of another RSV strain had, in comparison with strain A2, two additional amino acids in the upstream end of the protein, this would cause the amino acid numbering of downstream residues relative to strain A2 to increase by an increment of two. However, because these strains share a large degree of sequence identity, those skilled in the art would be able to determine the location of corresponding sequences by simply aligning the nucleotide or amino acid sequence of the A2 reference strain with that of the strain in question. Therefore, it should be understood that the amino acid and nucleotide positions described herein, though specifically enumerated in the context of this disclosure, can correspond to other positions when a sequence shift has occurred or due to sequence variation between virus strains. In the comparison of a protein, or protein segment, or gene, or genome, or genome segment between two or more related viruses, a "corresponding" amino acid or nucleotide residue is one that is thought to be exactly or approximately equivalent in function in the different species.

Unless context indicates otherwise, the numbering used in this disclosure is based on the sequence of the wild-type RSV A2 strain (GenBank accession number M74568) and viral genomic sequences described are in positive-sense.

In some embodiments of the present invention, the recombinant RSV strains were derived from the recombinant version of strain A2 that is called D46. The complete sequence of D46 is shown in U.S. Pat. No. 6,790,449 and is being made available as GenBank accession number KT992094. (In some instances and publications, the parent virus and sequence is called D53 rather than D46, a bookkeeping difference that refers to the strain of bacteria used to propagate the antigenomic cDNA and has no other known significance or effect. For the purposes of this disclosure, D46 and D53 are interchangeable.) The nucleotide sequence of D46 differs from the sequence of RSV A2 strain M74568 in 25 nucleotide positions, which includes a 1-nucleotide insert at position 1099.

With regard to sequence numbering of nucleotide and amino acid sequence positions for the described viruses, a convention was used whereby each nucleotide or amino acid residue in a given viral sequence retained the sequence position number that it has in the original 15,222-nucleotide biological wt strain A2 virus (Genbank accession number M74568), irrespective of any modifications. Thus, although a number of genomes contain deletions and/or insertions that cause changes in nucleotide length, and in some cases amino acid length, the numbering of all of the other residues (nucleotide or amino acid) in the genome and encoded proteins remains unchanged. It also is recognized that, even without the expedient of this convention, one skilled in the art can readily identify corresponding sequence positions between viral genomes or proteins that might differ in length, guided by sequence alignments as well as the positions of open reading frames, well-known RNA features such as gene-start and gene-end signals, and amino acid sequence features.

Recombinant viruses may be evaluated in cell culture, rodents and non-human primates for infectivity, replication kinetics, yield, efficiency of protein expression, and genetic stability using the methods known in the art. While these semi-permissive systems may not reliably detect every difference in replication, substantial differences in particular may be detected. Also recombinant strains may be evaluated successively in adults, seropositive children, and seronegative children. In some cases, where a previous similar strain has already been shown to be well-tolerated in seronegative children, a new strain may be evaluated directly in seronegative children. Evaluation may be done, for example, in groups of 10 vaccine recipients and 5 placebo recipients, which is a small number that allows simultaneous evaluation of multiple candidates. Candidates may be evaluated in the period immediately post-immunization for vaccine virus infectivity, replication kinetics, shedding, tolerability, immunogenicity, and genetic stability, and the vaccinees may be subjected to surveillance during the following RSV season for safety, RSV disease, and changes in RSV-specific serum antibodies, as described in Karron, et al. 2015, Science Transl Med 2015 7(312):312ra175, which is incorporated herein in its entirety. Thus, analysis of selected representative viruses may provide for relatively rapid triage to narrow down candidates to identify the most optimal.

Reference to a protein or a peptide includes its naturally occurring form, as well as any fragment, domain, or homolog of such protein. As used herein, the term "homolog" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes in one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation. A homolog can have either enhanced, decreased, or substantially similar properties as compared to the naturally occurring protein or peptide. A homolog of a given protein may comprise, consist essentially of, or consist of, an amino acid sequence that is at least about 50%, or at least about 55%, or at least about 60%, or at least about 65%, or at least about 70%, or at least about 75%, or at least about 80%, or at least about 85%, or at least about 90%, or at least about 95%, or at least about 96%, or at least about 97%, or at least about 98%, or at least about 99% identical (or any percent identity between 45% and 99%, in whole integer increments), to the amino acid sequence of the reference protein.

In one aspect of the invention, a selected gene segment, such as one encoding a selected protein or protein region (e.g., a cytoplasmic tail, transmembrane domain or ectodomain, an epitopic site or region, a binding site or region, an active site or region containing an active site, etc.) from one RSV, can be substituted for a counterpart gene segment from the same or different RSV or other source, to yield novel recombinants having desired phenotypic changes compared to wild-type or parent RSV strains. For example, recombinants of this type may express a chimeric protein having a cytoplasmic tail and/or transmembrane domain of one RSV fused to an ectodomain of another RSV. Other exemplary recombinants of this type express duplicate protein regions, such as duplicate immunogenic regions. As used herein, "counterpart" genes, gene segments, proteins or protein regions, are typically from heterologous sources (e.g., from different RSV genes, or representing the same (i.e., homologous or allelic) gene or gene segment in different RSV strains). Typical counterparts selected in this context share gross structural features, e.g., each counterpart may encode a comparable structural "domain," such as a cytoplasmic domain, transmembrane domain, ectodomain, binding site or region, epitopic site or region, etc. Counterpart domains and their encoding gene segments embrace an assemblage of species having a range of size and amino acid (or nucleotide) sequence variations, which range is defined by a common biological activity among the domain or gene segment variants. For example, two selected protein domains encoded by counterpart gene segments within the invention may share substantially the same qualitative activity, such as providing a membrane spanning function, a specific binding activity, an immunological recognition site, etc. More typically, a specific biological activity shared between counterparts, e.g., between selected protein segments or proteins, will be substantially similar in quantitative terms, i.e., they will not vary in respective quantitative activity profiles by more than 30%, preferably by no more than 20%, more preferably by no more than 5-10%.

In alternative aspects of the invention, the infectious RSV produced from a cDNA-expressed genome or antigenome can be any of the RSV or RSV-like strains, e.g., human, bovine, murine, etc., or of any pneumovirus or metapneumovirus, e.g., pneumonia virus of mice or avian metapneumovirus. To engender a protective immune response, the RSV strain may be one which is endogenous to the subject being immunized, such as human RSV being used to immunize humans. The genome or antigenome of endogenous RSV can be modified, however, to express RSV genes or gene segments from a combination of different sources, e.g., a combination of genes or gene segments from different RSV species, subgroups, or strains, or from an RSV and another respiratory pathogen such as human parainfluenza virus (PIV) (see, e.g., Hoffman et al. J. Virol. 71:4272-4277 (1997); Durbin et al. Virology 235(2):323-32 (1997); Murphy et al. U.S. Patent Application Ser. No. 60/047,575, filed May 23, 1997, and the following plasmids for producing infectious PIV clones: p3/7(131) (ATCC 97990); p3/7(131) 2G(ATCC 97889); and p218(131) (ATCC 97991); each deposited Apr. 18, 1997 under the terms of the Budapest Treaty with the American Type Culture Collection (ATCC) of 10801 University Blvd., Manassas, Va. 20110-2209, USA., and granted the above identified accession numbers.

In certain embodiments of the invention, recombinant RSV are provided wherein individual internal genes of a human RSV are replaced with, e.g., a bovine or other RSV counterpart, or with a counterpart or foreign gene from another respiratory pathogen such as PIV. Also, human RSV cis-acting sequences, such as promoter or transcription signals, can be replaced with, e.g., their bovine RSV counterpart. Reciprocally, means are provided to generate live attenuated bovine RSV by inserting human attenuating genes or cis-acting sequences into a bovine RSV genome or antigenome background.

Thus, infectious recombinant RSV intended for administration to humans can be a human RSV that has been modified to contain genes from, e.g., a bovine RSV or a PIV, such as for the purpose of attenuation. For example, by inserting a gene or gene segment from PIV, a bivalent vaccine to both PIV and RSV is provided. Alternatively, a heterologous RSV species, subgroup or strain, or a distinct respiratory pathogen such as PIV, may be modified, e.g., to contain genes that encode epitopes or proteins which elicit protection against human RSV infection. For example, the human RSV glycoprotein genes can be substituted for the bovine glycoprotein genes such that the resulting bovine RSV, which now bears the human RSV surface glycoproteins and would retain a restricted ability to replicate in a human host due to the remaining bovine genetic background, elicits a protective immune response in humans against human RSV strains.

The ability to analyze and incorporate other types of attenuating mutations into infectious RSV for vaccine development extends to a broad assemblage of targeted changes in RSV clones. For example, any RSV gene which is not essential for growth may be ablated or otherwise modified to yield desired effects on virulence, pathogenesis, immunogenicity and other phenotypic characters.

As used herein, “heterologous genes” refers to genes taken from different RSV strains or types or non-RSV sources. These heterologous genes can be inserted in whole or in part, the order of genes changed, gene overlap removed, the RSV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Deletions, insertions, substitutions and other mutations involving changes of whole viral genes or gene segments in recombinant RSV of the invention yield highly stable vaccine candidates, which may be relevant in the case of immunosuppressed individuals. Many of these mutations will result in attenuation of resultant vaccine strains, whereas others will specify different types of desired phenotypic changes. For example, certain viral genes are known which encode proteins that specifically interfere with host immunity (see, e.g., Kato et al., EMBO. J. 16:578-87 (1997). Ablation of such genes in vaccine viruses is expected to reduce virulence and pathogenesis and/or improve immunogenicity.

Other mutations within RSV of the present invention involve replacement of the 3' end of genome with its counterpart from antigenome, which is associated with changes in RNA replication and transcription. In addition, the intergenic regions (Collins et al., Proc. Natl. Acad. Sci. USA 83:4594-4598 (1986)) can be shortened or lengthened or changed in sequence content, and the naturally-occurring gene overlap (Collins et al., Proc. Natl. Acad. Sci. USA 84:5134-5138 (1987)) can be removed or changed to a different intergenic region by the methods described herein.

In another embodiment, a sequence surrounding a translational start site (preferably including a nucleotide in the -3 position) of a selected RSV gene is modified, alone or in combination with introduction of an upstream start codon, to modulate RSV gene expression by specifying up- or down-regulation of translation.

Alternatively, or in combination with other RSV modifications disclosed herein, RSV gene expression can be modulated by altering a transcriptional GS signal of a selected gene(s) of the virus. In one exemplary embodiment, the GS signal of M2 is modified to include a defined mutation to superimpose a is restriction on viral replication.

Yet additional RSV clones within the invention incorporate modifications to a transcriptional GE signal. For example, RSV clones are provided which substitute or mutate the GE signal of the NS1 and NS2 genes for that of the N gene, resulting in decreased levels of readthrough mRNAs and increased expression of proteins from downstream genes. The resulting recombinant virus exhibits increased growth kinetics and increased plaque size, providing but one example of alteration of RSV growth properties by modification of a cis-acting regulatory element in the RSV genome.

In another aspect, expression of the G protein may be increased by modification of the G mRNA. The G protein is expressed as both a membrane bound and a secreted form, the latter form being expressed by translational initiation at a start site within the G gene translational open reading frame. The secreted form may account for as much as one-half of the expressed G protein. Ablation of the internal start site (e.g., by sequence alteration, deletion, etc.), alone or together with altering the sequence context of the upstream start site yields desired changes in G protein expression. Ablation of the secreted form of the G protein also will improve the quality of the host immune response to exemplary, recombinant RSV, because the soluble form of the G protein is thought to act as a “decoy” to trap neutralizing antibodies. Also, soluble G protein has been implicated in enhanced immunopathology due to its preferential stimulation of a Th2-biased response.

In yet other embodiments, RSV useful in a vaccine formulation may be conveniently modified to accommodate antigenic drift in circulating virus. Typically the modification will be in the G and/or F proteins. The entire G or F gene, or the segments encoding particular immunogenic regions thereof, is incorporated into the RSV genome or antigenome cDNA by replacement of the corresponding region in the infectious clone or by adding one or more copies of the gene such that several antigenic forms are represented.

In addition to the above described modifications to recombinant RSV, different or additional modifications in RSV clones can be made to facilitate manipulations, such as the insertion of unique restriction sites in various intergenic regions or elsewhere. Nontranslated gene sequences can be removed to increase capacity for inserting foreign sequences.

Introduction of the foregoing, defined mutations into an infectious RSV clone can be achieved by a variety of well-known methods. By “infectious clone” is meant cDNA or its product, synthetic or otherwise, which can be transcribed into genomic or antigenomic RNA capable of producing an infectious virus. The term “infectious” refers to a virus or viral structure that is capable of replicating in a cultured cell or animal or human host to produce progeny virus or viral structures capable of the same activity. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA is well-known by those of ordinary skill in the art and has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. A mutated subfragment can then be assembled into the complete antigenome or genome cDNA. Mutations can vary from single nucleotide changes to replacement of large cDNA pieces containing one or more genes or genome regions.

Recombinant RSV may be produced by the intracellular coexpression of a cDNA that encodes the RSV genomic RNA, together with those viral proteins necessary to generate a transcribing, replicating nucleocapsid. Plasmids encoding other RSV proteins may also be included with these essential proteins. Alternatively, RNA may be synthesized in in vitro transcription reactions and transfected into cultured cells.

Accordingly, also described herein are isolated polynucleotides that encode the described mutated viruses, make up the described genomes or antigenomes, express the described genomes or antigenomes, or encode various proteins useful for making recombinant RSV in vitro. The nucleic acid sequences of a number of exemplary polynucleotides are also provided. Included within the scope of the invention are polynucleotides comprising sequences that consist or consist essentially of any of the aforementioned nucleic acid sequences. Further included are polynucleotides that possess at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent or more identity, or any number in between, to any of the aforementioned sequences or SEQ ID NOs, as well as polynucleotides that hybridize to, or are the complements of the aforementioned molecules.

These polynucleotides can be included within or expressed by vectors in order to produce a recombinant RSV. Accordingly, cells transfected with the isolated polynucleotides or vectors are also within the scope of the invention and are exemplified herein.

In related aspects of the invention, compositions (e.g., isolated polynucleotides and vectors incorporating an RSV-encoding cDNA) and methods are provided for producing an recombinant RSV. Included within these aspects of the invention are novel, isolated polynucleotide molecules and vectors incorporating such molecules that comprise a RSV genome or antigenome which is modified as described herein. Also provided is the same or different expression vector comprising one or more isolated polynucleotide molecules encoding the RSV proteins. These proteins also can be expressed directly from the genome or antigenome cDNA. The vector(s) are preferably expressed or coexpressed in a cell or cell-free lysate, thereby producing an infectious mutant RSV particle or subviral particle.

In one aspect, the invention includes a method for producing one or more purified RSV protein(s) which involves infecting a host cell permissive of RSV infection with a recombinant RSV strain under conditions that allow for RSV propagation in the infected cell. After a period of replication in culture, the cells are lysed and recombinant RSV is isolated therefrom. One or more desired RSV protein(s) is purified after isolation of the virus, yielding one or more RSV protein(s) for vaccine, diagnostic and other uses.

The above methods and compositions yield infectious viral or subviral particles, or derivatives thereof. An infectious virus is comparable to the authentic RSV virus particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, L and M2-1 proteins is an example of a subviral particle which can initiate an infection if introduced into the cytoplasm of cells. Subviral particles provided within the invention include viral particles which lack one or more protein(s), protein segment(s), or other viral component(s) not essential for infectivity.

In other embodiments the invention provides a cell or cell free lysate containing an expression vector which comprises an isolated polynucleotide molecule encoding mutant RSV genome or antigenome as described above, and an expression vector (the same or different vector) which comprises one or more isolated polynucleotide molecules encoding the N, P, L and RNA polymerase elongation factor proteins of RSV. One or more of these proteins also can be expressed from the genome or antigenome cDNA. Upon expression the genome or antigenome and N, P, L, and RNA polymerase elongation factor proteins combine to produce an infectious RSV viral or sub-viral particle.

The recombinant RSV of the invention are useful in various compositions to generate a desired immune response against RSV in a host susceptible to RSV infection. Attenuated mutant RSV strains of the invention are capable of eliciting a protective immune response in an infected human host, yet are sufficiently attenuated so as to not cause unacceptable symptoms of severe respiratory disease in the immunized host. The attenuated virus or subviral particle may be present in a cell culture supernatant, isolated from the culture, or partially or completely purified. The virus may also be lyophilized, and can be combined with a variety of other components for storage or delivery to a host, as desired.

In another aspect of the invention, the recombinant mutants may be employed as "vectors" for protective antigens of other pathogens, particularly respiratory tract pathogens such as parainfluenza virus (PIV). For example, recombinant RSV may be engineered which incorporate, sequences that encode protective antigens from PIV to produce infectious, attenuated vaccine virus.

In related aspects, the invention provides a method for stimulating the immune system of an individual to elicit an immune response against RSV in a mammalian subject. The method comprises administering an immunogenic formulation of an immunologically sufficient amount of an attenuated, recombinant mutant RSV in a physiologically acceptable carrier and/or adjuvant.

The invention further provides novel vaccines comprising a physiologically acceptable carrier and/or adjuvant and an isolated attenuated mutant RSV particle or subviral particle.

To select candidate vaccine viruses from the host of recombinant RSV strains provided herein, the criteria of viability, efficient replication in vitro, attenuation in vivo, immunogenicity, and phenotypic stability are determined according to well-known methods. Viruses which will be most desired in vaccines of the invention should maintain viability, should replicate sufficiently in vitro well under permissive conditions to make vaccine manufacture possible, should have a stable attenuation phenotype, should be well-tolerated, should exhibit replication in an immunized host (albeit at lower levels), and should effectively elicit production of an immune response in a vaccine sufficient to confer protection against serious disease caused by subsequent infection from wild-type virus. To propagate a RSV virus for vaccine use and other purposes, a number of cell lines which allow for RSV growth may be used. RSV grows in a variety of human and animal cells. Preferred cell lines for propagating attenuated RS virus for vaccine use include DBSFRhL-2, MRC-5, and Vero cells. Highest virus yields are usually achieved with epithelial cell lines such as Vero cells. Cells are typically inoculated with virus at a multiplicity of infection ranging from about 0.001 to 1.0, or more, and are cultivated under conditions permissive for replication of the virus, e.g., at about 30-37° C. and for about 3-10 days, or as long as necessary for virus to reach an adequate titer. Temperature-sensitive viruses often are grown using 32° C. as the "permissive temperature." Virus is removed from cell culture and separated from cellular components, typically by well-known clarification procedures, e.g., centrifugation, and may be further purified as desired using procedures well known to those skilled in the art.

RSV which has been attenuated as described herein can be tested in various well known and generally accepted in vitro and in vivo models to confirm adequate attenuation, resistance to phenotypic reversion, and immunogenicity for vaccine use. In in vitro assays, the modified virus, which can be a multiply attenuated, biologically derived or recombinant RSV, is tested for temperature sensitivity of virus replication or "ts phenotype," and for the small plaque phenotype. Modified virus also may be evaluated in an in vitro human airway epithelium (HAE) model, which appears to provide a means of ranking viruses in the order of their relative attenuation in non-human primates and humans (Zhang et al 2002 J Virol 76:5654-5666; Schaap-Nutt et al 2010 Vaccine 28:2788-2798; Ilyushina et al 2012 J Virol 86:11725-11734). Modified viruses are further tested in animal models of RSV infection. A variety of animal models (e.g., murine, cotton rat, and primate) have been described and are known to those skilled in the art.

In accordance with the foregoing description and based on the Examples below, the invention also provides isolated, infectious RSV compositions for vaccine use. The attenuated virus which is a component of a vaccine is in an isolated and typically purified form. By isolated is meant to refer to RSV which is in other than a native environment of a wild-type virus, such as the nasopharynx of an infected individual. More generally, isolated is meant to include the attenuated virus as a component of a cell culture or other artificial medium. For example, attenuated RSV of the invention may be produced by an infected cell culture, separated from the cell culture and added to a stabilizer.

RSV vaccines of the invention contain as an active ingredient an immunogenically effective amount of RSV produced as described herein. Biologically derived or recombinant RSV can be used directly in vaccine formulations. The biologically derived or recombinantly modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or in frozen form that is thawed prior to use, or lyophilized, the lyophilized preparation being combined with a sterile solution prior to administration, as mentioned above. The compositions may contain pharmaceutically acceptable auxiliary substances as required to approximate physiological conditions, which include, but are not limited to, pH adjusting and buffering agents, tonicity adjusting agents, wetting agents and the like, for example, sodium acetate, sodium lactate, sodium chloride, potassium chloride, calcium chloride, sucrose, magnesium sulfate, phosphate buffers, HEPES (4-(2-hydroxyethyl)-1-piperazineethanesulfonic acid) buffer, sorbitan monolaurate, and triethanolamine oleate. Acceptable adjuvants include incomplete Freund's adjuvant, aluminum phosphate, aluminum hydroxide, or alum, which are materials well known in the art. Preferred adjuvants also include Stimulon™ QS-21 (Aquila Biopharmaceuticals, Inc., Worchester, Mass.), MPL™ (3-0-deacylated monophosphoryl lipid A; RIBI ImmunoChem Research, Inc., Hamilton, Mont.), and interleukin-12 (Genetics Institute, Cambridge, Mass.).

Upon immunization with a RSV vaccine composition, the host responds to the vaccine by producing antibodies specific for RSV virus proteins, e.g., F and G glycoproteins. In addition, innate and cell-mediated immune responses are induced, which can provide antiviral effectors as well as regulating the immune response. As a result of the vaccination the host becomes at least partially or completely immune to RSV infection, or resistant to developing moderate or severe RSV disease, particularly of the lower respiratory tract.

The vaccine compositions containing the attenuated RSV of the invention are administered to a subject susceptible to or otherwise at risk of RSV infection in an "immunogenically effective dose" which is sufficient to induce or enhance the individual's immune response capabilities against RSV. An RSV vaccine composition may be administered by any suitable method, including but not limited to, via injection, aerosol delivery, nasal spray, nasal droplets, oral inoculation, or topical application. In the case of human subjects, the attenuated virus of the invention is administered according to well established human RSV vaccine protocols (Karron et al. JID 191:1093-104, 2005). Briefly, adults or children are inoculated intranasally via droplet with an immunogenically effective dose of RSV vaccine, typically in a volume of 0.5 ml of a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has not been observed with a live virus.

In some embodiments, the vaccine may be administered intranasally or subcutaneously or intramuscularly. In some embodiments, it may be administered to the upper respiratory tract. This may be performed by any suitable method, including but not limited to, by spray, droplet or aerosol delivery. Often, the composition will be administered to an individual seronegative for antibodies to RSV or possessing transplacentally acquired maternal antibodies to RSV.

In all subjects, the precise amount of RSV vaccine administered and the timing and repetition of administration will be determined by various factors, including the patient's state of health and weight, the mode of administration, the nature of the formulation, etc. Dosages will generally range from about 3.0 $\log_{10}$ to about 6.0 $\log_{10}$ plaque forming units ("PFU") or more of virus per patient, more commonly from about 4.0 $\log_{10}$ to 5.0 $\log_{10}$ PFU virus per patient. In one embodiment, about 5.0 $\log_{10}$ to 6.0 $\log_{10}$ PFU per patient may be administered during infancy, such as between 1 and 6 months of age, and one or more additional booster doses could be given 2-6 months or more following the first dose. In another embodiment, young infants could be given a dose of about 5.0 $\log_{10}$ to 6.0 $\log_{10}$ PFU per patient at approximately 2, 4, and 6 months of age, which is the recommended time of administration of a number of other childhood vaccines. In yet another embodiment, an additional booster dose could be administered at approximately 10-15 months of age. In any event, the vaccine formulations should provide a quantity of attenuated RSV of the invention sufficient to effectively stimulate or induce an anti-RSV immune response (an "effective amount").

In some embodiments, the vaccine may comprise attenuated recombinant virus that elicits an immune response against a single RSV strain or antigenic subgroup, e.g. A or B, or against multiple RSV strains or subgroups. In this regard, the recombinant mutant RSV can be combined in vaccine formulations with other RSV vaccine strains or subgroups having different immunogenic characteristics for more effective protection against one or multiple RSV strains or subgroups. They may be administered in a vaccine mixture, or administered separately in a coordinated treatment protocol to elicit more effective protection against one RSV strain, or against multiple RSV strains or subgroups.

The resulting immune response can be characterized by a variety of methods. These include taking samples of nasal washes or sera for analysis of RSV-specific antibodies, which can be detected by tests including, but not limited to, complement fixation, plaque neutralization, enzyme-linked immunosorbent assay, luciferase-immunoprecipitation assay, and flow cytometry. In addition, immune responses can be detected by assay of cytokines in nasal washes or sera, ELISPOT of immune cells from either source, quantitative RT-PCR or microarray analysis of nasal wash or serum samples, and restimulation of immune cells from nasal washes or serum by re-exposure to viral antigen in vitro and analysis for the production or display of cytokines, surface markers, or other immune correlates measures by flow cytometry or for cytotoxic activity against indicator target cells displaying RSV antigens. In this regard, individuals are also monitored for signs and symptoms of upper respiratory illness.

The level of attenuation of vaccine virus may be determined by, for example, quantifying the amount of virus present in the respiratory tract of an immunized host and comparing the amount to that produced by wild-type RSV or other attenuated RS viruses which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of RSV in the nasopharynx of an infected host are well known in the literature. Specimens are obtained by aspiration or washing out of nasopharyngeal secretions and virus quantified in tissue culture or other by laboratory procedure. See, for example, Belshe et al., J. Med. Virology 1:157-162 (1977), Friedewald et al., J. Amer. Med. Assoc. 204:690-694 (1968); Gharpure et al., J. Virol. 3:414-421 (1969); and Wright et al., Arch. Ges. Virusforsch. 41:238-247 (1973). The virus can conveniently be measured in the nasopharynx of host animals, such as chimpanzees.

In summary, the materials, information, and methods described in this disclosure provide an array of attenuated strains with graded attenuation phenotypes, and provide guidance in selecting suitable vaccine candidate strains based on clinical benchmarks. The following examples are provided by way of illustration, not limitation.

Additional Embodiments

Clause 1. An isolated polynucleotide molecule encoding a recombinant respiratory syncytial virus (RSV) variant having an attenuated phenotype comprising a RSV genome or antigenome sequence, wherein the RSV genome or antigenome comprises a modification selected from the group consisting of:

(a) the NS1 gene is in a gene position higher than position 1;

(b) the NS2 gene is in a gene position higher than position 2; and (c) a combination of (a) and (b), optionally, further comprising a reporter gene.

Clause 2. The isolated polynucleotide molecule of clause 1, wherein the modification is a combination of (a) and (b).

Clause 3. The isolated polynucleotide molecule of clause 2, wherein the NS1 gene is in gene position 7 and the NS2 gene is in gene position 8.

Clause 4. The isolated polynucleotide molecule of clause 2, wherein the NS1 gene is in gene position 9 and the NS2 gene is in gene position 10.

Clause 5. The isolated polynucleotide molecule of clause 1, wherein the modification is (a).

Clause 6. The isolated polynucleotide molecule of clause 5, wherein the NS1 gene is in gene position 7 or 9.

Clause 7. The isolated polynucleotide molecule of clause 1, wherein the modification is (b).

Clause 8. The isolated polynucleotide molecule of clause 5 or 6 or 7, wherein the RSV genome or antigenome further comprises a deletion of all or part of the NS1 or NS2 gene.

Clause 9. The isolated polynucleotide molecule of any one of clause 1-8, further comprising a deletion of all or part of the M2-2 gene.

Clause 10. The isolated polynucleotide molecule of clause 1, wherein the RSV genome or antigenome has a positive-sense sequence denoted by a sequence that is at least 90% identical to SEQ ID NO:2.

Clause 11. The isolated polynucleotide molecule of clause 1, wherein the RSV genome or antigenome has a positive-sense sequence denoted by SEQ ID NO:2.

Clause 12. The isolated polynucleotide molecule of clause 1, wherein the RSV genome or antigenome has a positive-sense sequence denoted by a sequence that is at least 90% identical to SEQ ID NO:4.

Clause 13. The isolated polynucleotide molecule of clause 1, wherein the RSV genome or antigenome has a positive-sense sequence denoted by SEQ ID NO:4.

Clause 14. The isolated polynucleotide molecule of clause 8, wherein the RSV genome or antigenome has a positive-sense sequence denoted by a sequence that is at least 90% identical to a sequence selected from the group consisting of SEQ ID NO:6 and SEQ ID NO:8.

Clause 15. The isolated polynucleotide molecule of clause 1, wherein the reporter gene encodes Green Fluorescent Protein (GFP).

Clause 16. The isolated polynucleotide molecule of clause 15, wherein the RSV genome or antigenome has a positive-sense sequence denoted by a sequence that is at least 90% identical to a sequence selected from the group consisting of SEQ ID NO:1, SEQ ID NO:3, SEQ ID NO:5 and SEQ ID NO:7.

Clause 17. The isolated polynucleotide molecule of any one of clauses 1-16, which exhibits reduced expression of the NS1 gene and/or NS2 gene compared to an RSV having the NS1 gene in gene position 1 and the NS2 gene in gene position 2.

Clause 18. The isolated polynucleotide molecule of any one of clauses 1-17, which exhibits reduced transcription of the NS1 gene and/or NS2 gene compared to an RSV having the NS1 gene in gene position 1 and the NS2 gene in gene position 2.

Clause 19. The isolated polynucleotide molecule of any one of clauses 1-16, which exhibits reduced inhibition of host interferon response compared to an RSV having the NS1 gene in gene position 1 and the NS2 gene in gene position 2.

Clause 20. The isolated polynucleotide molecule of any one of clauses 1-16, wherein the RSV variant is increasingly susceptible to restriction in cultured cells that can produce interferons in response to viral infection.

Clause 21. The isolated polynucleotide molecule of any one of clauses 1-16, wherein the RSV variant retains replication efficiency in cultured cells that cannot produce interferons in response to viral infection Clause 22. A vector comprising the isolated polynucleotide molecule of any one of clauses 1-21.

Clause 23. A cell comprising the isolated polynucleotide of any one of clauses 1-21.

Clause 24. A pharmaceutical composition comprising an immunologically effective amount of the recombinant RSV variant encoded by the isolated polynucleotide molecule of any one of clauses 1-21.

Clause 25. The pharmaceutical composition of clause 24 further comprising an adjuvant.

Clause 26. A method of vaccinating a subject against RSV comprising administering the pharmaceutical composition of clause 24.

Clause 27. The method of clause 26, wherein the pharmaceutical composition is administered intranasally.

Clause 28. The method of clause 26 or 27, wherein the pharmaceutical composition is administered via injection, aerosol delivery, nasal spray or nasal droplets.

```
Exemplary Sequences
Antigenomic cDNA sequence of RSV 6120/NS12FM2GFP (SEQ ID NO: 1)
ACGGGAAAAAATGCGTACAACAAACTTGCATAAACCAAAAAAATGGGGCAAATAAGAATTTGATAAGTACCACTTAA

ATTTAACTCCCTTGGTTAGAGATGGCTCTTAGCAAAGTCAAGTTGAATGATACACTCAACAAAGATCAACTTCTGTC

ATCCAGCAAATACACCATCCAACGGAGCACAGGAGATAGTATTGATACTCCTAATTATGATGTGCAGAAACACATCA

ATAAGTTATGTGGCATGTTATTAATCACAGAAGATGCTAATCATAAATTCACTGGGTTAATAGGTATGTTATATGCG

ATGTCTAGGTTAGGAAGAGAAGACACCATAAAAATACTCAGAGATGCGGGATATCATGTAAAAGCAAATGGAGTAGA

TGTAACAACACATCGTCAAGACATTAATGGAAAAGAAATGAAATTTGAAGTGTTAACATTGGCAAGCTTAACAACTG

AAATTCAAATCAACATTGAGATAGAATCTAGAAAATCCTACAAAAAAATGCTAAAAGAAATGGGAGAGGTAGCTCCA

GAATACAGGCATGACTCTCCTGATTGTGGGATGATAATATTATGTATAGCAGCATTAGTAATAACTAAATTAGCAGC

AGGGGACAGATCTGGTCTTACAGCCGTGATTAGGAGAGCTAATAATGTCCTAAAAAATGAAATGAAACGTTACAAAG

GCTTACTACCCAAGGACATAGCCAACAGCTTCTATGAAGTGTTTGAAAAACATCCCCACTTTATAGATGTTTTTGTT

CATTTTGGTATAGCACAATCTTCTACCAGAGGTGGCAGTAGAGTTGAAGGGATTTTTGCAGGATTGTTTATGAATGC

CTATGGTGCAGGGCAAGTGATGTTACGGTGGGGAGTCTTAGCAAAATCAGTTAAAAATATTATGTTAGGACATGCTA

GTGTGCAAGCAGAAATGGAACAAGTTGTTGAGGTTTATGAATATGCCCAAAAATTGGGTGGTGAAGCAGGATTCTAC

CATATATTGAACAACCCAAAAGCATCATTATTATCTTTGACTCAATTTCCTCACTTCTCCAGTGTAGTATTAGGCAA

TGCTGCTGGCCTAGGCATAATGGGAGAGTACAGAGGTACACCGAGGAATCAAGATCTATATGATGCAGCAAAGGCAT
```

-continued

ATGCTGAACAACTCAAAGAAAATGGTGTGATTAACTACAGTGTACTAGACTTGACAGCAGAAGAACTAGAGGCTATC

AAACATCAGCTTAATCCAAAAGATAATGATGTAGAGCTTTGAGTTAATAAAAAATGGGGCAAATAAATCATCATGGA

AAAGTTTGCTCCTGAATTCCATGGAGAAGATGCAAACAACAGGGCTACTAAATTCCTAGAATCAATAAAGGGCAAAT

TCACATCACCCAAAGATCCCAAGAAAAAAGATAGTATCATATCTGTCAACTCAATAGATATAGAAGTAACCAAAGAA

AGCCCTATAACATCAAATTCAACTATTATCAACCCAACAAATGAGACAGATGATACTGCAGGGAACAAGCCCAATTA

TCAAAGAAAACCTCTAGTAAGTTTCAAAGAAGACCCTACACCAAGTGATAATCCCTTTTCTAAACTATACAAAGAAA

CCATAGAAACATTTGATAACAATGAAGAAGAATCCAGCTATTCATACGAAGAAATAAATGATCAGACAAACGATAAT

ATAACAGCAAGATTAGATAGGATTGATGAAAAATTAAGTGAAATACTAGGAATGCTTCACACATTAGTAGTGGCAAG

TGCAGGACCTACATCTGCTCGGGATGGTATAAGAGATGCCATGGTTGGTTTAAGAGAAGAAATGATAGAAAAAATCA

GAACTGAAGCATTAATGACCAATGACAGATTAGAAGCTATGGCAAGACTCAGGAATGAGGAAAGTGAAAAGATGGCA

AAAGACACATCAGATGAAGTGTCTCTCAATCCAACATCAGAGAAATTGAACAACCTATTGGAAGGGAATGATAGTGA

CAATGATCTATCACTTGAAGATTTCTGATTAGTTACCAATCTTCACATCAACACACAATACCAACAGAAGACCAACA

AACTAACCAACCCAATCATCCAACCAAACATCCATCCGCCAATCAGCCAAACAGCCAACAAAACAACCAGCCAATCC

AAAACTAACCACCCGGAAAAAATCTATAATATAGTTACAAAAAAAGGAATCGATGGGGCAAATACAAGTATGGTGAG

CAAGGGCGAGGAGCTGTTCACCGGGGTGGTGCCCATCCTGGTCGAGCTGGACGGCGACGTAAACGGCCACAAGTTCA

GCGTGTCCGGCGAGGGCGAGGGCGATGCCACCTACGGCAAGCTGACCCTGAAGTTCATCTGCACCACCGGCAAGCTG

CCCGTGCCCTGGCCCACCCTCGTGACCACCCTGACCTACGGCGTGCAGTGCTTCAGCCGCTACCCCGACCACATGAA

GCAGCACGACTTCTTCAAGTCCGCCATGCCCGAAGGCTACGTCCAGGAGCGCACCATCTTCTTCAAGGACGACGGCA

ACTACAAGACCCGCGCCGAGGTGAAGTTCGAGGGCGACACCCTGGTGAACCGCATCGAGCTGAAGGGCATCGACTTC

AAGGAGGACGGCAACATCCTGGGGCACAAGCTGGAGTACAACTACAACAGCCACAACGTCTATATCATGGCCGACAA

GCAGAAGAACGGCATCAAGGTGAACTTCAAGATCCGCCACAACATCGAGGACGGCAGCGTGCAGCTCGCCGACCACT

ACCAGCAGAACACCCCCATCGGCGACGGCCCCGTGCTGCTGCCCGACAACCACTACCTGAGCACCCAGTCCGCCCTG

AGCAAAGACCCCAACGAGAAGCGCGATCACATGGTCCTGCTGGAGTTCGTGACCGCCGCCGGGATCACTCTCGGCAT

GGACGAGCTGTACAAGTAAAAGTAGTTACTTAAAAAGTCGACGGTGGGGCAAATATGGAAACATACGTGAACAAGCT

TCACGAAGGCTCCACATACACAGCTGCTGTTCAATACAATGTCTTAGAAAAAGACGATGACCCTGCATCACTTACAA

TATGGGTGCCCATGTTCCAATCATCTATGCCAGCAGATTTACTTATAAAAGAACTAGCTAATGTCAACATACTAGTG

AAACAAATATCCACACCCAAGGGACCTTCACTAAGAGTCATGATAAACTCAAGAAGTGCAGTGCTAGCACAAATGCC

CAGCAAATTTACCATATGCGCTAATGTGTCCTTGGATGAAAGAAGCAAACTAGCATATGATGTAACCACACCCTGTG

AAATCAAGGCATGTAGTCTAACATGCCTAAAATCAAAAAATATGTTGACTACAGTTAAAGATCTCACTATGAAGACA

CTCAACCCTACACATGATATTATTGCTTTATGTGAATTTGAAAACATAGTAACATCAAAAAAAGTCATAATACCAAC

ATACCTAAGATCCATCAGTGTCAGAAATAAAGATCTGAACACACTTGAAAATATAACAACCACTGAATTCAAAAATG

CTATCACAAATGCAAAAATCATCCCTTACTCAGGATTACTATTAGTCATCACAGTGACTGACAACAAAGGAGCATTC

AAATACATAAAGCCACAAAGTCAATTCATAGTAGATCTTGGAGCTTACCTAGAAAAAGAAAGTATATATTATGTTAC

CACAAATTGGAAGCACACAGCTACACGATTTGCAATCAAACCCATGGAAGATTAACCTTTTTCCTCTACATCAGTGT

GTTAATTCATACAAACTTTCTACCTACATTCTTCACTTCACCATCACAATCACAAACACTCTGTGGTTCAACCAATC

AAACAAAACTTATCTGAAGTCCCAGATCATCCCAAGTCATTGTTTATCAGATCTAGTACTCAAATAAGTTAATAAAA

AATATACACATGGGGCAAATAATCATTGGAGGAAATCCAACTAATCACAATATCTGTTAACATAGACAAGTCCACAC

ACCATACAGAATCAACCAATGGAAAATACATCCATAACAATAGAATTCTCAAGCAAATTCTGGCCTTACTTTACACT

AATACACATGATCACAACAATAATCTCTTTGCTAATCATAATCTCCATCATGATTGCAATACTAAACAAACTTTGTG

AATATAACGTATTCCATAACAAAACCTTTGAGTTACCAAGAGCTCGAGTTAATACTTGATAAAGTAGTTAATTAAAA

ATAGTCATAACAATGAACTAGGATATCAAGACTAACAATAACATTGGGGCAAATGCAAACATGTCCAAAAACAAGGA

-continued

CCAACGCACCGCTAAGACATTAGAAAGGACCTGGGACACTCTCAATCATTTATTATTCATATCATCGTGCTTATATA

AGTTAAATCTTAAATCTGTAGCACAAATCACATTATCCATTCTGGCAATGATAATCTCAACTTCACTTATAATTGCA

GCCATCATATTCATAGCCTCGGCAAACCACAAAGTCACACCAACAACTGCAATCATACAAGATGCAACAAGCCAGAT

CAAGAACACAACCCCAACATACCTCACCCAGAATCCTCAGCTTGGAATCAGTCCCTCTAATCCGTCTGAAATTACAT

CACAAATCACCACCATACTAGCTTCAACAACACCAGGAGTCAAGTCAACCCTGCAATCCACAACAGTCAAGACCAAA

AACACAACAACAACTCAAACACAACCCAGCAAGCCCACCACAAAACAACGCCAAAACAAACCACCAAGCAAACCCAA

TAATGATTTTCACTTTGAAGTGTTCAACTTTGTACCCTGCAGCATATGCAGCAACAATCCAACCTGCTGGGCTATCT

GCAAAAGAATACCAAACAAAAAACCAGGAAAGAAAACCACTACCAAGCCCACAAAAAAACCAACCCTCAAGACAACC

AAAAAAGATCCCAAACCTCAAACCACTAAATCAAAGGAAGTACCCACCACCAAGCCCACAGAAGAGCCAACCATCAA

CACCACCAAAACAAACATCATAACTACACTACTCACCTCCAACACCACAGGAAATCCAGAACTCACAAGTCAAATGG

AAACCTTCCACTCAACTTCCTCCGAAGGCAATCCAAGCCCTTCTCAAGTCTCTACAACATCCGAGTACCCATCACAA

CCTTCATCTCCACCCAACACACCACGCCAGTAGTTACTTAAAAACATATTATCACAAAAGGCCTTGACCAACTTAAA

CAGAATCAAAATAAACTCTGGGGCAAATAACAATGGAGTTGCTAATCCTCAAAGCAAATGCAATTACCACAATCCTC

ACTGCAGTCACATTTTGTTTTGCTTCTGGTCAAAACATCACTGAAGAATTTTATCAATCAACATGCAGTGCAGTTAG

CAAAGGCTATCTTAGTGCTCTGAGAACTGGTTGGTATACCAGTGTTATAACTATAGAATTAAGTAATATCAAGAAAA

ATAAGTGTAATGGAACAGATGCTAAGGTAAAATTGATAAAACAAGAATTAGATAAATATAAAAATGCTGTAACAGAA

TTGCAGTTGCTCATGCAAAGCACACAAGCAACAAACAATCGAGCCAGAAGAGAACTACCAAGGTTTATGAATTATAC

ACTCAACAATGCCAAAAAAACCAATGTAACATTAAGCAAGAAAAGGAAAAGAAGATTTCTTGGTTTTTTGTTAGGTG

TTGGATCTGCAATCGCCAGTGGCGTTGCTGTATCTAAGGTCCTGCACCTAGAAGGGGAAGTGAACAAGATCAAAAGT

GCTCTACTATCCACAAACAAGGCTGTAGTCAGCTTATCAAATGGAGTTAGTGTTTTAACCAGCAAAGTGTTAGACCT

CAAAAACTATATAGATAAACAATTGTTACCTATTGTGAACAAGCAAAGCTGCAGCATATCAAATATAGAAACTGTGA

TAGAGTTCCAACAAAAGAACAACAGACTACTAGAGATTACCAGGGAATTTAGTGTTAATGCAGGCGTAACTACACCT

GTAAGCACTTACATGTTAACTAATAGTGAATTATTGTCATTAATCAATGATATGCCTATAACAAATGATCAGAAAAA

GTTAATGTCCAACAATGTTCAAATAGTTAGACAGCAAAGTTACTCTATCATGTCCATAATAAAAGAGGAAGTCTTAG

CATATGTAGTACAATTACCACTATATGGTGTTATAGATACACCCTGTTGGAAACTACACACATCCCCTCTATGTACA

ACCAACACAAAAGAAGGGTCCAACATCTGTTTAACAAGAACTGACAGAGGATGGTACTGTGACAATGCAGGATCAGT

ATCTTTCTTCCCACAAGCTGAAACATGTAAAGTTCAATCAAATCGAGTATTTTGTGACACAATGAACAGTTTAACAT

TACCAAGTGAAGTAAATCTCTGCAATGTTGACATATTCAACCCCAAATATGATTGTAAAATTATGACTTCAAAAACA

GATGTAAGCAGCTCCGTTATCACATCTCTAGGAGCCATTGTGTCATGCTATGGCAAAACTAAATGTACAGCATCCAA

TAAAAATCGTGGAATCATAAAGACATTTTCTAACGGGTGCGATTATGTATCAAATAAAGGGGTGGACACTGTGTCTG

TAGGTAACACATTATATTATGTAAATAAGCAAGAAGGTAAAAGTCTCTATGTAAAAGGTGAACCAATAATAAATTTC

TATGACCCATTAGTATTCCCCTCTGATGAATTTGATGCATCAATATCTCAAGTCAACGAGAAGATTAACCAGAGCCT

AGCATTTATTCGTAAATCCGATGAATTATTACATAATGTAAATGCTGGTAAATCCACCACAAATATCATGATAACTA

CTATAATTATAGTGATTATAGTAATATTGTTATCATTAATTGCTGTTGGACTGCTCTTATACTGTAAGGCCAGAAGC

ACACCAGTCACACTAAGCAAAGATCAACTGAGTGGTATAAATAATATTGCATTTAGTAACTAAATAAAAATAGCACC

TAATCATGTTCTTACAATGGTTTACTATCTGCTCATAGACAACCCATCTGTCATTGGATTTTCTTAAAATCTGAACT

TCATCGAAACTCTCATCTATAAACCATCTCACTTACACTATTTAAGTAGATTCCTAGTTTATAGTTATATAAAACAC

AATTGCATGCCAGGTACCATGGGGCAAATAAGAATTTGATAAGTACCACTTAAATTTAACTCCCTTGGTTAGAGATG

GGCAGCAATTCATTGAGTATGATAAAAGTTAGATTACAAAATTTGTTTGACAATGATGAAGTAGCATTGTTAAAAAT

AACATGCTATACTGATAAATTAATACATTTAACTAATGCTTTGGCTAAGGCAGTGATACATACAATCAAATTGAATG

-continued

GCATTGTGTTTGTGCATGTTATTACAAGTAGTGATATTTGCCCTAATAATAATATTGTAGTAAAATCCAATTTCACA

ACAATGCCAGTACTACAAAATGGAGGTTATATATGGGAAATGATGGAATTAACACATTGCTCTCAACCTAATGGTCT

ACTAGATGACAATTGTGAAATTAAATTCTCCAAAAAACTAAGTGATTCAACAATGACCAATTATATGAATCAATTAT

CTGAATTACTTGGATTTGATCTTAATCCATAAATTATAATTAATATCAACTAGCAAATCAATGTCACTAACACCATT

AGTTAATATAAAACTTAACAGAAGACAAAAATGGGGCAAATAAATCAATTCAGCCAACCCAACCATGGACACAACCC

ACAATGATAATACACCACAAAGACTGATGATCACAGACATGAGACCGTTGTCACTTGAGACCATAATAACATCACTA

ACCAGAGACATCATAACACACAAATTTATATACTTGATAAATCATGAATGCATAGTGAGAAAACTTGATGAAAGACA

GGCCACATTTACATTCCTGGTCAACTATGAAATGAAACTATTACACAAAGTAGGAAGCACTAAATATAAAAAATATA

CTGAATACAACACAAAATATGGCACTTTCCCTATGCCAATATTCATCAATCATGATGGGTTCTTAGAATGCATTGGC

ATTAAGCCTACAAAGCATACTCCCATAATATACAAGTATGATCTCAATCCATAAATTTCAACACAATATTCACACAA

TCTAAAACAACAACTCTATGCATAACTATACTCCATAGTCCAGATGGAGCCTGAAAATTATAGTAATTTAAAACTTA

AGGAGAGATATAAGATAGAAGATGGTACCCTTACCATCTGTAAAAATGAAAACTGGGGCAAATATGTCACGAAGGAA

TCCTTGCAAATTTGAAATTCGAGGTCATTGCTTAAATGGTAAGAGGTGTCATTTTAGTCATAATTATTTTGAATGGC

CACCCCATGCACTGCTTGTAAGACAAAACTTTATGTTAAACAGAATACTTAAGTCTATGGATAAAAGTATAGATACC

TTATCAGAAATAAGTGGAGCTGCAGAGTTGGACAGAACAGAAGAGTATGCTCTTGGTGTAGTTGGAGTGCTAGAGAG

TTATATAGGATCAATAAACAATATAACTAAACAATCAGCATGTGTTGCCATGAGCAAACTCCTCACTGAACTCAATA

GTGATGATATCAAAAAGCTGAGGGACAATGAAGAGCTAAATTCACCCAAGATAAGAGTGTACAATACTGTCATATCA

TATATTGAAAGCAACAGGAAAAACAATAAACAAACTATCCATCTGTTAAAAAGATTGCCAGCAGACGTATTGAAGAA

AACCATCAAAAACACATTGGATATCCATAAGAGCATAACCATCAACAACCCAAAAGAATCAACTGTTAGTGATACAA

ATGACCATGCCAAAAATAATGATACTACCTGACAAATATCCTTGTAGTATAACTTCCATACTAATAACAAGTAGATG

TAGAGTTACTATGTATAATCAAAAGAACACACTATATTTCAATCAAAACAACCCAAATAACCATATGTACTCACCGA

ATCAAACATTCAATGAAATCCATTGGACCTCTCAAGAATTGATTGACACAATTCAAAATTTTCTACAACATCTAGGT

ATTATTGAGGATATATATACAATATATATATTAGTGTCATAACACTCAATTCTAACACTCACCACATCGTTACATTA

TTAATTCAAACAATTCAAGTTGTGGGACAAAATGGATCCCATTATTAATGGAAATTCTGCTAATGTTTATCTAACCG

ATAGTTATTTAAAAGGTGTTATCTCTTTCTCAGAGTGTAATGCTTTAGGAAGTTACATATTCAATGGTCCTTATCTC

AAAAATGATTATACCAACTTAATTAGTAGACAAAATCCATTAATAGAACACATGAATCTAAAGAAACTAAATATAAC

ACAGTCCTTAATATCTAAGTATCATAAAGGTGAAATAAAATTAGAAGAACCTACTTATTTTCAGTCATTACTTATGA

CATACAAGAGTATGACCTCGTCAGAACAGATTGCTACCACTAATTTACTTAAAAAGATAATAAGAAGAGCTATAGAA

ATAAGTGATGTCAAAGTCTATGCTATATTGAATAAACTAGGGCTTAAAGAAAAGGACAAGATTAAATCCAACAATGG

ACAAGATGAAGACAACTCAGTTATTACGACCATAATCAAAGATGATATACTTTCAGCTGTTAAAGATAATCAATCTC

ATCTTAAAGCAGACAAAAATCACTCTACAAAACAAAAAGACACAATCAAAACAACACTCTTGAAGAAATTGATGTGT

TCAATGCAACATCCTCCATCATGGTTAATACATTGGTTTAACTTATACACAAAATTAAACAACATATTAACACAGTA

TCGATCAAATGAGGTAAAAAACCATGGGTTTACATTGATAGATAATCAAACTCTTAGTGGATTTCAATTTATTTTGA

ACCAATATGGTTGTATAGTTTATCATAAGGAACTCAAAAGAATTACTGTGACAACCTATAATCAATTCTTGACATGG

AAAGATATTAGCCTTAGTAGATTAAATGTTTGTTTAATTACATGGATTAGTAACTGCTTGAACACATTAAATAAAAG

CTTAGGCTTAAGATGCGGATTCAATAATGTTATCTTGACACAACTATTCCTTTATGGAGATTGTATACTAAAGCTAT

TTCACAATGAGGGGTTCTACATAATAAAAGAGGTAGAGGGATTTATTATGTCTCTAATTTTAAATATAACAGAAGAA

GATCAATTCAGAAAACGATTTTATAATAGTATGCTCAACAACATCACAGATGCTGCTAATAAAGCTCAGAAAAATCT

GCTATCAAGAGTATGTCATACATTATTAGATAAGACAGTGTCCGATAATATAATAAATGGCAGATGGATAATTCTAT

TAAGTAAGTTCCTTAAATTAATTAAGCTTGCAGGTGACAATAACCTTAACAATCTGAGTGAACTATATTTTTTGTTC

AGAATATTTGGACACCCAATGGTAGATGAAAGACAAGCCATGGATGCTGTTAAAATTAATTGCAATGAGACCAAATT

-continued

TTACTTGTTAAGCAGTCTGAGTATGTTAAGAGGTGCCTTTATATATAGAATTATAAAAGGGTTTGTAAATAATTACA

ACAGATGGCCTACTTTAAGAAATGCTATTGTTTTACCCTTAAGATGGTTAACTTACTATAAACTAAACACTTATCCT

TCTTTGTTGGAACTTACAGAAAGAGATTTGATTGTGTTATCAGGACTACGTTTCTATCGTGAGTTTCGGTTGCCTAA

AAAAGTGGATCTTGAAATGATTATAAATGATAAAGCTATATCACCTCCTAAAAATTTGATATGGACTAGTTTCCCTA

GAAATTACATGCCATCACACATACAAAACTATATAGAACATGAAAAATTAAAATTTTCCGAGAGTGATAAATCAAGA

AGAGTATTAGAGTATTATTTAAGAGATAACAAATTCAATGAATGTGATTTATACAACTGTGTAGTTAATCAAAGTTA

TCTCAACAACCCTAATCATGTGGTATCATTGACAGGCAAAGAAAGAGAACTCAGTGTAGGTAGAATGTTTGCAATGC

AACCGGGAATGTTCAGACAGGTTCAAATATTGGCAGAGAAAATGATAGCTGAAAACATTTTACAATTCTTTCCTGAA

AGTCTTACAAGATATGGTGATCTAGAACTACAAAAAATATTAGAACTGAAAGCAGGAATAAGTAACAAATCAAATCG

CTACAATGATAATTACAACAATTACATTAGTAAGTGCTCTATCATCACAGATCTCAGCAAATTCAATCAAGCATTTC

GATATGAAACGTCATGTATTTGTAGTGATGTGCTGGATGAACTGCATGGTGTACAATCTCTATTTTCCTGGTTACAT

TTAACTATTCCTCATGTCACAATAATATGCACATATAGGCATGCACCCCCCTATATAGGAGATCATATTGTAGATCT

TAACAATGTAGATGAACAAAGTGGATTATATAGATATCACATGGGTGGCATCGAAGGGTGGTGTCAAAAACTATGGA

CCATAGAAGCTATATCACTATTGGATCTAATATCTCTCAAAGGGAAATTCTCAATTACTGCTTTAATTAATGGTGAC

AATCAATCAATAGATATAAGCAAACCAATCAGACTCATGGAAGGTCAAACTCATGCTCAAGCAGATTATTTGCTAGC

ATTAAATAGCCTTAAATTACTGTATAAAGAGTATGCAGGCATAGGCCACAAATTAAAAGGAACTGAGACTTATATAT

CACGAGATATGCAATTTATGAGTAAAACAATTCAACATAACGGTGTATATTACCCAGCTAGTATAAAGAAAGTCCTA

AGAGTGGGACCGTGGATAAACACTATACTTGATGATTTCAAAGTGAGTCTAGAATCTATAGGTAGTTTGACACAAGA

ATTAGAATATAGAGGTGAAAGTCTATTATGCAGTTTAATATTTAGAAATGTATGGTTATATAATCAGATTGCTCTAC

AATTAAAAAATCATGCATTATGTAACAATAAACTATATTTGGACATATTAAAGGTTCTGAAACACTTAAAAACCTTT

TTTAATCTTGATAATATTGATACAGCATTAACATTGTATATGAATTTACCCATGTTATTTGGTGGTGGTGATCCCAA

CTTGTTATATCGAAGTTTCTATAGAAGAACTCCTGACTTCCTCACAGAGGCTATAGTTCACTCTGTGTTCATACTTA

GTTATTATACAAACCATGACTTAAAAGATAAACTTCAAGATCTGTCAGATGATAGATTGAATAAGTTCTTAACATGC

ATAATCACGTTTGACAAAAACCCTAATGCTGAATTCGTAACATTGATGAGAGATCCTCAAGCTTTAGGGTCTGAGAG

ACAAGCTAAAATTACTAGCGAAATCAATAGACTGGCAGTTACAGAGGTTTTGAGTACAGCTCCAAACAAAATATTCT

CCAAAAGTGCACAACATTATACTACTACAGAGATAGATCTAAATGATATTATGCAAAATATAGAACCTACATATCCT

CATGGGCTAAGAGTTGTTTATGAAAGTTTACCCTTTTATAAAGCAGAGAAAATAGTAAATCTTATATCAGGTACAAA

ATCTATAACTAACATACTGGAAAAAACTTCTGCCATAGACTTAACAGATATTGATAGAGCCACTGAGATGATGAGGA

AAAACATAACTTTGCTTATAAGGATACTTCCATTGGATTGTAACAGAGATAAAAGAGAGATATTGAGTATGGAAAAC

CTAAGTATTACTGAATTAAGCAAATATGTTAGGGAAAGATCTTGGTCTTTATCCAATATAGTTGGTGTTACATCACC

CAGTATCATGTATACAATGGACATCAAATATACTACAAGCACTATATCTAGTGGCATAATTATAGAGAAATATAATG

TTAACAGTTTAACACGTGGTGAGAGAGGACCCACTAAACCATGGGTTGGTTCATCTACACAAGAGAAAAAAACAATG

CCAGTTTATAATAGACAAGTCTTAACCAAAAAACAGAGAGATCAAATAGATCTATTAGCAAAATTGGATTGGGTGTA

TGCATCTATAGATAACAAGGATGAATTCATGGAAGAACTCAGCATAGGAACCCTTGGGTTAACATATGAAAAGGCCA

AGAAATTATTTCCACAATATTTAAGTGTCAATTATTTGCATCGCCTTACAGTCAGTAGTAGACCATGTGAATTCCCT

GCATCAATACCAGCTTATAGAACAACAAATTATCACTTTGACACTAGCCCTATTAATCGCATATTAACAGAAAAGTA

TGGTGATGAAGATATTGACATAGTATTCCAAAACTGTATAAGCTTTGGCCTTAGTTTAATGTCAGTAGTAGAACAAT

TTACTAATGTATGTCCTAACAGAATTATTCTCATACCTAAGCTTAATGAGATACATTTGATGAAACCTCCCATATTC

ACAGGTGATGTTGATATTCACAAGTTAAAACAAGTGATACAAAAACAGCATATGTTTTTACCAGACAAAATAAGTTT

GACTCAATATGTGGAATTATTCTTAAGTAATAAAACACTCAAATCTGGATCTCATGTTAATTCTAATTTAATATTGG

-continued

CACATAAAATATCTGACTATTTTCATAATACTTACATTTTAAGTACTAATTTAGCTGGACATTGGATTCTGATTATA

CAACTTATGAAAGATTCTAAAGGTATTTTTGAAAAAGATTGGGGAGAGGGATATATAACTGATCATATGTTTATTAA

TTTGAAAGTTTTCTTCAATGCTTATAAGACCTATCTCTTGTGTTTTCATAAAGGTTATGGCAAAGCAAAGCTGGAGT

GTGATATGAACACTTCAGATCTTCTATGTGTATTGGAATTAATAGACAGTAGTTATTGGAAGTCTATGTCTAAGGTA

TTTTTAGAACAAAAAGTTATCAAATACATTCTTAGCCAAGATGCAAGTTTACATAGAGTAAAAGGATGTCATAGCTT

CAAATTATGGTTTCTTAAACGTCTTAATGTAGCAGAATTCACAGTTTGCCCTTGGGTTGTTAACATAGATTATCATC

CAACACATATGAAAGCAATATTAACTTATATAGATCTTGTTAGAATGGGATTGATAAATATAGATAGAATACACATT

AAAAATAAACACAAATTCAATGATGAATTTTATACTTCTAATCTCTTCTACATTAATTATAACTTCTCAGATAATAC

TCATCTATTAACTAAACATATAAGGATTGCTAATTCTGAATTAGAAAATAATTACAACAAATTATATCATCCTACAC

CAGAAACCCTAGAGAATATACTAGCCAATCCGATTAAAAGTAATGACAAAAAGACACTGAATGACTATTGTATAGGT

AAAAATGTTGACTCAATAATGTTACCATTGTTATCTAATAAGAAGCTTATTAAATCGTCTGCAATGATTAGAACCAA

TTACAGCAAACAAGATTTGTATAATTTATTCCCTATGGTTGTGATTGATAGAATTATAGATCATTCAGGCAATACAG

CCAAATCCAACCAACTTTACACTACTACTTCCCACCAAATATCCTTAGTGCACAATAGCACATCACTTTACTGCATG

CTTCCTTGGCATCATATTAATAGATTCAATTTTGTATTTAGTTCTACAGGTTGTAAAATTAGTATAGAGTATATTTT

AAAAGATCTTAAAATTAAAGATCCCAATTGTATAGCATTCATAGGTGAAGGAGCAGGGAATTTATTATTGCGTACAG

TAGTGGAACTTCATCCTGACATAAGATATATTTACAGAAGTCTGAAAGATTGCAATGATCATAGTTTACCTATTGAG

TTTTTAAGGCTGTACAATGGACATATCAACATTGATTATGGTGAAAATTTGACCATTCCTGCTACAGATGCAACCAA

CAACATTCATTGGTCTTATTTACATATAAAGTTTGCTGAACCTATCAGTCTTTTTGTCTGTGATGCCGAATTGTCTG

TAACAGTCAACTGGAGTAAAATTATAATAGAATGGAGCAAGCATGTAAGAAAGTGCAAGTACTGTTCCTCAGTTAAT

AAATGTATGTTAATAGTAAAATATCATGCTCAAGATGATATTGATTTCAAATTAGACAATATAACTATATTAAAAAC

TTATGTATGCTTAGGCAGTAAGTTAAAGGGATCGGAGGTTTACTTAGTCCTTACAATAGGTCCTGCGAATATATTCC

CAGTATTTAATGTAGTACAAAATGCTAAATTGATACTATCAAGAACCAAAAATTTCATCATGCCTAAGAAAGCTGAT

AAAGAGTCTATTGATGCAAATATTAAAAGTTTGATACCCTTTCTTTGTTACCCTATAACAAAAAAAGGAATTAATAC

TGCATTGTCAAAACTAAAGAGTGTTGTTAGTGGAGATATACTATCATATTCTATAGCTGGACGTAATGAAGTTTTCA

GCAATAAACTTATAAATCATAAGCATATGAACATCTTAAAATGGTTCAATCATGTTTTAAATTTCAGATCAACAGAA

CTAAACTATAACCATTTATATATGGTAGAATCTACATATCCTTACCTAAGTGAATTGTTAAACAGCTTGACAACCAA

TGAACTTAAAAAACTGATTAAAATCACAGGTAGTCTGTTATACAACTTTCATAATGAATAATGAATAAAGATCTTAT

AATAAAAATTCCCATAGCTATACACTAACACTGTATTCAATTATAGTTATTAAAAATTAAAAATCATATAATTTTTT

AAATAACTTTTAGTGAACTAATCCTAAAGTTATCATTTTAATCTTGGAGGAATAAATTTAAACCCTAATCTAATTGG

TTTATATGTGTATTAACTAAATTACGAGATATTAGTTTTTGACACTTTTTTTCTCGT

Antigenomic cDNA sequence of RSV 6120/NS12FM2 (SEQ ID NO: 2)

ACGGGAAAAAATGCGTACAACAAACTTGCATAAACCAAAAAAATGGGGCAAATAAGAATTTGATAAGTACCACTTAA

ATTTAACTCCCTTGGTTAGAGATGGCTCTTAGCAAAGTCAAGTTGAATGATACACTCAACAAAGATCAACTTCTGTC

ATCCAGCAAATACACCATCCAACGGAGCACAGGAGATAGTATTGATACTCCTAATTATGATGTGCAGAAACACATCA

ATAAGTTATGTGGCATGTTATTAATCACAGAAGATGCTAATCATAAATTCACTGGGTTAATAGGTATGTTATATGCG

ATGTCTAGGTTAGGAAGAGAAGACACCATAAAAATACTCAGAGATGCGGGATATCATGTAAAAGCAAATGGAGTAGA

TGTAACAACACATCGTCAAGACATTAATGGAAAAGAAATGAAATTTGAAGTGTTAACATTGGCAAGCTTAACAACTG

AAATTCAAATCAACATTGAGATAGAATCTAGAAAATCCTACAAAAAAATGCTAAAAGAAATGGGAGAGGTAGCTCCA

GAATACAGGCATGACTCTCCTGATTGTGGGATGATAATATTATGTATAGCAGCATTAGTAATAACTAAATTAGCAGC

AGGGGACAGATCTGGTCTTACAGCCGTGATTAGGAGAGCTAATAATGTCCTAAAAAATGAAATGAAACGTTACAAAG

GCTTACTACCCAAGGACATAGCCAACAGCTTCTATGAAGTGTTTGAAAAACATCCCCACTTTATAGATGTTTTTGTT

-continued

CATTTTGGTATAGCACAATCTTCTACCAGAGGTGGCAGTAGAGTTGAAGGGATTTTTGCAGGATTGTTTATGAATGC

CTATGGTGCAGGGCAAGTGATGTTACGGTGGGGAGTCTTAGCAAAATCAGTTAAAAATATTATGTTAGGACATGCTA

GTGTGCAAGCAGAAATGGAACAAGTTGTTGAGGTTTATGAATATGCCCAAAAATTGGGTGGTGAAGCAGGATTCTAC

CATATATTGAACAACCCAAAAGCATCATTATTATCTTTGACTCAATTTCCTCACTTCTCCAGTGTAGTATTAGGCAA

TGCTGCTGGCCTAGGCATAATGGGAGAGTACAGAGGTACACCGAGGAATCAAGATCTATATGATGCAGCAAAGGCAT

ATGCTGAACAACTCAAAGAAAATGGTGTGATTAACTACAGTGTACTAGACTTGACAGCAGAAGAACTAGAGGCTATC

AAACATCAGCTTAATCCAAAAGATAATGATGTAGAGCTTTGAGTTAATAAAAAATGGGGCAAATAAATCATCATGGA

AAAGTTTGCTCCTGAATTCCATGGAGAAGATGCAAACAACAGGGCTACTAAATTCCTAGAATCAATAAAGGGCAAAT

TCACATCACCCAAAGATCCCAAGAAAAAAGATAGTATCATATCTGTCAACTCAATAGATATAGAAGTAACCAAAGAA

AGCCCTATAACATCAAATTCAACTATTATCAACCCAACAAATGAGACAGATGATACTGCAGGGAACAAGCCCAATTA

TCAAAGAAAACCTCTAGTAAGTTTCAAAGAAGACCCTACACCAAGTGATAATCCCTTTTCTAAACTATACAAAGAAA

CCATAGAAACATTTGATAACAATGAAGAAGAATCCAGCTATTCATACGAAGAAATAAATGATCAGACAAACGATAAT

ATAACAGCAAGATTAGATAGGATTGATGAAAAATTAAGTGAAATACTAGGAATGCTTCACACATTAGTAGTGGCAAG

TGCAGGACCTACATCTGCTCGGGATGGTATAAGAGATGCCATGGTTGGTTTAAGAGAAGAAATGATAGAAAAAATCA

GAACTGAAGCATTAATGACCAATGACAGATTAGAAGCTATGGCAAGACTCAGGAATGAGGAAAGTGAAAAGATGGCA

AAAGACACATCAGATGAAGTGTCTCTCAATCCAACATCAGAGAAATTGAACAACCTATTGGAAGGGAATGATAGTGA

CAATGATCTATCACTTGAAGATTTCTGATTAGTTACCAATCTTCACATCAACACACAATACCAACAGAAGACCAACA

AACTAACCAACCCAATCATCCAACCAAACATCCATCCGCCAATCAGCCAAACAGCCAACAAAACAACCAGCCAATCC

AAAACTAACCACCCGGAAAAAATCTATAATATAGTTACAAAAAAAGGAAAGGGTGGGGCAAATATGGAAACATACGT

GAACAAGCTTCACGAAGGCTCCACATACACAGCTGCTGTTCAATACAATGTCTTAGAAAAAGACGATGACCCTGCAT

CACTTACAATATGGGTGCCCATGTTCCAATCATCTATGCCAGCAGATTTACTTATAAAAGAACTAGCTAATGTCAAC

ATACTAGTGAAACAAATATCCACACCCAAGGGACCTTCACTAAGAGTCATGATAAACTCAAGAAGTGCAGTGCTAGC

ACAAATGCCCAGCAAATTTACCATATGCGCTAATGTGTCCTTGGATGAAAGAAGCAAACTAGCATATGATGTAACCA

CACCCTGTGAAATCAAGGCATGTAGTCTAACATGCCTAAAATCAAAAAATATGTTGACTACAGTTAAAGATCTCACT

ATGAAGACACTCAACCCTACACATGATATTATTGCTTTATGTGAATTTGAAAACATAGTAACATCAAAAAAAGTCAT

AATACCAACATACCTAAGATCCATCAGTGTCAGAAATAAAGATCTGAACACACTTGAAAATATAACAACCACTGAAT

TCAAAAATGCTATCACAAATGCAAAAATCATCCCTTACTCAGGATTACTATTAGTCATCACAGTGACTGACAACAAA

GGAGCATTCAAATACATAAAGCCACAAAGTCAATTCATAGTAGATCTTGGAGCTTACCTAGAAAAAGAAAGTATATA

TTATGTTACCACAAATTGGAAGCACACAGCTACACGATTTGCAATCAAACCCATGGAAGATTAACCTTTTTCCTCTA

CATCAGTGTGTTAATTCATACAAACTTTCTACCTACATTCTTCACTTCACCATCACAATCACAAACACTCTGTGGTT

CAACCAATCAAACAAAACTTATCTGAAGTCCCAGATCATCCCAAGTCATTGTTTATCAGATCTAGTACTCAAATAAG

TTAATAAAAAATATACACATGGGGCAAATAATCATTGGAGGAAATCCAACTAATCACAATATCTGTTAACATAGACA

AGTCCACACACCATACAGAATCAACCAATGGAAAATACATCCATAACAATAGAATTCTCAAGCAAATTCTGGCCTTA

CTTTACACTAATACACATGATCACAACAATAATCTCTTTGCTAATCATAATCTCCATCATGATTGCAATACTAAACA

AACTTTGTGAATATAACGTATTCCATAACAAAACCTTTGAGTTACCAAGAGCTCGAGTTAATACTTGATAAAGTAGT

TAATTAAAAATAGTCATAACAATGAACTAGGATATCAAGACTAACAATAACATTGGGGCAAATGCAAACATGTCCAA

AAACAAGGACCAACGCACCGCTAAGACATTAGAAAGGACCTGGGACACTCTCAATCATTTATTATTCATATCATCGT

GCTTATATAAGTTAAATCTTAAATCTGTAGCACAAATCACATTATCCATTCTGGCAATGATAATCTCAACTTCACTT

ATAATTGCAGCCATCATATTCATAGCCTCGGCAAACCACAAAGTCACACCAACAACTGCAATCATACAAGATGCAAC

AAGCCAGATCAAGAACACAACCCCAACATACCTCACCCAGAATCCTCAGCTTGGAATCAGTCCCTCTAATCCGTCTG

AAATTACATCACAAATCACCACCATACTAGCTTCAACAACACCAGGAGTCAAGTCAACCCTGCAATCCACAACAGTC

-continued

AAGACCAAAAACACAACAACAACTCAAACACAACCCAGCAAGCCCACCACAAAACAACGCCAAAACAAACCACCAAG

CAAACCCAATAATGATTTTCACTTTGAAGTGTTCAACTTTGTACCCTGCAGCATATGCAGCAACAATCCAACCTGCT

GGGCTATCTGCAAAAGAATACCAAACAAAAAACCAGGAAAGAAAACCACTACCAAGCCCACAAAAAAACCAACCCTC

AAGACAACCAAAAAAGATCCCAAACCTCAAACCACTAAATCAAAGGAAGTACCCACCACCAAGCCCACAGAAGAGCC

AACCATCAACACCACCAAAACAAACATCATAACTACACTACTCACCTCCAACACCACAGGAAATCCAGAACTCACAA

GTCAAATGGAAACCTTCCACTCAACTTCCTCCGAAGGCAATCCAAGCCCTTCTCAAGTCTCTACAACATCCGAGTAC

CCATCACAACCTTCATCTCCACCCAACACACCACGCCAGTAGTTACTTAAAAACATATTATCACAAAAGGCCTTGAC

CAACTTAAACAGAATCAAAATAAACTCTGGGGCAAATAACAATGGAGTTGCTAATCCTCAAAGCAAATGCAATTACC

ACAATCCTCACTGCAGTCACATTTTGTTTTGCTTCTGGTCAAAACATCACTGAAGAATTTTATCAATCAACATGCAG

TGCAGTTAGCAAAGGCTATCTTAGTGCTCTGAGAACTGGTTGGTATACCAGTGTTATAACTATAGAATTAAGTAATA

TCAAGAAAAATAAGTGTAATGGAACAGATGCTAAGGTAAAATTGATAAAACAAGAATTAGATAAATATAAAAATGCT

GTAACAGAATTGCAGTTGCTCATGCAAAGCACACAAGCAACAAACAATCGAGCCAGAAGAGAACTACCAAGGTTTAT

GAATTATACACTCAACAATGCCAAAAAAACCAATGTAACATTAAGCAAGAAAAGGAAAAGAAGATTTCTTGGTTTTT

TGTTAGGTGTTGGATCTGCAATCGCCAGTGGCGTTGCTGTATCTAAGGTCCTGCACCTAGAAGGGGAAGTGAACAAG

ATCAAAAGTGCTCTACTATCCACAAACAAGGCTGTAGTCAGCTTATCAAATGGAGTTAGTGTTTTAACCAGCAAAGT

GTTAGACCTCAAAAACTATATAGATAAACAATTGTTACCTATTGTGAACAAGCAAAGCTGCAGCATATCAAATATAG

AAACTGTGATAGAGTTCCAACAAAAGAACAACAGACTACTAGAGATTACCAGGGAATTTAGTGTTAATGCAGGCGTA

ACTACACCTGTAAGCACTTACATGTTAACTAATAGTGAATTATTGTCATTAATCAATGATATGCCTATAACAAATGA

TCAGAAAAAGTTAATGTCCAACAATGTTCAAATAGTTAGACAGCAAAGTTACTCTATCATGTCCATAATAAAAGAGG

AAGTCTTAGCATATGTAGTACAATTACCACTATATGGTGTTATAGATACACCCTGTTGGAAACTACACACATCCCCT

CTATGTACAACCAACACAAAAGAAGGGTCCAACATCTGTTTAACAAGAACTGACAGAGGATGGTACTGTGACAATGC

AGGATCAGTATCTTTCTTCCCACAAGCTGAAACATGTAAAGTTCAATCAAATCGAGTATTTTGTGACACAATGAACA

GTTTAACATTACCAAGTGAAGTAAATCTCTGCAATGTTGACATATTCAACCCCAAATATGATTGTAAAATTATGACT

TCAAAAACAGATGTAAGCAGCTCCGTTATCACATCTCTAGGAGCCATTGTGTCATGCTATGGCAAAACTAAATGTAC

AGCATCCAATAAAAATCGTGGAATCATAAAGACATTTTCTAACGGGTGCGATTATGTATCAAATAAAGGGGTGGACA

CTGTGTCTGTAGGTAACACATTATATTATGTAAATAAGCAAGAAGGTAAAAGTCTCTATGTAAAAGGTGAACCAATA

ATAAATTTCTATGACCCATTAGTATTCCCCTCTGATGAATTTGATGCATCAATATCTCAAGTCAACGAGAAGATTAA

CCAGAGCCTAGCATTTATTCGTAAATCCGATGAATTATTACATAATGTAAATGCTGGTAAATCCACCACAAATATCA

TGATAACTACTATAATTATAGTGATTATAGTAATATTGTTATCATTAATTGCTGTTGGACTGCTCTTATACTGTAAG

GCCAGAAGCACACCAGTCACACTAAGCAAAGATCAACTGAGTGGTATAAATAATATTGCATTTAGTAACTAAATAAA

AATAGCACCTAATCATGTTCTTACAATGGTTTACTATCTGCTCATAGACAACCCATCTGTCATTGGATTTTCTTAAA

ATCTGAACTTCATCGAAACTCTCATCTATAAACCATCTCACTTACACTATTTAAGTAGATTCCTAGTTTATAGTTAT

ATAAAACACAATTGCATGCCAGGTACCATGGGGCAAATAAGAATTTGATAAGTACCACTTAAATTTAACTCCCTTGG

TTAGAGATGGGCAGCAATTCATTGAGTATGATAAAAGTTAGATTACAAAATTTGTTTGACAATGATGAAGTAGCATT

GTTAAAAATAACATGCTATACTGATAAATTAATACATTTAACTAATGCTTTGGCTAAGGCAGTGATACATACAATCA

AATTGAATGGCATTGTGTTTGTGCATGTTATTACAAGTAGTGATATTTGCCCTAATAATAATATTGTAGTAAAATCC

AATTTCACAACAATGCCAGTACTACAAAATGGAGGTTATATATGGGAAATGATGGAATTAACACATTGCTCTCAACC

TAATGGTCTACTAGATGACAATTGTGAAATTAAATTCTCCAAAAAACTAAGTGATTCAACAATGACCAATTATATGA

ATCAATTATCTGAATTACTTGGATTTGATCTTAATCCATAAATTATAATTAATATCAACTAGCAAATCAATGTCACT

AACACCATTAGTTAATATAAAACTTAACAGAAGACAAAAATGGGGCAAATAAATCAATTCAGCCAACCCAACCATGG

-continued

ACACAACCCACAATGATAATACACCACAAAGACTGATGATCACAGACATGAGACCGTTGTCACTTGAGACCATAATA

ACATCACTAACCAGAGACATCATAACACACAAATTTATATACTTGATAAATCATGAATGCATAGTGAGAAAACTTGA

TGAAAGACAGGCCACATTTACATTCCTGGTCAACTATGAAATGAAACTATTACACAAAGTAGGAAGCACTAAATATA

AAAAATATACTGAATACAACACAAAATATGGCACTTTCCCTATGCCAATATTCATCAATCATGATGGGTTCTTAGAA

TGCATTGGCATTAAGCCTACAAAGCATACTCCCATAATATACAAGTATGATCTCAATCCATAAATTTCAACACAATA

TTCACACAATCTAAAACAACAACTCTATGCATAACTATACTCCATAGTCCAGATGGAGCCTGAAAATTATAGTAATT

TAAAACTTAAGGAGAGATATAAGATAGAAGATGGTACCCTTACCATCTGTAAAAATGAAAACTGGGGCAAATATGTC

ACGAAGGAATCCTTGCAAATTTGAAATTCGAGGTCATTGCTTAAATGGTAAGAGGTGTCATTTTAGTCATAATTATT

TTGAATGGCCACCCCATGCACTGCTTGTAAGACAAAACTTTATGTTAAACAGAATACTTAAGTCTATGGATAAAAGT

ATAGATACCTTATCAGAAATAAGTGGAGCTGCAGAGTTGGACAGAACAGAAGAGTATGCTCTTGGTGTAGTTGGAGT

GCTAGAGAGTTATATAGGATCAATAAACAATATAACTAAACAATCAGCATGTGTTGCCATGAGCAAACTCCTCACTG

AACTCAATAGTGATGATATCAAAAAGCTGAGGGACAATGAAGAGCTAAATTCACCCAAGATAAGAGTGTACAATACT

GTCATATCATATATTGAAAGCAACAGGAAAAACAATAAACAAACTATCCATCTGTTAAAAAGATTGCCAGCAGACGT

ATTGAAGAAAACCATCAAAAACACATTGGATATCCATAAGAGCATAACCATCAACAACCCAAAAGAATCAACTGTTA

GTGATACAAATGACCATGCCAAAAATAATGATACTACCTGACAAATATCCTTGTAGTATAACTTCCATACTAATAAC

AAGTAGATGTAGAGTTACTATGTATAATCAAAAGAACACACTATATTTCAATCAAAACAACCCAAATAACCATATGT

ACTCACCGAATCAAACATTCAATGAAATCCATTGGACCTCTCAAGAATTGATTGACACAATTCAAAATTTTCTACAA

CATCTAGGTATTATTGAGGATATATATACAATATATATATTAGTGTCATAACACTCAATTCTAACACTCACCACATC

GTTACATTATTAATTCAAACAATTCAAGTTGTGGGACAAAATGGATCCCATTATTAATGGAAATTCTGCTAATGTTT

ATCTAACCGATAGTTATTTAAAAGGTGTTATCTCTTTCTCAGAGTGTAATGCTTTAGGAAGTTACATATTCAATGGT

CCTTATCTCAAAAATGATTATACCAACTTAATTAGTAGACAAAATCCATTAATAGAACACATGAATCTAAAGAAACT

AAATATAACACAGTCCTTAATATCTAAGTATCATAAAGGTGAAATAAAATTAGAAGAACCTACTTATTTTCAGTCAT

TACTTATGACATACAAGAGTATGACCTCGTCAGAACAGATTGCTACCACTAATTTACTTAAAAAGATAATAAGAAGA

GCTATAGAAATAAGTGATGTCAAAGTCTATGCTATATTGAATAAACTAGGGCTTAAAGAAAAGGACAAGATTAAATC

CAACAATGGACAAGATGAAGACAACTCAGTTATTACGACCATAATCAAAGATGATATACTTTCAGCTGTTAAAGATA

ATCAATCTCATCTTAAAGCAGACAAAAATCACTCTACAAAACAAAAAGACACAATCAAAACAACACTCTTGAAGAAA

TTGATGTGTTCAATGCAACATCCTCCATCATGGTTAATACATTGGTTTAACTTATACACAAAATTAAACAACATATT

AACACAGTATCGATCAAATGAGGTAAAAAACCATGGGTTTACATTGATAGATAATCAAACTCTTAGTGGATTTCAAT

TTATTTTGAACCAATATGGTTGTATAGTTTATCATAAGGAACTCAAAAGAATTACTGTGACAACCTATAATCAATTC

TTGACATGGAAAGATATTAGCCTTAGTAGATTAAATGTTTGTTTAATTACATGGATTAGTAACTGCTTGAACACATT

AAATAAAAGCTTAGGCTTAAGATGCGGATTCAATAATGTTATCTTGACACAACTATTCCTTTATGGAGATTGTATAC

TAAAGCTATTTCACAATGAGGGGTTCTACATAATAAAAGAGGTAGAGGGATTTATTATGTCTCTAATTTTAAATATA

ACAGAAGAAGATCAATTCAGAAAACGATTTTATAATAGTATGCTCAACAACATCACAGATGCTGCTAATAAAGCTCA

GAAAAATCTGCTATCAAGAGTATGTCATACATTATTAGATAAGACAGTGTCCGATAATATAATAAATGGCAGATGGA

TAATTCTATTAAGTAAGTTCCTTAAATTAATTAAGCTTGCAGGTGACAATAACCTTAACAATCTGAGTGAACTATAT

TTTTTGTTCAGAATATTTGGACACCCAATGGTAGATGAAAGACAAGCCATGGATGCTGTTAAAATTAATTGCAATGA

GACCAAATTTTACTTGTTAAGCAGTCTGAGTATGTTAAGAGGTGCCTTTATATATAGAATTATAAAAGGGTTTGTAA

ATAATTACAACAGATGGCCTACTTTAAGAAATGCTATTGTTTTACCCTTAAGATGGTTAACTTACTATAAACTAAAC

ACTTATCCTTCTTTGTTGGAACTTACAGAAAGAGATTTGATTGTGTTATCAGGACTACGTTTCTATCGTGAGTTTCG

GTTGCCTAAAAAAGTGGATCTTGAAATGATTATAAATGATAAAGCTATATCACCTCCTAAAAATTTGATATGGACTA

GTTTCCCTAGAAATTACATGCCATCACACATACAAAACTATATAGAACATGAAAAATTAAAATTTTCCGAGAGTGAT

-continued

AAATCAAGAAGAGTATTAGAGTATTATTTAAGAGATAACAAATTCAATGAATGTGATTTATACAACTGTGTAGTTAA

TCAAAGTTATCTCAACAACCCTAATCATGTGGTATCATTGACAGGCAAAGAAAGAGAACTCAGTGTAGGTAGAATGT

TTGCAATGCAACCGGGAATGTTCAGACAGGTTCAAATATTGGCAGAGAAAATGATAGCTGAAAACATTTTACAATTC

TTTCCTGAAAGTCTTACAAGATATGGTGATCTAGAACTACAAAAAATATTAGAACTGAAAGCAGGAATAAGTAACAA

ATCAAATCGCTACAATGATAATTACAACAATTACATTAGTAAGTGCTCTATCATCACAGATCTCAGCAAATTCAATC

AAGCATTTCGATATGAAACGTCATGTATTTGTAGTGATGTGCTGGATGAACTGCATGGTGTACAATCTCTATTTTCC

TGGTTACATTTAACTATTCCTCATGTCACAATAATATGCACATATAGGCATGCACCCCCCTATATAGGAGATCATAT

TGTAGATCTTAACAATGTAGATGAACAAAGTGGATTATATAGATATCACATGGGTGGCATCGAAGGGTGGTGTCAAA

AACTATGGACCATAGAAGCTATATCACTATTGGATCTAATATCTCTCAAAGGGAAATTCTCAATTACTGCTTTAATT

AATGGTGACAATCAATCAATAGATATAAGCAAACCAATCAGACTCATGGAAGGTCAAACTCATGCTCAAGCAGATTA

TTTGCTAGCATTAAATAGCCTTAAATTACTGTATAAAGAGTATGCAGGCATAGGCCACAAATTAAAAGGAACTGAGA

CTTATATATCACGAGATATGCAATTTATGAGTAAAACAATTCAACATAACGGTGTATATTACCCAGCTAGTATAAAG

AAAGTCCTAAGAGTGGGACCGTGGATAAACACTATACTTGATGATTTCAAAGTGAGTCTAGAATCTATAGGTAGTTT

GACACAAGAATTAGAATATAGAGGTGAAAGTCTATTATGCAGTTTAATATTTAGAAATGTATGGTTATATAATCAGA

TTGCTCTACAATTAAAAAATCATGCATTATGTAACAATAAACTATATTTGGACATATTAAAGGTTCTGAAACACTTA

AAAACCTTTTTTAATCTTGATAATATTGATACAGCATTAACATTGTATATGAATTTACCCATGTTATTTGGTGGTGG

TGATCCCAACTTGTTATATCGAAGTTTCTATAGAAGAACTCCTGACTTCCTCACAGAGGCTATAGTTCACTCTGTGT

TCATACTTAGTTATTATACAAACCATGACTTAAAAGATAAACTTCAAGATCTGTCAGATGATAGATTGAATAAGTTC

TTAACATGCATAATCACGTTTGACAAAAACCCTAATGCTGAATTCGTAACATTGATGAGAGATCCTCAAGCTTTAGG

GTCTGAGAGACAAGCTAAAATTACTAGCGAAATCAATAGACTGGCAGTTACAGAGGTTTTGAGTACAGCTCCAAACA

AAATATTCTCCAAAAGTGCACAACATTATACTACTACAGAGATAGATCTAAATGATATTATGCAAAATATAGAACCT

ACATATCCTCATGGGCTAAGAGTTGTTTATGAAAGTTTACCCTTTTATAAAGCAGAGAAAATAGTAAATCTTATATC

AGGTACAAAATCTATAACTAACATACTGGAAAAAACTTCTGCCATAGACTTAACAGATATTGATAGAGCCACTGAGA

TGATGAGGAAAAACATAACTTTGCTTATAAGGATACTTCCATTGGATTGTAACAGAGATAAAAGAGAGATATTGAGT

ATGGAAAACCTAAGTATTACTGAATTAAGCAAATATGTTAGGGAAAGATCTTGGTCTTTATCCAATATAGTTGGTGT

TACATCACCCAGTATCATGTATACAATGGACATCAAATATACTACAAGCACTATATCTAGTGGCATAATTATAGAGA

AATATAATGTTAACAGTTTAACACGTGGTGAGAGAGGACCCACTAAACCATGGGTTGGTTCATCTACACAAGAGAAA

AAAACAATGCCAGTTTATAATAGACAAGTCTTAACCAAAAAACAGAGAGATCAAATAGATCTATTAGCAAAATTGGA

TTGGGTGTATGCATCTATAGATAACAAGGATGAATTCATGGAAGAACTCAGCATAGGAACCCTTGGGTTAACATATG

AAAAGGCCAAGAAATTATTTCCACAATATTTAAGTGTCAATTATTTGCATCGCCTTACAGTCAGTAGTAGACCATGT

GAATTCCCTGCATCAATACCAGCTTATAGAACAACAAATTATCACTTTGACACTAGCCCTATTAATCGCATATTAAC

AGAAAAGTATGGTGATGAAGATATTGACATAGTATTCCAAAACTGTATAAGCTTTGGCCTTAGTTTAATGTCAGTAG

TAGAACAATTTACTAATGTATGTCCTAACAGAATTATTCTCATACCTAAGCTTAATGAGATACATTTGATGAAACCT

CCCATATTCACAGGTGATGTTGATATTCACAAGTTAAAACAAGTGATACAAAAACAGCATATGTTTTTACCAGACAA

AATAAGTTTGACTCAATATGTGGAATTATTCTTAAGTAATAAAACACTCAAATCTGGATCTCATGTTAATTCTAATT

TAATATTGGCACATAAAATATCTGACTATTTTCATAATACTTACATTTTAAGTACTAATTTAGCTGGACATTGGATT

CTGATTATACAACTTATGAAAGATTCTAAAGGTATTTTTGAAAAAGATTGGGGAGAGGGATATATAACTGATCATAT

GTTTATTAATTTGAAAGTTTTCTTCAATGCTTATAAGACCTATCTCTTGTGTTTTCATAAAGGTTATGGCAAAGCAA

AGCTGGAGTGTGATATGAACACTTCAGATCTTCTATGTGTATTGGAATTAATAGACAGTAGTTATTGGAAGTCTATG

TCTAAGGTATTTTTAGAACAAAAAGTTATCAAATACATTCTTAGCCAAGATGCAAGTTTACATAGAGTAAAAGGATG

-continued

TCATAGCTTCAAATTATGGTTTCTTAAACGTCTTAATGTAGCAGAATTCACAGTTTGCCCTTGGGTTGTTAACATAG

ATTATCATCCAACACATATGAAAGCAATATTAACTTATATAGATCTTGTTAGAATGGGATTGATAAATATAGATAGA

ATACACATTAAAAATAAACACAAATTCAATGATGAATTTTATACTTCTAATCTCTTCTACATTAATTATAACTTCTC

AGATAATACTCATCTATTAACTAAACATATAAGGATTGCTAATTCTGAATTAGAAAATAATTACAACAAATTATATC

ATCCTACACCAGAAACCCTAGAGAATATACTAGCCAATCCGATTAAAAGTAATGACAAAAAGACACTGAATGACTAT

TGTATAGGTAAAAATGTTGACTCAATAATGTTACCATTGTTATCTAATAAGAAGCTTATTAAATCGTCTGCAATGAT

TAGAACCAATTACAGCAAACAAGATTTGTATAATTTATTCCCTATGGTTGTGATTGATAGAATTATAGATCATTCAG

GCAATACAGCCAAATCCAACCAACTTTACACTACTACTTCCCACCAAATATCCTTAGTGCACAATAGCACATCACTT

TACTGCATGCTTCCTTGGCATCATATTAATAGATTCAATTTTGTATTTAGTTCTACAGGTTGTAAAATTAGTATAGA

GTATATTTTAAAAGATCTTAAAATTAAAGATCCCAATTGTATAGCATTCATAGGTGAAGGAGCAGGGAATTTATTAT

TGCGTACAGTAGTGGAACTTCATCCTGACATAAGATATATTTACAGAAGTCTGAAAGATTGCAATGATCATAGTTTA

CCTATTGAGTTTTTAAGGCTGTACAATGGACATATCAACATTGATTATGGTGAAAATTTGACCATTCCTGCTACAGA

TGCAACCAACAACATTCATTGGTCTTATTTACATATAAAGTTTGCTGAACCTATCAGTCTTTTTGTCTGTGATGCCG

AATTGTCTGTAACAGTCAACTGGAGTAAAATTATAATAGAATGGAGCAAGCATGTAAGAAAGTGCAAGTACTGTTCC

TCAGTTAATAAATGTATGTTAATAGTAAAATATCATGCTCAAGATGATATTGATTTCAAATTAGACAATATAACTAT

ATTAAAAACTTATGTATGCTTAGGCAGTAAGTTAAAGGGATCGGAGGTTTACTTAGTCCTTACAATAGGTCCTGCGA

ATATATTCCCAGTATTTAATGTAGTACAAAATGCTAAATTGATACTATCAAGAACCAAAAATTTCATCATGCCTAAG

AAAGCTGATAAAGAGTCTATTGATGCAAATATTAAAAGTTTGATACCCTTTCTTTGTTACCCTATAACAAAAAAAGG

AATTAATACTGCATTGTCAAAACTAAAGAGTGTTGTTAGTGGAGATATACTATCATATTCTATAGCTGGACGTAATG

AAGTTTTCAGCAATAAACTTATAAATCATAAGCATATGAACATCTTAAAATGGTTCAATCATGTTTTAAATTTCAGA

TCAACAGAACTAAACTATAACCATTTATATATGGTAGAATCTACATATCCTTACCTAAGTGAATTGTTAAACAGCTT

GACAACCAATGAACTTAAAAAACTGATTAAAATCACAGGTAGTCTGTTATACAACTTTCATAATGAATAATGAATAA

AGATCTTATAATAAAAATTCCCATAGCTATACACTAACACTGTATTCAATTATAGTTATTAAAAATTAAAAATCATA

TAATTTTTTAAATAACTTTTAGTGAACTAATCCTAAAGTTATCATTTTAATCTTGGAGGAATAAATTTAAACCCTAA

TCTAATTGGTTTATATGTGTATTAACTAAATTACGAGATATTAGTTTTTGACACTTTTTTTCTCGT

Antigenomic cDNA sequence of RSV 6120/NS12LtrGFP (SEQ ID NO: 3)

ACGGGAAAAAATGCGTACAACAAACTTGCATAAACCAAAAAAATGGGGCAAATAAGAATTTGATAAGTACCACTTAA

ATTTAACTCCCTTGGTTAGAGATGGCTCTTAGCAAAGTCAAGTTGAATGATACACTCAACAAAGATCAACTTCTGTC

ATCCAGCAAATACACCATCCAACGGAGCACAGGAGATAGTATTGATACTCCTAATTATGATGTGCAGAAACACATCA

ATAAGTTATGTGGCATGTTATTAATCACAGAAGATGCTAATCATAAATTCACTGGGTTAATAGGTATGTTATATGCG

ATGTCTAGGTTAGGAAGAGAAGACACCATAAAAATACTCAGAGATGCGGGATATCATGTAAAAGCAAATGGAGTAGA

TGTAACAACACATCGTCAAGACATTAATGGAAAAGAAATGAAATTTGAAGTGTTAACATTGGCAAGCTTAACAACTG

AAATTCAAATCAACATTGAGATAGAATCTAGAAAATCCTACAAAAAAATGCTAAAAGAAATGGGAGAGGTAGCTCCA

GAATACAGGCATGACTCTCCTGATTGTGGGATGATAATATTATGTATAGCAGCATTAGTAATAACTAAATTAGCAGC

AGGGGACAGATCTGGTCTTACAGCCGTGATTAGGAGAGCTAATAATGTCCTAAAAAATGAAATGAAACGTTACAAAG

GCTTACTACCCAAGGACATAGCCAACAGCTTCTATGAAGTGTTTGAAAAACATCCCCACTTTATAGATGTTTTTGTT

CATTTTGGTATAGCACAATCTTCTACCAGAGGTGGCAGTAGAGTTGAAGGGATTTTTGCAGGATTGTTTATGAATGC

CTATGGTGCAGGGCAAGTGATGTTACGGTGGGGAGTCTTAGCAAAATCAGTTAAAAATATTATGTTAGGACATGCTA

GTGTGCAAGCAGAAATGGAACAAGTTGTTGAGGTTTATGAATATGCCCAAAAATTGGGTGGTGAAGCAGGATTCTAC

CATATATTGAACAACCCAAAAGCATCATTATTATCTTTGACTCAATTTCCTCACTTCTCCAGTGTAGTATTAGGCAA

TGCTGCTGGCCTAGGCATAATGGGAGAGTACAGAGGTACACCGAGGAATCAAGATCTATATGATGCAGCAAAGGCAT

-continued

ATGCTGAACAACTCAAAGAAAATGGTGTGATTAACTACAGTGTACTAGACTTGACAGCAGAAGAACTAGAGGCTATC

AAACATCAGCTTAATCCAAAAGATAATGATGTAGAGCTTTGAGTTAATAAAAAATGGGGCAAATAAATCATCATGGA

AAAGTTTGCTCCTGAATTCCATGGAGAAGATGCAAACAACAGGGCTACTAAATTCCTAGAATCAATAAAGGGCAAAT

TCACATCACCCAAAGATCCCAAGAAAAAAGATAGTATCATATCTGTCAACTCAATAGATATAGAAGTAACCAAAGAA

AGCCCTATAACATCAAATTCAACTATTATCAACCCAACAAATGAGACAGATGATACTGCAGGGAACAAGCCCAATTA

TCAAAGAAAACCTCTAGTAAGTTTCAAAGAAGACCCTACACCAAGTGATAATCCCTTTTCTAAACTATACAAAGAAA

CCATAGAAACATTTGATAACAATGAAGAAGAATCCAGCTATTCATACGAAGAAATAAATGATCAGACAAACGATAAT

ATAACAGCAAGATTAGATAGGATTGATGAAAAATTAAGTGAAATACTAGGAATGCTTCACACATTAGTAGTGGCAAG

TGCAGGACCTACATCTGCTCGGGATGGTATAAGAGATGCCATGGTTGGTTTAAGAGAAGAAATGATAGAAAAAATCA

GAACTGAAGCATTAATGACCAATGACAGATTAGAAGCTATGGCAAGACTCAGGAATGAGGAAAGTGAAAAGATGGCA

AAAGACACATCAGATGAAGTGTCTCTCAATCCAACATCAGAGAAATTGAACAACCTATTGGAAGGGAATGATAGTGA

CAATGATCTATCACTTGAAGATTTCTGATTAGTTACCAATCTTCACATCAACACACAATACCAACAGAAGACCAACA

AACTAACCAACCCAATCATCCAACCAAACATCCATCCGCCAATCAGCCAAACAGCCAACAAAACAACCAGCCAATCC

AAAACTAACCACCCGGAAAAAATCTATAATATAGTTACAAAAAAAGGAATCGATGGGGCAAATACAAGTATGGTGAG

CAAGGGCGAGGAGCTGTTCACCGGGGTGGTGCCCATCCTGGTCGAGCTGGACGGCGACGTAAACGGCCACAAGTTCA

GCGTGTCCGGCGAGGGCGAGGGCGATGCCACCTACGGCAAGCTGACCCTGAAGTTCATCTGCACCACCGGCAAGCTG

CCCGTGCCCTGGCCCACCCTCGTGACCACCCTGACCTACGGCGTGCAGTGCTTCAGCCGCTACCCCGACCACATGAA

GCAGCACGACTTCTTCAAGTCCGCCATGCCCGAAGGCTACGTCCAGGAGCGCACCATCTTCTTCAAGGACGACGGCA

ACTACAAGACCCGCGCCGAGGTGAAGTTCGAGGGCGACACCCTGGTGAACCGCATCGAGCTGAAGGGCATCGACTTC

AAGGAGGACGGCAACATCCTGGGGCACAAGCTGGAGTACAACTACAACAGCCACAACGTCTATATCATGGCCGACAA

GCAGAAGAACGGCATCAAGGTGAACTTCAAGATCCGCCACAACATCGAGGACGGCAGCGTGCAGCTCGCCGACCACT

ACCAGCAGAACACCCCCATCGGCGACGGCCCCGTGCTGCTGCCCGACAACCACTACCTGAGCACCCAGTCCGCCCTG

AGCAAAGACCCCAACGAGAAGCGCGATCACATGGTCCTGCTGGAGTTCGTGACCGCCGCCGGGATCACTCTCGGCAT

GGACGAGCTGTACAAGTAAAAGTAGTTACTTAAAAAGTCGACGGTGGGGCAAATATGGAAACATACGTGAACAAGCT

TCACGAAGGCTCCACATACACAGCTGCTGTTCAATACAATGTCTTAGAAAAAGACGATGACCCTGCATCACTTACAA

TATGGGTGCCCATGTTCCAATCATCTATGCCAGCAGATTTACTTATAAAAGAACTAGCTAATGTCAACATACTAGTG

AAACAAATATCCACACCCAAGGGACCTTCACTAAGAGTCATGATAAACTCAAGAAGTGCAGTGCTAGCACAAATGCC

CAGCAAATTTACCATATGCGCTAATGTGTCCTTGGATGAAAGAAGCAAACTAGCATATGATGTAACCACACCCTGTG

AAATCAAGGCATGTAGTCTAACATGCCTAAAATCAAAAAATATGTTGACTACAGTTAAAGATCTCACTATGAAGACA

CTCAACCCTACACATGATATTATTGCTTTATGTGAATTTGAAAACATAGTAACATCAAAAAAAGTCATAATACCAAC

ATACCTAAGATCCATCAGTGTCAGAAATAAAGATCTGAACACACTTGAAAATATAACAACCACTGAATTCAAAAATG

CTATCACAAATGCAAAAATCATCCCTTACTCAGGATTACTATTAGTCATCACAGTGACTGACAACAAAGGAGCATTC

AAATACATAAAGCCACAAAGTCAATTCATAGTAGATCTTGGAGCTTACCTAGAAAAAGAAAGTATATATTATGTTAC

CACAAATTGGAAGCACACAGCTACACGATTTGCAATCAAACCCATGGAAGATTAACCTTTTTCCTCTACATCAGTGT

GTTAATTCATACAAACTTTCTACCTACATTCTTCACTTCACCATCACAATCACAAACACTCTGTGGTTCAACCAATC

AAACAAAACTTATCTGAAGTCCCAGATCATCCCAAGTCATTGTTTATCAGATCTAGTACTCAAATAAGTTAATAAAA

AATATACACATGGGGCAAATAATCATTGGAGGAAATCCAACTAATCACAATATCTGTTAACATAGACAAGTCCACAC

ACCATACAGAATCAACCAATGGAAAATACATCCATAACAATAGAATTCTCAAGCAAATTCTGGCCTTACTTTACACT

AATACACATGATCACAACAATAATCTCTTTGCTAATCATAATCTCCATCATGATTGCAATACTAAACAAACTTTGTG

AATATAACGTATTCCATAACAAAACCTTTGAGTTACCAAGAGCTCGAGTTAATACTTGATAAAGTAGTTAATTAAAA

ATAGTCATAACAATGAACTAGGATATCAAGACTAACAATAACATTGGGGCAAATGCAAACATGTCCAAAAACAAGGA

-continued

CCAACGCACCGCTAAGACATTAGAAAGGACCTGGGACACTCTCAATCATTTATTATTCATATCATCGTGCTTATATA

AGTTAAATCTTAAATCTGTAGCACAAATCACATTATCCATTCTGGCAATGATAATCTCAACTTCACTTATAATTGCA

GCCATCATATTCATAGCCTCGGCAAACCACAAAGTCACACCAACAACTGCAATCATACAAGATGCAACAAGCCAGAT

CAAGAACACAACCCCAACATACCTCACCCAGAATCCTCAGCTTGGAATCAGTCCCTCTAATCCGTCTGAAATTACAT

CACAAATCACCACCATACTAGCTTCAACAACACCAGGAGTCAAGTCAACCCTGCAATCCACAACAGTCAAGACCAAA

AACACAACAACAACTCAAACACAACCCAGCAAGCCCACCACAAAACAACGCCAAAACAAACCACCAAGCAAACCCAA

TAATGATTTTCACTTTGAAGTGTTCAACTTTGTACCCTGCAGCATATGCAGCAACAATCCAACCTGCTGGGCTATCT

GCAAAAGAATACCAAACAAAAAACCAGGAAAGAAAACCACTACCAAGCCCACAAAAAAACCAACCCTCAAGACAACC

AAAAAAGATCCCAAACCTCAAACCACTAAATCAAAGGAAGTACCCACCACCAAGCCCACAGAAGAGCCAACCATCAA

CACCACCAAAACAAACATCATAACTACACTACTCACCTCCAACACCACAGGAAATCCAGAACTCACAAGTCAAATGG

AAACCTTCCACTCAACTTCCTCCGAAGGCAATCCAAGCCCTTCTCAAGTCTCTACAACATCCGAGTACCCATCACAA

CCTTCATCTCCACCCAACACACCACGCCAGTAGTTACTTAAAAACATATTATCACAAAAGGCCTTGACCAACTTAAA

CAGAATCAAAATAAACTCTGGGGCAAATAACAATGGAGTTGCTAATCCTCAAAGCAAATGCAATTACCACAATCCTC

ACTGCAGTCACATTTTGTTTTGCTTCTGGTCAAAACATCACTGAAGAATTTTATCAATCAACATGCAGTGCAGTTAG

CAAAGGCTATCTTAGTGCTCTGAGAACTGGTTGGTATACCAGTGTTATAACTATAGAATTAAGTAATATCAAGAAAA

ATAAGTGTAATGGAACAGATGCTAAGGTAAAATTGATAAAACAAGAATTAGATAAATATAAAAATGCTGTAACAGAA

TTGCAGTTGCTCATGCAAAGCACACAAGCAACAAACAATCGAGCCAGAAGAGAACTACCAAGGTTTATGAATTATAC

ACTCAACAATGCCAAAAAAACCAATGTAACATTAAGCAAGAAAAGGAAAAGAAGATTTCTTGGTTTTTTGTTAGGTG

TTGGATCTGCAATCGCCAGTGGCGTTGCTGTATCTAAGGTCCTGCACCTAGAAGGGGAAGTGAACAAGATCAAAAGT

GCTCTACTATCCACAAACAAGGCTGTAGTCAGCTTATCAAATGGAGTTAGTGTTTTAACCAGCAAAGTGTTAGACCT

CAAAAACTATATAGATAAACAATTGTTACCTATTGTGAACAAGCAAAGCTGCAGCATATCAAATATAGAAACTGTGA

TAGAGTTCCAACAAAAGAACAACAGACTACTAGAGATTACCAGGGAATTTAGTGTTAATGCAGGCGTAACTACACCT

GTAAGCACTTACATGTTAACTAATAGTGAATTATTGTCATTAATCAATGATATGCCTATAACAAATGATCAGAAAAA

GTTAATGTCCAACAATGTTCAAATAGTTAGACAGCAAAGTTACTCTATCATGTCCATAATAAAAGAGGAAGTCTTAG

CATATGTAGTACAATTACCACTATATGGTGTTATAGATACACCCTGTTGGAAACTACACACATCCCCTCTATGTACA

ACCAACACAAAAGAAGGGTCCAACATCTGTTTAACAAGAACTGACAGAGGATGGTACTGTGACAATGCAGGATCAGT

ATCTTTCTTCCCACAAGCTGAAACATGTAAAGTTCAATCAAATCGAGTATTTTGTGACACAATGAACAGTTTAACAT

TACCAAGTGAAGTAAATCTCTGCAATGTTGACATATTCAACCCCAAATATGATTGTAAAATTATGACTTCAAAAACA

GATGTAAGCAGCTCCGTTATCACATCTCTAGGAGCCATTGTGTCATGCTATGGCAAAACTAAATGTACAGCATCCAA

TAAAAATCGTGGAATCATAAAGACATTTTCTAACGGGTGCGATTATGTATCAAATAAAGGGGTGGACACTGTGTCTG

TAGGTAACACATTATATTATGTAAATAAGCAAGAAGGTAAAAGTCTCTATGTAAAAGGTGAACCAATAATAAATTTC

TATGACCCATTAGTATTCCCCTCTGATGAATTTGATGCATCAATATCTCAAGTCAACGAGAAGATTAACCAGAGCCT

AGCATTTATTCGTAAATCCGATGAATTATTACATAATGTAAATGCTGGTAAATCCACCACAAATATCATGATAACTA

CTATAATTATAGTGATTATAGTAATATTGTTATCATTAATTGCTGTTGGACTGCTCTTATACTGTAAGGCCAGAAGC

ACACCAGTCACACTAAGCAAAGATCAACTGAGTGGTATAAATAATATTGCATTTAGTAACTAAATAAAAATAGCACC

TAATCATGTTCTTACAATGGTTTACTATCTGCTCATAGACAACCCATCTGTCATTGGATTTTCTTAAAATCTGAACT

TCATCGAAACTCTCATCTATAAACCATCTCACTTACACTATTTAAGTAGATTCCTAGTTTATAGTTATATAAAACAC

AATTGCATGCCAGATTAACTTACCATCTGTAAAAATGAAAACTGGGGCAAATATGTCACGAAGGAATCCTTGCAAAT

TTGAAATTCGAGGTCATTGCTTAAATGGTAAGAGGTGTCATTTTAGTCATAATTATTTTGAATGGCCACCCCATGCA

CTGCTTGTAAGACAAAACTTTATGTTAAACAGAATACTTAAGTCTATGGATAAAAGTATAGATACCTTATCAGAAAT

-continued
AAGTGGAGCTGCAGAGTTGGACAGAACAGAAGAGTATGCTCTTGGTGTAGTTGGAGTGCTAGAGAGTTATATAGGAT

CAATAAACAATATAACTAAACAATCAGCATGTGTTGCCATGAGCAAACTCCTCACTGAACTCAATAGTGATGATATC

AAAAAGCTGAGGGACAATGAAGAGCTAAATTCACCCAAGATAAGAGTGTACAATACTGTCATATCATATATTGAAAG

CAACAGGAAAAACAATAAACAAACTATCCATCTGTTAAAAAGATTGCCAGCAGACGTATTGAAGAAAACCATCAAAA

ACACATTGGATATCCATAAGAGCATAACCATCAACAACCCAAAAGAATCAACTGTTAGTGATACAAATGACCATGCC

AAAAATAATGATACTACCTGACAAATATCCTTGTAGTATAACTTCCATACTAATAACAAGTAGATGTAGAGTTACTA

TGTATAATCAAAAGAACACACTATATTTCAATCAAAACAACCCAAATAACCATATGTACTCACCGAATCAAACATTC

AATGAAATCCATTGGACCTCTCAAGAATTGATTGACACAATTCAAAATTTTCTACAACATCTAGGTATTATTGAGGA

TATATATACAATATATATATTAGTGTCATAACACTCAATTCTAACACTCACCACATCGTTACATTATTAATTCAAAC

AATTCAAGTTGTGGGACAAAATGGATCCCATTATTAATGGAAATTCTGCTAATGTTTATCTAACCGATAGTTATTTA

AAAGGTGTTATCTCTTTCTCAGAGTGTAATGCTTTAGGAAGTTACATATTCAATGGTCCTTATCTCAAAAATGATTA

TACCAACTTAATTAGTAGACAAAATCCATTAATAGAACACATGAATCTAAAGAAACTAAATATAACACAGTCCTTAA

TATCTAAGTATCATAAAGGTGAAATAAAATTAGAAGAACCTACTTATTTTCAGTCATTACTTATGACATACAAGAGT

ATGACCTCGTCAGAACAGATTGCTACCACTAATTTACTTAAAAAGATAATAAGAAGAGCTATAGAAATAAGTGATGT

CAAAGTCTATGCTATATTGAATAAACTAGGGCTTAAAGAAAAGGACAAGATTAAATCCAACAATGGACAAGATGAAG

ACAACTCAGTTATTACGACCATAATCAAAGATGATATACTTTCAGCTGTTAAAGATAATCAATCTCATCTTAAAGCA

GACAAAAATCACTCTACAAAACAAAAAGACACAATCAAAACAACACTCTTGAAGAAATTGATGTGTTCAATGCAACA

TCCTCCATCATGGTTAATACATTGGTTTAACTTATACACAAAATTAAACAACATATTAACACAGTATCGATCAAATG

AGGTAAAAAACCATGGGTTTACATTGATAGATAATCAAACTCTTAGTGGATTTCAATTTATTTTGAACCAATATGGT

TGTATAGTTTATCATAAGGAACTCAAAAGAATTACTGTGACAACCTATAATCAATTCTTGACATGGAAAGATATTAG

CCTTAGTAGATTAAATGTTTGTTTAATTACATGGATTAGTAACTGCTTGAACACATTAAATAAAAGCTTAGGCTTAA

GATGCGGATTCAATAATGTTATCTTGACACAACTATTCCTTTATGGAGATTGTATACTAAAGCTATTTCACAATGAG

GGGTTCTACATAATAAAAGAGGTAGAGGGATTTATTATGTCTCTAATTTTAAATATAACAGAAGAAGATCAATTCAG

AAAACGATTTTATAATAGTATGCTCAACAACATCACAGATGCTGCTAATAAAGCTCAGAAAAATCTGCTATCAAGAG

TATGTCATACATTATTAGATAAGACAGTGTCCGATAATATAATAAATGGCAGATGGATAATTCTATTAAGTAAGTTC

CTTAAATTAATTAAGCTTGCAGGTGACAATAACCTTAACAATCTGAGTGAACTATATTTTTTGTTCAGAATATTTGG

ACACCCAATGGTAGATGAAAGACAAGCCATGGATGCTGTTAAAATTAATTGCAATGAGACCAAATTTTACTTGTTAA

GCAGTCTGAGTATGTTAAGAGGTGCCTTTATATATAGAATTATAAAAGGGTTTGTAAATAATTACAACAGATGGCCT

ACTTTAAGAAATGCTATTGTTTTACCCTTAAGATGGTTAACTTACTATAAACTAAACACTTATCCTTCTTTGTTGGA

ACTTACAGAAAGAGATTTGATTGTGTTATCAGGACTACGTTTCTATCGTGAGTTTCGGTTGCCTAAAAAAGTGGATC

TTGAAATGATTATAAATGATAAAGCTATATCACCTCCTAAAAATTTGATATGGACTAGTTTCCCTAGAAATTACATG

CCATCACACATACAAAACTATATAGAACATGAAAAATTAAAATTTTCCGAGAGTGATAAATCAAGAAGAGTATTAGA

GTATTATTTAAGAGATAACAAATTCAATGAATGTGATTTATACAACTGTGTAGTTAATCAAAGTTATCTCAACAACC

CTAATCATGTGGTATCATTGACAGGCAAAGAAAGAGAACTCAGTGTAGGTAGAATGTTTGCAATGCAACCGGGAATG

TTCAGACAGGTTCAAATATTGGCAGAGAAAATGATAGCTGAAAACATTTTACAATTCTTTCCTGAAAGTCTTACAAG

ATATGGTGATCTAGAACTACAAAAAATATTAGAACTGAAAGCAGGAATAAGTAACAAATCAAATCGCTACAATGATA

ATTACAACAATTACATTAGTAAGTGCTCTATCATCACAGATCTCAGCAAATTCAATCAAGCATTTCGATATGAAACG

TCATGTATTTGTAGTGATGTGCTGGATGAACTGCATGGTGTACAATCTCTATTTTCCTGGTTACATTTAACTATTCC

TCATGTCACAATAATATGCACATATAGGCATGCACCCCCCTATATAGGAGATCATATTGTAGATCTTAACAATGTAG

ATGAACAAAGTGGATTATATAGATATCACATGGGTGGCATCGAAGGGTGGTGTCAAAAACTATGGACCATAGAAGCT

ATATCACTATTGGATCTAATATCTCTCAAAGGGAAATTCTCAATTACTGCTTTAATTAATGGTGACAATCAATCAAT

-continued

AGATATAAGCAAACCAATCAGACTCATGGAAGGTCAAACTCATGCTCAAGCAGATTATTTGCTAGCATTAAATAGCC

TTAAATTACTGTATAAAGAGTATGCAGGCATAGGCCACAAATTAAAAGGAACTGAGACTTATATATCACGAGATATG

CAATTTATGAGTAAAACAATTCAACATAACGGTGTATATTACCCAGCTAGTATAAAGAAAGTCCTAAGAGTGGGACC

GTGGATAAACACTATACTTGATGATTTCAAAGTGAGTCTAGAATCTATAGGTAGTTTGACACAAGAATTAGAATATA

GAGGTGAAAGTCTATTATGCAGTTTAATATTTAGAAATGTATGGTTATATAATCAGATTGCTCTACAATTAAAAAAT

CATGCATTATGTAACAATAAACTATATTTGGACATATTAAAGGTTCTGAAACACTTAAAAACCTTTTTTAATCTTGA

TAATATTGATACAGCATTAACATTGTATATGAATTTACCCATGTTATTTGGTGGTGGTGATCCCAACTTGTTATATC

GAAGTTTCTATAGAAGAACTCCTGACTTCCTCACAGAGGCTATAGTTCACTCTGTGTTCATACTTAGTTATTATACA

AACCATGACTTAAAAGATAAACTTCAAGATCTGTCAGATGATAGATTGAATAAGTTCTTAACATGCATAATCACGTT

TGACAAAAACCCTAATGCTGAATTCGTAACATTGATGAGAGATCCTCAAGCTTTAGGGTCTGAGAGACAAGCTAAAA

TTACTAGCGAAATCAATAGACTGGCAGTTACAGAGGTTTTGAGTACAGCTCCAAACAAAATATTCTCCAAAAGTGCA

CAACATTATACTACTACAGAGATAGATCTAAATGATATTATGCAAAATATAGAACCTACATATCCTCATGGGCTAAG

AGTTGTTTATGAAAGTTTACCCTTTTATAAAGCAGAGAAAATAGTAAATCTTATATCAGGTACAAAATCTATAACTA

ACATACTGGAAAAAACTTCTGCCATAGACTTAACAGATATTGATAGAGCCACTGAGATGATGAGGAAAAACATAACT

TTGCTTATAAGGATACTTCCATTGGATTGTAACAGAGATAAAAGAGAGATATTGAGTATGGAAAACCTAAGTATTAC

TGAATTAAGCAAATATGTTAGGGAAAGATCTTGGTCTTTATCCAATATAGTTGGTGTTACATCACCCAGTATCATGT

ATACAATGGACATCAAATATACTACAAGCACTATATCTAGTGGCATAATTATAGAGAAATATAATGTTAACAGTTTA

ACACGTGGTGAGAGAGGACCCACTAAACCATGGGTTGGTTCATCTACACAAGAGAAAAAAACAATGCCAGTTTATAA

TAGACAAGTCTTAACCAAAAAACAGAGAGATCAAATAGATCTATTAGCAAAATTGGATTGGGTGTATGCATCTATAG

ATAACAAGGATGAATTCATGGAAGAACTCAGCATAGGAACCCTTGGGTTAACATATGAAAAGGCCAAGAAATTATTT

CCACAATATTTAAGTGTCAATTATTTGCATCGCCTTACAGTCAGTAGTAGACCATGTGAATTCCCTGCATCAATACC

AGCTTATAGAACAACAAATTATCACTTTGACACTAGCCCTATTAATCGCATATTAACAGAAAAGTATGGTGATGAAG

ATATTGACATAGTATTCCAAAACTGTATAAGCTTTGGCCTTAGTTTAATGTCAGTAGTAGAACAATTTACTAATGTA

TGTCCTAACAGAATTATTCTCATACCTAAGCTTAATGAGATACATTTGATGAAACCTCCCATATTCACAGGTGATGT

TGATATTCACAAGTTAAAACAAGTGATACAAAAACAGCATATGTTTTTACCAGACAAAATAAGTTTGACTCAATATG

TGGAATTATTCTTAAGTAATAAAACACTCAAATCTGGATCTCATGTTAATTCTAATTTAATATTGGCACATAAAATA

TCTGACTATTTTCATAATACTTACATTTTAAGTACTAATTTAGCTGGACATTGGATTCTGATTATACAACTTATGAA

AGATTCTAAAGGTATTTTTGAAAAAGATTGGGGAGAGGGATATATAACTGATCATATGTTTATTAATTTGAAAGTTT

TCTTCAATGCTTATAAGACCTATCTCTTGTGTTTTCATAAAGGTTATGGCAAAGCAAAGCTGGAGTGTGATATGAAC

ACTTCAGATCTTCTATGTGTATTGGAATTAATAGACAGTAGTTATTGGAAGTCTATGTCTAAGGTATTTTTAGAACA

AAAAGTTATCAAATACATTCTTAGCCAAGATGCAAGTTTACATAGAGTAAAAGGATGTCATAGCTTCAAATTATGGT

TTCTTAAACGTCTTAATGTAGCAGAATTCACAGTTTGCCCTTGGGTTGTTAACATAGATTATCATCCAACACATATG

AAAGCAATATTAACTTATATAGATCTTGTTAGAATGGGATTGATAAATATAGATAGAATACACATTAAAAATAAACA

CAAATTCAATGATGAATTTTATACTTCTAATCTCTTCTACATTAATTATAACTTCTCAGATAATACTCATCTATTAA

CTAAACATATAAGGATTGCTAATTCTGAATTAGAAAATAATTACAACAAATTATATCATCCTACACCAGAAACCCTA

GAGAATATACTAGCCAATCCGATTAAAAGTAATGACAAAAAGACACTGAATGACTATTGTATAGGTAAAAATGTTGA

CTCAATAATGTTACCATTGTTATCTAATAAGAAGCTTATTAAATCGTCTGCAATGATTAGAACCAATTACAGCAAAC

AAGATTTGTATAATTTATTCCCTATGGTTGTGATTGATAGAATTATAGATCATTCAGGCAATACAGCCAAATCCAAC

CAACTTTACACTACTACTTCCCACCAAATATCCTTAGTGCACAATAGCACATCACTTTACTGCATGCTTCCTTGGCA

TCATATTAATAGATTCAATTTTGTATTTAGTTCTACAGGTTGTAAAATTAGTATAGAGTATATTTTAAAAGATCTTA

-continued

AAATTAAAGATCCCAATTGTATAGCATTCATAGGTGAAGGAGCAGGGAATTTATTATTGCGTACAGTAGTGGAACTT

CATCCTGACATAAGATATATTTACAGAAGTCTGAAAGATTGCAATGATCATAGTTTACCTATTGAGTTTTTAAGGCT

GTACAATGGACATATCAACATTGATTATGGTGAAAATTTGACCATTCCTGCTACAGATGCAACCAACAACATTCATT

GGTCTTATTTACATATAAAGTTTGCTGAACCTATCAGTCTTTTTGTCTGTGATGCCGAATTGTCTGTAACAGTCAAC

TGGAGTAAAATTATAATAGAATGGAGCAAGCATGTAAGAAAGTGCAAGTACTGTTCCTCAGTTAATAAATGTATGTT

AATAGTAAAATATCATGCTCAAGATGATATTGATTTCAAATTAGACAATATAACTATATTAAAAACTTATGTATGCT

TAGGCAGTAAGTTAAAGGGATCGGAGGTTTACTTAGTCCTTACAATAGGTCCTGCGAATATATTCCCAGTATTTAAT

GTAGTACAAAATGCTAAATTGATACTATCAAGAACCAAAAATTTCATCATGCCTAAGAAAGCTGATAAAGAGTCTAT

TGATGCAAATATTAAAAGTTTGATACCCTTTCTTTGTTACCCTATAACAAAAAAAGGAATTAATACTGCATTGTCAA

AACTAAAGAGTGTTGTTAGTGGAGATATACTATCATATTCTATAGCTGGACGTAATGAAGTTTTCAGCAATAAACTT

ATAAATCATAAGCATATGAACATCTTAAAATGGTTCAATCATGTTTTAAATTTCAGATCAACAGAACTAAACTATAA

CCATTTATATATGGTAGAATCTACATATCCTTACCTAAGTGAATTGTTAAACAGCTTGACAACCAATGAACTTAAAA

AACTGATTAAAATCACAGGTAGTCTGTTATACAACTTTCATAATGAATAATGAATAAAGATCTTATAATAAAAATTC

CCATAGCTATACACTAACACTGTATTCAATTATAGTTATAAAAATTAAAAATGGTACCATGGGGCAAATAAGAATTT

GATAAGTACCACTTAAATTTAACTCCCTTGGTTAGAGATGGGCAGCAATTCATTGAGTATGATAAAAGTTAGATTAC

AAAATTTGTTTGACAATGATGAAGTAGCATTGTTAAAAATAACATGCTATACTGATAAATTAATACATTTAACTAAT

GCTTTGGCTAAGGCAGTGATACATACAATCAAATTGAATGGCATTGTGTTTGTGCATGTTATTACAAGTAGTGATAT

TTGCCCTAATAATAATATTGTAGTAAAATCCAATTTCACAACAATGCCAGTACTACAAAATGGAGGTTATATATGGG

AAATGATGGAATTAACACATTGCTCTCAACCTAATGGTCTACTAGATGACAATTGTGAAATTAAATTCTCCAAAAAA

CTAAGTGATTCAACAATGACCAATTATATGAATCAATTATCTGAATTACTTGGATTTGATCTTAATCCATAAATTAT

AATTAATATCAACTAGCAAATCAATGTCACTAACACCATTAGTTAATATAAAACTTAACAGAAGACAAAAATGGGGC

AAATAAATCAATTCAGCCAACCCAACCATGGACACAACCCACAATGATAATACACCACAAAGACTGATGATCACAGA

CATGAGACCGTTGTCACTTGAGACCATAATAACATCACTAACCAGAGACATCATAACACACAAATTTATATACTTGA

TAAATCATGAATGCATAGTGAGAAAACTTGATGAAAGACAGGCCACATTTACATTCCTGGTCAACTATGAAATGAAA

CTATTACACAAAGTAGGAAGCACTAAATATAAAAAATATACTGAATACAACACAAAATATGGCACTTTCCCTATGCC

AATATTCATCAATCATGATGGGTTCTTAGAATGCATTGGCATTAAGCCTACAAAGCATACTCCCATAATATACAAGT

ATGATCTCAATCCATAAATTTCAACACAATATTCACACAATCTAAAACAACAACTCTATGCATAACTATACTCCATA

GTCCAGATGGAGCCTGAAAATTATAGTAATTTAAAACTTAAGGAGAGATATAAGATAGAAGATGGTACCATTTTTTA

AATAACTTTTAGTGAACTAATCCTAAAGTTATCATTTTAATCTTGGAGGAATAAATTTAAACCCTAATCTAATTGGT

TTATATGTGTATTAACTAAATTACGAGATATTAGTTTTTGACACTTTTTTTCTCGT

Antigenomic cDNA sequence of RSV 6120/NS12Ltr (SEQ ID NO: 4)

ACGgGAAAAAATGCGTACAACAAACTTGCATAAACCAAAAAAATGGGGCAAATAAGAATTTGATAAGTACCACTTAA

ATTTAACTCCCTTGGTTAGAGATGGCTCTTAGCAAAGTCAAGTTGAATGATACACTCAACAAAGATCAACTTCTGTC

ATCCAGCAAATACACCATCCAACGGAGCACAGGAGATAGTATTGATACTCCTAATTATGATGTGCAGAAACACATCA

ATAAGTTATGTGGCATGTTATTAATCACAGAAGATGCTAATCATAAATTCACTGGGTTAATAGGTATGTTATATGCG

ATGTCTAGGTTAGGAAGAGAAGACACCATAAAAATACTCAGAGATGCGGGATATCATGTAAAAGCAAATGGAGTAGA

TGTAACAACACATCGTCAAGACATTAATGGAAAAGAAATGAAATTTGAAGTGTTAACATTGGCAAGCTTAACAACTG

AAATTCAAATCAACATTGAGATAGAATCTAGAAAATCCTACAAAAAAATGCTAAAAGAAATGGGAGAGGTAGCTCCA

GAATACAGGCATGACTCTCCTGATTGTGGGATGATAATATTATGTATAGCAGCATTAGTAATAACTAAATTAGCAGC

AGGGGACAGATCTGGTCTTACAGCCGTGATTAGGAGAGCTAATAATGTCCTAAAAAATGAAATGAAACGTTACAAAG

GCTTACTACCCAAGGACATAGCCAACAGCTTCTATGAAGTGTTTGAAAAACATCCCCACTTTATAGATGTTTTTGTT

-continued

CATTTTGGTATAGCACAATCTTCTACCAGAGGTGGCAGTAGAGTTGAAGGGATTTTTGCAGGATTGTTTATGAATGC

CTATGGTGCAGGGCAAGTGATGTTACGGTGGGGAGTCTTAGCAAAATCAGTTAAAAATATTATGTTAGGACATGCTA

GTGTGCAAGCAGAAATGGAACAAGTTGTTGAGGTTTATGAATATGCCCAAAAATTGGGTGGTGAAGCAGGATTCTAC

CATATATTGAACAACCCAAAAGCATCATTATTATCTTTGACTCAATTTCCTCACTTCTCCAGTGTAGTATTAGGCAA

TGCTGCTGGCCTAGGCATAATGGGAGAGTACAGAGGTACACCGAGGAATCAAGATCTATATGATGCAGCAAAGGCAT

ATGCTGAACAACTCAAAGAAAATGGTGTGATTAACTACAGTGTACTAGACTTGACAGCAGAAGAACTAGAGGCTATC

AAACATCAGCTTAATCCAAAAGATAATGATGTAGAGCTTTGAGTTAATAAAAAATGGGGCAAATAAATCATCATGGA

AAAGTTTGCTCCTGAATTCCATGGAGAAGATGCAAACAACAGGGCTACTAAATTCCTAGAATCAATAAAGGGCAAAT

TCACATCACCCAAAGATCCCAAGAAAAAAGATAGTATCATATCTGTCAACTCAATAGATATAGAAGTAACCAAAGAA

AGCCCTATAACATCAAATTCAACTATTATCAACCCAACAAATGAGACAGATGATACTGCAGGGAACAAGCCCAATTA

TCAAAGAAAACCTCTAGTAAGTTTCAAAGAAGACCCTACACCAAGTGATAATCCCTTTTCTAAACTATACAAAGAAA

CCATAGAAACATTTGATAACAATGAAGAAGAATCCAGCTATTCATACGAAGAAATAAATGATCAGACAAACGATAAT

ATAACAGCAAGATTAGATAGGATTGATGAAAAATTAAGTGAAATACTAGGAATGCTTCACACATTAGTAGTGGCAAG

TGCAGGACCTACATCTGCTCGGGATGGTATAAGAGATGCCATGGTTGGTTTAAGAGAAGAAATGATAGAAAAAATCA

GAACTGAAGCATTAATGACCAATGACAGATTAGAAGCTATGGCAAGACTCAGGAATGAGGAAAGTGAAAAGATGGCA

AAAGACACATCAGATGAAGTGTCTCTCAATCCAACATCAGAGAAATTGAACAACCTATTGGAAGGGAATGATAGTGA

CAATGATCTATCACTTGAAGATTTCTGATTAGTTACCAATCTTCACATCAACACACAATACCAACAGAAGACCAACA

AACTAACCAACCCAATCATCCAACCAAACATCCATCCGCCAATCAGCCAAACAGCCAACAAAACAACCAGCCAATCC

AAAACTAACCACCCGGAAAAAATCTATAATATAGTTACAAAAAAAGGAAagGGTGGGGCAAATATGGAAACATACGT

GAACAAGCTTCACGAAGGCTCCACATACACAGCTGCTGTTCAATACAATGTCTTAGAAAAAGACGATGACCCTGCAT

CACTTACAATATGGGTGCCCATGTTCCAATCATCTATGCCAGCAGATTTACTTATAAAAGAACTAGCTAATGTCAAC

ATACTAGTGAAACAAATATCCACACCCAAGGGACCTTCACTAAGAGTCATGATAAACTCAAGAAGTGCAGTGCTAGC

ACAAATGCCCAGCAAATTTACCATATGCGCTAATGTGTCCTTGGATGAAAGAAGCAAACTAGCATATGATGTAACCA

CACCCTGTGAAATCAAGGCATGTAGTCTAACATGCCTAAAATCAAAAAATATGTTGACTACAGTTAAAGATCTCACT

ATGAAGACACTCAACCCTACACATGATATTATTGCTTTATGTGAATTTGAAAACATAGTAACATCAAAAAAAGTCAT

AATACCAACATACCTAAGATCCATCAGTGTCAGAAATAAAGATCTGAACACACTTGAAAATATAACAACCACTGAAT

TCAAAAATGCTATCACAAATGCAAAAATCATCCCTTACTCAGGATTACTATTAGTCATCACAGTGACTGACAACAAA

GGAGCATTCAAATACATAAAGCCACAAAGTCAATTCATAGTAGATCTTGGAGCTTACCTAGAAAAAGAAAGTATATA

TTATGTTACCACAAATTGGAAGCACACAGCTACACGATTTGCAATCAAACCCATGGAAGATTAACCTTTTTCCTCTA

CATCAGTGTGTTAATTCATACAAACTTTCTACCTACATTCTTCACTTCACCATCACAATCACAAACACTCTGTGGTT

CAACCAATCAAACAAAACTTATCTGAAGTCCCAGATCATCCCAAGTCATTGTTTATCAGATCTAGTACTCAAATAAG

TTAATAAAAAATATACACATGGGGCAAATAATCATTGGAGGAAATCCAACTAATCACAATATCTGTTAACATAGACA

AGTCCACACACCATACAGAATCAACCAATGGAAAATACATCCATAACAATAGAATTCTCAAGCAAATTCTGGCCTTA

CTTTACACTAATACACATGATCACAACAATAATCTCTTTGCTAATCATAATCTCCATCATGATTGCAATACTAAACA

AACTTTGTGAATATAACGTATTCCATAACAAAACCTTTGAGTTACCAAGAGCTCGAGTTAATACTTGATAAAGTAGT

TAATTAAAAATAGTCATAACAATGAACTAGGATATCAAGACTAACAATAACATTGGGGCAAATGCAAACATGTCCAA

AAACAAGGACCAACGCACCGCTAAGACATTAGAAAGGACCTGGGACACTCTCAATCATTTATTATTCATATCATCGT

GCTTATATAAGTTAAATCTTAAATCTGTAGCACAAATCACATTATCCATTCTGGCAATGATAATCTCAACTTCACTT

ATAATTGCAGCCATCATATTCATAGCCTCGGCAAACCACAAAGTCACACCAACAACTGCAATCATACAAGATGCAAC

AAGCCAGATCAAGAACACAACCCCAACATACCTCACCCAGAATCCTCAGCTTGGAATCAGTCCCTCTAATCCGTCTG

AAATTACATCACAAATCACCACCATACTAGCTTCAACAACACCAGGAGTCAAGTCAACCCTGCAATCCACAACAGTC

-continued

AAGACCAAAAACACAACAACAACTCAAACACAACCCAGCAAGCCCACCACAAAACAACGCCAAAACAAACCACCAAG

CAAACCCAATAATGATTTTCACTTTGAAGTGTTCAACTTTGTACCCTGCAGCATATGCAGCAACAATCCAACCTGCT

GGGCTATCTGCAAAAGAATACCAAACAAAAAACCAGGAAAGAAAACCACTACCAAGCCCACAAAAAAACCAACCCTC

AAGACAACCAAAAAAGATCCCAAACCTCAAACCACTAAATCAAAGGAAGTACCCACCACCAAGCCCACAGAAGAGCC

AACCATCAACACCACCAAAACAAACATCATAACTACACTACTCACCTCCAACACCACAGGAAATCCAGAACTCACAA

GTCAAATGGAAACCTTCCACTCAACTTCCTCCGAAGGCAATCCAAGCCCTTCTCAAGTCTCTACAACATCCGAGTAC

CCATCACAACCTTCATCTCCACCCAACACACCACGCCAGTAGTTACTTAAAAACATATTATCACAAAAGGCCTTGAC

CAACTTAAACAGAATCAAAATAAACTCTGGGGCAAATAACAATGGAGTTGCTAATCCTCAAAGCAAATGCAATTACC

ACAATCCTCACTGCAGTCACATTTTGTTTTGCTTCTGGTCAAAACATCACTGAAGAATTTTATCAATCAACATGCAG

TGCAGTTAGCAAAGGCTATCTTAGTGCTCTGAGAACTGGTTGGTATACCAGTGTTATAACTATAGAATTAAGTAATA

TCAAGAAAAATAAGTGTAATGGAACAGATGCTAAGGTAAAATTGATAAAACAAGAATTAGATAAATATAAAAATGCT

GTAACAGAATTGCAGTTGCTCATGCAAAGCACACAAGCAACAAACAATCGAGCCAGAAGAGAACTACCAAGGTTTAT

GAATTATACACTCAACAATGCCAAAAAAACCAATGTAACATTAAGCAAGAAAAGGAAAAGAAGATTTCTTGGTTTTT

TGTTAGGTGTTGGATCTGCAATCGCCAGTGGCGTTGCTGTATCTAAGGTCCTGCACCTAGAAGGGGAAGTGAACAAG

ATCAAAAGTGCTCTACTATCCACAAACAAGGCTGTAGTCAGCTTATCAAATGGAGTTAGTGTTTTAACCAGCAAAGT

GTTAGACCTCAAAAACTATATAGATAAACAATTGTTACCTATTGTGAACAAGCAAAGCTGCAGCATATCAAATATAG

AAACTGTGATAGAGTTCCAACAAAAGAACAACAGACTACTAGAGATTACCAGGGAATTTAGTGTTAATGCAGGCGTA

ACTACACCTGTAAGCACTTACATGTTAACTAATAGTGAATTATTGTCATTAATCAATGATATGCCTATAACAAATGA

TCAGAAAAAGTTAATGTCCAACAATGTTCAAATAGTTAGACAGCAAAGTTACTCTATCATGTCCATAATAAAAGAGG

AAGTCTTAGCATATGTAGTACAATTACCACTATATGGTGTTATAGATACACCCTGTTGGAAACTACACACATCCCCT

CTATGTACAACCAACACAAAAGAAGGGTCCAACATCTGTTTAACAAGAACTGACAGAGGATGGTACTGTGACAATGC

AGGATCAGTATCTTTCTTCCCACAAGCTGAAACATGTAAAGTTCAATCAAATCGAGTATTTTGTGACACAATGAACA

GTTTAACATTACCAAGTGAAGTAAATCTCTGCAATGTTGACATATTCAACCCCAAATATGATTGTAAAATTATGACT

TCAAAAACAGATGTAAGCAGCTCCGTTATCACATCTCTAGGAGCCATTGTGTCATGCTATGGCAAAACTAAATGTAC

AGCATCCAATAAAAATCGTGGAATCATAAAGACATTTTCTAACGGGTGCGATTATGTATCAAATAAAGGGGTGGACA

CTGTGTCTGTAGGTAACACATTATATTATGTAAATAAGCAAGAAGGTAAAAGTCTCTATGTAAAAGGTGAACCAATA

ATAAATTTCTATGACCCATTAGTATTCCCCTCTGATGAATTTGATGCATCAATATCTCAAGTCAACGAGAAGATTAA

CCAGAGCCTAGCATTTATTCGTAAATCCGATGAATTATTACATAATGTAAATGCTGGTAAATCCACCACAAATATCA

TGATAACTACTATAATTATAGTGATTATAGTAATATTGTTATCATTAATTGCTGTTGGACTGCTCTTATACTGTAAG

GCCAGAAGCACACCAGTCACACTAAGCAAAGATCAACTGAGTGGTATAAATAATATTGCATTTAGTAACTAAATAAA

AATAGCACCTAATCATGTTCTTACAATGGTTTACTATCTGCTCATAGACAACCCATCTGTCATTGGATTTTCTTAAA

ATCTGAACTTCATCGAAACTCTCATCTATAAACCATCTCACTTACACTATTTAAGTAGATTCCTAGTTTATAGTTAT

ATAAAACACAATTGCATGCCAGATTAACTTACCATCTGTAAAAATGAAAACTGGGGCAAATATGTCACGAAGGAATC

CTTGCAAATTTGAAATTCGAGGTCATTGCTTAAATGGTAAGAGGTGTCATTTTAGTCATAATTATTTTGAATGGCCA

CCCCATGCACTGCTTGTAAGACAAAACTTTATGTTAAACAGAATACTTAAGTCTATGGATAAAAGTATAGATACCTT

ATCAGAAATAAGTGGAGCTGCAGAGTTGGACAGAACAGAAGAGTATGCTCTTGGTGTAGTTGGAGTGCTAGAGAGTT

ATATAGGATCAATAAACAATATAACTAAACAATCAGCATGTGTTGCCATGAGCAAACTCCTCACTGAACTCAATAGT

GATGATATCAAAAAGCTGAGGGACAATGAAGAGCTAAATTCACCCAAGATAAGAGTGTACAATACTGTCATATCATA

TATTGAAAGCAACAGGAAAAACAATAAACAAACTATCCATCTGTTAAAAAGATTGCCAGCAGACGTATTGAAGAAAA

CCATCAAAAACACATTGGATATCCATAAGAGCATAACCATCAACAACCCAAAAGAATCAACTGTTAGTGATACAAAT

-continued

GACCATGCCAAAAATAATGATACTACCTGACAAATATCCTTGTAGTATAACTTCCATACTAATAACAAGTAGATGTA

GAGTTACTATGTATAATCAAAAGAACACACTATATTTCAATCAAAACAACCCAAATAACCATATGTACTCACCGAAT

CAAACATTCAATGAAATCCATTGGACCTCTCAAGAATTGATTGACACAATTCAAAATTTTCTACAACATCTAGGTAT

TATTGAGGATATATATACAATATATATATTAGTGTCATAACACTCAATTCTAACACTCACCACATCGTTACATTATT

AATTCAAACAATTCAAGTTGTGGGACAAAATGGATCCCATTATTAATGGAAATTCTGCTAATGTTTATCTAACCGAT

AGTTATTTAAAAGGTGTTATCTCTTTCTCAGAGTGTAATGCTTTAGGAAGTTACATATTCAATGGTCCTTATCTCAA

AAATGATTATACCAACTTAATTAGTAGACAAAATCCATTAATAGAACACATGAATCTAAAGAAACTAAATATAACAC

AGTCCTTAATATCTAAGTATCATAAAGGTGAAATAAAATTAGAAGAACCTACTTATTTTCAGTCATTACTTATGACA

TACAAGAGTATGACCTCGTCAGAACAGATTGCTACCACTAATTTACTTAAAAAGATAATAAGAAGAGCTATAGAAAT

AAGTGATGTCAAAGTCTATGCTATATTGAATAAACTAGGGCTTAAAGAAAAGGACAAGATTAAATCCAACAATGGAC

AAGATGAAGACAACTCAGTTATTACGACCATAATCAAAGATGATATACTTTCAGCTGTTAAAGATAATCAATCTCAT

CTTAAAGCAGACAAAAATCACTCTACAAAACAAAAAGACACAATCAAAACAACACTCTTGAAGAAATTGATGTGTTC

AATGCAACATCCTCCATCATGGTTAATACATTGGTTTAACTTATACACAAAATTAAACAACATATTAACACAGTATC

GATCAAATGAGGTAAAAAACCATGGGTTTACATTGATAGATAATCAAACTCTTAGTGGATTTCAATTTATTTTGAAC

CAATATGGTTGTATAGTTTATCATAAGGAACTCAAAAGAATTACTGTGACAACCTATAATCAATTCTTGACATGGAA

AGATATTAGCCTTAGTAGATTAAATGTTTGTTTAATTACATGGATTAGTAACTGCTTGAACACATTAAATAAAAGCT

TAGGCTTAAGATGCGGATTCAATAATGTTATCTTGACACAACTATTCCTTTATGGAGATTGTATACTAAAGCTATTT

CACAATGAGGGGTTCTACATAATAAAAGAGGTAGAGGGATTTATTATGTCTCTAATTTTAAATATAACAGAAGAAGA

TCAATTCAGAAAACGATTTTATAATAGTATGCTCAACAACATCACAGATGCTGCTAATAAAGCTCAGAAAAATCTGC

TATCAAGAGTATGTCATACATTATTAGATAAGACAGTGTCCGATAATATAATAAATGGCAGATGGATAATTCTATTA

AGTAAGTTCCTTAAATTAATTAAGCTTGCAGGTGACAATAACCTTAACAATCTGAGTGAACTATATTTTTTGTTCAG

AATATTTGGACACCCAATGGTAGATGAAAGACAAGCCATGGATGCTGTTAAAATTAATTGCAATGAGACCAAATTTT

ACTTGTTAAGCAGTCTGAGTATGTTAAGAGGTGCCTTTATATATAGAATTATAAAAGGGTTTGTAAATAATTACAAC

AGATGGCCTACTTTAAGAAATGCTATTGTTTTACCCTTAAGATGGTTAACTTACTATAAACTAAACACTTATCCTTC

TTTGTTGGAACTTACAGAAAGAGATTTGATTGTGTTATCAGGACTACGTTTCTATCGTGAGTTTCGGTTGCCTAAAA

AAGTGGATCTTGAAATGATTATAAATGATAAAGCTATATCACCTCCTAAAAATTTGATATGGACTAGTTTCCCTAGA

AATTACATGCCATCACACATACAAAACTATATAGAACATGAAAAATTAAAATTTTCCGAGAGTGATAAATCAAGAAG

AGTATTAGAGTATTATTTAAGAGATAACAAATTCAATGAATGTGATTTATACAACTGTGTAGTTAATCAAAGTTATC

TCAACAACCCTAATCATGTGGTATCATTGACAGGCAAAGAAAGAGAACTCAGTGTAGGTAGAATGTTTGCAATGCAA

CCGGGAATGTTCAGACAGGTTCAAATATTGGCAGAGAAAATGATAGCTGAAAACATTTTACAATTCTTTCCTGAAAG

TCTTACAAGATATGGTGATCTAGAACTACAAAAAATATTAGAACTGAAAGCAGGAATAAGTAACAAATCAAATCGCT

ACAATGATAATTACAACAATTACATTAGTAAGTGCTCTATCATCACAGATCTCAGCAAATTCAATCAAGCATTTCGA

TATGAAACGTCATGTATTTGTAGTGATGTGCTGGATGAACTGCATGGTGTACAATCTCTATTTTCCTGGTTACATTT

AACTATTCCTCATGTCACAATAATATGCACATATAGGCATGCACCCCCCTATATAGGAGATCATATTGTAGATCTTA

ACAATGTAGATGAACAAAGTGGATTATATAGATATCACATGGGTGGCATCGAAGGGTGGTGTCAAAAACTATGGACC

ATAGAAGCTATATCACTATTGGATCTAATATCTCTCAAAGGGAAATTCTCAATTACTGCTTTAATTAATGGTGACAA

TCAATCAATAGATATAAGCAAACCAATCAGACTCATGGAAGGTCAAACTCATGCTCAAGCAGATTATTTGCTAGCAT

TAAATAGCCTTAAATTACTGTATAAAGAGTATGCAGGCATAGGCCACAAATTAAAAGGAACTGAGACTTATATATCA

CGAGATATGCAATTTATGAGTAAAACAATTCAACATAACGGTGTATATTACCCAGCTAGTATAAAGAAAGTCCTAAG

AGTGGGACCGTGGATAAACACTATACTTGATGATTTCAAAGTGAGTCTAGAATCTATAGGTAGTTTGACACAAGAAT

TAGAATATAGAGGTGAAAGTCTATTATGCAGTTTAATATTTAGAAATGTATGGTTATATAATCAGATTGCTCTACAA

-continued

TTAAAAAATCATGCATTATGTAACAATAAACTATATTTGGACATATTAAAGGTTCTGAAACACTTAAAAACCTTTTT

TAATCTTGATAATATTGATACAGCATTAACATTGTATATGAATTTACCCATGTTATTTGGTGGTGGTGATCCCAACT

TGTTATATCGAAGTTTCTATAGAAGAACTCCTGACTTCCTCACAGAGGCTATAGTTCACTCTGTGTTCATACTTAGT

TATTATACAAACCATGACTTAAAAGATAAACTTCAAGATCTGTCAGATGATAGATTGAATAAGTTCTTAACATGCAT

AATCACGTTTGACAAAAACCCTAATGCTGAATTCGTAACATTGATGAGAGATCCTCAAGCTTTAGGGTCTGAGAGAC

AAGCTAAAATTACTAGCGAAATCAATAGACTGGCAGTTACAGAGGTTTTGAGTACAGCTCCAAACAAAATATTCTCC

AAAAGTGCACAACATTATACTACTACAGAGATAGATCTAAATGATATTATGCAAAATATAGAACCTACATATCCTCA

TGGGCTAAGAGTTGTTTATGAAAGTTTACCCTTTTATAAAGCAGAGAAAATAGTAAATCTTATATCAGGTACAAAAT

CTATAACTAACATACTGGAAAAAACTTCTGCCATAGACTTAACAGATATTGATAGAGCCACTGAGATGATGAGGAAA

AACATAACTTTGCTTATAAGGATACTTCCATTGGATTGTAACAGAGATAAAAGAGAGATATTGAGTATGGAAAACCT

AAGTATTACTGAATTAAGCAAATATGTTAGGGAAAGATCTTGGTCTTTATCCAATATAGTTGGTGTTACATCACCCA

GTATCATGTATACAATGGACATCAAATATACTACAAGCACTATATCTAGTGGCATAATTATAGAGAAATATAATGTT

AACAGTTTAACACGTGGTGAGAGAGGACCCACTAAACCATGGGTTGGTTCATCTACACAAGAGAAAAAAACAATGCC

AGTTTATAATAGACAAGTCTTAACCAAAAAACAGAGAGATCAAATAGATCTATTAGCAAAATTGGATTGGGTGTATG

CATCTATAGATAACAAGGATGAATTCATGGAAGAACTCAGCATAGGAACCCTTGGGTTAACATATGAAAAGGCCAAG

AAATTATTTCCACAATATTTAAGTGTCAATTATTTGCATCGCCTTACAGTCAGTAGTAGACCATGTGAATTCCCTGC

ATCAATACCAGCTTATAGAACAACAAATTATCACTTTGACACTAGCCCTATTAATCGCATATTAACAGAAAAGTATG

GTGATGAAGATATTGACATAGTATTCCAAAACTGTATAAGCTTTGGCCTTAGTTTAATGTCAGTAGTAGAACAATTT

ACTAATGTATGTCCTAACAGAATTATTCTCATACCTAAGCTTAATGAGATACATTTGATGAAACCTCCCATATTCAC

AGGTGATGTTGATATTCACAAGTTAAAACAAGTGATACAAAAACAGCATATGTTTTTACCAGACAAAATAAGTTTGA

CTCAATATGTGGAATTATTCTTAAGTAATAAAACACTCAAATCTGGATCTCATGTTAATTCTAATTTAATATTGGCA

CATAAAATATCTGACTATTTTCATAATACTTACATTTTAAGTACTAATTTAGCTGGACATTGGATTCTGATTATACA

ACTTATGAAAGATTCTAAAGGTATTTTTGAAAAAGATTGGGGAGAGGGATATATAACTGATCATATGTTTATTAATT

TGAAAGTTTTCTTCAATGCTTATAAGACCTATCTCTTGTGTTTTCATAAAGGTTATGGCAAAGCAAAGCTGGAGTGT

GATATGAACACTTCAGATCTTCTATGTGTATTGGAATTAATAGACAGTAGTTATTGGAAGTCTATGTCTAAGGTATT

TTTAGAACAAAAAGTTATCAAATACATTCTTAGCCAAGATGCAAGTTTACATAGAGTAAAAGGATGTCATAGCTTCA

AATTATGGTTTCTTAAACGTCTTAATGTAGCAGAATTCACAGTTTGCCCTTGGGTTGTTAACATAGATTATCATCCA

ACACATATGAAAGCAATATTAACTTATATAGATCTTGTTAGAATGGGATTGATAAATATAGATAGAATACACATTAA

AAATAAACACAAATTCAATGATGAATTTTATACTTCTAATCTCTTCTACATTAATTATAACTTCTCAGATAATACTC

ATCTATTAACTAAACATATAAGGATTGCTAATTCTGAATTAGAAAATAATTACAACAAATTATATCATCCTACACCA

GAAACCCTAGAGAATATACTAGCCAATCCGATTAAAAGTAATGACAAAAAGACACTGAATGACTATTGTATAGGTAA

AAATGTTGACTCAATAATGTTACCATTGTTATCTAATAAGAAGCTTATTAAATCGTCTGCAATGATTAGAACCAATT

ACAGCAAACAAGATTTGTATAATTTATTCCCTATGGTTGTGATTGATAGAATTATAGATCATTCAGGCAATACAGCC

AAATCCAACCAACTTTACACTACTACTTCCCACCAAATATCCTTAGTGCACAATAGCACATCACTTTACTGCATGCT

TCCTTGGCATCATATTAATAGATTCAATTTTGTATTTAGTTCTACAGGTTGTAAAATTAGTATAGAGTATATTTTAA

AAGATCTTAAAATTAAAGATCCCAATTGTATAGCATTCATAGGTGAAGGAGCAGGGAATTTATTATTGCGTACAGTA

GTGGAACTTCATCCTGACATAAGATATATTTACAGAAGTCTGAAAGATTGCAATGATCATAGTTTACCTATTGAGTT

TTTAAGGCTGTACAATGGACATATCAACATTGATTATGGTGAAAATTTGACCATTCCTGCTACAGATGCAACCAACA

ACATTCATTGGTCTTATTTACATATAAAGTTTGCTGAACCTATCAGTCTTTTTGTCTGTGATGCCGAATTGTCTGTA

ACAGTCAACTGGAGTAAAATTATAATAGAATGGAGCAAGCATGTAAGAAAGTGCAAGTACTGTTCCTCAGTTAATAA

-continued

ATGTATGTTAATAGTAAAATATCATGCTCAAGATGATATTGATTTCAAATTAGACAATATAACTATATTAAAAACTT

ATGTATGCTTAGGCAGTAAGTTAAAGGGATCGGAGGTTTACTTAGTCCTTACAATAGGTCCTGCGAATATATTCCCA

GTATTTAATGTAGTACAAAATGCTAAATTGATACTATCAAGAACCAAAAATTTCATCATGCCTAAGAAAGCTGATAA

AGAGTCTATTGATGCAAATATTAAAAGTTTGATACCCTTTCTTTGTTACCCTATAACAAAAAAAGGAATTAATACTG

CATTGTCAAAACTAAAGAGTGTTGTTAGTGGAGATATACTATCATATTCTATAGCTGGACGTAATGAAGTTTTCAGC

AATAAACTTATAAATCATAAGCATATGAACATCTTAAAATGGTTCAATCATGTTTTAAATTTCAGATCAACAGAACT

AAACTATAACCATTTATATATGGTAGAATCTACATATCCTTACCTAAGTGAATTGTTAAACAGCTTGACAACCAATG

AACTTAAAAAACTGATTAAAATCACAGGTAGTCTGTTATACAACTTTCATAATGAATAATGAATAAAGATCTTATAA

TAAAAATTCCCATAGCTATACACTAACACTGTATTCAATTATAGTTATAAAAATTAAAAATggtaccATGGGGCAAA

TAAGAATTTGATAAGTACCACTTAAATTTAACTCCCTTGGTTAGAGATGGGCAGCAATTCATTGAGTATGATAAAAG

TTAGATTACAAAATTTGTTTGACAATGATGAAGTAGCATTGTTAAAAATAACATGCTATACTGATAAATTAATACAT

TTAACTAATGCTTTGGCTAAGGCAGTGATACATACAATCAAATTGAATGGCATTGTGTTTGTGCATGTTATTACAAG

TAGTGATATTTGCCCTAATAATAATATTGTAGTAAAATCCAATTTCACAACAATGCCAGTACTACAAAATGGAGGTT

ATATATGGGAAATGATGGAATTAACACATTGCTCTCAACCTAATGGTCTACTAGATGACAATTGTGAAATTAAATTC

TCCAAAAAACTAAGTGATTCAACAATGACCAATTATATGAATCAATTATCTGAATTACTTGGATTTGATCTTAATCC

ATAAATTATAATTAATATCAACTAGCAAATCAATGTCACTAACACCATTAGTTAATATAAAACTTAACAGAAGACAA

AAATGGGGCAAATAAATCAATTCAGCCAACCCAACCATGGACACAACCCACAATGATAATACACCACAAAGACTGAT

GATCACAGACATGAGACCGTTGTCACTTGAGACCATAATAACATCACTAACCAGAGACATCATAACACACAAATTTA

TATACTTGATAAATCATGAATGCATAGTGAGAAAACTTGATGAAAGACAGGCCACATTTACATTCCTGGTCAACTAT

GAAATGAAACTATTACACAAAGTAGGAAGCACTAAATATAAAAAATATACTGAATACAACACAAAATATGGCACTTT

CCCTATGCCAATATTCATCAATCATGATGGGTTCTTAGAATGCATTGGCATTAAGCCTACAAAGCATACTCCCATAA

TATACAAGTATGATCTCAATCCATAAATTTCAACACAATATTCACACAATCTAAAACAACAACTCTATGCATAACTA

TACTCCATAGTCCAGATGGAGCCTGAAAATTATAGTAATTTAAAACTTAAGGAGAGATATAAGATAGAAGATggtac cATTTTTTAAATAACTTTTAGTGAACTAATCCTAAAGTTATCATTTTAATCTTGGAGGAATAAATTTAAACCCTAAT

CTAATTGGTTTATATGTGTATTAACTAAATTACGAGATATTAGTTTTTGACACTTTTTTTCTCGT

Antigenomic cDNA sequence of RSV 6120/NS12FM2/ΔNS2GFP (SEQ ID NO: 5)
ACGGGAAAAAATGCGTACAACAAACTTGCATAAACCAAAAAAATGGGGCAAATAAGAATTTGATAAGTACCACTTAA

ATTTAACTCCCTTGGTTAGAGATGGCTCTTAGCAAAGTCAAGTTGAATGATACACTCAACAAAGATCAACTTCTGTC

ATCCAGCAAATACACCATCCAACGGAGCACAGGAGATAGTATTGATACTCCTAATTATGATGTGCAGAAACACATCA

ATAAGTTATGTGGCATGTTATTAATCACAGAAGATGCTAATCATAAATTCACTGGGTTAATAGGTATGTTATATGCG

ATGTCTAGGTTAGGAAGAGAAGACACCATAAAAATACTCAGAGATGCGGGATATCATGTAAAAGCAAATGGAGTAGA

TGTAACAACACATCGTCAAGACATTAATGGAAAAGAAATGAAATTTGAAGTGTTAACATTGGCAAGCTTAACAACTG

AAATTCAAATCAACATTGAGATAGAATCTAGAAAATCCTACAAAAAAATGCTAAAAGAAATGGGAGAGGTAGCTCCA

GAATACAGGCATGACTCTCCTGATTGTGGGATGATAATATTATGTATAGCAGCATTAGTAATAACTAAATTAGCAGC

AGGGGACAGATCTGGTCTTACAGCCGTGATTAGGAGAGCTAATAATGTCCTAAAAAATGAAATGAAACGTTACAAAG

GCTTACTACCCAAGGACATAGCCAACAGCTTCTATGAAGTGTTTGAAAAACATCCCCACTTTATAGATGTTTTTGTT

CATTTTGGTATAGCACAATCTTCTACCAGAGGTGGCAGTAGAGTTGAAGGGATTTTTGCAGGATTGTTTATGAATGC

CTATGGTGCAGGGCAAGTGATGTTACGGTGGGGAGTCTTAGCAAAATCAGTTAAAAATATTATGTTAGGACATGCTA

GTGTGCAAGCAGAAATGGAACAAGTTGTTGAGGTTTATGAATATGCCCAAAAATTGGGTGGTGAAGCAGGATTCTAC

CATATATTGAACAACCCAAAAGCATCATTATTATCTTTGACTCAATTTCCTCACTTCTCCAGTGTAGTATTAGGCAA

TGCTGCTGGCCTAGGCATAATGGGAGAGTACAGAGGTACACCGAGGAATCAAGATCTATATGATGCAGCAAAGGCAT

-continued

ATGCTGAACAACTCAAAGAAAATGGTGTGATTAACTACAGTGTACTAGACTTGACAGCAGAAGAACTAGAGGCTATC

AAACATCAGCTTAATCCAAAAGATAATGATGTAGAGCTTTGAGTTAATAAAAAATGGGGCAAATAAATCATCATGGA

AAAGTTTGCTCCTGAATTCCATGGAGAAGATGCAAACAACAGGGCTACTAAATTCCTAGAATCAATAAAGGGCAAAT

TCACATCACCCAAAGATCCCAAGAAAAAAGATAGTATCATATCTGTCAACTCAATAGATATAGAAGTAACCAAAGAA

AGCCCTATAACATCAAATTCAACTATTATCAACCCAACAAATGAGACAGATGATACTGCAGGGAACAAGCCCAATTA

TCAAAGAAAACCTCTAGTAAGTTTCAAAGAAGACCCTACACCAAGTGATAATCCCTTTTCTAAACTATACAAAGAAA

CCATAGAAACATTTGATAACAATGAAGAAGAATCCAGCTATTCATACGAAGAAATAAATGATCAGACAAACGATAAT

ATAACAGCAAGATTAGATAGGATTGATGAAAAATTAAGTGAAATACTAGGAATGCTTCACACATTAGTAGTGGCAAG

TGCAGGACCTACATCTGCTCGGGATGGTATAAGAGATGCCATGGTTGGTTTAAGAGAAGAAATGATAGAAAAAATCA

GAACTGAAGCATTAATGACCAATGACAGATTAGAAGCTATGGCAAGACTCAGGAATGAGGAAAGTGAAAAGATGGCA

AAAGACACATCAGATGAAGTGTCTCTCAATCCAACATCAGAGAAATTGAACAACCTATTGGAAGGGAATGATAGTGA

CAATGATCTATCACTTGAAGATTTCTGATTAGTTACCAATCTTCACATCAACACACAATACCAACAGAAGACCAACA

AACTAACCAACCCAATCATCCAACCAAACATCCATCCGCCAATCAGCCAAACAGCCAACAAAACAACCAGCCAATCC

AAAACTAACCACCCGGAAAAAATCTATAATATAGTTACAAAAAAAGGAATCGATGGGGCAAATACAAGTATGGTGAG

CAAGGGCGAGGAGCTGTTCACCGGGGTGGTGCCCATCCTGGTCGAGCTGGACGGCGACGTAAACGGCCACAAGTTCA

GCGTGTCCGGCGAGGGCGAGGGCGATGCCACCTACGGCAAGCTGACCCTGAAGTTCATCTGCACCACCGGCAAGCTG

CCCGTGCCCTGGCCCACCCTCGTGACCACCCTGACCTACGGCGTGCAGTGCTTCAGCCGCTACCCCGACCACATGAA

GCAGCACGACTTCTTCAAGTCCGCCATGCCCGAAGGCTACGTCCAGGAGCGCACCATCTTCTTCAAGGACGACGGCA

ACTACAAGACCCGCGCCGAGGTGAAGTTCGAGGGCGACACCCTGGTGAACCGCATCGAGCTGAAGGGCATCGACTTC

AAGGAGGACGGCAACATCCTGGGGCACAAGCTGGAGTACAACTACAACAGCCACAACGTCTATATCATGGCCGACAA

GCAGAAGAACGGCATCAAGGTGAACTTCAAGATCCGCCACAACATCGAGGACGGCAGCGTGCAGCTCGCCGACCACT

ACCAGCAGAACACCCCCATCGGCGACGGCCCCGTGCTGCTGCCCGACAACCACTACCTGAGCACCCAGTCCGCCCTG

AGCAAAGACCCCAACGAGAAGCGCGATCACATGGTCCTGCTGGAGTTCGTGACCGCCGCCGGGATCACTCTCGGCAT

GGACGAGCTGTACAAGTAAAAGTAGTTACTTAAAAAGTCGACGGTGGGGCAAATATGGAAACATACGTGAACAAGCT

TCACGAAGGCTCCACATACACAGCTGCTGTTCAATACAATGTCTTAGAAAAAGACGATGACCCTGCATCACTTACAA

TATGGGTGCCCATGTTCCAATCATCTATGCCAGCAGATTTACTTATAAAAGAACTAGCTAATGTCAACATACTAGTG

AAACAAATATCCACACCCAAGGGACCTTCACTAAGAGTCATGATAAACTCAAGAAGTGCAGTGCTAGCACAAATGCC

CAGCAAATTTACCATATGCGCTAATGTGTCCTTGGATGAAAGAAGCAAACTAGCATATGATGTAACCACACCCTGTG

AAATCAAGGCATGTAGTCTAACATGCCTAAAATCAAAAAATATGTTGACTACAGTTAAAGATCTCACTATGAAGACA

CTCAACCCTACACATGATATTATTGCTTTATGTGAATTTGAAAACATAGTAACATCAAAAAAAGTCATAATACCAAC

ATACCTAAGATCCATCAGTGTCAGAAATAAAGATCTGAACACACTTGAAAATATAACAACCACTGAATTCAAAAATG

CTATCACAAATGCAAAAATCATCCCTTACTCAGGATTACTATTAGTCATCACAGTGACTGACAACAAAGGAGCATTC

AAATACATAAAGCCACAAAGTCAATTCATAGTAGATCTTGGAGCTTACCTAGAAAAAGAAAGTATATATTATGTTAC

CACAAATTGGAAGCACACAGCTACACGATTTGCAATCAAACCCATGGAAGATTAACCTTTTTCCTCTACATCAGTGT

GTTAATTCATACAAACTTTCTACCTACATTCTTCACTTCACCATCACAATCACAAACACTCTGTGGTTCAACCAATC

AAACAAAACTTATCTGAAGTCCCAGATCATCCCAAGTCATTGTTTATCAGATCTAGTACTCAAATAAGTTAATAAAA

AATATACACATGGGGCAAATAATCATTGGAGGAAATCCAACTAATCACAATATCTGTTAACATAGACAAGTCCACAC

ACCATACAGAATCAACCAATGGAAAATACATCCATAACAATAGAATTCTCAAGCAAATTCTGGCCTTACTTTACACT

AATACACATGATCACAACAATAATCTCTTTGCTAATCATAATCTCCATCATGATTGCAATACTAAACAAACTTTGTG

AATATAACGTATTCCATAACAAAACCTTTGAGTTACCAAGAGCTCGAGTTAATACTTGATAAAGTAGTTAATTAAAA

ATAGTCATAACAATGAACTAGGATATCAAGACTAACAATAACATTGGGGCAAATGCAAACATGTCCAAAAACAAGGA

-continued

CCAACGCACCGCTAAGACATTAGAAAGGACCTGGGACACTCTCAATCATTTATTATTCATATCATCGTGCTTATATA

AGTTAAATCTTAAATCTGTAGCACAAATCACATTATCCATTCTGGCAATGATAATCTCAACTTCACTTATAATTGCA

GCCATCATATTCATAGCCTCGGCAAACCACAAAGTCACACCAACAACTGCAATCATACAAGATGCAACAAGCCAGAT

CAAGAACACAACCCCAACATACCTCACCCAGAATCCTCAGCTTGGAATCAGTCCCTCTAATCCGTCTGAAATTACAT

CACAAATCACCACCATACTAGCTTCAACAACACCAGGAGTCAAGTCAACCCTGCAATCCACAACAGTCAAGACCAAA

AACACAACAACAACTCAAACACAACCCAGCAAGCCCACCACAAAACAACGCCAAAACAAACCACCAAGCAAACCCAA

TAATGATTTTCACTTTGAAGTGTTCAACTTTGTACCCTGCAGCATATGCAGCAACAATCCAACCTGCTGGGCTATCT

GCAAAAGAATACCAAACAAAAAACCAGGAAAGAAAACCACTACCAAGCCCACAAAAAAACCAACCCTCAAGACAACC

AAAAAAGATCCCAAACCTCAAACCACTAAATCAAAGGAAGTACCCACCACCAAGCCCACAGAAGAGCCAACCATCAA

CACCACCAAAACAAACATCATAACTACACTACTCACCTCCAACACCACAGGAAATCCAGAACTCACAAGTCAAATGG

AAACCTTCCACTCAACTTCCTCCGAAGGCAATCCAAGCCCTTCTCAAGTCTCTACAACATCCGAGTACCCATCACAA

CCTTCATCTCCACCCAACACACCACGCCAGTAGTTACTTAAAAACATATTATCACAAAAGGCCTTGACCAACTTAAA

CAGAATCAAAATAAACTCTGGGGCAAATAACAATGGAGTTGCTAATCCTCAAAGCAAATGCAATTACCACAATCCTC

ACTGCAGTCACATTTTGTTTTGCTTCTGGTCAAAACATCACTGAAGAATTTTATCAATCAACATGCAGTGCAGTTAG

CAAAGGCTATCTTAGTGCTCTGAGAACTGGTTGGTATACCAGTGTTATAACTATAGAATTAAGTAATATCAAGAAAA

ATAAGTGTAATGGAACAGATGCTAAGGTAAAATTGATAAAACAAGAATTAGATAAATATAAAAATGCTGTAACAGAA

TTGCAGTTGCTCATGCAAAGCACACAAGCAACAAACAATCGAGCCAGAAGAGAACTACCAAGGTTTATGAATTATAC

ACTCAACAATGCCAAAAAAACCAATGTAACATTAAGCAAGAAAAGGAAAAGAAGATTTCTTGGTTTTTTGTTAGGTG

TTGGATCTGCAATCGCCAGTGGCGTTGCTGTATCTAAGGTCCTGCACCTAGAAGGGGAAGTGAACAAGATCAAAAGT

GCTCTACTATCCACAAACAAGGCTGTAGTCAGCTTATCAAATGGAGTTAGTGTTTTAACCAGCAAAGTGTTAGACCT

CAAAAACTATATAGATAAACAATTGTTACCTATTGTGAACAAGCAAAGCTGCAGCATATCAAATATAGAAACTGTGA

TAGAGTTCCAACAAAAGAACAACAGACTACTAGAGATTACCAGGGAATTTAGTGTTAATGCAGGCGTAACTACACCT

GTAAGCACTTACATGTTAACTAATAGTGAATTATTGTCATTAATCAATGATATGCCTATAACAAATGATCAGAAAAA

GTTAATGTCCAACAATGTTCAAATAGTTAGACAGCAAAGTTACTCTATCATGTCCATAATAAAAGAGGAAGTCTTAG

CATATGTAGTACAATTACCACTATATGGTGTTATAGATACACCCTGTTGGAAACTACACACATCCCCTCTATGTACA

ACCAACACAAAAGAAGGGTCCAACATCTGTTTAACAAGAACTGACAGAGGATGGTACTGTGACAATGCAGGATCAGT

ATCTTTCTTCCCACAAGCTGAAACATGTAAAGTTCAATCAAATCGAGTATTTTGTGACACAATGAACAGTTTAACAT

TACCAAGTGAAGTAAATCTCTGCAATGTTGACATATTCAACCCCAAATATGATTGTAAAATTATGACTTCAAAAACA

GATGTAAGCAGCTCCGTTATCACATCTCTAGGAGCCATTGTGTCATGCTATGGCAAAACTAAATGTACAGCATCCAA

TAAAAATCGTGGAATCATAAAGACATTTTCTAACGGGTGCGATTATGTATCAAATAAAGGGGTGGACACTGTGTCTG

TAGGTAACACATTATATTATGTAAATAAGCAAGAAGGTAAAAGTCTCTATGTAAAAGGTGAACCAATAATAAATTTC

TATGACCCATTAGTATTCCCCTCTGATGAATTTGATGCATCAATATCTCAAGTCAACGAGAAGATTAACCAGAGCCT

AGCATTTATTCGTAAATCCGATGAATTATTACATAATGTAAATGCTGGTAAATCCACCACAAATATCATGATAACTA

CTATAATTATAGTGATTATAGTAATATTGTTATCATTAATTGCTGTTGGACTGCTCTTATACTGTAAGGCCAGAAGC

ACACCAGTCACACTAAGCAAAGATCAACTGAGTGGTATAAATAATATTGCATTTAGTAACTAAATAAAAATAGCACC

TAATCATGTTCTTACAATGGTTTACTATCTGCTCATAGACAACCCATCTGTCATTGGATTTTCTTAAAATCTGAACT

TCATCGAAACTCTCATCTATAAACCATCTCACTTACACTATTTAAGTAGATTCCTAGTTTATAGTTATATAAAACAC

AATTGCATGCCAGGTACCATGGGGCAAATAAGAATTTGATAAGTACCACTTAAATTTAACTCCCTTGGTTAGAGATG

GGCAGCAATTCATTGAGTATGATAAAAGTTAGATTACAAAATTTGTTTGACAATGATGAAGTAGCATTGTTAAAAAT

AACATGCTATACTGATAAATTAATACATTTAACTAATGCTTTGGCTAAGGCAGTGATACATACAATCAAATTGAATG

-continued

GCATTGTGTTTGTGCATGTTATTACAAGTAGTGATATTTGCCCTAATAATAATATTGTAGTAAAATCCAATTTCACA

ACAATGCCAGTACTACAAAATGGAGGTTATATATGGGAAATGATGGAATTAACACATTGCTCTCAACCTAATGGTCT

ACTAGATGACAATTGTGAAATTAAATTCTCCAAAAAACTAAGTGATTCAACAATGACCAATTATATGAATCAATTAT

CTGAATTACTTGGATTTGATCTTAATCCATAAATTATAATTAATATCAACTAGCAAATCAATGTCACTAACACCATT

AGTTAATATAAAACTTAACAGAAGACAAAAATGGGGCAAATATGTCACGAAGGAATCCTTGCAAATTTGAAATTCGA

GGTCATTGCTTAAATGGTAAGAGGTGTCATTTTAGTCATAATTATTTTGAATGGCCACCCCATGCACTGCTTGTAAG

ACAAAACTTTATGTTAAACAGAATACTTAAGTCTATGGATAAAAGTATAGATACCTTATCAGAAATAAGTGGAGCTG

CAGAGTTGGACAGAACAGAAGAGTATGCTCTTGGTGTAGTTGGAGTGCTAGAGAGTTATATAGGATCAATAAACAAT

ATAACTAAACAATCAGCATGTGTTGCCATGAGCAAACTCCTCACTGAACTCAATAGTGATGATATCAAAAAGCTGAG

GGACAATGAAGAGCTAAATTCACCCAAGATAAGAGTGTACAATACTGTCATATCATATATTGAAAGCAACAGGAAAA

ACAATAAACAAACTATCCATCTGTTAAAAAGATTGCCAGCAGACGTATTGAAGAAAACCATCAAAAACACATTGGAT

ATCCATAAGAGCATAACCATCAACAACCCAAAAGAATCAACTGTTAGTGATACAAATGACCATGCCAAAAATAATGA

TACTACCTGACAAATATCCTTGTAGTATAACTTCCATACTAATAACAAGTAGATGTAGAGTTACTATGTATAATCAA

AAGAACACACTATATTTCAATCAAAACAACCCAAATAACCATATGTACTCACCGAATCAAACATTCAATGAAATCCA

TTGGACCTCTCAAGAATTGATTGACACAATTCAAAATTTTCTACAACATCTAGGTATTATTGAGGATATATATACAA

TATATATATTAGTGTCATAACACTCAATTCTAACACTCACCACATCGTTACATTATTAATTCAAACAATTCAAGTTG

TGGGACAAAATGGATCCCATTATTAATGGAAATTCTGCTAATGTTTATCTAACCGATAGTTATTTAAAAGGTGTTAT

CTCTTTCTCAGAGTGTAATGCTTTAGGAAGTTACATATTCAATGGTCCTTATCTCAAAAATGATTATACCAACTTAA

TTAGTAGACAAAATCCATTAATAGAACACATGAATCTAAAGAAACTAAATATAACACAGTCCTTAATATCTAAGTAT

CATAAAGGTGAAATAAAATTAGAAGAACCTACTTATTTTCAGTCATTACTTATGACATACAAGAGTATGACCTCGTC

AGAACAGATTGCTACCACTAATTTACTTAAAAAGATAATAAGAAGAGCTATAGAAATAAGTGATGTCAAAGTCTATG

CTATATTGAATAAACTAGGGCTTAAAGAAAAGGACAAGATTAAATCCAACAATGGACAAGATGAAGACAACTCAGTT

ATTACGACCATAATCAAAGATGATATACTTTCAGCTGTTAAAGATAATCAATCTCATCTTAAAGCAGACAAAAATCA

CTCTACAAAACAAAAAGACACAATCAAAACAACACTCTTGAAGAAATTGATGTGTTCAATGCAACATCCTCCATCAT

GGTTAATACATTGGTTTAACTTATACACAAAATTAAACAACATATTAACACAGTATCGATCAAATGAGGTAAAAAAC

CATGGGTTTACATTGATAGATAATCAAACTCTTAGTGGATTTCAATTTATTTTGAACCAATATGGTTGTATAGTTTA

TCATAAGGAACTCAAAAGAATTACTGTGACAACCTATAATCAATTCTTGACATGGAAAGATATTAGCCTTAGTAGAT

TAAATGTTTGTTTAATTACATGGATTAGTAACTGCTTGAACACATTAAATAAAAGCTTAGGCTTAAGATGCGGATTC

AATAATGTTATCTTGACACAACTATTCCTTTATGGAGATTGTATACTAAAGCTATTTCACAATGAGGGGTTCTACAT

AATAAAAGAGGTAGAGGGATTTATTATGTCTCTAATTTTAAATATAACAGAAGAAGATCAATTCAGAAAACGATTTT

ATAATAGTATGCTCAACAACATCACAGATGCTGCTAATAAAGCTCAGAAAAATCTGCTATCAAGAGTATGTCATACA

TTATTAGATAAGACAGTGTCCGATAATATAATAAATGGCAGATGGATAATTCTATTAAGTAAGTTCCTTAAATTAAT

TAAGCTTGCAGGTGACAATAACCTTAACAATCTGAGTGAACTATATTTTTTGTTCAGAATATTTGGACACCCAATGG

TAGATGAAAGACAAGCCATGGATGCTGTTAAAATTAATTGCAATGAGACCAAATTTTACTTGTTAAGCAGTCTGAGT

ATGTTAAGAGGTGCCTTTATATATAGAATTATAAAAGGGTTTGTAAATAATTACAACAGATGGCCTACTTTAAGAAA

TGCTATTGTTTTACCCTTAAGATGGTTAACTTACTATAAACTAAACACTTATCCTTCTTTGTTGGAACTTACAGAAA

GAGATTTGATTGTGTTATCAGGACTACGTTTCTATCGTGAGTTTCGGTTGCCTAAAAAAGTGGATCTTGAAATGATT

ATAAATGATAAAGCTATATCACCTCCTAAAAATTTGATATGGACTAGTTTCCCTAGAAATTACATGCCATCACACAT

ACAAAACTATATAGAACATGAAAAATTAAAATTTTCCGAGAGTGATAAATCAAGAAGAGTATTAGAGTATTATTTAA

GAGATAACAAATTCAATGAATGTGATTTATACAACTGTGTAGTTAATCAAAGTTATCTCAACAACCCTAATCATGTG

GTATCATTGACAGGCAAAGAAAGAGAACTCAGTGTAGGTAGAATGTTTGCAATGCAACCGGGAATGTTCAGACAGGT

-continued

TCAAATATTGGCAGAGAAAATGATAGCTGAAAACATTTTACAATTCTTTCCTGAAAGTCTTACAAGATATGGTGATC

TAGAACTACAAAAAATATTAGAACTGAAAGCAGGAATAAGTAACAAATCAAATCGCTACAATGATAATTACAACAAT

TACATTAGTAAGTGCTCTATCATCACAGATCTCAGCAAATTCAATCAAGCATTTCGATATGAAACGTCATGTATTTG

TAGTGATGTGCTGGATGAACTGCATGGTGTACAATCTCTATTTTCCTGGTTACATTTAACTATTCCTCATGTCACAA

TAATATGCACATATAGGCATGCACCCCCCTATATAGGAGATCATATTGTAGATCTTAACAATGTAGATGAACAAAGT

GGATTATATAGATATCACATGGGTGGCATCGAAGGGTGGTGTCAAAAACTATGGACCATAGAAGCTATATCACTATT

GGATCTAATATCTCTCAAAGGGAAATTCTCAATTACTGCTTTAATTAATGGTGACAATCAATCAATAGATATAAGCA

AACCAATCAGACTCATGGAAGGTCAAACTCATGCTCAAGCAGATTATTTGCTAGCATTAAATAGCCTTAAATTACTG

TATAAAGAGTATGCAGGCATAGGCCACAAATTAAAAGGAACTGAGACTTATATATCACGAGATATGCAATTTATGAG

TAAAACAATTCAACATAACGGTGTATATTACCCAGCTAGTATAAAGAAAGTCCTAAGAGTGGGACCGTGGATAAACA

CTATACTTGATGATTTCAAAGTGAGTCTAGAATCTATAGGTAGTTTGACACAAGAATTAGAATATAGAGGTGAAAGT

CTATTATGCAGTTTAATATTTAGAAATGTATGGTTATATAATCAGATTGCTCTACAATTAAAAAATCATGCATTATG

TAACAATAAACTATATTTGGACATATTAAAGGTTCTGAAACACTTAAAAACCTTTTTAATCTTGATAATATTGATA

CAGCATTAACATTGTATATGAATTTACCCATGTTATTTGGTGGTGGTGATCCCAACTTGTTATATCGAAGTTTCTAT

AGAAGAACTCCTGACTTCCTCACAGAGGCTATAGTTCACTCTGTGTTCATACTTAGTTATTATACAAACCATGACTT

AAAAGATAAACTTCAAGATCTGTCAGATGATAGATTGAATAAGTTCTTAACATGCATAATCACGTTTGACAAAAACC

CTAATGCTGAATTCGTAACATTGATGAGAGATCCTCAAGCTTTAGGGTCTGAGAGACAAGCTAAAATTACTAGCGAA

ATCAATAGACTGGCAGTTACAGAGGTTTTGAGTACAGCTCCAAACAAAATATTCTCCAAAAGTGCACAACATTATAC

TACTACAGAGATAGATCTAAATGATATTATGCAAAATATAGAACCTACATATCCTCATGGGCTAAGAGTTGTTTATG

AAAGTTTACCCTTTTATAAAGCAGAGAAAATAGTAAATCTTATATCAGGTACAAAATCTATAACTAACATACTGGAA

AAAACTTCTGCCATAGACTTAACAGATATTGATAGAGCCACTGAGATGATGAGGAAAAACATAACTTTGCTTATAAG

GATACTTCCATTGGATTGTAACAGAGATAAAAGAGAGATATTGAGTATGGAAAACCTAAGTATTACTGAATTAAGCA

AATATGTTAGGGAAAGATCTTGGTCTTTATCCAATATAGTTGGTGTTACATCACCCAGTATCATGTATACAATGGAC

ATCAAATATACTACAAGCACTATATCTAGTGGCATAATTATAGAGAAATATAATGTTAACAGTTTAACACGTGGTGA

GAGAGGACCCACTAAACCATGGGTTGGTTCATCTACACAAGAGAAAAAAACAATGCCAGTTTATAATAGACAAGTCT

TAACCAAAAAACAGAGAGATCAAATAGATCTATTAGCAAAATTGGATTGGGTGTATGCATCTATAGATAACAAGGAT

GAATTCATGGAAGAACTCAGCATAGGAACCCTTGGGTTAACATATGAAAAGGCCAAGAAATTATTTCCACAATATTT

AAGTGTCAATTATTTGCATCGCCTTACAGTCAGTAGTAGACCATGTGAATTCCCTGCATCAATACCAGCTTATAGAA

CAACAAATTATCACTTTGACACTAGCCCTATTAATCGCATATTAACAGAAAAGTATGGTGATGAAGATATTGACATA

GTATTCCAAAACTGTATAAGCTTTGGCCTTAGTTTAATGTCAGTAGTAGAACAATTTACTAATGTATGTCCTAACAG

AATTATTCTCATACCTAAGCTTAATGAGATACATTTGATGAAACCTCCCATATTCACAGGTGATGTTGATATTCACA

AGTTAAAACAAGTGATACAAAAACAGCATATGTTTTTACCAGACAAAATAAGTTTGACTCAATATGTGGAATTATTC

TTAAGTAATAAAACACTCAAATCTGGATCTCATGTTAATTCTAATTTAATATTGGCACATAAAATATCTGACTATTT

TCATAATACTTACATTTTAAGTACTAATTTAGCTGGACATTGGATTCTGATTATACAACTTATGAAAGATTCTAAAG

GTATTTTTGAAAAAGATTGGGGAGAGGGATATATAACTGATCATATGTTTATTAATTTGAAAGTTTTCTTCAATGCT

TATAAGACCTATCTCTTGTGTTTTCATAAAGGTTATGGCAAAGCAAAGCTGGAGTGTGATATGAACACTTCAGATCT

TCTATGTGTATTGGAATTAATAGACAGTAGTTATTGGAAGTCTATGTCTAAGGTATTTTTAGAACAAAAAGTTATCA

AATACATTCTTAGCCAAGATGCAAGTTTACATAGAGTAAAAGGATGTCATAGCTTCAAATTATGGTTTCTTAAACGT

CTTAATGTAGCAGAATTCACAGTTTGCCCTTGGGTTGTTAACATAGATTATCATCCAACACATATGAAAGCAATATT

AACTTATATAGATCTTGTTAGAATGGGATTGATAAATATAGATAGAATACACATTAAAAATAAACACAAATTCAATG

-continued

ATGAATTTTATACTTCTAATCTCTTCTACATTAATTATAACTTCTCAGATAATACTCATCTATTAACTAAACATATA

AGGATTGCTAATTCTGAATTAGAAAATAATTACAACAAATTATATCATCCTACACCAGAAACCCTAGAGAATATACT

AGCCAATCCGATTAAAAGTAATGACAAAAAGACACTGAATGACTATTGTATAGGTAAAAATGTTGACTCAATAATGT

TACCATTGTTATCTAATAAGAAGCTTATTAAATCGTCTGCAATGATTAGAACCAATTACAGCAAACAAGATTTGTAT

AATTTATTCCCTATGGTTGTGATTGATAGAATTATAGATCATTCAGGCAATACAGCCAAATCCAACCAACTTTACAC

TACTACTTCCCACCAAATATCCTTAGTGCACAATAGCACATCACTTTACTGCATGCTTCCTTGGCATCATATTAATA

GATTCAATTTTGTATTTAGTTCTACAGGTTGTAAAATTAGTATAGAGTATATTTTAAAAGATCTTAAAATTAAAGAT

CCCAATTGTATAGCATTCATAGGTGAAGGAGCAGGGAATTTATTATTGCGTACAGTAGTGGAACTTCATCCTGACAT

AAGATATATTTACAGAAGTCTGAAAGATTGCAATGATCATAGTTTACCTATTGAGTTTTTAAGGCTGTACAATGGAC

ATATCAACATTGATTATGGTGAAAATTTGACCATTCCTGCTACAGATGCAACCAACAACATTCATTGGTCTTATTTA

CATATAAAGTTTGCTGAACCTATCAGTCTTTTTGTCTGTGATGCCGAATTGTCTGTAACAGTCAACTGGAGTAAAAT

TATAATAGAATGGAGCAAGCATGTAAGAAAGTGCAAGTACTGTTCCTCAGTTAATAAATGTATGTTAATAGTAAAAT

ATCATGCTCAAGATGATATTGATTTCAAATTAGACAATATAACTATATTAAAAACTTATGTATGCTTAGGCAGTAAG

TTAAAGGGATCGGAGGTTTACTTAGTCCTTACAATAGGTCCTGCGAATATATTCCCAGTATTTAATGTAGTACAAAA

TGCTAAATTGATACTATCAAGAACCAAAAATTTCATCATGCCTAAGAAAGCTGATAAAGAGTCTATTGATGCAAATA

TTAAAAGTTTGATACCCTTTCTTTGTTACCCTATAACAAAAAAAGGAATTAATACTGCATTGTCAAAACTAAAGAGT

GTTGTTAGTGGAGATATACTATCATATTCTATAGCTGGACGTAATGAAGTTTTCAGCAATAAACTTATAAATCATAA

GCATATGAACATCTTAAAATGGTTCAATCATGTTTTAAATTTCAGATCAACAGAACTAAACTATAACCATTTATATA

TGGTAGAATCTACATATCCTTACCTAAGTGAATTGTTAAACAGCTTGACAACCAATGAACTTAAAAAACTGATTAAA

ATCACAGGTAGTCTGTTATACAACTTTCATAATGAATAATGAATAAAGATCTTATAATAAAAATTCCCATAGCTATA

CACTAACACTGTATTCAATTATAGTTATTAAAAATTAAAAATCATATAATTTTTTAAATAACTTTTAGTGAACTAAT

CCTAAAGTTATCATTTTAATCTTGGAGGAATAAATTTAAACCCTAATCTAATTGGTTTATATGTGTATTAACTAAAT

TACGAGATATTAGTTTTTGACACTTTTTTTCTCGT

Antigenomic cDNA sequence of RSV 6120/NS12FM2/ΔNS2 (SEQ ID NO: 6)

ACGGGAAAAAATGCGTACAACAAACTTGCATAAACCAAAAAAATGGGGCAAATAAGAATTTGATAAGTACCACTTAA

ATTTAACTCCCTTGGTTAGAGATGGCTCTTAGCAAAGTCAAGTTGAATGATACACTCAACAAAGATCAACTTCTGTC

ATCCAGCAAATACACCATCCAACGGAGCACAGGAGATAGTATTGATACTCCTAATTATGATGTGCAGAAACACATCA

ATAAGTTATGTGGCATGTTATTAATCACAGAAGATGCTAATCATAAATTCACTGGGTTAATAGGTATGTTATATGCG

ATGTCTAGGTTAGGAAGAGAAGACACCATAAAAATACTCAGAGATGCGGGATATCATGTAAAAGCAAATGGAGTAGA

TGTAACAACACATCGTCAAGACATTAATGGAAAAGAAATGAAATTTGAAGTGTTAACATTGGCAAGCTTAACAACTG

AAATTCAAATCAACATTGAGATAGAATCTAGAAAATCCTACAAAAAAATGCTAAAAGAAATGGGAGAGGTAGCTCCA

GAATACAGGCATGACTCTCCTGATTGTGGGATGATAATATTATGTATAGCAGCATTAGTAATAACTAAATTAGCAGC

AGGGGACAGATCTGGTCTTACAGCCGTGATTAGGAGAGCTAATAATGTCCTAAAAAATGAAATGAAACGTTACAAAG

GCTTACTACCCAAGGACATAGCCAACAGCTTCTATGAAGTGTTTGAAAAACATCCCCACTTTATAGATGTTTTTGTT

CATTTTGGTATAGCACAATCTTCTACCAGAGGTGGCAGTAGAGTTGAAGGGATTTTTGCAGGATTGTTTATGAATGC

CTATGGTGCAGGGCAAGTGATGTTACGGTGGGGAGTCTTAGCAAAATCAGTTAAAAATATTATGTTAGGACATGCTA

GTGTGCAAGCAGAAATGGAACAAGTTGTTGAGGTTTATGAATATGCCCAAAAATTGGGTGGTGAAGCAGGATTCTAC

CATATATTGAACAACCCAAAAGCATCATTATTATCTTTGACTCAATTTCCTCACTTCTCCAGTGTAGTATTAGGCAA

TGCTGCTGGCCTAGGCATAATGGGAGAGTACAGAGGTACACCGAGGAATCAAGATCTATATGATGCAGCAAAGGCAT

ATGCTGAACAACTCAAAGAAAATGGTGTGATTAACTACAGTGTACTAGACTTGACAGCAGAAGAACTAGAGGCTATC

AAACATCAGCTTAATCCAAAAGATAATGATGTAGAGCTTTGAGTTAATAAAAAATGGGGCAAATAAATCATCATGGA

-continued

AAAGTTTGCTCCTGAATTCCATGGAGAAGATGCAAACAACAGGGCTACTAAATTCCTAGAATCAATAAAGGGCAAAT

TCACATCACCCAAAGATCCCAAGAAAAAAGATAGTATCATATCTGTCAACTCAATAGATATAGAAGTAACCAAAGAA

AGCCCTATAACATCAAATTCAACTATTATCAACCCAACAAATGAGACAGATGATACTGCAGGGAACAAGCCCAATTA

TCAAAGAAAACCTCTAGTAAGTTTCAAAGAAGACCCTACACCAAGTGATAATCCCTTTTCTAAACTATACAAAGAAA

CCATAGAAACATTTGATAACAATGAAGAAGAATCCAGCTATTCATACGAAGAAATAAATGATCAGACAAACGATAAT

ATAACAGCAAGATTAGATAGGATTGATGAAAAATTAAGTGAAATACTAGGAATGCTTCACACATTAGTAGTGGCAAG

TGCAGGACCTACATCTGCTCGGGATGGTATAAGAGATGCCATGGTTGGTTTAAGAGAAGAAATGATAGAAAAAATCA

GAACTGAAGCATTAATGACCAATGACAGATTAGAAGCTATGGCAAGACTCAGGAATGAGGAAAGTGAAAAGATGGCA

AAAGACACATCAGATGAAGTGTCTCTCAATCCAACATCAGAGAAATTGAACAACCTATTGGAAGGGAATGATAGTGA

CAATGATCTATCACTTGAAGATTTCTGATTAGTTACCAATCTTCACATCAACACACAATACCAACAGAAGACCAACA

AACTAACCAACCCAATCATCCAACCAAACATCCATCCGCCAATCAGCCAAACAGCCAACAAAACAACCAGCCAATCC

AAAACTAACCACCCGGAAAAAATCTATAATATAGTTACAAAAAAAGGAAAGGGTGGGGCAAATATGGAAACATACGT

GAACAAGCTTCACGAAGGCTCCACATACACAGCTGCTGTTCAATACAATGTCTTAGAAAAAGACGATGACCCTGCAT

CACTTACAATATGGGTGCCCATGTTCCAATCATCTATGCCAGCAGATTTACTTATAAAAGAACTAGCTAATGTCAAC

ATACTAGTGAAACAAATATCCACACCCAAGGGACCTTCACTAAGAGTCATGATAAACTCAAGAAGTGCAGTGCTAGC

ACAAATGCCCAGCAAATTTACCATATGCGCTAATGTGTCCTTGGATGAAAGAAGCAAACTAGCATATGATGTAACCA

CACCCTGTGAAATCAAGGCATGTAGTCTAACATGCCTAAAATCAAAAAATATGTTGACTACAGTTAAAGATCTCACT

ATGAAGACACTCAACCCTACACATGATATTATTGCTTTATGTGAATTTGAAAACATAGTAACATCAAAAAAAGTCAT

AATACCAACATACCTAAGATCCATCAGTGTCAGAAATAAAGATCTGAACACACTTGAAAATATAACAACCACTGAAT

TCAAAAATGCTATCACAAATGCAAAAATCATCCCTTACTCAGGATTACTATTAGTCATCACAGTGACTGACAACAAA

GGAGCATTCAAATACATAAAGCCACAAAGTCAATTCATAGTAGATCTTGGAGCTTACCTAGAAAAAGAAAGTATATA

TTATGTTACCACAAATTGGAAGCACACAGCTACACGATTTGCAATCAAACCCATGGAAGATTAACCTTTTTCCTCTA

CATCAGTGTGTTAATTCATACAAACTTTCTACCTACATTCTTCACTTCACCATCACAATCACAAACACTCTGTGGTT

CAACCAATCAAACAAAACTTATCTGAAGTCCCAGATCATCCCAAGTCATTGTTTATCAGATCTAGTACTCAAATAAG

TTAATAAAAAATATACACATGGGGCAAATAATCATTGGAGGAAATCCAACTAATCACAATATCTGTTAACATAGACA

AGTCCACACACCATACAGAATCAACCAATGGAAAATACATCCATAACAATAGAATTCTCAAGCAAATTCTGGCCTTA

CTTTACACTAATACACATGATCACAACAATAATCTCTTTGCTAATCATAATCTCCATCATGATTGCAATACTAAACA

AACTTTGTGAATATAACGTATTCCATAACAAAACCTTTGAGTTACCAAGAGCTCGAGTTAATACTTGATAAAGTAGT

TAATTAAAAATAGTCATAACAATGAACTAGGATATCAAGACTAACAATAACATTGGGGCAAATGCAAACATGTCCAA

AAACAAGGACCAACGCACCGCTAAGACATTAGAAAGGACCTGGGACACTCTCAATCATTTATTATTCATATCATCGT

GCTTATATAAGTTAAATCTTAAATCTGTAGCACAAATCACATTATCCATTCTGGCAATGATAATCTCAACTTCACTT

ATAATTGCAGCCATCATATTCATAGCCTCGGCAAACCACAAAGTCACACCAACAACTGCAATCATACAAGATGCAAC

AAGCCAGATCAAGAACACAACCCCAACATACCTCACCCAGAATCCTCAGCTTGGAATCAGTCCCTCTAATCCGTCTG

AAATTACATCACAAATCACCACCATACTAGCTTCAACAACACCAGGAGTCAAGTCAACCCTGCAATCCACAACAGTC

AAGACCAAAAACACAACAACAACTCAAACACAACCCAGCAAGCCCACCACAAAACAACGCCAAAACAAACCACCAAG

CAAACCCAATAATGATTTTCACTTTGAAGTGTTCAACTTTGTACCCTGCAGCATATGCAGCAACAATCCAACCTGCT

GGGCTATCTGCAAAAGAATACCAAACAAAAAACCAGGAAAGAAAACCACTACCAAGCCCACAAAAAAACCAACCCTC

AAGACAACCAAAAAAGATCCCAAACCTCAAACCACTAAATCAAAGGAAGTACCCACCACCAAGCCCACAGAAGAGCC

AACCATCAACACCACCAAAACAAACATCATAACTACACTACTCACCTCCAACACCACAGGAAATCCAGAACTCACAA

GTCAAATGGAAACCTTCCACTCAACTTCCTCCGAAGGCAATCCAAGCCCTTCTCAAGTCTCTACAACATCCGAGTAC

CCATCACAACCTTCATCTCCACCCAACACACCACGCCAGTAGTTACTTAAAAACATATTATCACAAAAGGCCTTGAC

-continued

CAACTTAAACAGAATCAAAATAAACTCTGGGGCAAATAACAATGGAGTTGCTAATCCTCAAAGCAAATGCAATTACC

ACAATCCTCACTGCAGTCACATTTTGTTTTGCTTCTGGTCAAAACATCACTGAAGAATTTTATCAATCAACATGCAG

TGCAGTTAGCAAAGGCTATCTTAGTGCTCTGAGAACTGGTTGGTATACCAGTGTTATAACTATAGAATTAAGTAATA

TCAAGAAAAATAAGTGTAATGGAACAGATGCTAAGGTAAAATTGATAAAACAAGAATTAGATAAATATAAAAATGCT

GTAACAGAATTGCAGTTGCTCATGCAAAGCACACAAGCAACAAACAATCGAGCCAGAAGAGAACTACCAAGGTTTAT

GAATTATACACTCAACAATGCCAAAAAAACCAATGTAACATTAAGCAAGAAAAGGAAAAGAAGATTTCTTGGTTTTT

TGTTAGGTGTTGGATCTGCAATCGCCAGTGGCGTTGCTGTATCTAAGGTCCTGCACCTAGAAGGGGAAGTGAACAAG

ATCAAAAGTGCTCTACTATCCACAAACAAGGCTGTAGTCAGCTTATCAAATGGAGTTAGTGTTTTAACCAGCAAAGT

GTTAGACCTCAAAAACTATATAGATAAACAATTGTTACCTATTGTGAACAAGCAAAGCTGCAGCATATCAAATATAG

AAACTGTGATAGAGTTCCAACAAAAGAACAACAGACTACTAGAGATTACCAGGGAATTTAGTGTTAATGCAGGCGTA

ACTACACCTGTAAGCACTTACATGTTAACTAATAGTGAATTATTGTCATTAATCAATGATATGCCTATAACAAATGA

TCAGAAAAAGTTAATGTCCAACAATGTTCAAATAGTTAGACAGCAAAGTTACTCTATCATGTCCATAATAAAAGAGG

AAGTCTTAGCATATGTAGTACAATTACCACTATATGGTGTTATAGATACACCCTGTTGGAAACTACACACATCCCCT

CTATGTACAACCAACACAAAAGAAGGGTCCAACATCTGTTTAACAAGAACTGACAGAGGATGGTACTGTGACAATGC

AGGATCAGTATCTTTCTTCCCACAAGCTGAAACATGTAAAGTTCAATCAAATCGAGTATTTTGTGACACAATGAACA

GTTTAACATTACCAAGTGAAGTAAATCTCTGCAATGTTGACATATTCAACCCCAAATATGATTGTAAAATTATGACT

TCAAAAACAGATGTAAGCAGCTCCGTTATCACATCTCTAGGAGCCATTGTGTCATGCTATGGCAAAACTAAATGTAC

AGCATCCAATAAAAATCGTGGAATCATAAAGACATTTTCTAACGGGTGCGATTATGTATCAAATAAAGGGGTGGACA

CTGTGTCTGTAGGTAACACATTATATTATGTAAATAAGCAAGAAGGTAAAAGTCTCTATGTAAAAGGTGAACCAATA

ATAAATTTCTATGACCCATTAGTATTCCCCTCTGATGAATTTGATGCATCAATATCTCAAGTCAACGAGAAGATTAA

CCAGAGCCTAGCATTTATTCGTAAATCCGATGAATTATTACATAATGTAAATGCTGGTAAATCCACCACAAATATCA

TGATAACTACTATAATTATAGTGATTATAGTAATATTGTTATCATTAATTGCTGTTGGACTGCTCTTATACTGTAAG

GCCAGAAGCACACCAGTCACACTAAGCAAAGATCAACTGAGTGGTATAAATAATATTGCATTTAGTAACTAAATAAA

AATAGCACCTAATCATGTTCTTACAATGGTTTACTATCTGCTCATAGACAACCCATCTGTCATTGGATTTTCTTAAA

ATCTGAACTTCATCGAAACTCTCATCTATAAACCATCTCACTTACACTATTTAAGTAGATTCCTAGTTTATAGTTAT

ATAAAACACAATTGCATGCCAGGTACCATGGGGCAAATAAGAATTTGATAAGTACCACTTAAATTTAACTCCCTTGG

TTAGAGATGGGCAGCAATTCATTGAGTATGATAAAAGTTAGATTACAAAATTTGTTTGACAATGATGAAGTAGCATT

GTTAAAAATAACATGCTATACTGATAAATTAATACATTTAACTAATGCTTTGGCTAAGGCAGTGATACATACAATCA

AATTGAATGGCATTGTGTTTGTGCATGTTATTACAAGTAGTGATATTTGCCCTAATAATAATATTGTAGTAAAATCC

AATTTCACAACAATGCCAGTACTACAAAATGGAGGTTATATATGGGAAATGATGGAATTAACACATTGCTCTCAACC

TAATGGTCTACTAGATGACAATTGTGAAATTAAATTCTCCAAAAAACTAAGTGATTCAACAATGACCAATTATATGA

ATCAATTATCTGAATTACTTGGATTTGATCTTAATCCATAAATTATAATTAATATCAACTAGCAAATCAATGTCACT

AACACCATTAGTTAATATAAAACTTAACAGAAGACAAAAATGGGGCAAATATGTCACGAAGGAATCCTTGCAAATTT

GAAATTCGAGGTCATTGCTTAAATGGTAAGAGGTGTCATTTTAGTCATAATTATTTTGAATGGCCACCCCATGCACT

GCTTGTAAGACAAAACTTTATGTTAAACAGAATACTTAAGTCTATGGATAAAAGTATAGATACCTTATCAGAAATAA

GTGGAGCTGCAGAGTTGGACAGAACAGAAGAGTATGCTCTTGGTGTAGTTGGAGTGCTAGAGAGTTATATAGGATCA

ATAAACAATATAACTAAACAATCAGCATGTGTTGCCATGAGCAAACTCCTCACTGAACTCAATAGTGATGATATCAA

AAAGCTGAGGGACAATGAAGAGCTAAATTCACCCAAGATAAGAGTGTACAATACTGTCATATCATATATTGAAAGCA

ACAGGAAAAACAATAAACAAACTATCCATCTGTTAAAAAGATTGCCAGCAGACGTATTGAAGAAAACCATCAAAAAC

ACATTGGATATCCATAAGAGCATAACCATCAACAACCCAAAAGAATCAACTGTTAGTGATACAAATGACCATGCCAA

-continued

AAATAATGATACTACCTGACAAATATCCTTGTAGTATAACTTCCATACTAATAACAAGTAGATGTAGAGTTACTATG

TATAATCAAAAGAACACACTATATTTCAATCAAAACAACCCAAATAACCATATGTACTCACCGAATCAAACATTCAA

TGAAATCCATTGGACCTCTCAAGAATTGATTGACACAATTCAAAATTTTCTACAACATCTAGGTATTATTGAGGATA

TATATACAATATATATATTAGTGTCATAACACTCAATTCTAACACTCACCACATCGTTACATTATTAATTCAAACAA

TTCAAGTTGTGGGACAAAATGGATCCCATTATTAATGGAAATTCTGCTAATGTTTATCTAACCGATAGTTATTTAAA

AGGTGTTATCTCTTTCTCAGAGTGTAATGCTTTAGGAAGTTACATATTCAATGGTCCTTATCTCAAAAATGATTATA

CCAACTTAATTAGTAGACAAAATCCATTAATAGAACACATGAATCTAAAGAAACTAAATATAACACAGTCCTTAATA

TCTAAGTATCATAAAGGTGAAATAAAATTAGAAGAACCTACTTATTTTCAGTCATTACTTATGACATACAAGAGTAT

GACCTCGTCAGAACAGATTGCTACCACTAATTTACTTAAAAAGATAATAAGAAGAGCTATAGAAATAAGTGATGTCA

AAGTCTATGCTATATTGAATAAACTAGGGCTTAAAGAAAAGGACAAGATTAAATCCAACAATGGACAAGATGAAGAC

AACTCAGTTATTACGACCATAATCAAAGATGATATACTTTCAGCTGTTAAAGATAATCAATCTCATCTTAAAGCAGA

CAAAAATCACTCTACAAAACAAAAAGACACAATCAAAACAACACTCTTGAAGAAATTGATGTGTTCAATGCAACATC

CTCCATCATGGTTAATACATTGGTTTAACTTATACACAAAATTAAACAACATATTAACACAGTATCGATCAAATGAG

GTAAAAAACCATGGGTTTACATTGATAGATAATCAAACTCTTAGTGGATTTCAATTTATTTTGAACCAATATGGTTG

TATAGTTTATCATAAGGAACTCAAAAGAATTACTGTGACAACCTATAATCAATTCTTGACATGGAAAGATATTAGCC

TTAGTAGATTAAATGTTTGTTTAATTACATGGATTAGTAACTGCTTGAACACATTAAATAAAAGCTTAGGCTTAAGA

TGCGGATTCAATAATGTTATCTTGACACAACTATTCCTTTATGGAGATTGTATACTAAAGCTATTTCACAATGAGGG

GTTCTACATAATAAAAGAGGTAGAGGGATTTATTATGTCTCTAATTTTAAATATAACAGAAGAAGATCAATTCAGAA

AACGATTTTATAATAGTATGCTCAACAACATCACAGATGCTGCTAATAAAGCTCAGAAAAATCTGCTATCAAGAGTA

TGTCATACATTATTAGATAAGACAGTGTCCGATAATATAATAAATGGCAGATGGATAATTCTATTAAGTAAGTTCCT

TAAATTAATTAAGCTTGCAGGTGACAATAACCTTAACAATCTGAGTGAACTATATTTTTTGTTCAGAATATTTGGAC

ACCCAATGGTAGATGAAAGACAAGCCATGGATGCTGTTAAAATTAATTGCAATGAGACCAAATTTTACTTGTTAAGC

AGTCTGAGTATGTTAAGAGGTGCCTTTATATATAGAATTATAAAAGGGTTTGTAAATAATTACAACAGATGGCCTAC

TTTAAGAAATGCTATTGTTTTACCCTTAAGATGGTTAACTTACTATAAACTAAACACTTATCCTTCTTTGTTGGAAC

TTACAGAAAGAGATTTGATTGTGTTATCAGGACTACGTTTCTATCGTGAGTTTCGGTTGCCTAAAAAAGTGGATCTT

GAAATGATTATAAATGATAAAGCTATATCACCTCCTAAAAATTTGATATGGACTAGTTTCCCTAGAAATTACATGCC

ATCACACATACAAAACTATATAGAACATGAAAAATTAAAATTTTCCGAGAGTGATAAATCAAGAAGAGTATTAGAGT

ATTATTTAAGAGATAACAAATTCAATGAATGTGATTTATACAACTGTGTAGTTAATCAAAGTTATCTCAACAACCCT

AATCATGTGGTATCATTGACAGGCAAAGAAAGAGAACTCAGTGTAGGTAGAATGTTTGCAATGCAACCGGGAATGTT

CAGACAGGTTCAAATATTGGCAGAGAAAATGATAGCTGAAAACATTTTACAATTCTTTCCTGAAAGTCTTACAAGAT

ATGGTGATCTAGAACTACAAAAAATATTAGAACTGAAAGCAGGAATAAGTAACAAATCAAATCGCTACAATGATAAT

TACAACAATTACATTAGTAAGTGCTCTATCATCACAGATCTCAGCAAATTCAATCAAGCATTTCGATATGAAACGTC

ATGTATTTGTAGTGATGTGCTGGATGAACTGCATGGTGTACAATCTCTATTTTCCTGGTTACATTTAACTATTCCTC

ATGTCACAATAATATGCACATATAGGCATGCACCCCCCTATATAGGAGATCATATTGTAGATCTTAACAATGTAGAT

GAACAAAGTGGATTATATAGATATCACATGGGTGGCATCGAAGGGTGGTGTCAAAAACTATGGACCATAGAAGCTAT

ATCACTATTGGATCTAATATCTCTCAAAGGGAAATTCTCAATTACTGCTTTAATTAATGGTGACAATCAATCAATAG

ATATAAGCAAACCAATCAGACTCATGGAAGGTCAAACTCATGCTCAAGCAGATTATTTGCTAGCATTAAATAGCCTT

AAATTACTGTATAAAGAGTATGCAGGCATAGGCCACAAATTAAAAGGAACTGAGACTTATATATCACGAGATATGCA

ATTTATGAGTAAAACAATTCAACATAACGGTGTATATTACCCAGCTAGTATAAAGAAAGTCCTAAGAGTGGGACCGT

GGATAAACACTATACTTGATGATTTCAAAGTGAGTCTAGAATCTATAGGTAGTTTGACACAAGAATTAGAATATAGA

GGTGAAAGTCTATTATGCAGTTTAATATTTAGAAATGTATGGTTATATAATCAGATTGCTCTACAATTAAAAAATCA

-continued

TGCATTATGTAACAATAAACTATATTTGGACATATTAAAGGTTCTGAAACACTTAAAAACCTTTTTTAATCTTGATA

ATATTGATACAGCATTAACATTGTATATGAATTTACCCATGTTATTTGGTGGTGGTGATCCCAACTTGTTATATCGA

AGTTTCTATAGAAGAACTCCTGACTTCCTCACAGAGGCTATAGTTCACTCTGTGTTCATACTTAGTTATTATACAAA

CCATGACTTAAAAGATAAACTTCAAGATCTGTCAGATGATAGATTGAATAAGTTCTTAACATGCATAATCACGTTTG

ACAAAAACCCTAATGCTGAATTCGTAACATTGATGAGAGATCCTCAAGCTTTAGGGTCTGAGAGACAAGCTAAAATT

ACTAGCGAAATCAATAGACTGGCAGTTACAGAGGTTTTGAGTACAGCTCCAAACAAAATATTCTCCAAAAGTGCACA

ACATTATACTACTACAGAGATAGATCTAAATGATATTATGCAAAATATAGAACCTACATATCCTCATGGGCTAAGAG

TTGTTTATGAAAGTTTACCCTTTTATAAAGCAGAGAAAATAGTAAATCTTATATCAGGTACAAAATCTATAACTAAC

ATACTGGAAAAAACTTCTGCCATAGACTTAACAGATATTGATAGAGCCACTGAGATGATGAGGAAAAACATAACTTT

GCTTATAAGGATACTTCCATTGGATTGTAACAGAGATAAAAGAGAGATATTGAGTATGGAAAACCTAAGTATTACTG

AATTAAGCAAATATGTTAGGGAAAGATCTTGGTCTTTATCCAATATAGTTGGTGTTACATCACCCAGTATCATGTAT

ACAATGGACATCAAATATACTACAAGCACTATATCTAGTGGCATAATTATAGAGAAATATAATGTTAACAGTTTAAC

ACGTGGTGAGAGAGGACCCACTAAACCATGGGTTGGTTCATCTACACAAGAGAAAAAAACAATGCCAGTTTATAATA

GACAAGTCTTAACCAAAAAACAGAGAGATCAAATAGATCTATTAGCAAAATTGGATTGGGTGTATGCATCTATAGAT

AACAAGGATGAATTCATGGAAGAACTCAGCATAGGAACCCTTGGGTTAACATATGAAAAGGCCAAGAAATTATTTCC

ACAATATTTAAGTGTCAATTATTTGCATCGCCTTACAGTCAGTAGTAGACCATGTGAATTCCCTGCATCAATACCAG

CTTATAGAACAACAAATTATCACTTTGACACTAGCCCTATTAATCGCATATTAACAGAAAAGTATGGTGATGAAGAT

ATTGACATAGTATTCCAAAACTGTATAAGCTTTGGCCTTAGTTTAATGTCAGTAGTAGAACAATTTACTAATGTATG

TCCTAACAGAATTATTCTCATACCTAAGCTTAATGAGATACATTTGATGAAACCTCCCATATTCACAGGTGATGTTG

ATATTCACAAGTTAAAACAAGTGATACAAAAACAGCATATGTTTTTACCAGACAAAATAAGTTTGACTCAATATGTG

GAATTATTCTTAAGTAATAAAACACTCAAATCTGGATCTCATGTTAATTCTAATTTAATATTGGCACATAAAATATC

TGACTATTTTCATAATACTTACATTTTAAGTACTAATTTAGCTGGACATTGGATTCTGATTATACAACTTATGAAAG

ATTCTAAAGGTATTTTTGAAAAAGATTGGGGAGAGGGATATATAACTGATCATATGTTTATTAATTTGAAAGTTTTC

TTCAATGCTTATAAGACCTATCTCTTGTGTTTTCATAAAGGTTATGGCAAAGCAAAGCTGGAGTGTGATATGAACAC

TTCAGATCTTCTATGTGTATTGGAATTAATAGACAGTAGTTATTGGAAGTCTATGTCTAAGGTATTTTTAGAACAAA

AAGTTATCAAATACATTCTTAGCCAAGATGCAAGTTTACATAGAGTAAAAGGATGTCATAGCTTCAAATTATGGTTT

CTTAAACGTCTTAATGTAGCAGAATTCACAGTTTGCCCTTGGGTTGTTAACATAGATTATCATCCAACACATATGAA

AGCAATATTAACTTATATAGATCTTGTTAGAATGGGATTGATAAATATAGATAGAATACACATTAAAAATAAACACA

AATTCAATGATGAATTTTATACTTCTAATCTCTTCTACATTAATTATAACTTCTCAGATAATACTCATCTATTAACT

AAACATATAAGGATTGCTAATTCTGAATTAGAAAATAATTACAACAAATTATATCATCCTACACCAGAAACCCTAGA

GAATATACTAGCCAATCCGATTAAAAGTAATGACAAAAAGACACTGAATGACTATTGTATAGGTAAAAATGTTGACT

CAATAATGTTACCATTGTTATCTAATAAGAAGCTTATTAAATCGTCTGCAATGATTAGAACCAATTACAGCAAACAA

GATTTGTATAATTTATTCCCTATGGTTGTGATTGATAGAATTATAGATCATTCAGGCAATACAGCCAAATCCAACCA

ACTTTACACTACTACTTCCCACCAAATATCCTTAGTGCACAATAGCACATCACTTTACTGCATGCTTCCTTGGCATC

ATATTAATAGATTCAATTTTGTATTTAGTTCTACAGGTTGTAAAATTAGTATAGAGTATATTTTAAAAGATCTTAAA

ATTAAAGATCCCAATTGTATAGCATTCATAGGTGAAGGAGCAGGGAATTTATTATTGCGTACAGTAGTGGAACTTCA

TCCTGACATAAGATATATTTACAGAAGTCTGAAAGATTGCAATGATCATAGTTTACCTATTGAGTTTTTAAGGCTGT

ACAATGGACATATCAACATTGATTATGGTGAAAATTTGACCATTCCTGCTACAGATGCAACCAACAACATTCATTGG

TCTTATTTACATATAAAGTTTGCTGAACCTATCAGTCTTTTTGTCTGTGATGCCGAATTGTCTGTAACAGTCAACTG

GAGTAAAATTATAATAGAATGGAGCAAGCATGTAAGAAAGTGCAAGTACTGTTCCTCAGTTAATAAATGTATGTTAA

-continued

TAGTAAAATATCATGCTCAAGATGATATTGATTTCAAATTAGACAATATAACTATATTAAAAACTTATGTATGCTTA

GGCAGTAAGTTAAAGGGATCGGAGGTTTACTTAGTCCTTACAATAGGTCCTGCGAATATATTCCCAGTATTTAATGT

AGTACAAAATGCTAAATTGATACTATCAAGAACCAAAAATTTCATCATGCCTAAGAAAGCTGATAAAGAGTCTATTG

ATGCAAATATTAAAAGTTTGATACCCTTTCTTTGTTACCCTATAACAAAAAAAGGAATTAATACTGCATTGTCAAAA

CTAAAGAGTGTTGTTAGTGGAGATATACTATCATATTCTATAGCTGGACGTAATGAAGTTTTCAGCAATAAACTTAT

AAATCATAAGCATATGAACATCTTAAAATGGTTCAATCATGTTTTAAATTTCAGATCAACAGAACTAAACTATAACC

ATTTATATATGGTAGAATCTACATATCCTTACCTAAGTGAATTGTTAAACAGCTTGACAACCAATGAACTTAAAAAA

CTGATTAAAATCACAGGTAGTCTGTTATACAACTTTCATAATGAATAATGAATAAAGATCTTATAATAAAAATTCCC

ATAGCTATACACTAACACTGTATTCAATTATAGTTATTAAAAATTAAAAATCATATAATTTTTTAAATAACTTTTAG

TGAACTAATCCTAAAGTTATCATTTTAATCTTGGAGGAATAAATTTAAACCCTAATCTAATTGGTTTATATGTGTAT

TAACTAAATTACGAGATATTAGTTTTTGACACTTTTTTTCTCGT

Antigenomic cDNA sequence of RSV 6120/NS12Ltr/ΔNS2/GFP (SEQ ID NO: 7)

ACGGGAAAAAATGCGTACAACAAACTTGCATAAACCAAAAAAATGGGGCAAATAAGAATTTGATAAGTACCACTTAA

ATTTAACTCCCTTGGTTAGAGATGGCTCTTAGCAAAGTCAAGTTGAATGATACACTCAACAAAGATCAACTTCTGTC

ATCCAGCAAATACACCATCCAACGGAGCACAGGAGATAGTATTGATACTCCTAATTATGATGTGCAGAAACACATCA

ATAAGTTATGTGGCATGTTATTAATCACAGAAGATGCTAATCATAAATTCACTGGGTTAATAGGTATGTTATATGCG

ATGTCTAGGTTAGGAAGAGAAGACACCATAAAAATACTCAGAGATGCGGGATATCATGTAAAAGCAAATGGAGTAGA

TGTAACAACACATCGTCAAGACATTAATGGAAAAGAAATGAAATTTGAAGTGTTAACATTGGCAAGCTTAACAACTG

AAATTCAAATCAACATTGAGATAGAATCTAGAAAATCCTACAAAAAAATGCTAAAAGAAATGGGAGAGGTAGCTCCA

GAATACAGGCATGACTCTCCTGATTGTGGGATGATAATATTATGTATAGCAGCATTAGTAATAACTAAATTAGCAGC

AGGGGACAGATCTGGTCTTACAGCCGTGATTAGGAGAGCTAATAATGTCCTAAAAAATGAAATGAAACGTTACAAAG

GCTTACTACCCAAGGACATAGCCAACAGCTTCTATGAAGTGTTTGAAAAACATCCCCACTTTATAGATGTTTTTGTT

CATTTTGGTATAGCACAATCTTCTACCAGAGGTGGCAGTAGAGTTGAAGGGATTTTTGCAGGATTGTTTATGAATGC

CTATGGTGCAGGGCAAGTGATGTTACGGTGGGGAGTCTTAGCAAAATCAGTTAAAAATATTATGTTAGGACATGCTA

GTGTGCAAGCAGAAATGGAACAAGTTGTTGAGGTTTATGAATATGCCCAAAAATTGGGTGGTGAAGCAGGATTCTAC

CATATATTGAACAACCCAAAAGCATCATTATTATCTTTGACTCAATTTCCTCACTTCTCCAGTGTAGTATTAGGCAA

TGCTGCTGGCCTAGGCATAATGGGAGAGTACAGAGGTACACCGAGGAATCAAGATCTATATGATGCAGCAAAGGCAT

ATGCTGAACAACTCAAAGAAAATGGTGTGATTAACTACAGTGTACTAGACTTGACAGCAGAAGAACTAGAGGCTATC

AAACATCAGCTTAATCCAAAAGATAATGATGTAGAGCTTTGAGTTAATAAAAAATGGGGCAAATAAATCATCATGGA

AAAGTTTGCTCCTGAATTCCATGGAGAAGATGCAAACAACAGGGCTACTAAATTCCTAGAATCAATAAAGGGCAAAT

TCACATCACCCAAAGATCCCAAGAAAAAAGATAGTATCATATCTGTCAACTCAATAGATATAGAAGTAACCAAAGAA

AGCCCTATAACATCAAATTCAACTATTATCAACCCAACAAATGAGACAGATGATACTGCAGGGAACAAGCCCAATTA

TCAAAGAAAACCTCTAGTAAGTTTCAAAGAAGACCCTACACCAAGTGATAATCCCTTTTCTAAACTATACAAAGAAA

CCATAGAAACATTTGATAACAATGAAGAAGAATCCAGCTATTCATACGAAGAAATAAATGATCAGACAAACGATAAT

ATAACAGCAAGATTAGATAGGATTGATGAAAAATTAAGTGAAATACTAGGAATGCTTCACACATTAGTAGTGGCAAG

TGCAGGACCTACATCTGCTCGGGATGGTATAAGAGATGCCATGGTTGGTTTAAGAGAAGAAATGATAGAAAAAATCA

GAACTGAAGCATTAATGACCAATGACAGATTAGAAGCTATGGCAAGACTCAGGAATGAGGAAAGTGAAAAGATGGCA

AAAGACACATCAGATGAAGTGTCTCTCAATCCAACATCAGAGAAATTGAACAACCTATTGGAAGGGAATGATAGTGA

CAATGATCTATCACTTGAAGATTTCTGATTAGTTACCAATCTTCACATCAACACACAATACCAACAGAAGACCAACA

AACTAACCAACCCAATCATCCAACCAAACATCCATCCGCCAATCAGCCAAACAGCCAACAAAACAACCAGCCAATCC

AAAACTAACCACCCGGAAAAAATCTATAATATAGTTACAAAAAAAGGAATCGATGGGGCAAATACAAGTATGGTGAG

-continued

CAAGGGCGAGGAGCTGTTCACCGGGGTGGTGCCCATCCTGGTCGAGCTGGACGGCGACGTAAACGGCCACAAGTTCA

GCGTGTCCGGCGAGGGCGAGGGCGATGCCACCTACGGCAAGCTGACCCTGAAGTTCATCTGCACCACCGGCAAGCTG

CCCGTGCCCTGGCCCACCCTCGTGACCACCCTGACCTACGGCGTGCAGTGCTTCAGCCGCTACCCCGACCACATGAA

GCAGCACGACTTCTTCAAGTCCGCCATGCCCGAAGGCTACGTCCAGGAGCGCACCATCTTCTTCAAGGACGACGGCA

ACTACAAGACCCGCGCCGAGGTGAAGTTCGAGGGCGACACCCTGGTGAACCGCATCGAGCTGAAGGGCATCGACTTC

AAGGAGGACGGCAACATCCTGGGGCACAAGCTGGAGTACAACTACAACAGCCACAACGTCTATATCATGGCCGACAA

GCAGAAGAACGGCATCAAGGTGAACTTCAAGATCCGCCACAACATCGAGGACGGCAGCGTGCAGCTCGCCGACCACT

ACCAGCAGAACACCCCCATCGGCGACGGCCCCGTGCTGCTGCCCGACAACCACTACCTGAGCACCCAGTCCGCCCTG

AGCAAAGACCCCAACGAGAAGCGCGATCACATGGTCCTGCTGGAGTTCGTGACCGCCGCCGGGATCACTCTCGGCAT

GGACGAGCTGTACAAGTAAAAGTAGTTACTTAAAAAGTCGACGGTGGGGCAAATATGGAAACATACGTGAACAAGCT

TCACGAAGGCTCCACATACACAGCTGCTGTTCAATACAATGTCTTAGAAAAAGACGATGACCCTGCATCACTTACAA

TATGGGTGCCCATGTTCCAATCATCTATGCCAGCAGATTTACTTATAAAAGAACTAGCTAATGTCAACATACTAGTG

AAACAAATATCCACACCCAAGGGACCTTCACTAAGAGTCATGATAAACTCAAGAAGTGCAGTGCTAGCACAAATGCC

CAGCAAATTTACCATATGCGCTAATGTGTCCTTGGATGAAAGAAGCAAACTAGCATATGATGTAACCACACCCTGTG

AAATCAAGGCATGTAGTCTAACATGCCTAAAATCAAAAAATATGTTGACTACAGTTAAAGATCTCACTATGAAGACA

CTCAACCCTACACATGATATTATTGCTTTATGTGAATTTGAAAACATAGTAACATCAAAAAAAGTCATAATACCAAC

ATACCTAAGATCCATCAGTGTCAGAAATAAAGATCTGAACACACTTGAAAATATAACAACCACTGAATTCAAAAATG

CTATCACAAATGCAAAAATCATCCCTTACTCAGGATTACTATTAGTCATCACAGTGACTGACAACAAAGGAGCATTC

AAATACATAAAGCCACAAAGTCAATTCATAGTAGATCTTGGAGCTTACCTAGAAAAAGAAAGTATATATTATGTTAC

CACAAATTGGAAGCACACAGCTACACGATTTGCAATCAAACCCATGGAAGATTAACCTTTTTCCTCTACATCAGTGT

GTTAATTCATACAAACTTTCTACCTACATTCTTCACTTCACCATCACAATCACAAACACTCTGTGGTTCAACCAATC

AAACAAAACTTATCTGAAGTCCCAGATCATCCCAAGTCATTGTTTATCAGATCTAGTACTCAAATAAGTTAATAAAA

AATATACACATGGGGCAAATAATCATTGGAGGAAATCCAACTAATCACAATATCTGTTAACATAGACAAGTCCACAC

ACCATACAGAATCAACCAATGGAAAATACATCCATAACAATAGAATTCTCAAGCAAATTCTGGCCTTACTTTACACT

AATACACATGATCACAACAATAATCTCTTTGCTAATCATAATCTCCATCATGATTGCAATACTAAACAAACTTTGTG

AATATAACGTATTCCATAACAAAACCTTTGAGTTACCAAGAGCTCGAGTTAATACTTGATAAAGTAGTTAATTAAAA

ATAGTCATAACAATGAACTAGGATATCAAGACTAACAATAACATTGGGGCAAATGCAAACATGTCCAAAAACAAGGA

CCAACGCACCGCTAAGACATTAGAAAGGACCTGGGACACTCTCAATCATTTATTATTCATATCATCGTGCTTATATA

AGTTAAATCTTAAATCTGTAGCACAAATCACATTATCCATTCTGGCAATGATAATCTCAACTTCACTTATAATTGCA

GCCATCATATTCATAGCCTCGGCAAACCACAAAGTCACACCAACAACTGCAATCATACAAGATGCAACAAGCCAGAT

CAAGAACACAACCCCAACATACCTCACCCAGAATCCTCAGCTTGGAATCAGTCCCTCTAATCCGTCTGAAATTACAT

CACAAATCACCACCATACTAGCTTCAACAACACCAGGAGTCAAGTCAACCCTGCAATCCACAACAGTCAAGACCAAA

AACACAACAACAACTCAAACACAACCCAGCAAGCCCACCACAAAACAACGCCAAAACAAACCACCAAGCAAACCCAA

TAATGATTTTCACTTTGAAGTGTTCAACTTTGTACCCTGCAGCATATGCAGCAACAATCCAACCTGCTGGGCTATCT

GCAAAAGAATACCAAACAAAAAACCAGGAAAGAAAACCACTACCAAGCCCACAAAAAAACCAACCCTCAAGACAACC

AAAAAAGATCCCAAACCTCAAACCACTAAATCAAAGGAAGTACCCACCACCAAGCCCACAGAAGAGCCAACCATCAA

CACCACCAAAACAAACATCATAACTACACTACTCACCTCCAACACCACAGGAAATCCAGAACTCACAAGTCAAATGG

AAACCTTCCACTCAACTTCCTCCGAAGGCAATCCAAGCCCTTCTCAAGTCTCTACAACATCCGAGTACCCATCACAA

CCTTCATCTCCACCCAACACACCACGCCAGTAGTTACTTAAAAACATATTATCACAAAAGGCCTTGACCAACTTAAA

CAGAATCAAAATAAACTCTGGGGCAAATAACAATGGAGTTGCTAATCCTCAAAGCAAATGCAATTACCACAATCCTC

ACTGCAGTCACATTTTGTTTTGCTTCTGGTCAAAACATCACTGAAGAATTTTATCAATCAACATGCAGTGCAGTTAG

-continued

CAAAGGCTATCTTAGTGCTCTGAGAACTGGTTGGTATACCAGTGTTATAACTATAGAATTAAGTAATATCAAGAAAA

ATAAGTGTAATGGAACAGATGCTAAGGTAAAATTGATAAAACAAGAATTAGATAAATATAAAAATGCTGTAACAGAA

TTGCAGTTGCTCATGCAAAGCACACAAGCAACAAACAATCGAGCCAGAAGAGAACTACCAAGGTTTATGAATTATAC

ACTCAACAATGCCAAAAAAACCAATGTAACATTAAGCAAGAAAAGGAAAAGAAGATTTCTTGGTTTTTTGTTAGGTG

TTGGATCTGCAATCGCCAGTGGCGTTGCTGTATCTAAGGTCCTGCACCTAGAAGGGGAAGTGAACAAGATCAAAAGT

GCTCTACTATCCACAAACAAGGCTGTAGTCAGCTTATCAAATGGAGTTAGTGTTTTAACCAGCAAAGTGTTAGACCT

CAAAAACTATATAGATAAACAATTGTTACCTATTGTGAACAAGCAAAGCTGCAGCATATCAAATATAGAAACTGTGA

TAGAGTTCCAACAAAAGAACAACAGACTACTAGAGATTACCAGGGAATTTAGTGTTAATGCAGGCGTAACTACACCT

GTAAGCACTTACATGTTAACTAATAGTGAATTATTGTCATTAATCAATGATATGCCTATAACAAATGATCAGAAAAA

GTTAATGTCCAACAATGTTCAAATAGTTAGACAGCAAAGTTACTCTATCATGTCCATAATAAAAGAGGAAGTCTTAG

CATATGTAGTACAATTACCACTATATGGTGTTATAGATACACCCTGTTGGAAACTACACACATCCCCTCTATGTACA

ACCAACACAAAAGAAGGGTCCAACATCTGTTTAACAAGAACTGACAGAGGATGGTACTGTGACAATGCAGGATCAGT

ATCTTTCTTCCCACAAGCTGAAACATGTAAAGTTCAATCAAATCGAGTATTTTGTGACACAATGAACAGTTTAACAT

TACCAAGTGAAGTAAATCTCTGCAATGTTGACATATTCAACCCCAAATATGATTGTAAAATTATGACTTCAAAAACA

GATGTAAGCAGCTCCGTTATCACATCTCTAGGAGCCATTGTGTCATGCTATGGCAAAACTAAATGTACAGCATCCAA

TAAAAATCGTGGAATCATAAAGACATTTTCTAACGGGTGCGATTATGTATCAAATAAAGGGGTGGACACTGTGTCTG

TAGGTAACACATTATATTATGTAAATAAGCAAGAAGGTAAAAGTCTCTATGTAAAAGGTGAACCAATAATAAATTTC

TATGACCCATTAGTATTCCCCTCTGATGAATTTGATGCATCAATATCTCAAGTCAACGAGAAGATTAACCAGAGCCT

AGCATTTATTCGTAAATCCGATGAATTATTACATAATGTAAATGCTGGTAAATCCACCACAAATATCATGATAACTA

CTATAATTATAGTGATTATAGTAATATTGTTATCATTAATTGCTGTTGGACTGCTCTTATACTGTAAGGCCAGAAGC

ACACCAGTCACACTAAGCAAAGATCAACTGAGTGGTATAAATAATATTGCATTTAGTAACTAAATAAAAATAGCACC

TAATCATGTTCTTACAATGGTTTACTATCTGCTCATAGACAACCCATCTGTCATTGGATTTTCTTAAAATCTGAACT

TCATCGAAACTCTCATCTATAAACCATCTCACTTACACTATTTAAGTAGATTCCTAGTTTATAGTTATATAAAACAC

AATTGCATGCCAGATTAACTTACCATCTGTAAAAATGAAAACTGGGGCAAATATGTCACGAAGGAATCCTTGCAAAT

TTGAAATTCGAGGTCATTGCTTAAATGGTAAGAGGTGTCATTTTAGTCATAATTATTTTGAATGGCCACCCCATGCA

CTGCTTGTAAGACAAAACTTTATGTTAAACAGAATACTTAAGTCTATGGATAAAAGTATAGATACCTTATCAGAAAT

AAGTGGAGCTGCAGAGTTGGACAGAACAGAAGAGTATGCTCTTGGTGTAGTTGGAGTGCTAGAGAGTTATATAGGAT

CAATAAACAATATAACTAAACAATCAGCATGTGTTGCCATGAGCAAACTCCTCACTGAACTCAATAGTGATGATATC

AAAAAGCTGAGGGACAATGAAGAGCTAAATTCACCCAAGATAAGAGTGTACAATACTGTCATATCATATATTGAAAG

CAACAGGAAAAACAATAAACAAACTATCCATCTGTTAAAAAGATTGCCAGCAGACGTATTGAAGAAAACCATCAAAA

ACACATTGGATATCCATAAGAGCATAACCATCAACAACCCAAAAGAATCAACTGTTAGTGATACAAATGACCATGCC

AAAAATAATGATACTACCTGACAAATATCCTTGTAGTATAACTTCCATACTAATAACAAGTAGATGTAGAGTTACTA

TGTATAATCAAAAGAACACACTATATTTCAATCAAAACAACCCAAATAACCATATGTACTCACCGAATCAAACATTC

AATGAAATCCATTGGACCTCTCAAGAATTGATTGACACAATTCAAAATTTTCTACAACATCTAGGTATTATTGAGGA

TATATATACAATATATATATTAGTGTCATAACACTCAATTCTAACACTCACCACATCGTTACATTATTAATTCAAAC

AATTCAAGTTGTGGGACAAAATGGATCCCATTATTAATGGAAATTCTGCTAATGTTTATCTAACCGATAGTTATTTA

AAAGGTGTTATCTCTTTCTCAGAGTGTAATGCTTTAGGAAGTTACATATTCAATGGTCCTTATCTCAAAAATGATTA

TACCAACTTAATTAGTAGACAAAATCCATTAATAGAACACATGAATCTAAAGAAACTAAATATAACACAGTCCTTAA

TATCTAAGTATCATAAAGGTGAAATAAAATTAGAAGAACCTACTTATTTTCAGTCATTACTTATGACATACAAGAGT

ATGACCTCGTCAGAACAGATTGCTACCACTAATTTACTTAAAAAGATAATAAGAAGAGCTATAGAAATAAGTGATGT

-continued

CAAAGTCTATGCTATATTGAATAAACTAGGGCTTAAAGAAAAGGACAAGATTAAATCCAACAATGGACAAGATGAAG

ACAACTCAGTTATTACGACCATAATCAAAGATGATATACTTTCAGCTGTTAAAGATAATCAATCTCATCTTAAAGCA

GACAAAAATCACTCTACAAAACAAAAAGACACAATCAAAACAACACTCTTGAAGAAATTGATGTGTTCAATGCAACA

TCCTCCATCATGGTTAATACATTGGTTTAACTTATACACAAAATTAAACAACATATTAACACAGTATCGATCAAATG

AGGTAAAAAACCATGGGTTTACATTGATAGATAATCAAACTCTTAGTGGATTTCAATTTATTTTGAACCAATATGGT

TGTATAGTTTATCATAAGGAACTCAAAAGAATTACTGTGACAACCTATAATCAATTCTTGACATGGAAAGATATTAG

CCTTAGTAGATTAAATGTTTGTTTAATTACATGGATTAGTAACTGCTTGAACACATTAAATAAAAGCTTAGGCTTAA

GATGCGGATTCAATAATGTTATCTTGACACAACTATTCCTTTATGGAGATTGTATACTAAAGCTATTTCACAATGAG

GGGTTCTACATAATAAAAGAGGTAGAGGGATTTATTATGTCTCTAATTTTAAATATAACAGAAGAAGATCAATTCAG

AAAACGATTTTATAATAGTATGCTCAACAACATCACAGATGCTGCTAATAAAGCTCAGAAAAATCTGCTATCAAGAG

TATGTCATACATTATTAGATAAGACAGTGTCCGATAATATAATAAATGGCAGATGGATAATTCTATTAAGTAAGTTC

CTTAAATTAATTAAGCTTGCAGGTGACAATAACCTTAACAATCTGAGTGAACTATATTTTTTGTTCAGAATATTTGG

ACACCCAATGGTAGATGAAAGACAAGCCATGGATGCTGTTAAAATTAATTGCAATGAGACCAAATTTTACTTGTTAA

GCAGTCTGAGTATGTTAAGAGGTGCCTTTATATATAGAATTATAAAAGGGTTTGTAAATAATTACAACAGATGGCCT

ACTTTAAGAAATGCTATTGTTTTACCCTTAAGATGGTTAACTTACTATAAACTAAACACTTATCCTTCTTTGTTGGA

ACTTACAGAAAGAGATTTGATTGTGTTATCAGGACTACGTTTCTATCGTGAGTTTCGGTTGCCTAAAAAAGTGGATC

TTGAAATGATTATAAATGATAAAGCTATATCACCTCCTAAAAATTTGATATGGACTAGTTTCCCTAGAAATTACATG

CCATCACACATACAAAACTATATAGAACATGAAAAATTAAAATTTTCCGAGAGTGATAAATCAAGAAGAGTATTAGA

GTATTATTTAAGAGATAACAAATTCAATGAATGTGATTTATACAACTGTGTAGTTAATCAAAGTTATCTCAACAACC

CTAATCATGTGGTATCATTGACAGGCAAAGAAAGAGAACTCAGTGTAGGTAGAATGTTTGCAATGCAACCGGGAATG

TTCAGACAGGTTCAAATATTGGCAGAGAAAATGATAGCTGAAAACATTTTACAATTCTTTCCTGAAAGTCTTACAAG

ATATGGTGATCTAGAACTACAAAAAATATTAGAACTGAAAGCAGGAATAAGTAACAAATCAAATCGCTACAATGATA

ATTACAACAATTACATTAGTAAGTGCTCTATCATCACAGATCTCAGCAAATTCAATCAAGCATTTCGATATGAAACG

TCATGTATTTGTAGTGATGTGCTGGATGAACTGCATGGTGTACAATCTCTATTTTCCTGGTTACATTTAACTATTCC

TCATGTCACAATAATATGCACATATAGGCATGCACCCCCCTATATAGGAGATCATATTGTAGATCTTAACAATGTAG

ATGAACAAAGTGGATTATATAGATATCACATGGGTGGCATCGAAGGGTGGTGTCAAAAACTATGGACCATAGAAGCT

ATATCACTATTGGATCTAATATCTCTCAAAGGGAAATTCTCAATTACTGCTTTAATTAATGGTGACAATCAATCAAT

AGATATAAGCAAACCAATCAGACTCATGGAAGGTCAAACTCATGCTCAAGCAGATTATTTGCTAGCATTAAATAGCC

TTAAATTACTGTATAAAGAGTATGCAGGCATAGGCCACAAATTAAAAGGAACTGAGACTTATATATCACGAGATATG

CAATTTATGAGTAAAACAATTCAACATAACGGTGTATATTACCCAGCTAGTATAAAGAAAGTCCTAAGAGTGGGACC

GTGGATAAACACTATACTTGATGATTTCAAAGTGAGTCTAGAATCTATAGGTAGTTTGACACAAGAATTAGAATATA

GAGGTGAAAGTCTATTATGCAGTTTAATATTTAGAAATGTATGGTTATATAATCAGATTGCTCTACAATTAAAAAAT

CATGCATTATGTAACAATAAACTATATTTGGACATATTAAAGGTTCTGAAACACTTAAAAACCTTTTTTAATCTTGA

TAATATTGATACAGCATTAACATTGTATATGAATTTACCCATGTTATTTGGTGGTGGTGATCCCAACTTGTTATATC

GAAGTTTCTATAGAAGAACTCCTGACTTCCTCACAGAGGCTATAGTTCACTCTGTGTTCATACTTAGTTATTATACA

AACCATGACTTAAAAGATAAACTTCAAGATCTGTCAGATGATAGATTGAATAAGTTCTTAACATGCATAATCACGTT

TGACAAAAACCCTAATGCTGAATTCGTAACATTGATGAGAGATCCTCAAGCTTTAGGGTCTGAGAGACAAGCTAAAA

TTACTAGCGAAATCAATAGACTGGCAGTTACAGAGGTTTTGAGTACAGCTCCAAACAAAATATTCTCCAAAAGTGCA

CAACATTATACTACTACAGAGATAGATCTAAATGATATTATGCAAAATATAGAACCTACATATCCTCATGGGCTAAG

AGTTGTTTATGAAAGTTTACCCTTTTATAAAGCAGAGAAAATAGTAAATCTTATATCAGGTACAAAATCTATAACTA

ACATACTGGAAAAAACTTCTGCCATAGACTTAACAGATATTGATAGAGCCACTGAGATGATGAGGAAAAACATAACT

-continued

TTGCTTATAAGGATACTTCCATTGGATTGTAACAGAGATAAAAGAGAGATATTGAGTATGGAAAACCTAAGTATTAC
TGAATTAAGCAAATATGTTAGGGAAAGATCTTGGTCTTTATCCAATATAGTTGGTGTTACATCACCCAGTATCATGT
ATACAATGGACATCAAATATACTACAAGCACTATATCTAGTGGCATAATTATAGAGAAATATAATGTTAACAGTTTA
ACACGTGGTGAGAGAGGACCCACTAAACCATGGGTTGGTTCATCTACACAAGAGAAAAAAACAATGCCAGTTTATAA
TAGACAAGTCTTAACCAAAAAACAGAGAGATCAAATAGATCTATTAGCAAAATTGGATTGGGTGTATGCATCTATAG
ATAACAAGGATGAATTCATGGAAGAACTCAGCATAGGAACCCTTGGGTTAACATATGAAAAGGCCAAGAAATTATTT
CCACAATATTTAAGTGTCAATTATTTGCATCGCCTTACAGTCAGTAGTAGACCATGTGAATTCCCTGCATCAATACC
AGCTTATAGAACAACAAATTATCACTTTGACACTAGCCCTATTAATCGCATATTAACAGAAAAGTATGGTGATGAAG
ATATTGACATAGTATTCCAAAACTGTATAAGCTTTGGCCTTAGTTTAATGTCAGTAGTAGAACAATTTACTAATGTA
TGTCCTAACAGAATTATTCTCATACCTAAGCTTAATGAGATACATTTGATGAAACCTCCCATATTCACAGGTGATGT
TGATATTCACAAGTTAAAACAAGTGATACAAAAACAGCATATGTTTTTACCAGACAAAATAAGTTTGACTCAATATG
TGGAATTATTCTTAAGTAATAAAACACTCAAATCTGGATCTCATGTTAATTCTAATTTAATATTGGCACATAAAATA
TCTGACTATTTTCATAATACTTACATTTTAAGTACTAATTTAGCTGGACATTGGATTCTGATTATACAACTTATGAA
AGATTCTAAAGGTATTTTTGAAAAAGATTGGGGAGAGGGATATATAACTGATCATATGTTTATTAATTTGAAAGTTT
TCTTCAATGCTTATAAGACCTATCTCTTGTGTTTTCATAAAGGTTATGGCAAAGCAAAGCTGGAGTGTGATATGAAC
ACTTCAGATCTTCTATGTGTATTGGAATTAATAGACAGTAGTTATTGGAAGTCTATGTCTAAGGTATTTTTAGAACA
AAAAGTTATCAAATACATTCTTAGCCAAGATGCAAGTTTACATAGAGTAAAAGGATGTCATAGCTTCAAATTATGGT
TTCTTAAACGTCTTAATGTAGCAGAATTCACAGTTTGCCCTTGGGTTGTTAACATAGATTATCATCCAACACATATG
AAAGCAATATTAACTTATATAGATCTTGTTAGAATGGGATTGATAAATATAGATAGAATACACATTAAAAATAAACA
CAAATTCAATGATGAATTTTATACTTCTAATCTCTTCTACATTAATTATAACTTCTCAGATAATACTCATCTATTAA
CTAAACATATAAGGATTGCTAATTCTGAATTAGAAAATAATTACAACAAATTATATCATCCTACACCAGAAACCCTA
GAGAATATACTAGCCAATCCGATTAAAAGTAATGACAAAAAGACACTGAATGACTATTGTATAGGTAAAAATGTTGA
CTCAATAATGTTACCATTGTTATCTAATAAGAAGCTTATTAAATCGTCTGCAATGATTAGAACCAATTACAGCAAAC
AAGATTTGTATAATTTATTCCCTATGGTTGTGATTGATAGAATTATAGATCATTCAGGCAATACAGCCAAATCCAAC
CAACTTTACACTACTACTTCCCACCAAATATCCTTAGTGCACAATAGCACATCACTTTACTGCATGCTTCCTTGGCA
TCATATTAATAGATTCAATTTTGTATTTAGTTCTACAGGTTGTAAAATTAGTATAGAGTATATTTTAAAAGATCTTA
AAATTAAAGATCCCAATTGTATAGCATTCATAGGTGAAGGAGCAGGGAATTTATTATTGCGTACAGTAGTGGAACTT
CATCCTGACATAAGATATATTTACAGAAGTCTGAAAGATTGCAATGATCATAGTTTACCTATTGAGTTTTTAAGGCT
GTACAATGGACATATCAACATTGATTATGGTGAAAATTTGACCATTCCTGCTACAGATGCAACCAACAACATTCATT
GGTCTTATTTACATATAAAGTTTGCTGAACCTATCAGTCTTTTTGTCTGTGATGCCGAATTGTCTGTAACAGTCAAC
TGGAGTAAAATTATAATAGAATGGAGCAAGCATGTAAGAAAGTGCAAGTACTGTTCCTCAGTTAATAAATGTATGTT
AATAGTAAAATATCATGCTCAAGATGATATTGATTTCAAATTAGACAATATAACTATATTAAAAACTTATGTATGCT
TAGGCAGTAAGTTAAAGGGATCGGAGGTTTACTTAGTCCTTACAATAGGTCCTGCGAATATATTCCCAGTATTTAAT
GTAGTACAAAATGCTAAATTGATACTATCAAGAACCAAAAATTTCATCATGCCTAAGAAAGCTGATAAAGAGTCTAT
TGATGCAAATATTAAAAGTTTGATACCCTTTCTTTGTTACCCTATAACAAAAAAAGGAATTAATACTGCATTGTCAA
AACTAAAGAGTGTTGTTAGTGGAGATATACTATCATATTCTATAGCTGGACGTAATGAAGTTTTCAGCAATAAACTT
ATAAATCATAAGCATATGAACATCTTAAAATGGTTCAATCATGTTTTAAATTTCAGATCAACAGAACTAAACTATAA
CCATTTATATATGGTAGAATCTACATATCCTTACCTAAGTGAATTGTTAAACAGCTTGACAACCAATGAACTTAAAA
AACTGATTAAAATCACAGGTAGTCTGTTATACAACTTTCATAATGAATAATGAATAAAGATCTTATAATAAAAATTC
CCATAGCTATACACTAACACTGTATTCAATTATAGTTATAAAAATTAAAAATGGTACCATGGGGCAAATAAGAATTT

-continued

GATAAGTACCACTTAAATTTAACTCCCTTGGTTAGAGATGGGCAGCAATTCATTGAGTATGATAAAAGTTAGATTAC

AAAATTTGTTTGACAATGATGAAGTAGCATTGTTAAAAATAACATGCTATACTGATAAATTAATACATTTAACTAAT

GCTTTGGCTAAGGCAGTGATACATACAATCAAATTGAATGGCATTGTGTTTGTGCATGTTATTACAAGTAGTGATAT

TTGCCCTAATAATAATATTGTAGTAAAATCCAATTTCACAACAATGCCAGTACTACAAAATGGAGGTTATATATGGG

AAATGATGGAATTAACACATTGCTCTCAACCTAATGGTCTACTAGATGACAATTGTGAAATTAAATTCTCCAAAAAA

CTAAGTGATTCAACAATGACCAATTATATGAATCAATTATCTGAATTACTTGGATTTGATCTTAATCCATAAATTAT

AATTAATATCAACTAGCAAATCAATGTCACTAACACCATTAGTTAATATAAAACTTAACAGAAGACAAAAATCTTAA

GGAGAGATATAAGATAGAAGATGGTACCATTTTTTAAATAACTTTTAGTGAACTAATCCTAAAGTTATCATTTTAAT

CTTGGAGGAATAAATTTAAACCCTAATCTAATTGGTTTATATGTGTATTAACTAAATTACGAGATATTAGTTTTTGA

CACTTTTTTTCTCGT

Antigenomic cDNA sequence of RSV 6120/NS12Ltr/ΔNS2 (SEQ ID NO: 8):

ACGGGAAAAAATGCGTACAACAAACTTGCATAAACCAAAAAAATGGGGCAAATAAGAATTTGATAAGTACCACTTAA

ATTTAACTCCCTTGGTTAGAGATGGCTCTTAGCAAAGTCAAGTTGAATGATACACTCAACAAAGATCAACTTCTGTC

ATCCAGCAAATACACCATCCAACGGAGCACAGGAGATAGTATTGATACTCCTAATTATGATGTGCAGAAACACATCA

ATAAGTTATGTGGCATGTTATTAATCACAGAAGATGCTAATCATAAATTCACTGGGTTAATAGGTATGTTATATGCG

ATGTCTAGGTTAGGAAGAGAAGACACCATAAAAATACTCAGAGATGCGGGATATCATGTAAAAGCAAATGGAGTAGA

TGTAACAACACATCGTCAAGACATTAATGGAAAAGAAATGAAATTTGAAGTGTTAACATTGGCAAGCTTAACAACTG

AAATTCAAATCAACATTGAGATAGAATCTAGAAAATCCTACAAAAAAATGCTAAAAGAAATGGGAGAGGTAGCTCCA

GAATACAGGCATGACTCTCCTGATTGTGGGATGATAATATTATGTATAGCAGCATTAGTAATAACTAAATTAGCAGC

AGGGGACAGATCTGGTCTTACAGCCGTGATTAGGAGAGCTAATAATGTCCTAAAAAATGAAATGAAACGTTACAAAG

GCTTACTACCCAAGGACATAGCCAACAGCTTCTATGAAGTGTTTGAAAAACATCCCCACTTTATAGATGTTTTTGTT

CATTTTGGTATAGCACAATCTTCTACCAGAGGTGGCAGTAGAGTTGAAGGGATTTTTGCAGGATTGTTTATGAATGC

CTATGGTGCAGGGCAAGTGATGTTACGGTGGGGAGTCTTAGCAAAATCAGTTAAAAATATTATGTTAGGACATGCTA

GTGTGCAAGCAGAAATGGAACAAGTTGTTGAGGTTTATGAATATGCCCAAAAATTGGGTGGTGAAGCAGGATTCTAC

CATATATTGAACAACCCAAAAGCATCATTATTATCTTTGACTCAATTTCCTCACTTCTCCAGTGTAGTATTAGGCAA

TGCTGCTGGCCTAGGCATAATGGGAGAGTACAGAGGTACACCGAGGAATCAAGATCTATATGATGCAGCAAAGGCAT

ATGCTGAACAACTCAAAGAAAATGGTGTGATTAACTACAGTGTACTAGACTTGACAGCAGAAGAACTAGAGGCTATC

AAACATCAGCTTAATCCAAAAGATAATGATGTAGAGCTTTGAGTTAATAAAAAATGGGGCAAATAAATCATCATGGA

AAAGTTTGCTCCTGAATTCCATGGAGAAGATGCAAACAACAGGGCTACTAAATTCCTAGAATCAATAAAGGGCAAAT

TCACATCACCCAAAGATCCCAAGAAAAAAGATAGTATCATATCTGTCAACTCAATAGATATAGAAGTAACCAAAGAA

AGCCCTATAACATCAAATTCAACTATTATCAACCCAACAAATGAGACAGATGATACTGCAGGGAACAAGCCCAATTA

TCAAAGAAAACCTCTAGTAAGTTTCAAAGAAGACCCTACACCAAGTGATAATCCCTTTTCTAAACTATACAAAGAAA

CCATAGAAACATTTGATAACAATGAAGAAGAATCCAGCTATTCATACGAAGAAATAAATGATCAGACAAACGATAAT

ATAACAGCAAGATTAGATAGGATTGATGAAAAATTAAGTGAAATACTAGGAATGCTTCACACATTAGTAGTGGCAAG

TGCAGGACCTACATCTGCTCGGGATGGTATAAGAGATGCCATGGTTGGTTTAAGAGAAGAAATGATAGAAAAAATCA

GAACTGAAGCATTAATGACCAATGACAGATTAGAAGCTATGGCAAGACTCAGGAATGAGGAAAGTGAAAAGATGGCA

AAAGACACATCAGATGAAGTGTCTCTCAATCCAACATCAGAGAAATTGAACAACCTATTGGAAGGGAATGATAGTGA

CAATGATCTATCACTTGAAGATTTCTGATTAGTTACCAATCTTCACATCAACACACAATACCAACAGAAGACCAACA

AACTAACCAACCCAATCATCCAACCAAACATCCATCCGCCAATCAGCCAAACAGCCAACAAAACAACCAGCCAATCC

AAAACTAACCACCCGGAAAAAATCTATAATATAGTTACAAAAAAAGGAAAGGGTGGGGCAAATATGGAAACATACGT

GAACAAGCTTCACGAAGGCTCCACATACACAGCTGCTGTTCAATACAATGTCTTAGAAAAAGACGATGACCCTGCAT

-continued

CACTTACAATATGGGTGCCCATGTTCCAATCATCTATGCCAGCAGATTTACTTATAAAAGAACTAGCTAATGTCAAC

ATACTAGTGAAACAAATATCCACACCCAAGGGACCTTCACTAAGAGTCATGATAAACTCAAGAAGTGCAGTGCTAGC

ACAAATGCCCAGCAAATTTACCATATGCGCTAATGTGTCCTTGGATGAAAGAAGCAAACTAGCATATGATGTAACCA

CACCCTGTGAAATCAAGGCATGTAGTCTAACATGCCTAAAATCAAAAAATATGTTGACTACAGTTAAAGATCTCACT

ATGAAGACACTCAACCCTACACATGATATTATTGCTTTATGTGAATTTGAAAACATAGTAACATCAAAAAAAGTCAT

AATACCAACATACCTAAGATCCATCAGTGTCAGAAATAAAGATCTGAACACACTTGAAAATATAACAACCACTGAAT

TCAAAAATGCTATCACAAATGCAAAAATCATCCCTTACTCAGGATTACTATTAGTCATCACAGTGACTGACAACAAA

GGAGCATTCAAATACATAAAGCCACAAAGTCAATTCATAGTAGATCTTGGAGCTTACCTAGAAAAAGAAAGTATATA

TTATGTTACCACAAATTGGAAGCACACAGCTACACGATTTGCAATCAAACCCATGGAAGATTAACCTTTTTCCTCTA

CATCAGTGTGTTAATTCATACAAACTTTCTACCTACATTCTTCACTTCACCATCACAATCACAAACACTCTGTGGTT

CAACCAATCAAACAAAACTTATCTGAAGTCCCAGATCATCCCAAGTCATTGTTTATCAGATCTAGTACTCAAATAAG

TTAATAAAAAATATACACATGGGGCAAATAATCATTGGAGGAAATCCAACTAATCACAATATCTGTTAACATAGACA

AGTCCACACACCATACAGAATCAACCAATGGAAAATACATCCATAACAATAGAATTCTCAAGCAAATTCTGGCCTTA

CTTTACACTAATACACATGATCACAACAATAATCTCTTTGCTAATCATAATCTCCATCATGATTGCAATACTAAACA

AACTTTGTGAATATAACGTATTCCATAACAAAACCTTTGAGTTACCAAGAGCTCGAGTTAATACTTGATAAAGTAGT

TAATTAAAAATAGTCATAACAATGAACTAGGATATCAAGACTAACAATAACATTGGGGCAAATGCAAACATGTCCAA

AAACAAGGACCAACGCACCGCTAAGACATTAGAAAGGACCTGGGACACTCTCAATCATTTATTATTCATATCATCGT

GCTTATATAAGTTAAATCTTAAATCTGTAGCACAAATCACATTATCCATTCTGGCAATGATAATCTCAACTTCACTT

ATAATTGCAGCCATCATATTCATAGCCTCGGCAAACCACAAAGTCACACCAACAACTGCAATCATACAAGATGCAAC

AAGCCAGATCAAGAACACAACCCCAACATACCTCACCCAGAATCCTCAGCTTGGAATCAGTCCCTCTAATCCGTCTG

AAATTACATCACAAATCACCACCATACTAGCTTCAACAACACCAGGAGTCAAGTCAACCCTGCAATCCACAACAGTC

AAGACCAAAAACACAACAACAACTCAAACACAACCCAGCAAGCCCACCACAAAACAACGCCAAAACAAACCCACCAAG

CAAACCCAATAATGATTTTCACTTTGAAGTGTTCAACTTTGTACCCTGCAGCATATGCAGCAACAATCCAACCTGCT

GGGCTATCTGCAAAAGAATACCAAACAAAAAACCAGGAAAGAAAACCACTACCAAGCCCACAAAAAAACCAACCCTC

AAGACAACCAAAAAAGATCCCAAACCTCAAACCACTAAATCAAAGGAAGTACCCACCACCAAGCCCACAGAAGAGCC

AACCATCAACACCACCAAAACAAACATCATAACTACACTACTCACCTCCAACACCACAGGAAATCCAGAACTCACAA

GTCAAATGGAAACCTTCCACTCAACTTCCTCCGAAGGCAATCCAAGCCCTTCTCAAGTCTCTACAACATCCGAGTAC

CCATCACAACCTTCATCTCCACCCAACACACCACGCCAGTAGTTACTTAAAAACATATTATCACAAAAGGCCTTGAC

CAACTTAAACAGAATCAAAATAAACTCTGGGGCAAATAACAATGGAGTTGCTAATCCTCAAAGCAAATGCAATTACC

ACAATCCTCACTGCAGTCACATTTTGTTTTGCTTCTGGTCAAAACATCACTGAAGAATTTTATCAATCAACATGCAG

TGCAGTTAGCAAAGGCTATCTTAGTGCTCTGAGAACTGGTTGGTATACCAGTGTTATAACTATAGAATTAAGTAATA

TCAAGAAAAATAAGTGTAATGGAACAGATGCTAAGGTAAAATTGATAAAACAAGAATTAGATAAATATAAAAATGCT

GTAACAGAATTGCAGTTGCTCATGCAAAGCACACAAGCAACAAACAATCGAGCCAGAAGAGAACTACCAAGGTTTAT

GAATTATACACTCAACAATGCCAAAAAAACCAATGTAACATTAAGCAAGAAAAGGAAAAGAAGATTTCTTGGTTTTT

TGTTAGGTGTTGGATCTGCAATCGCCAGTGGCGTTGCTGTATCTAAGGTCCTGCACCTAGAAGGGGAAGTGAACAAG

ATCAAAAGTGCTCTACTATCCACAAACAAGGCTGTAGTCAGCTTATCAAATGGAGTTAGTGTTTTAACCAGCAAAGT

GTTAGACCTCAAAAACTATATAGATAAACAATTGTTACCTATTGTGAACAAGCAAAGCTGCAGCATATCAAATATAG

AAACTGTGATAGAGTTCCAACAAAAGAACAACAGACTACTAGAGATTACCAGGGAATTTAGTGTTAATGCAGGCGTA

ACTACACCTGTAAGCACTTACATGTTAACTAATAGTGAATTATTGTCATTAATCAATGATATGCCTATAACAAATGA

TCAGAAAAAGTTAATGTCCAACAATGTTCAAATAGTTAGACAGCAAAGTTACTCTATCATGTCCATAATAAAAGAGG

AAGTCTTAGCATATGTAGTACAATTACCACTATATGGTGTTATAGATACACCCTGTTGGAAACTACACACATCCCCT

-continued

CTATGTACAACCAACACAAAAGAAGGGTCCAACATCTGTTTAACAAGAACTGACAGAGGATGGTACTGTGACAATGC

AGGATCAGTATCTTTCTTCCCACAAGCTGAAACATGTAAAGTTCAATCAAATCGAGTATTTTGTGACACAATGAACA

GTTTAACATTACCAAGTGAAGTAAATCTCTGCAATGTTGACATATTCAACCCCAAATATGATTGTAAAATTATGACT

TCAAAAACAGATGTAAGCAGCTCCGTTATCACATCTCTAGGAGCCATTGTGTCATGCTATGGCAAAACTAAATGTAC

AGCATCCAATAAAAATCGTGGAATCATAAAGACATTTTCTAACGGGTGCGATTATGTATCAAATAAAGGGGTGGACA

CTGTGTCTGTAGGTAACACATTATATTATGTAAATAAGCAAGAAGGTAAAAGTCTCTATGTAAAAGGTGAACCAATA

ATAAATTTCTATGACCCATTAGTATTCCCCTCTGATGAATTTGATGCATCAATATCTCAAGTCAACGAGAAGATTAA

CCAGAGCCTAGCATTTATTCGTAAATCCGATGAATTATTACATAATGTAAATGCTGGTAAATCCACCACAAATATCA

TGATAACTACTATAATTATAGTGATTATAGTAATATTGTTATCATTAATTGCTGTTGGACTGCTCTTATACTGTAAG

GCCAGAAGCACACCAGTCACACTAAGCAAAGATCAACTGAGTGGTATAAATAATATTGCATTTAGTAACTAAATAAA

AATAGCACCTAATCATGTTCTTACAATGGTTTACTATCTGCTCATAGACAACCCATCTGTCATTGGATTTTCTTAAA

ATCTGAACTTCATCGAAACTCTCATCTATAAACCATCTCACTTACACTATTTAAGTAGATTCCTAGTTTATAGTTAT

ATAAAACACAATTGCATGCCAGATTAACTTACCATCTGTAAAAATGAAAACTGGGGCAAATATGTCACGAAGGAATC

CTTGCAAATTTGAAATTCGAGGTCATTGCTTAAATGGTAAGAGGTGTCATTTTAGTCATAATTATTTTGAATGGCCA

CCCCATGCACTGCTTGTAAGACAAAACTTTATGTTAAACAGAATACTTAAGTCTATGGATAAAAGTATAGATACCTT

ATCAGAAATAAGTGGAGCTGCAGAGTTGGACAGAACAGAAGAGTATGCTCTTGGTGTAGTTGGAGTGCTAGAGAGTT

ATATAGGATCAATAAACAATATAACTAAACAATCAGCATGTGTTGCCATGAGCAAACTCCTCACTGAACTCAATAGT

GATGATATCAAAAAGCTGAGGGACAATGAAGAGCTAAATTCACCCAAGATAAGAGTGTACAATACTGTCATATCATA

TATTGAAAGCAACAGGAAAAACAATAAACAAACTATCCATCTGTTAAAAAGATTGCCAGCAGACGTATTGAAGAAAA

CCATCAAAAACACATTGGATATCCATAAGAGCATAACCATCAACAACCCAAAAGAATCAACTGTTAGTGATACAAAT

GACCATGCCAAAAATAATGATACTACCTGACAAATATCCTTGTAGTATAACTTCCATACTAATAACAAGTAGATGTA

GAGTTACTATGTATAATCAAAAGAACACACTATATTTCAATCAAAACAACCCAAATAACCATATGTACTCACCGAAT

CAAACATTCAATGAAATCCATTGGACCTCTCAAGAATTGATTGACACAATTCAAAATTTTCTACAACATCTAGGTAT

TATTGAGGATATATATACAATATATATATTAGTGTCATAACACTCAATTCTAACACTCACCACATCGTTACATTATT

AATTCAAACAATTCAAGTTGTGGGACAAAATGGATCCCATTATTAATGGAAATTCTGCTAATGTTTATCTAACCGAT

AGTTATTTAAAAGGTGTTATCTCTTTCTCAGAGTGTAATGCTTTAGGAAGTTACATATTCAATGGTCCTTATCTCAA

AAATGATTATACCAACTTAATTAGTAGACAAAATCCATTAATAGAACACATGAATCTAAAGAAACTAAATATAACAC

AGTCCTTAATATCTAAGTATCATAAAGGTGAAATAAAATTAGAAGAACCTACTTATTTTCAGTCATTACTTATGACA

TACAAGAGTATGACCTCGTCAGAACAGATTGCTACCACTAATTTACTTAAAAAGATAATAAGAAGAGCTATAGAAAT

AAGTGATGTCAAAGTCTATGCTATATTGAATAAACTAGGGCTTAAAGAAAAGGACAAGATTAAATCCAACAATGGAC

AAGATGAAGACAACTCAGTTATTACGACCATAATCAAAGATGATATACTTTCAGCTGTTAAAGATAATCAATCTCAT

CTTAAAGCAGACAAAAATCACTCTACAAAACAAAAAGACACAATCAAAACAACACTCTTGAAGAAATTGATGTGTTC

AATGCAACATCCTCCATCATGGTTAATACATTGGTTTAACTTATACACAAAATTAAACAACATATTAACACAGTATC

GATCAAATGAGGTAAAAAACCATGGGTTTACATTGATAGATAATCAAACTCTTAGTGGATTTCAATTTATTTTGAAC

CAATATGGTTGTATAGTTTATCATAAGGAACTCAAAAGAATTACTGTGACAACCTATAATCAATTCTTGACATGGAA

AGATATTAGCCTTAGTAGATTAAATGTTTGTTTAATTACATGGATTAGTAACTGCTTGAACACATTAAATAAAAGCT

TAGGCTTAAGATGCGGATTCAATAATGTTATCTTGACACAACTATTCCTTTATGGAGATTGTATACTAAAGCTATTT

CACAATGAGGGGTTCTACATAATAAAAGAGGTAGAGGGATTTATTATGTCTCTAATTTTAAATATAACAGAAGAAGA

TCAATTCAGAAAACGATTTTATAATAGTATGCTCAACAACATCACAGATGCTGCTAATAAAGCTCAGAAAAATCTGC

TATCAAGAGTATGTCATACATTATTAGATAAGACAGTGTCCGATAATATAATAAATGGCAGATGGATAATTCTATTA

-continued

AGTAAGTTCCTTAAATTAATTAAGCTTGCAGGTGACAATAACCTTAACAATCTGAGTGAACTATATTTTTTGTTCAG

AATATTTGGACACCCAATGGTAGATGAAAGACAAGCCATGGATGCTGTTAAAATTAATTGCAATGAGACCAAATTTT

ACTTGTTAAGCAGTCTGAGTATGTTAAGAGGTGCCTTTATATATAGAATTATAAAAGGGTTTGTAAATAATTACAAC

AGATGGCCTACTTTAAGAAATGCTATTGTTTTACCCTTAAGATGGTTAACTTACTATAAACTAAACACTTATCCTTC

TTTGTTGGAACTTACAGAAAGAGATTTGATTGTGTTATCAGGACTACGTTTCTATCGTGAGTTTCGGTTGCCTAAAA

AAGTGGATCTTGAAATGATTATAAATGATAAAGCTATATCACCTCCTAAAAATTTGATATGGACTAGTTTCCCTAGA

AATTACATGCCATCACACATACAAAACTATATAGAACATGAAAAATTAAAATTTTCCGAGAGTGATAAATCAAGAAG

AGTATTAGAGTATTATTTAAGAGATAACAAATTCAATGAATGTGATTTATACAACTGTGTAGTTAATCAAAGTTATC

TCAACAACCCTAATCATGTGGTATCATTGACAGGCAAAGAAAGAGAACTCAGTGTAGGTAGAATGTTTGCAATGCAA

CCGGGAATGTTCAGACAGGTTCAAATATTGGCAGAGAAAATGATAGCTGAAAACATTTTACAATTCTTTCCTGAAAG

TCTTACAAGATATGGTGATCTAGAACTACAAAAAATATTAGAACTGAAAGCAGGAATAAGTAACAAATCAAATCGCT

ACAATGATAATTACAACAATTACATTAGTAAGTGCTCTATCATCACAGATCTCAGCAAATTCAATCAAGCATTTCGA

TATGAAACGTCATGTATTTGTAGTGATGTGCTGGATGAACTGCATGGTGTACAATCTCTATTTTCCTGGTTACATTT

AACTATTCCTCATGTCACAATAATATGCACATATAGGCATGCACCCCCCTATATAGGAGATCATATTGTAGATCTTA

ACAATGTAGATGAACAAAGTGGATTATATAGATATCACATGGGTGGCATCGAAGGGTGGTGTCAAAAACTATGGACC

ATAGAAGCTATATCACTATTGGATCTAATATCTCTCAAAGGGAAATTCTCAATTACTGCTTTAATTAATGGTGACAA

TCAATCAATAGATATAAGCAAACCAATCAGACTCATGGAAGGTCAAACTCATGCTCAAGCAGATTATTTGCTAGCAT

TAAATAGCCTTAAATTACTGTATAAAGAGTATGCAGGCATAGGCCACAAATTAAAAGGAACTGAGACTTATATATCA

CGAGATATGCAATTTATGAGTAAAACAATTCAACATAACGGTGTATATTACCCAGCTAGTATAAAGAAAGTCCTAAG

AGTGGGACCGTGGATAAACACTATACTTGATGATTTCAAAGTGAGTCTAGAATCTATAGGTAGTTTGACACAAGAAT

TAGAATATAGAGGTGAAAGTCTATTATGCAGTTTAATATTTAGAAATGTATGGTTATATAATCAGATTGCTCTACAA

TTAAAAAATCATGCATTATGTAACAATAAACTATATTTGGACATATTAAAGGTTCTGAAACACTTAAAAACCTTTTT

TAATCTTGATAATATTGATACAGCATTAACATTGTATATGAATTTACCCATGTTATTTGGTGGTGGTGATCCCAACT

TGTTATATCGAAGTTTCTATAGAAGAACTCCTGACTTCCTCACAGAGGCTATAGTTCACTCTGTGTTCATACTTAGT

TATTATACAAACCATGACTTAAAAGATAAACTTCAAGATCTGTCAGATGATAGATTGAATAAGTTCTTAACATGCAT

AATCACGTTTGACAAAAACCCTAATGCTGAATTCGTAACATTGATGAGAGATCCTCAAGCTTTAGGGTCTGAGAGAC

AAGCTAAAATTACTAGCGAAATCAATAGACTGGCAGTTACAGAGGTTTTGAGTACAGCTCCAAACAAAATATTCTCC

AAAAGTGCACAACATTATACTACTACAGAGATAGATCTAAATGATATTATGCAAAATATAGAACCTACATATCCTCA

TGGGCTAAGAGTTGTTTATGAAAGTTTACCCTTTTATAAAGCAGAGAAAATAGTAAATCTTATATCAGGTACAAAAT

CTATAACTAACATACTGGAAAAAACTTCTGCCATAGACTTAACAGATATTGATAGAGCCACTGAGATGATGAGGAAA

AACATAACTTTGCTTATAAGGATACTTCCATTGGATTGTAACAGAGATAAAAGAGAGATATTGAGTATGGAAAACCT

AAGTATTACTGAATTAAGCAAATATGTTAGGGAAAGATCTTGGTCTTTATCCAATATAGTTGGTGTTACATCACCCA

GTATCATGTATACAATGGACATCAAATATACTACAAGCACTATATCTAGTGGCATAATTATAGAGAAATATAATGTT

AACAGTTTAACACGTGGTGAGAGAGGACCCACTAAACCATGGGTTGGTTCATCTACACAAGAGAAAAAAACAATGCC

AGTTTATAATAGACAAGTCTTAACCAAAAAACAGAGAGATCAAATAGATCTATTAGCAAAATTGGATTGGGTGTATG

CATCTATAGATAACAAGGATGAATTCATGGAAGAACTCAGCATAGGAACCCTTGGGTTAACATATGAAAAGGCCAAG

AAATTATTTCCACAATATTTAAGTGTCAATTATTTGCATCGCCTTACAGTCAGTAGTAGACCATGTGAATTCCCTGC

ATCAATACCAGCTTATAGAACAACAAATTATCACTTTGACACTAGCCCTATTAATCGCATATTAACAGAAAAGTATG

GTGATGAAGATATTGACATAGTATTCCAAAACTGTATAAGCTTTGGCCTTAGTTTAATGTCAGTAGTAGAACAATTT

ACTAATGTATGTCCTAACAGAATTATTCTCATACCTAAGCTTAATGAGATACATTTGATGAAACCTCCCATATTCAC

AGGTGATGTTGATATTCACAAGTTAAAACAAGTGATACAAAAACAGCATATGTTTTTACCAGACAAAATAAGTTTGA

-continued

CTCAATATGTGGAATTATTCTTAAGTAATAAAACACTCAAATCTGGATCTCATGTTAATTCTAATTTAATATTGGCA

CATAAAATATCTGACTATTTTCATAATACTTACATTTTAAGTACTAATTTAGCTGGACATTGGATTCTGATTATACA

ACTTATGAAAGATTCTAAAGGTATTTTTGAAAAAGATTGGGGAGAGGGATATATAACTGATCATATGTTTATTAATT

TGAAAGTTTTCTTCAATGCTTATAAGACCTATCTCTTGTGTTTTCATAAAGGTTATGGCAAAGCAAAGCTGGAGTGT

GATATGAACACTTCAGATCTTCTATGTGTATTGGAATTAATAGACAGTAGTTATTGGAAGTCTATGTCTAAGGTATT

TTTAGAACAAAAAGTTATCAAATACATTCTTAGCCAAGATGCAAGTTTACATAGAGTAAAAGGATGTCATAGCTTCA

AATTATGGTTTCTTAAACGTCTTAATGTAGCAGAATTCACAGTTTGCCCTTGGGTTGTTAACATAGATTATCATCCA

ACACATATGAAAGCAATATTAACTTATATAGATCTTGTTAGAATGGGATTGATAAATATAGATAGAATACACATTAA

AAATAAACACAAATTCAATGATGAATTTTATACTTCTAATCTCTTCTACATTAATTATAACTTCTCAGATAATACTC

ATCTATTAACTAAACATATAAGGATTGCTAATTCTGAATTAGAAAATAATTACAACAAATTATATCATCCTACACCA

GAAACCCTAGAGAATATACTAGCCAATCCGATTAAAAGTAATGACAAAAAGACACTGAATGACTATTGTATAGGTAA

AAATGTTGACTCAATAATGTTACCATTGTTATCTAATAAGAAGCTTATTAAATCGTCTGCAATGATTAGAACCAATT

ACAGCAAACAAGATTTGTATAATTTATTCCCTATGGTTGTGATTGATAGAATTATAGATCATTCAGGCAATACAGCC

AAATCCAACCAACTTTACACTACTACTTCCCACCAAATATCCTTAGTGCACAATAGCACATCACTTTACTGCATGCT

TCCTTGGCATCATATTAATAGATTCAATTTTGTATTTAGTTCTACAGGTTGTAAAATTAGTATAGAGTATATTTTAA

AAGATCTTAAAATTAAAGATCCCAATTGTATAGCATTCATAGGTGAAGGAGCAGGGAATTTATTATTGCGTACAGTA

GTGGAACTTCATCCTGACATAAGATATATTTACAGAAGTCTGAAAGATTGCAATGATCATAGTTTACCTATTGAGTT

TTTAAGGCTGTACAATGGACATATCAACATTGATTATGGTGAAAATTTGACCATTCCTGCTACAGATGCAACCAACA

ACATTCATTGGTCTTATTTACATATAAAGTTTGCTGAACCTATCAGTCTTTTTGTCTGTGATGCCGAATTGTCTGTA

ACAGTCAACTGGAGTAAAATTATAATAGAATGGAGCAAGCATGTAAGAAAGTGCAAGTACTGTTCCTCAGTTAATAA

ATGTATGTTAATAGTAAAATATCATGCTCAAGATGATATTGATTTCAAATTAGACAATATAACTATATTAAAAACTT

ATGTATGCTTAGGCAGTAAGTTAAAGGGATCGGAGGTTTACTTAGTCCTTACAATAGGTCCTGCGAATATATTCCCA

GTATTTAATGTAGTACAAAATGCTAAATTGATACTATCAAGAACCAAAAATTTCATCATGCCTAAGAAAGCTGATAA

AGAGTCTATTGATGCAAATATTAAAAGTTTGATACCCTTTCTTTGTTACCCTATAACAAAAAAAGGAATTAATACTG

CATTGTCAAAACTAAAGAGTGTTGTTAGTGGAGATATACTATCATATTCTATAGCTGGACGTAATGAAGTTTTCAGC

AATAAACTTATAAATCATAAGCATATGAACATCTTAAAATGGTTCAATCATGTTTTAAATTTCAGATCAACAGAACT

AAACTATAACCATTTATATATGGTAGAATCTACATATCCTTACCTAAGTGAATTGTTAAACAGCTTGACAACCAATG

AACTTAAAAAACTGATTAAAATCACAGGTAGTCTGTTATACAACTTTCATAATGAATAATGAATAAAGATCTTATAA

TAAAAATTCCCATAGCTATACACTAACACTGTATTCAATTATAGTTATAAAAATTAAAAATGGTACCATGGGGCAAA

TAAGAATTTGATAAGTACCACTTAAATTTAACTCCCTTGGTTAGAGATGGGCAGCAATTCATTGAGTATGATAAAAG

TTAGATTACAAAATTTGTTTGACAATGATGAAGTAGCATTGTTAAAAATAACATGCTATACTGATAAATTAATACAT

TTAACTAATGCTTTGGCTAAGGCAGTGATACATACAATCAAATTGAATGGCATTGTGTTTGTGCATGTTATTACAAG

TAGTGATATTTGCCCTAATAATAATATTGTAGTAAAATCCAATTTCACAACAATGCCAGTACTACAAAATGGAGGTT

ATATATGGGAAATGATGGAATTAACACATTGCTCTCAACCTAATGGTCTACTAGATGACAATTGTGAAATTAAATTC

TCCAAAAAACTAAGTGATTCAACAATGACCAATTATATGAATCAATTATCTGAATTACTTGGATTTGATCTTAATCC

ATAAATTATAATTAATATCAACTAGCAAATCAATGTCACTAACACCATTAGTTAATATAAAACTTAACAGAAGACAA

AAATCTTAAGGAGAGATATAAGATAGAAGATGGTACCATTTTTTAAATAACTTTTAGTGAACTAATCCTAAAGTTAT

CATTTTAATCTTGGAGGAATAAATTTAAACCCTAATCTAATTGGTTTATATGTGTATTAACTAAATTACGAGATATT

AGTTTTTGACACTTTTTTTCTCGT

EXAMPLES

In summary, the materials, information, and methods described in this disclosure provide an array of attenuated strains with graded attenuation phenotypes, and provide guidance in selecting suitable vaccine candidate strains based on clinical benchmarks. The following examples are provided by way of illustration, not limitation.

Example 1

This example illustrates design, construction, and recovery of recombinant RSV 6120/NS12FM2/GFP and 6120/NS12FM2.

The RSV antigenome that was used for constructing 6120/NS12FM2/GFP was the "6120" derivative of the unmodified WT RSV strain A2 antigenomic cDNA called D46 (or D53). D46/D53 is the basis for the present reverse genetics system (Collins, et al. 1995. Proc Natl Acad Sci USA 92:11563-11567), and its complete sequence is shown in U.S. Pat. No. 6,790,449 and in GenBank KT992094, with a single difference at position 1938 (in the N gene ORF) compared to the constructs in the present invention. Specifically, the nucleotide assignment at position 1938 in U.S. Pat. No. 6,790,449 and in GenBank KT992094 is A, but in the sequences provided herein it is G. This difference does not change amino acid coding and is understood to be inconsequential. The 6120 derivative contained a 112-nucleotide deletion of the downstream non-translated region of the SH gene together with 5 nucleotide substitutions that involve the last three codons and stop codon of the SH ORF and do not change amino acid coding (Bukreyev, et al. 2001. J Virol 75:12128-12140). In addition, the antigenome cDNA had previously been modified to contain a gene encoding enhanced green fluorescent protein (GFP) inserted between the RSV P and M genes as the third gene (Munir et al 2008 J Virol 82:8780-8796). Insertion of a GFP gene in the first gene position was previously shown to have little or no effect on RSV replication or pathogenesis in cell lines and in an in vitro human airway epithelium (HAE) culture (Zhang et al 2002 J Virol 76:5654-5666), and the same appeared to be the case for GFP inserted between the P and M genes (Munir et al 2008 J Virol 82:8780-8796). The purpose of expressing GFP from the viral genome was to facilitate monitoring infection in initial experiments, because it allows visualization of infections in live cells without interfering with the infection. GFP is often used in this fashion in initial experiments. Note that the GFP gene was not included in the gene position numbering.

The top part of FIG. 1 (above the "RSV genome" diagram) illustrates the deletion of the NS1 and NS2 ORFs along with most of their flanking gene sequences from their native positions 1 and 2 in the genome. This deletion has the result of fusing the upstream nontranslated region of the NS1 gene to the N gene ORF. The bottom part of the FIG. 1 (below the "RSV genome" diagram) illustrates the creation of a KpnI site in the intergenic region between the F and M2 genes and the insertion of an NS1/NS2 gene cassette at this site. In 6120/NS12FM2/GFP, the NS1 and NS2 genes were shifted by recombinant DNA methods from their native positions 1 and 2 in the RSV antigenomic cDNA to positions 7 and 8. Note that the GFP gene was not included in the gene position numbering. The shifts are shown in FIG. 1. The recombinant RSV 6120/NS12FM2/GFP virus was recovered by reverse genetics.

For a final vaccine product, GFP preferably would not be present. Therefore, site-directed mutagenesis was used to remove the GFP gene from the RSV 6120/NS12FM2/GFP cDNA, creating RSV 6120/NS12FM2. This construct otherwise is identical to that shown in FIG. 1. RSV 6120/NS12FM2 was recovered by reverse genetics and was found to replicate similarly to RSV 6120/NS12FM2/GFP in Vero cells.

With regard to nomenclature, note that of necessity there is some flexibility in usage. For example, 6120/NS12FM2/ΔNS2 also can be referred to as 6120_NS12FM2_ΔNS2 and to 6120_NS12FM2_DNS2 (reflecting that some symbols can be altered in silico), or 6120/NS12FM2/ΔNS2, or 6120/NS12FM2/ΔNS2, or 6120NS12FM2/ΔNS2, etc. As another example, RSV 6120/NS12FM2 is equivalent to 6120/NS12FM2 (some descriptors are not essential to the meaning). As another example, various names can be abbreviated for simplicity, as will be noted in the text; for example, 6120/NS12FM2 can be abbreviated as F-M2.

Example 2

This example illustrates design and construction of rRSV 6120/NS12Ltr/GFP and 6120/NS12Ltr.

The RSV antigenome that was used for constructing 6120/NS12Ltr/GFP was the "6120" derivative of the WT RSV antigenomic cDNA, which also contained the GFP gene between the viral M and P genes, as described in Example 1.

In RSV 6120/NS12Ltr/GFP, the NS1 and NS2 genes were shifted by recombinant DNA methods from their native positions 1 and 2 in the antigenomic cDNA to positions 9 and 10. Note that the GFP gene is not included in gene position numbering. The top part of the FIG. 2 (above the "RSV genome" diagram) illustrates the deletion of the NS1 and NS2 ORFs as in FIG. 1. The bottom part of FIG. 2 (below the "RSV genome" diagram) illustrates the creation of a KpnI site in the trailer region shortly after the L gene, and the insertion of an NS1/NS2 gene cassette at this site. The RSV 6120/NS12Ltr/GFP virus was recovered by reverse genetics.

In addition, a subsequent version called RSV 6120/NS12Ltr was constructed, in which the GFP gene was deleted by site-directed mutagenesis. This construct otherwise is identical to that shown in FIG. 2.

Example 3

This example describes the replication characteristics of the recombinant RSV 6120/NS12FM2/GFP.

The kinetics and yield of multi-cycle replication of recombinant RSV 6120/NS12FM2/GFP (F-M2) virus was compared to that of wt RSV/GFP (wt RSV) and RSV ΔNS1/ΔNS2/GFP (delNS1_NS2) in African green monkey Vero cells, which are unable to produce type I interferons in response to virus infection. Note that the wt RSV and delNS1_NS2 viruses also are in the 6120 backbone and contain the GFP gene between viral genes P and M. Thus, the F-M2 virus and the control viruses are based on the same viral backbone and can be compared directly.

Figure 3:
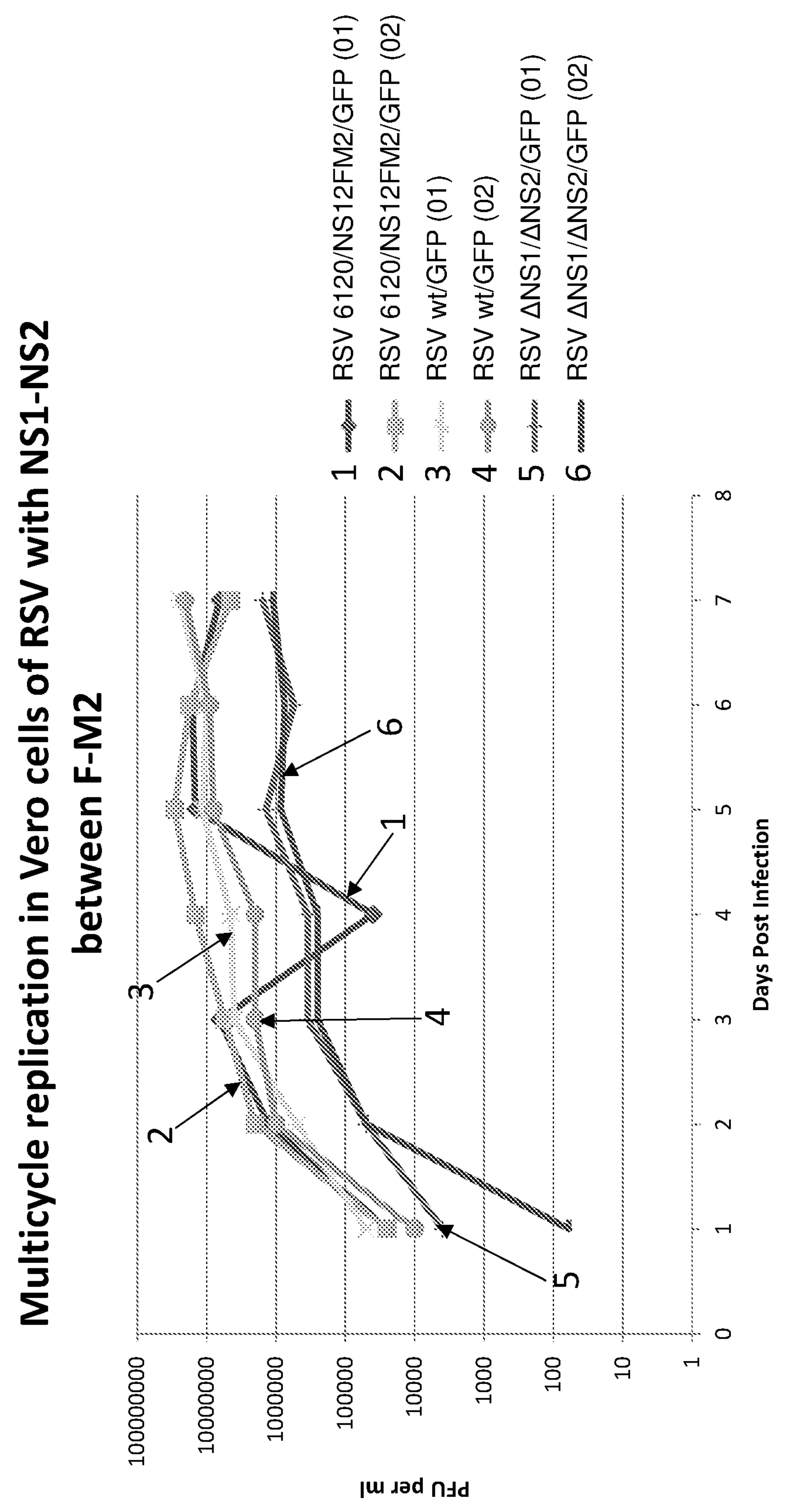
FIG. 3 shows replication of RSV 6120/NS12FM2/GFP, RSV ΔNS1/ΔNS2/GFP and wt RSV/GFP in African green monkey Vero cells.

Two independent cultures (01 and 02) were evaluated per virus, using virus stocks that were prepared in Vero cells and infected at an MOI of 0.01. Following infection, cell supernatant samples were taken daily and subsequently evaluated in parallel by plaque titration in Vero cells. These results showed that the F-M2 virus replicated as efficiently as wt RSV in Vero cells, which is the substrate for vaccine virus manufacture, whereas delNS1_NS2 virus was restricted. See FIG. 3. Thus, the F-M2 virus retains the capacity for efficient vaccine manufacture. This result was not predictable because deletion of NS1 or NS2 has been shown to substantially reduce the efficiency of RSV replication in cell culture, including Vero cells used in vaccine manufacture, because deletion of either or both of these viral proteins results in increased apoptosis resulting in deterioration of the cell monolayer (Bitko et al 2007 J Virol 81:1786-1795). This is evidenced in FIG. 3 by the substantially decreased replication of the delNS1_NS2 mutant. Further, attempts to produce clinical trial material with a ΔNS1 mutant of RSV were unsuccessful because of insufficient titer. The ability of the F-M2 virus to replicate with an efficiency indistinguishable from that of wt RSV indicates that the reduced levels of expression of NS1 and NS2 were sufficient to maintain inhibition of apoptosis sufficient for efficient viral replication.

Figure 4:
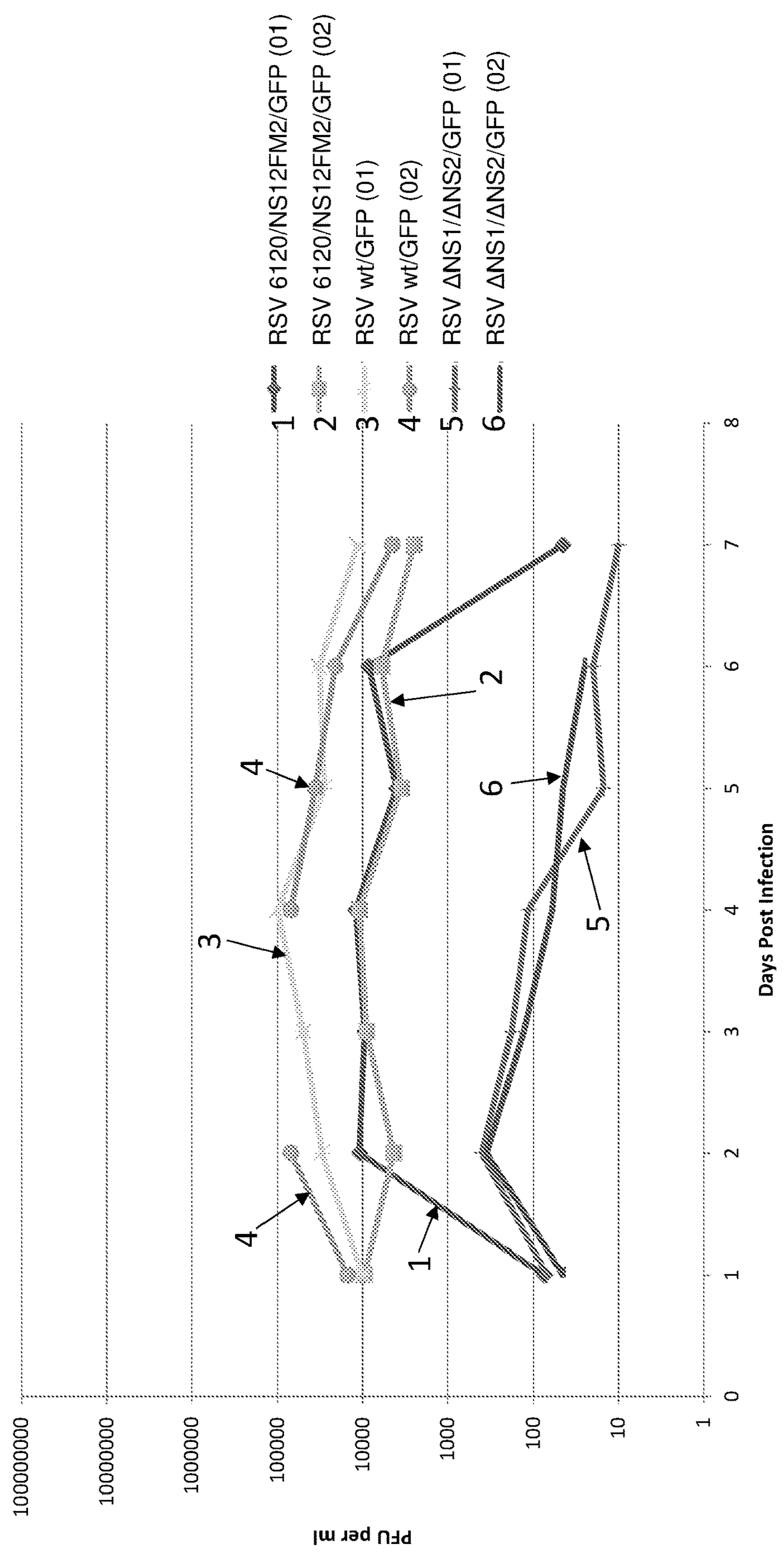
FIG. 4 shows replication of RSV 6120/NS12FM2/GFP, RSV ΔNS1/ΔNS2/GFP and wt RSV/GFP in human airway A549 cells.

A similar comparison of virus replication was performed in parallel in human airway A549 cells, which are competent for interferon responses to viral infection. Infections were performed with the same Vero-grown virus as in FIG. 3, infected at an MOI of 0.01, with virus replication quantified by plaque assay on Vero cells. These results showed that the F-M2 virus replicated less efficiently than wt RSV, but more efficiently than the delNS1_NS2 virus. See FIG. 4. Growth efficiency in A549 cells by viruses with mutation/deletion in the NS1 and NS2 accessory proteins is a marker for attenuation in vivo. A similar ΔNS1ΔNS2 virus has been shown to be over-attenuated in vivo (Jin et al 203 Vaccine 21:3647-3652). The intermediate level of restriction of the F-M2 virus indicates that this gene shift is a useful attenuating mutation in a vaccine virus, either alone or combined with another attenuating mutation.

Example 4

This example describes the replication characteristics of the recombinant RSV 6120/NS12Ltr/GFP.

Figure 5:
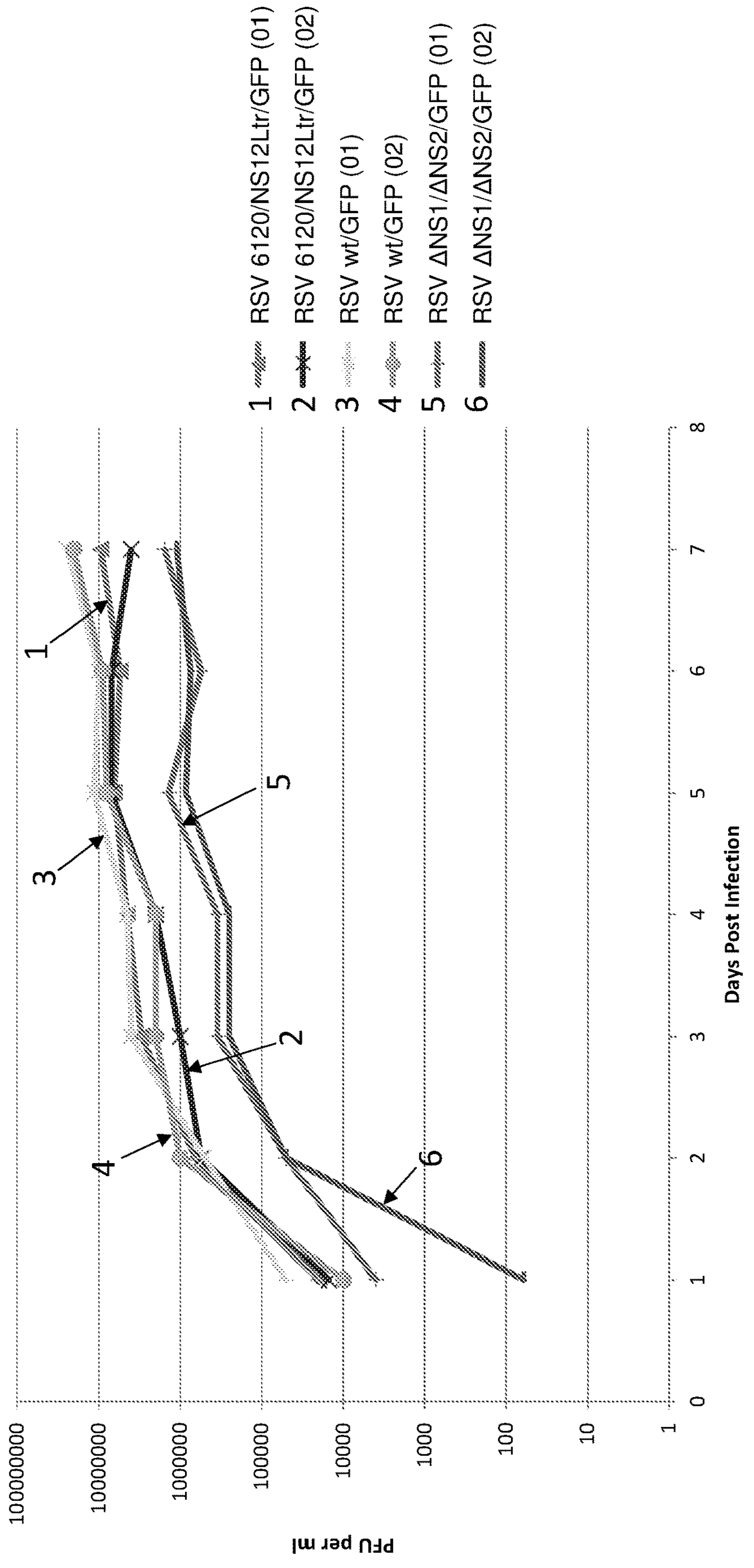
FIG. 5 shows replication of RSV 6120/NS12Ltr/GFP, RSV ΔNS1/ΔNS2/GFP and wt RSV/GFP in African green monkey Vero cells.

The RSV 6120/NS12Ltr/GFP (L-tr) virus was compared to wt RSV/GFP (wt RSV) and RSV ΔNS1/ΔNS2GFP (delNS1_NS2) for multi-cycle replication in Vero cells, following the experimental design in Example 3. These results showed that the L-tr virus replicated as efficiently as wt RSV in Vero cells, and thus retains the capacity for efficient vaccine manufacture. See FIG. 5.

Figure 6:
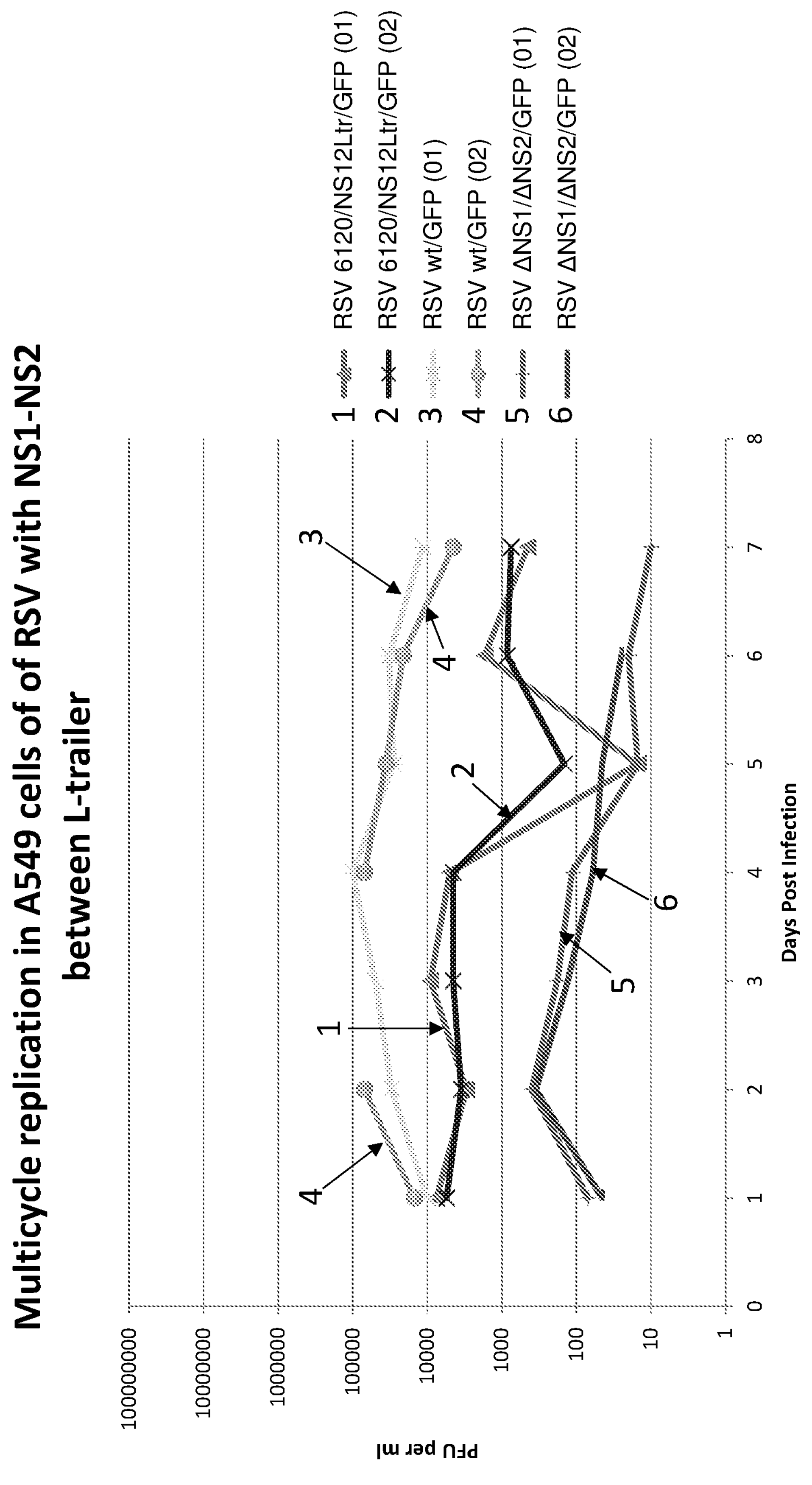
FIG. 6 shows replication of RSV 6120/NS12Ltr/GFP, RSV ΔNS1/ΔNS2/GFP and wt RSV/GFP in human airway A549 cells.

A similar comparison of virus replication was done in parallel in human airway A549 cells. These results showed that the L-tr virus replicated less efficiently than wt RSV, but more efficiently than the delNS1_NS2 virus. See FIG. 6. Furthermore, the L-tr virus replicated less efficiently than the F-M2 virus (see FIG. 4), consistent with the interpretation that moving the NS1 and NS2 genes to increasingly promoter-distal positions increased the level of restriction. This gene shift provided a more attenuated alternative to the F-M2 virus, and is a useful vaccine virus as-is (preferably with the GFP gene deleted) or further modified by the addition of another attenuating mutation.

Example 5

This example describes the deletion of the NS2 gene from RSV 6120/NS12M2F/GFP and RSV 6120/NS12FM2

Figure 7:
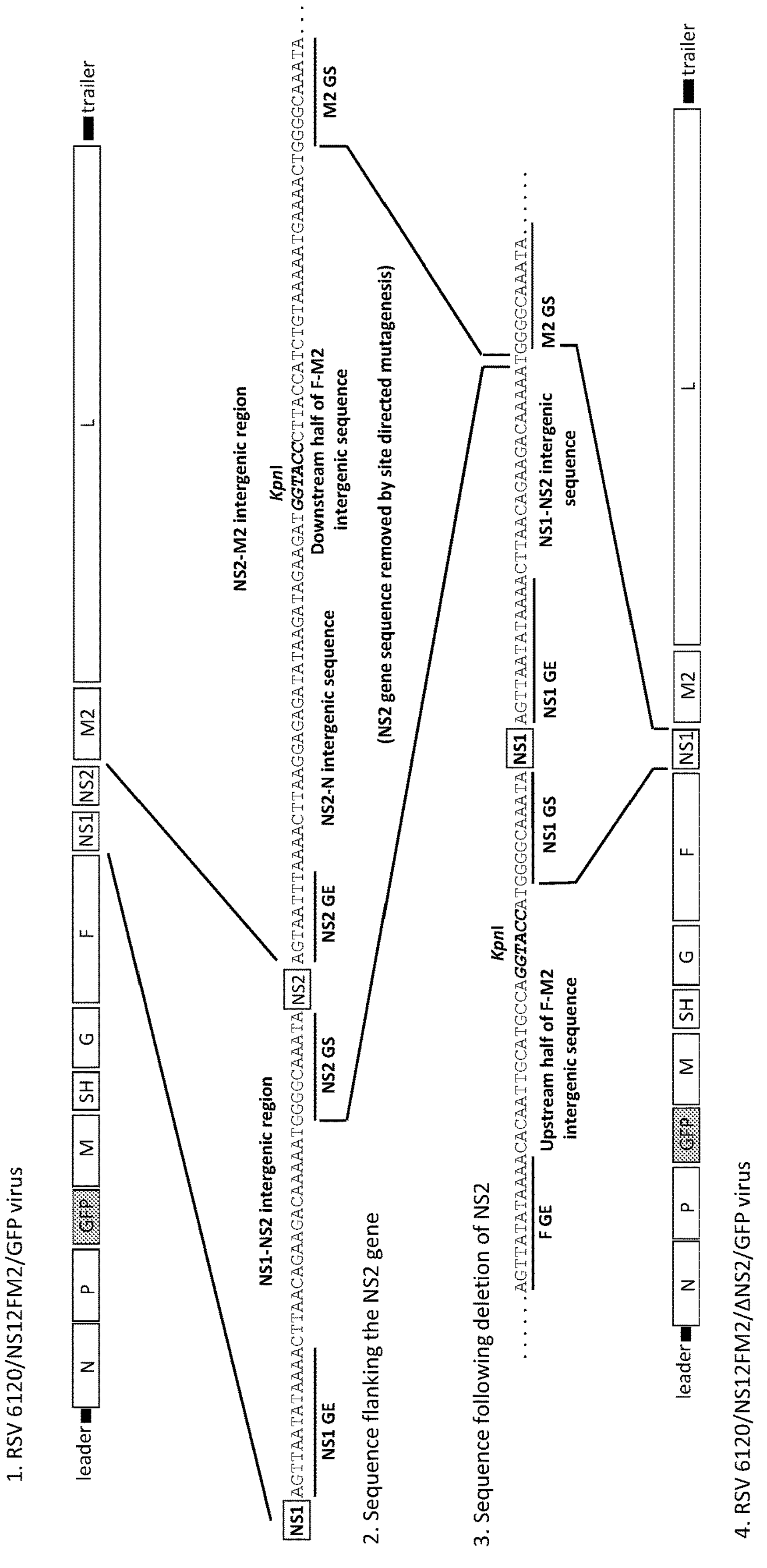
FIG. 7 shows schematic diagrams illustrating the deletion of the NS2 gene from RSV 6120/NS12FM2/GFP. The upper sequence line shows SEQ ID NOs: 18 and 19. The lower sequence line shows SEQ ID NOs: 20 and 21.

To exemplify how gene-shift of NS1 and/or NS2 could be combined with another attenuating mutation, the NS2 gene was deleted from RSV 6120/NS12FM2/GFP and RSV 6120/NS12FM2, resulting in RSV 6120/NS12FM2/ΔNS2/GFP and RSV 6120/NS12FM2/ΔNS2, respectively. The creation of RSV 6120/NS12FM2/ΔNS2/GFP is illustrated in FIG. 7. RSV 6120/NS12FM2/GFP (top), identical to that in FIG. 1, was modified by site-directed mutagenesis to delete the region from the first nucleotide of the GS signal of the NS2 gene to the first nucleotide of the M2-2 gene, inclusive. This deleted the complete NS2 gene as well as the long NS2-M2 intergenic region in 6120/NS12FM2/GFP. Deletion of the NS2 gene on its own has previously been shown to provide a modest amount of attenuation (Whitehead et al 1999 J Virol 73:3438-3442), compared to the much higher level of attenuation associated with deletion of the NS1 gene (Teng et al 2000 J Virol 74:9317-9321). Both viruses were readily recovered by reverse genetics.

Example 6

This example describes the deletion of the NS2 gene from RSV 6120/NS12Ltr/GFP and RSV 6120/NS12Ltr.

The NS2 gene was also deleted from RSV 6120/NS12Ltr/GFP and RSV 6120/NS12Ltr, resulting in RSV 6120/NS12Ltr/ΔNS2/GFP and RSV 6120/NS12Ltr/ΔNS2. The creation of RSV 6120/NS12Ltr/ΔNS2/GFP is shown in FIG. 8. RSV 6120/NS12Ltr/GFP (top), identical to that in FIG. 2, was modified by site-directed mutagenesis to delete the region from the first nucleotide of the GS signal of the NS2 gene to the last nucleotide of the GE signal of the NS2 gene, inclusive. This deleted the complete NS2 gene.

Example 7

Figure 9:
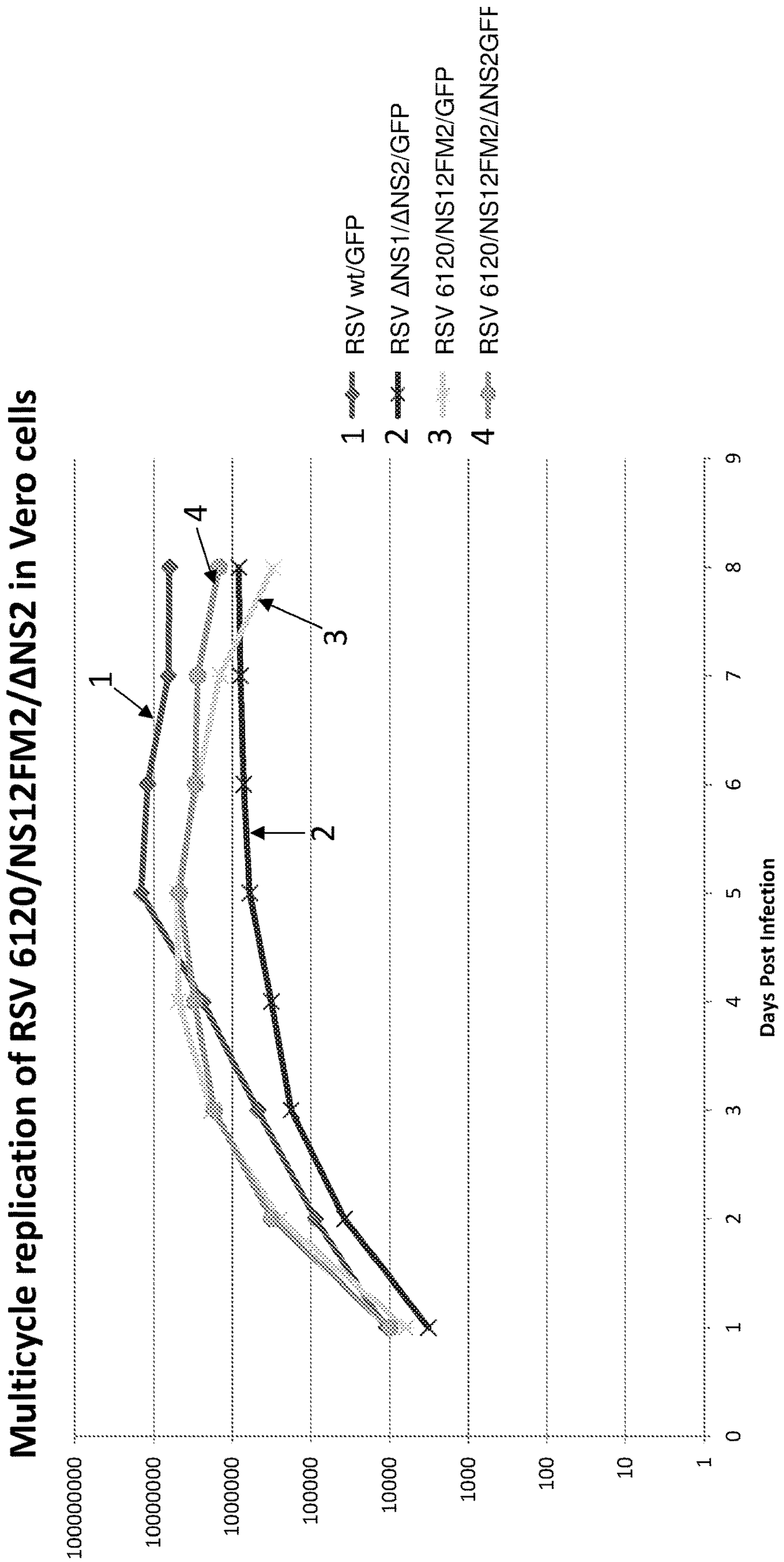
FIG. 9 shows replication of RSV 6120/NS12FM2/ΔNS2/GFP, RSV 6120/NS12FM2/GFP, RSV ΔNS1/ΔNS2/GFP and wt RSV/GFP in African green monkey Vero cells.

This example describes the replication characteristics of the recombinant virus 6120/NS12FM2/ΔNS2/GFP The kinetics and yield of multi-cycle replication of recombinant RSV 6120/NS12FM2/ΔNS2/GFP (F-M2/delNS2) virus were compared to those of its immediate parent RSV 6120/NS12FM2/GFP (F-M2), wt RSV/GFP (wt RSV), and RSV ΔNS1/ΔNS2/GFP (delNS1_NS2) in African green monkey Vero cells following the general experimental design of Example 3. These results (FIG. 9) showed that the F-M2/delNS2 virus replicated approximately as efficiently as F-M2 and wt RSV in Vero cells, which is the substrate for vaccine virus manufacture, whereas delNS1_NS2 was restricted, as previously shown. Thus, the F-M2/delNS2 virus retains the capacity for efficient vaccine manufacture even though it now contains two attenuating elements: F-M2 and ΔNS2.

Figure 10:
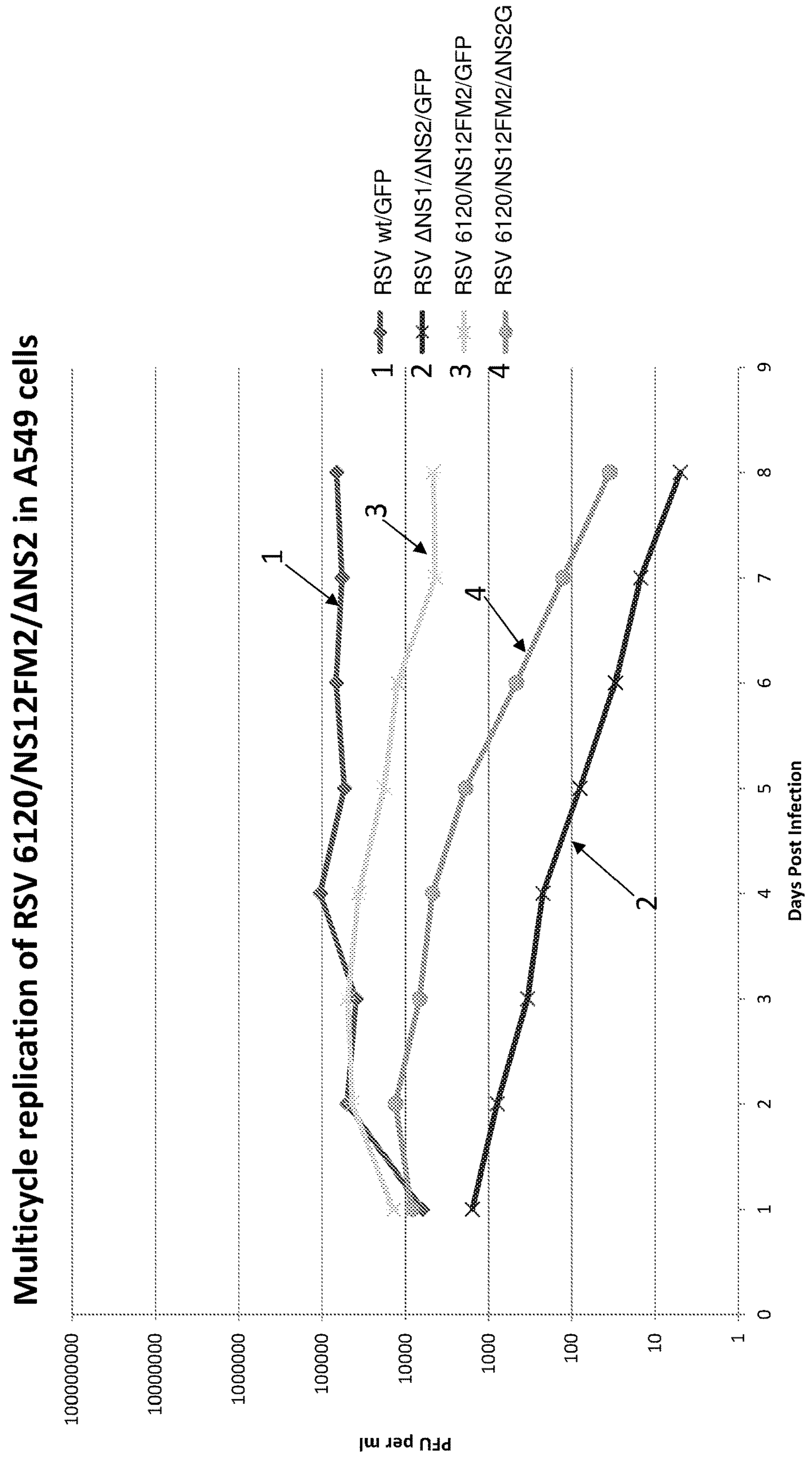
FIG. 10 shows replication of RSV 6120/NS12FM2/ΔNS2/GFP, RSV 6120/NS12FM2/GFP, RSV ΔNS1/ΔNS2/GFP and wt RSV/GFP in human airway A549 cells.

A similar comparison of virus replication was performed in parallel in human airway A549 cells, following the general experimental design of Example 3. These results (FIG. 10) showed that these viruses had a range of increasing restriction, in the order: wt RSV<F-M2<F-M2/delNS2<delNS1_NS2. As noted, growth restriction in A549 cells by viruses with mutation/deletion in the NS1 and/or NS2 accessory proteins is a marker for attenuation in vivo. The observation that F-M2/delNS2 is more restricted than F-M2 shows that the combination of these mutations indeed yielded a further-restricted derivative. A ΔNS1ΔNS2 virus similar to the delNS1_NS2 virus in FIG. 10 was previously shown to be over-attenuated in African green monkeys (Jin et al 203 Vaccine 21:3647-3652). Therefore, the availability of the F-M2 and F-M2/delNS2 viruses provides two alternatives that are less restricted and exhibit a range of restriction. These can now be evaluated in HAE cultures, rodents, and African green monkeys in parallel with previous vaccine candidates as benchmarks (Karron et al 2013 Curr Top Microbiol Immunol 372:259-284). Preferably, this analysis would involve the versions of F-M2 and F-M2/delNS2 that do not contain the GFP gene, as described. In addition, the RSV 6120/NS12Ltr/ΔNS2/GFP (L-tr/delNS2) construct described in FIG. 8, and its derivative lacking GFP, also can be evaluated in parallel. Since the L-tr shift is more attenuating than the F-M2 shift (FIG. 6 versus FIG. 4), this will provide a further range of restriction. One or more appropriate candidates can be evaluated in human volunteers as described (e.g. Karron, et al. 2015, Science Transl Med 2015 7(312):312ra175).

It will be apparent that the precise details of the methods or compositions described may be varied or modified without departing from the spirit of the described embodiments. We claim all such modifications and variations that fall within the scope and spirit of the claims below.

The invention claimed is:

1. A recombinant respiratory syncytial virus (RSV) attenuated by one or more modifications to an RSV genome, wherein the one or more modifications comprise:
a NS1 gene and a NS2 gene shifted from gene positions 1 and 2 to gene positions 9 and 10 of the RSV genome, respectively.

2. The recombinant RSV of claim 1, wherein the RSV genome further comprises a modification comprising a deletion of all or part of the NS1 gene or the NS2 gene.

3. The recombinant RSV of claim 1, wherein the RSV genome further comprises a modification comprising deletion of all or part of the M2-2 gene.

4. The recombinant RSV of claim 1, wherein the RSV genome comprises a positive-sense sequence denoted by SEQ ID NO: 4 (6120/NS12Ltr).

5. The recombinant RSV of claim 1, which exhibits:
reduced expression of the NS1 gene and/or NS2 gene compared to an RSV having the NS1 gene in gene position 1 and the NS2 gene in gene position 2.

6. The recombinant RSV of claim 1, wherein the recombinant RSV retains replication efficiency in cultured cells that cannot produce interferons in response to viral infection.

7. The recombinant RSV of claim 1, wherein the recombinant RSV is a subtype A RSV or a subtype B RSV.

8. The recombinant RSV of claim 1, wherein the recombinant RSV is infectious, attenuated, and self-replicating.

9. An isolated polynucleotide molecule comprising the nucleotide sequence of the recombinant RSV genome of claim 1, or an antigenomic cDNA or RNA sequence of the RSV genome.

10. A vector comprising the isolated polynucleotide molecule of claim 9.

11. A cell comprising the isolated polynucleotide or vector of claim 9.

12. A method of producing a recombinant RSV, comprising:

transfecting a permissive cell culture with the vector of claim 10;

incubating the cell culture for a sufficient period of time to allow for viral replication; and purifying the replicated recombinant RSV.

13. A recombinant RSV produced by the method of claim 12.

14. A pharmaceutical composition comprising the recombinant RSV of claim 1.

15. A method of eliciting an immune response to RSV in a subject comprising administering an immunogenically effective amount of the pharmaceutical composition of claim 14 to the subject.

16. The method of claim 15, wherein:

the pharmaceutical composition is administered intranasally.

17. The recombinant RSV of claim 1, which exhibits reduced transcription of the NS1 gene and/or NS2 gene compared to an RSV having the NS1 gene in gene position 1 and the NS2 gene in gene position 2.

18. The recombinant RSV of claim 1, which exhibits reduced inhibition of host interferon response compared to an RSV having the NS1 gene in gene position 1 and the NS2 gene in gene position 2.

19. The method of claim 15, wherein the pharmaceutical composition is administered via aerosol delivery, nasal spray or nasal droplets.

20. The method of claim 15, wherein the subject is a human.

21. The method of claim 20, wherein the human subject is between 1 and 6 months of age.

22. The method of claim 15, wherein the subject is seronegative for RSV.

* * * * *

SEQUENCE LISTING

<160> NUMBER OF SEQ ID NOS: 26

<210> SEQ ID NO 1
<211> LENGTH: 15919
<212> TYPE: DNA
<213> ORGANISM: Artificial Sequence
<220> FEATURE:
<223> OTHER INFORMATION: recombinant RSV sequence

<400> SEQUENCE: 1

```
acgggaaaaa atgcgtacaa caaacttgca taaaccaaaa aaatggggca aataagaatt      60
tgataagtac cacttaaatt taactccctt ggttagagat ggctcttagc aaagtcaagt     120
tgaatgatac actcaacaaa gatcaacttc tgtcatccag caaatacacc atccaacgga     180
gcacaggaga tagtattgat actcctaatt atgatgtgca gaaacacatc aataagttat     240
gtggcatgtt attaatcaca gaagatgcta atcataaatt cactgggtta ataggtatgt     300
tatatgcgat gtctaggtta ggaagagaag acaccataaa aatactcaga gatgcgggat     360
atcatgtaaa agcaaatgga gtagatgtaa caacacatcg tcaagacatt aatggaaaag     420
aaatgaaatt tgaagtgtta acattggcaa gcttaacaac tgaaattcaa atcaacattg     480
agatagaatc tagaaaatcc tacaaaaaaa tgctaaaaga aatgggagag gtagctccag     540
aatacaggca tgactctcct gattgtggga tgataatatt atgtatagca gcattagtaa     600
taactaaatt agcagcaggg gacagatctg gtcttacagc cgtgattagg agagctaata     660
atgtcctaaa aaatgaaatg aaacgttaca aaggcttact acccaaggac atagccaaca     720
gcttctatga agtgtttgaa aaacatcccc actttataga tgtttttgtt cattttggta     780
tagcacaatc ttctaccaga ggtggcagta gagttgaagg gatttttgca ggattgttta     840
tgaatgccta tggtgcaggg caagtgatgt tacggtgggg agtcttagca aaatcagtta     900
aaaatattat gttaggacat gctagtgtgc aagcagaaat ggaacaagtt gttgaggttt     960
atgaatatgc ccaaaaattg ggtggtgaag caggattcta ccatatattg aacaacccaa    1020
aagcatcatt attatctttg actcaatttc ctcacttctc cagtgtagta ttaggcaatg    1080
ctgctggcct aggcataatg ggagagtaca gaggtacacc gaggaatcaa gatctatatg    1140
atgcagcaaa ggcatatgct gaacaactca aagaaaatgg tgtgattaac tacagtgtac    1200
tagacttgac agcagaagaa ctagaggcta tcaaacatca gcttaatcca aaagataatg    1260
atgtagagct ttgagttaat aaaaaatggg gcaaataaat catcatggaa aagtttgctc    1320
ctgaattcca tggagaagat gcaaacaaca gggctactaa attcctagaa tcaataaagg    1380
gcaaattcac atcacccaaa gatcccaaga aaaaagatag tatcatatct gtcaactcaa    1440
tagatataga agtaaccaaa gaaagcccta taacatcaaa ttcaactatt atcaacccaa    1500
caaatgagac agatgatact gcagggaaca agcccaatta tcaaagaaaa cctctagtaa    1560
gtttcaaaga agaccctaca ccaagtgata atcccttttc taaactatac aaagaaacca    1620
```

```
tagaaacatt tgataacaat gaagaagaat ccagctattc atacgaagaa ataaatgatc   1680
agacaaacga taatataaca gcaagattag ataggattga tgaaaaatta agtgaaatac   1740
taggaatgct tcacacatta gtagtggcaa gtgcaggacc tacatctgct cgggatggta   1800
taagagatgc catggttggt ttaagagaag aaatgataga aaaaatcaga actgaagcat   1860
taatgaccaa tgacagatta gaagctatgg caagactcag gaatgaggaa agtgaaaaga   1920
tggcaaaaga cacatcagat gaagtgtctc tcaatccaac atcagagaaa ttgaacaacc   1980
tattggaagg gaatgatagt gacaatgatc tatcacttga agatttctga ttagttacca   2040
atcttcacat caacacacaa taccaacaga agaccaacaa actaaccaac ccaatcatcc   2100
aaccaaacat ccatccgcca atcagccaaa cagccaacaa aacaaccagc caatccaaaa   2160
ctaaccaccc ggaaaaaatc tataatatag ttacaaaaaa aggaatcgat ggggcaaata   2220
caagtatggt gagcaagggc gaggagctgt tcaccggggt ggtgcccatc ctggtcgagc   2280
tggacggcga cgtaaacggc cacaagttca gcgtgtccgg cgagggcgag ggcgatgcca   2340
cctacggcaa gctgaccctg aagttcatct gcaccaccgg caagctgccc gtgccctggc   2400
ccaccctcgt gaccaccctg acctacggcg tgcagtgctt cagccgctac cccgaccaca   2460
tgaagcagca cgacttcttc aagtccgcca tgcccgaagg ctacgtccag gagcgcacca   2520
tcttcttcaa ggacgacggc aactacaaga cccgcgccga ggtgaagttc gagggcgaca   2580
ccctggtgaa ccgcatcgag ctgaagggca tcgacttcaa ggaggacggc aacatcctgg   2640
ggcacaagct ggagtacaac tacaacagcc acaacgtcta tatcatggcc gacaagcaga   2700
agaacggcat caaggtgaac ttcaagatcc gccacaacat cgaggacggc agcgtgcagc   2760
tcgccgacca ctaccagcag aacaccccca tcggcgacgg ccccgtgctg ctgcccgaca   2820
accactacct gagcacccag tccgccctga gcaaagaccc caacgagaag cgcgatcaca   2880
tggtcctgct ggagttcgtg accgccgccg ggatcactct cggcatggac gagctgtaca   2940
agtaaaagta gttacttaaa aagtcgacgg tggggcaaat atggaaacat acgtgaacaa   3000
gcttcacgaa ggctccacat acacagctgc tgttcaatac aatgtcttag aaaaagacga   3060
tgaccctgca tcacttacaa tatgggtgcc catgttccaa tcatctatgc cagcagattt   3120
acttataaaa gaactagcta atgtcaacat actagtgaaa caaatatcca cacccaaggg   3180
accttcacta agagtcatga taaactcaag aagtgcagtg ctagcacaaa tgcccagcaa   3240
atttaccata tgcgctaatg tgtccttgga tgaaagaagc aaactagcat atgatgtaac   3300
cacaccctgt gaaatcaagg catgtagtct aacatgccta aaatcaaaaa atatgttgac   3360
tacagttaaa gatctcacta tgaagacact caaccctaca catgatatta ttgctttatg   3420
tgaatttgaa aacatagtaa catcaaaaaa agtcataata ccaacatacc taagatccat   3480
cagtgtcaga aataaagatc tgaacacact tgaaaatata acaaccactg aattcaaaaa   3540
tgctatcaca aatgcaaaaa tcatccctta ctcaggatta ctattagtca tcacagtgac   3600
tgacaacaaa ggagcattca aatacataaa gccacaaagt caattcatag tagatcttgg   3660
agcttaccta gaaaaagaaa gtatatatta tgttaccaca aattggaagc acacagctac   3720
acgatttgca atcaaaccca tggaagatta accttttttcc tctacatcag tgtgttaatt   3780
catacaaact ttctacctac attcttcact tcaccatcac aatcacaaac actctgtggt   3840
tcaaccaatc aaacaaaact tatctgaagt cccagatcat cccaagtcat tgtttatcag   3900
atctagtact caaataagtt aataaaaaat atacacatgg ggcaaataat cattggagga   3960
aatccaacta atcacaatat ctgttaacat agacaagtcc acacaccata cagaatcaac   4020
```

-continued

```
caatggaaaa tacatccata acaatagaat tctcaagcaa attctggcct tactttacac   4080
taatacacat gatcacaaca ataatctctt tgctaatcat aatctccatc atgattgcaa   4140
tactaaacaa actttgtgaa tataacgtat tccataacaa aacctttgag ttaccaagag   4200
ctcgagttaa tacttgataa agtagttaat taaaaatagt cataacaatg aactaggata   4260
tcaagactaa caataacatt ggggcaaatg caaacatgtc caaaaacaag gaccaacgca   4320
ccgctaagac attagaaagg acctgggaca ctctcaatca tttattattc atatcatcgt   4380
gcttatataa gttaaatctt aaatctgtag cacaaatcac attatccatt ctggcaatga   4440
taatctcaac ttcacttata attgcagcca tcatattcat agcctcggca aaccacaaag   4500
tcacaccaac aactgcaatc atacaagatg caacaagcca gatcaagaac acaaccccaa   4560
catacctcac ccagaatcct cagcttggaa tcagtccctc taatccgtct gaaattacat   4620
cacaaatcac caccatacta gcttcaacaa caccaggagt caagtcaacc ctgcaatcca   4680
caacagtcaa gaccaaaaac acaacaacaa ctcaaacaca acccagcaag cccaccacaa   4740
aacaacgcca aaacaaacca ccaagcaaac ccaataatga ttttcacttt gaagtgttca   4800
actttgtacc ctgcagcata tgcagcaaca atccaacctg ctgggctatc tgcaaaagaa   4860
taccaaacaa aaaaccagga aagaaaacca ctaccaagcc cacaaaaaaa ccaaccctca   4920
agacaaccaa aaaagatccc aaacctcaaa ccactaaatc aaaggaagta cccaccacca   4980
agcccacaga agagccaacc atcaacacca ccaaaacaaa catcataact acactactca   5040
cctccaacac cacaggaaat ccagaactca caagtcaaat ggaaaccttc cactcaactt   5100
cctccgaagg caatccaagc ccttctcaag tctctacaac atccgagtac ccatcacaac   5160
cttcatctcc acccaacaca ccacgccagt agttacttaa aaacatatta tcacaaaagg   5220
ccttgaccaa cttaaacaga atcaaaataa actctggggc aaataacaat ggagttgcta   5280
atcctcaaag caaatgcaat taccacaatc ctcactgcag tcacattttg ttttgcttct   5340
ggtcaaaaca tcactgaaga attttatcaa tcaacatgca gtgcagttag caaaggctat   5400
cttagtgctc tgagaactgg ttggtatacc agtgttataa ctatagaatt aagtaatatc   5460
aagaaaaata agtgtaatgg aacagatgct aaggtaaaat tgataaaaca agaattagat   5520
aaatataaaa atgctgtaac agaattgcag ttgctcatgc aaagcacaca agcaacaaac   5580
aatcgagcca gaagagaact accaaggttt atgaattata cactcaacaa tgccaaaaaa   5640
accaatgtaa cattaagcaa gaaaaggaaa agaagatttc ttggtttttt gttaggtgtt   5700
ggatctgcaa tcgccagtgg cgttgctgta tctaaggtcc tgcacctaga aggggaagtg   5760
aacaagatca aaagtgctct actatccaca aacaaggctg tagtcagctt atcaaatgga   5820
gttagtgttt taaccagcaa agtgttagac ctcaaaaact atatagataa acaattgtta   5880
cctattgtga acaagcaaag ctgcagcata tcaaatatag aaactgtgat agagttccaa   5940
caaaagaaca acagactact agagattacc agggaattta gtgttaatgc aggcgtaact   6000
acacctgtaa gcacttacat gttaactaat agtgaattat tgtcattaat caatgatatg   6060
cctataacaa atgatcagaa aaagttaatg tccaacaatg ttcaaatagt tagacagcaa   6120
agttactcta tcatgtccat aataaaagag gaagtcttag catatgtagt acaattacca   6180
ctatatggtg ttatagatac accctgttgg aaactacaca catcccctct atgtacaacc   6240
aacacaaaag aagggtccaa catctgttta acaagaactg acagaggatg gtactgtgac   6300
aatgcaggat cagtatcttt cttcccacaa gctgaaacat gtaaagttca atcaaatcga   6360
```

```
gtattttgtg acacaatgaa cagtttaaca ttaccaagtg aagtaaatct ctgcaatgtt   6420
gacatattca accccaaata tgattgtaaa attatgactt caaaaacaga tgtaagcagc   6480
tccgttatca catctctagg agccattgtg tcatgctatg gcaaaactaa atgtacagca   6540
tccaataaaa atcgtggaat cataaagaca ttttctaacg ggtgcgatta tgtatcaaat   6600
aaaggggtgg acactgtgtc tgtaggtaac acattatatt atgtaaataa gcaagaaggt   6660
aaaagtctct atgtaaaagg tgaaccaata ataaatttct atgacccatt agtattcccc   6720
tctgatgaat ttgatgcatc aatatctcaa gtcaacgaga agattaacca gagcctagca   6780
tttattcgta aatccgatga attattacat aatgtaaatg ctggtaaatc caccacaaat   6840
atcatgataa ctactataat tatagtgatt atagtaatat tgttatcatt aattgctgtt   6900
ggactgctct tatactgtaa ggccagaagc acaccagtca cactaagcaa agatcaactg   6960
agtggtataa ataatattgc atttagtaac taaataaaaa tagcacctaa tcatgttctt   7020
acaatggttt actatctgct catagacaac ccatctgtca ttggattttc ttaaaatctg   7080
aacttcatcg aaactctcat ctataaacca tctcacttac actatttaag tagattccta   7140
gtttatagtt atataaaaca caattgcatg ccaggtacca tggggcaaat aagaatttga   7200
taagtaccac ttaaatttaa ctcccttggt tagagatggg cagcaattca ttgagtatga   7260
taaaagttag attacaaaat ttgtttgaca atgatgaagt agcattgtta aaaataacat   7320
gctatactga taaattaata catttaacta atgctttggc taaggcagtg atacatacaa   7380
tcaaattgaa tggcattgtg tttgtgcatg ttattacaag tagtgatatt tgccctaata   7440
ataatattgt agtaaaatcc aatttcacaa caatgccagt actacaaaat ggaggttata   7500
tatgggaaat gatggaatta acacattgct ctcaacctaa tggtctacta gatgacaatt   7560
gtgaaattaa attctccaaa aaactaagtg attcaacaat gaccaattat atgaatcaat   7620
tatctgaatt acttggattt gatcttaatc cataaattat aattaatatc aactagcaaa   7680
tcaatgtcac taacaccatt agttaatata aaacttaaca gaagacaaaa atggggcaaa   7740
taaatcaatt cagccaaccc aaccatggac acaacccaca atgataatac accacaaaga   7800
ctgatgatca cagacatgag accgttgtca cttgagacca taataacatc actaaccaga   7860
gacatcataa cacacaaatt tatatacttg ataaatcatg aatgcatagt gagaaaactt   7920
gatgaaagac aggccacatt tacattcctg gtcaactatg aaatgaaact attacacaaa   7980
gtaggaagca ctaaatataa aaaatatact gaatacaaca caaaatatgg cactttccct   8040
atgccaatat tcatcaatca tgatgggttc ttagaatgca ttggcattaa gcctacaaag   8100
catactccca taatatacaa gtatgatctc aatccataaa tttcaacaca atattcacac   8160
aatctaaaac aacaactcta tgcataacta tactccatag tccagatgga gcctgaaaat   8220
tatagtaatt taaaacttaa ggagagatat aagatagaag atggtaccct taccatctgt   8280
aaaaatgaaa actggggcaa atatgtcacg aaggaatcct tgcaaatttg aaattcgagg   8340
tcattgctta aatggtaaga ggtgtcattt tagtcataat tattttgaat ggccacccca   8400
tgcactgctt gtaagacaaa actttatgtt aaacagaata cttaagtcta tggataaaag   8460
tatagatacc ttatcagaaa taagtggagc tgcagagttg gacagaacag aagagtatgc   8520
tcttggtgta gttggagtgc tagagagtta tataggatca ataaacaata taactaaaca   8580
atcagcatgt gttgccatga gcaaactcct cactgaactc aatagtgatg atatcaaaaa   8640
gctgagggac aatgaagagc taaattcacc caagataaga gtgtacaata ctgtcatatc   8700
atatattgaa agcaacagga aaaacaataa acaaactatc catctgttaa aaagattgcc   8760
```

```
agcagacgta ttgaagaaaa ccatcaaaaa cacattggat atccataaga gcataaccat   8820
caacaaccca aaagaatcaa ctgttagtga tacaaatgac catgccaaaa ataatgatac   8880
tacctgacaa atatccttgt agtataactt ccatactaat aacaagtaga tgtagagtta   8940
ctatgtataa tcaaaagaac acactatatt tcaatcaaaa caacccaaat aaccatatgt   9000
actcaccgaa tcaaacattc aatgaaatcc attggacctc tcaagaattg attgacacaa   9060
ttcaaaattt tctacaacat ctaggtatta ttgaggatat atatacaata tatatattag   9120
tgtcataaca ctcaattcta acactcacca catcgttaca ttattaattc aaacaattca   9180
agttgtggga caaaatggat cccattatta atggaaattc tgctaatgtt tatctaaccg   9240
atagttattt aaaaggtgtt atctctttct cagagtgtaa tgctttagga agttacatat   9300
tcaatggtcc ttatctcaaa aatgattata ccaacttaat tagtagacaa aatccattaa   9360
tagaacacat gaatctaaag aaactaaata taacacagtc cttaatatct aagtatcata   9420
aaggtgaaat aaaattagaa gaacctactt attttcagtc attacttatg acatacaaga   9480
gtatgacctc gtcagaacag attgctacca ctaatttact taaaaagata ataagaagag   9540
ctatagaaat aagtgatgtc aaagtctatg ctatattgaa taaactaggg cttaaagaaa   9600
aggacaagat taaatccaac aatggacaag atgaagacaa ctcagttatt acgaccataa   9660
tcaaagatga tatactttca gctgttaaag ataatcaatc tcatcttaaa gcagacaaaa   9720
atcactctac aaaacaaaaa gacacaatca aaacaacact cttgaagaaa ttgatgtgtt   9780
caatgcaaca tcctccatca tggttaatac attggtttaa cttatacaca aaattaaaca   9840
acatattaac acagtatcga tcaaatgagg taaaaaacca tgggtttaca ttgatagata   9900
atcaaactct tagtggattt caatttattt tgaaccaata tggttgtata gtttatcata   9960
aggaactcaa aagaattact gtgacaacct ataatcaatt cttgacatgg aaagatatta  10020
gccttagtag attaaatgtt tgtttaatta catggattag taactgcttg aacacattaa  10080
ataaaagctt aggcttaaga tgcggattca ataatgttat cttgacacaa ctattccttt  10140
atggagattg tatactaaag ctatttcaca atgaggggtt ctacataata aaagaggtag  10200
agggatttat tatgtctcta attttaaata taacagaaga agatcaattc agaaaacgat  10260
tttataatag tatgctcaac aacatcacag atgctgctaa taaagctcag aaaaatctgc  10320
tatcaagagt atgtcataca ttattagata agacagtgtc cgataatata ataaatggca  10380
gatggataat tctattaagt aagttcctta aattaattaa gcttgcaggt gacaataacc  10440
ttaacaatct gagtgaacta tattttttgt tcagaatatt tggacaccca atggtagatg  10500
aaagacaagc catggatgct gttaaaatta attgcaatga gaccaaattt tacttgttaa  10560
gcagtctgag tatgttaaga ggtgccttta tatatagaat tataaaaggg tttgtaaata  10620
attacaacag atggcctact ttaagaaatg ctattgtttt acccttaaga tggttaactt  10680
actataaact aaacacttat ccttctttgt tggaacttac agaaagagat ttgattgtgt  10740
tatcaggact acgtttctat cgtgagtttc ggttgcctaa aaaagtggat cttgaaatga  10800
ttataaatga taaagctata tcacctccta aaaatttgat atggactagt ttccctagaa  10860
attacatgcc atcacacata caaaactata tagaacatga aaaattaaaa ttttccgaga  10920
gtgataaatc aagaagagta ttagagtatt atttaagaga taacaaattc aatgaatgtg  10980
atttatacaa ctgtgtagtt aatcaaagtt atctcaacaa ccctaatcat gtggtatcat  11040
tgacaggcaa agaaagagaa ctcagtgtag gtagaatgtt tgcaatgcaa ccgggaatgt  11100
```

-continued tcagacaggt tcaaatattg gcagagaaaa tgatagctga aaacatttta caattctttc 11160
ctgaaagtct tacaagatat ggtgatctag aactacaaaa aatattagaa ctgaaagcag 11220
gaataagtaa caaatcaaat cgctacaatg ataattacaa caattacatt agtaagtgct 11280
ctatcatcac agatctcagc aaattcaatc aagcatttcg atatgaaacg tcatgtattt 11340
gtagtgatgt gctggatgaa ctgcatggtg tacaatctct attttcctgg ttacatttaa 11400
ctattcctca tgtcacaata atatgcacat ataggcatgc accccccctat ataggagatc 11460 atattgtaga tcttaacaat gtagatgaac aaagtggatt atatagatat cacatgggtg 11520
gcatcgaagg gtggtgtcaa aaactatgga ccatagaagc tatatcacta ttggatctaa 11580
tatctctcaa agggaaattc tcaattactg ctttaattaa tggtgacaat caatcaatag 11640
atataagcaa accaatcaga ctcatggaag gtcaaactca tgctcaagca gattatttgc 11700
tagcattaaa tagccttaaa ttactgtata aagagtatgc aggcataggc cacaaattaa 11760
aaggaactga gacttatata tcacgagata tgcaatttat gagtaaaaca attcaacata 11820
acggtgtata ttacccagct agtataaaga aagtcctaag agtgggaccg tggataaaca 11880
ctatacttga tgatttcaaa gtgagtctag aatctatagg tagtttgaca caagaattag 11940
aatatagagg tgaaagtcta ttatgcagtt taatatttag aaatgtatgg ttatataatc 12000
agattgctct acaattaaaa aatcatgcat tatgtaacaa taaactatat ttggacatat 12060
taaaggttct gaaacactta aaaacctttt ttaatcttga taatattgat acagcattaa 12120
cattgtatat gaatttaccc atgttatttg gtggtggtga tcccaacttg ttatatcgaa 12180
gtttctatag aagaactcct gacttcctca cagaggctat agttcactct gtgttcatac 12240
ttagttatta tacaaaccat gacttaaaag ataaacttca agatctgtca gatgatagat 12300
tgaataagtt cttaacatgc ataatcacgt ttgacaaaaa ccctaatgct gaattcgtaa 12360
cattgatgag agatcctcaa gctttagggt ctgagagaca agctaaaatt actagcgaaa 12420
tcaatagact ggcagttaca gaggttttga gtacagctcc aaacaaaata ttctccaaaa 12480
gtgcacaaca ttatactact acagagatag atctaaatga tattatgcaa aatatagaac 12540
ctacatatcc tcatgggcta agagttgttt atgaaagttt accccttttat aaagcagaga 12600 aaatagtaaa tcttatatca ggtacaaaat ctataactaa catactggaa aaaacttctg 12660
ccatagactt aacagatatt gatagagcca ctgagatgat gaggaaaaac ataactttgc 12720
ttataaggat acttccattg gattgtaaca gagataaaag agagatattg agtatggaaa 12780
acctaagtat tactgaatta agcaaatatg ttagggaaag atcttggtct ttatccaata 12840
tagttggtgt tacatcaccc agtatcatgt atacaatgga catcaaatat actacaagca 12900
ctatatctag tggcataatt atagagaaat ataatgttaa cagtttaaca cgtggtgaga 12960
gaggacccac taaaccatgg gttggttcat ctacacaaga gaaaaaaaca atgccagttt 13020
ataatagaca agtcttaacc aaaaaacaga gagatcaaat agatctatta gcaaaattgg 13080
attgggtgta tgcatctata gataacaagg atgaattcat ggaagaactc agcataggaa 13140
cccttgggtt aacatatgaa aaggccaaga aattatttcc acaatattta agtgtcaatt 13200
atttgcatcg ccttacagtc agtagtagac catgtgaatt ccctgcatca ataccagctt 13260
atagaacaac aaattatcac tttgacacta gccctattaa tcgcatatta acagaaaagt 13320
atggtgatga agatattgac atagtattcc aaaactgtat aagctttggc cttagtttaa 13380
tgtcagtagt agaacaattt actaatgtat gtcctaacag aattattctc atacctaagc 13440
ttaatgagat acatttgatg aaacctccca tattcacagg tgatgttgat attcacaagt 13500
taaaacaagt gatacaaaaa cagcatatgt ttttaccaga caaaataagt ttgactcaat 13560
atgtggaatt attcttaagt aataaaacac tcaaatctgg atctcatgtt aattctaatt 13620
taatattggc acataaaata tctgactatt ttcataatac ttacatttta agtactaatt 13680
tagctggaca ttggattctg attatacaac ttatgaaaga ttctaaaggt atttttgaaa 13740
aagattgggg agagggatat ataactgatc atatgtttat taatttgaaa gttttcttca 13800
atgcttataa gacctatctc ttgtgttttc ataaaggtta tggcaaagca aagctggagt 13860
gtgatatgaa cacttcagat cttctatgtg tattggaatt aatagacagt agttattgga 13920
agtctatgtc taaggtattt ttagaacaaa aagttatcaa atacattctt agccaagatg 13980
caagtttaca tagagtaaaa ggatgtcata gcttcaaatt atggtttctt aaacgtctta 14040
atgtagcaga attcacagtt tgcccttggg ttgttaacat agattatcat ccaacacata 14100
tgaaagcaat attaacttat atagatcttg ttagaatggg attgataaat atagatagaa 14160
tacacattaa aaataaacac aaattcaatg atgaatttta tacttctaat ctcttctaca 14220
ttaattataa cttctcagat aatactcatc tattaactaa acatataagg attgctaatt 14280
ctgaattaga aaataattac aacaaattat atcatcctac accagaaacc ctagagaata 14340
tactagccaa tccgattaaa agtaatgaca aaaagacact gaatgactat tgtataggta 14400
aaaatgttga ctcaataatg ttaccattgt tatctaataa gaagcttatt aaatcgtctg 14460
caatgattag aaccaattac agcaaacaag atttgtataa tttattccct atggttgtga 14520
ttgatagaat tatagatcat tcaggcaata cagccaaatc caaccaactt tacactacta 14580
cttcccacca aatatcctta gtgcacaata gcacatcact ttactgcatg cttccttggc 14640
atcatattaa tagattcaat tttgtattta gttctacagg ttgtaaaatt agtatagagt 14700
atattttaaa agatcttaaa attaaagatc ccaattgtat agcattcata ggtgaaggag 14760
cagggaattt attattgcgt acagtagtgg aacttcatcc tgacataaga tatatttaca 14820
gaagtctgaa agattgcaat gatcatagtt tacctattga gtttttaagg ctgtacaatg 14880
gacatatcaa cattgattat ggtgaaaatt tgaccattcc tgctacagat gcaaccaaca 14940
acattcattg gtcttattta catataaagt ttgctgaacc tatcagtctt tttgtctgtg 15000
atgccgaatt gtctgtaaca gtcaactgga gtaaaattat aatagaatgg agcaagcatg 15060
taagaaagtg caagtactgt tcctcagtta ataaatgtat gttaatagta aaatatcatg 15120
ctcaagatga tattgatttc aaattagaca atataactat attaaaaact tatgtatgct 15180
taggcagtaa gttaaaggga tcggaggttt acttagtcct tacaataggt cctgcgaata 15240
tattcccagt atttaatgta gtacaaaatg ctaaattgat actatcaaga accaaaaatt 15300
tcatcatgcc taagaaagct gataaagagt ctattgatgc aaatattaaa agtttgatac 15360
cctttctttg ttaccctata acaaaaaaag gaattaatac tgcattgtca aaactaaaga 15420
gtgttgttag tggagatata ctatcatatt ctatagctgg acgtaatgaa gttttcagca 15480
ataaacttat aaatcataag catatgaaca tcttaaaatg gttcaatcat gttttaaatt 15540
tcagatcaac agaactaaac tataaccatt tatatatggt agaatctaca tatccttacc 15600
taagtgaatt gttaaacagc ttgacaacca atgaacttaa aaaactgatt aaaatcacag 15660
gtagtctgtt atacaacttt cataatgaat aatgaataaa gatcttataa taaaaattcc 15720
catagctata cactaacact gtattcaatt atagttatta aaaattaaaa atcatataat 15780
tttttaaata acttttagtg aactaatcct aaagttatca ttttaatctt ggaggaataa 15840

-continued atttaaaccc taatctaatt ggtttatatg tgtattaact aaattacgag atattagttt 15900
ttgacacttt ttttctcgt 15919

<210> SEQ ID NO 2
<211> LENGTH: 15158
<212> TYPE: DNA
<213> ORGANISM: Artificial Sequence
<220> FEATURE:
<223> OTHER INFORMATION: recombinant RSV sequence

<400> SEQUENCE: 2
acgggaaaaa atgcgtacaa caaacttgca taaaccaaaa aaatggggca aataagaatt 60
tgataagtac cacttaaatt taactccctt ggttagagat ggctcttagc aaagtcaagt 120
tgaatgatac actcaacaaa gatcaacttc tgtcatccag caaatacacc atccaacgga 180
gcacaggaga tagtattgat actcctaatt atgatgtgca gaaacacatc aataagttat 240
gtggcatgtt attaatcaca gaagatgcta atcataaatt cactgggtta ataggtatgt 300
tatatgcgat gtctaggtta ggaagagaag acaccataaa aatactcaga gatgcgggat 360
atcatgtaaa agcaaatgga gtagatgtaa caacacatcg tcaagacatt aatggaaaag 420
aaatgaaatt tgaagtgtta acattggcaa gcttaacaac tgaaattcaa atcaacattg 480
agatagaatc tagaaaatcc tacaaaaaaa tgctaaaaga aatgggagag gtagctccag 540
aatacaggca tgactctcct gattgtggga tgataatatt atgtatagca gcattagtaa 600
taactaaatt agcagcaggg gacagatctg gtcttacagc cgtgattagg agagctaata 660
atgtcctaaa aaatgaaatg aaacgttaca aaggcttact acccaaggac atagccaaca 720
gcttctatga agtgtttgaa aaacatcccc actttataga tgtttttgtt cattttggta 780
tagcacaatc ttctaccaga ggtggcagta gagttgaagg gatttttgca ggattgttta 840
tgaatgccta tggtgcaggg caagtgatgt tacggtgggg agtcttagca aaatcagtta 900
aaaatattat gttaggacat gctagtgtgc aagcagaaat ggaacaagtt gttgaggttt 960
atgaatatgc ccaaaaattg ggtggtgaag caggattcta ccatatattg aacaacccaa 1020
aagcatcatt attatctttg actcaatttc ctcacttctc cagtgtagta ttaggcaatg 1080
ctgctggcct aggcataatg ggagagtaca gaggtacacc gaggaatcaa gatctatatg 1140
atgcagcaaa ggcatatgct gaacaactca aagaaaatgg tgtgattaac tacagtgtac 1200
tagacttgac agcagaagaa ctagaggcta tcaaacatca gcttaatcca aaagataatg 1260
atgtagagct ttgagttaat aaaaaatggg gcaaataaat catcatggaa aagtttgctc 1320
ctgaattcca tggagaagat gcaaacaaca gggctactaa attcctagaa tcaataaagg 1380
gcaaattcac atcacccaaa gatcccaaga aaaaagatag tatcatatct gtcaactcaa 1440
tagatataga agtaaccaaa gaaagcccta taacatcaaa ttcaactatt atcaacccaa 1500
caaatgagac agatgatact gcagggaaca agcccaatta tcaaagaaaa cctctagtaa 1560
gtttcaaaga agaccctaca ccaagtgata atcccttttc taaactatac aaagaaacca 1620
tagaaacatt tgataacaat gaagaagaat ccagctattc atacgaagaa ataaatgatc 1680
agacaaacga taatataaca gcaagattag ataggattga tgaaaaatta agtgaaatac 1740
taggaatgct tcacacatta gtagtggcaa gtgcaggacc tacatctgct cgggatggta 1800
taagagatgc catggttggt ttaagagaag aaatgataga aaaaatcaga actgaagcat 1860
taatgaccaa tgacagatta gaagctatgg caagactcag gaatgaggaa agtgaaaaga 1920
tggcaaaaga cacatcagat gaagtgtctc tcaatccaac atcagagaaa ttgaacaacc 1980
tattggaagg gaatgatagt gacaatgatc tatcacttga agatttctga ttagttacca 2040
atcttcacat caacacacaa taccaacaga agaccaacaa actaaccaac ccaatcatcc 2100
aaccaaacat ccatccgcca atcagccaaa cagccaacaa aacaaccagc caatccaaaa 2160
ctaaccaccc ggaaaaaatc tataatatag ttacaaaaaa aggaaagggt ggggcaaata 2220
tggaaacata cgtgaacaag cttcacgaag gctccacata cacagctgct gttcaataca 2280
atgtcttaga aaaagacgat gaccctgcat cacttacaat atgggtgccc atgttccaat 2340
catctatgcc agcagattta cttataaaag aactagctaa tgtcaacata ctagtgaaac 2400
aaatatccac acccaaggga ccttcactaa gagtcatgat aaactcaaga agtgcagtgc 2460
tagcacaaat gcccagcaaa tttaccatat gcgctaatgt gtccttggat gaaagaagca 2520
aactagcata tgatgtaacc acaccctgtg aaatcaaggc atgtagtcta acatgcctaa 2580
aatcaaaaaa tatgttgact acagttaaag atctcactat gaagacactc aaccctacac 2640
atgatattat tgctttatgt gaatttgaaa acatagtaac atcaaaaaaa gtcataatac 2700
caacatacct aagatccatc agtgtcagaa ataaagatct gaacacactt gaaaatataa 2760
caaccactga attcaaaaat gctatcacaa atgcaaaaat catcccttac tcaggattac 2820
tattagtcat cacagtgact gacaacaaag gagcattcaa atacataaag ccacaaagtc 2880
aattcatagt agatcttgga gcttacctag aaaaagaaag tatatattat gttaccacaa 2940
attggaagca cacagctaca cgatttgcaa tcaaacccat ggaagattaa cctttttcct 3000
ctacatcagt gtgttaattc atacaaactt tctacctaca ttcttcactt caccatcaca 3060
atcacaaaca ctctgtggtt caaccaatca aacaaaactt atctgaagtc ccagatcatc 3120
ccaagtcatt gtttatcaga tctagtactc aaataagtta ataaaaaata tacacatggg 3180
gcaaataatc attggaggaa atccaactaa tcacaatatc tgttaacata gacaagtcca 3240
cacaccatac agaatcaacc aatggaaaat acatccataa caatagaatt ctcaagcaaa 3300
ttctggcctt actttacact aatacacatg atcacaacaa taatctcttt gctaatcata 3360
atctccatca tgattgcaat actaaacaaa ctttgtgaat ataacgtatt ccataacaaa 3420
acctttgagt taccaagagc tcgagttaat acttgataaa gtagttaatt aaaaatagtc 3480
ataacaatga actaggatat caagactaac aataacattg gggcaaatgc aaacatgtcc 3540
aaaaacaagg accaacgcac cgctaagaca ttagaaagga cctgggacac tctcaatcat 3600
ttattattca tatcatcgtg cttatataag ttaaatctta aatctgtagc acaaatcaca 3660
ttatccattc tggcaatgat aatctcaact tcacttataa ttgcagccat catattcata 3720
gcctcggcaa accacaaagt cacaccaaca actgcaatca tacaagatgc aacaagccag 3780
atcaagaaca caaccccaac atacctcacc cagaatcctc agcttggaat cagtccctct 3840
aatccgtctg aaattacatc acaaatcacc accatactag cttcaacaac accaggagtc 3900
aagtcaaccc tgcaatccac aacagtcaag accaaaaaca caacaacaac tcaaacacaa 3960
cccagcaagc ccaccacaaa acaacgccaa aacaaaccac caagcaaacc caataatgat 4020
tttcactttg aagtgttcaa ctttgtaccc tgcagcatat gcagcaacaa tccaacctgc 4080
tgggctatct gcaaaagaat accaaacaaa aaaccaggaa agaaaaccac taccaagccc 4140
acaaaaaaac caaccctcaa gacaaccaaa aaagatccca aacctcaaac cactaaatca 4200
aaggaagtac ccaccaccaa gcccacagaa gagccaacca tcaacaccac caaaacaaac 4260
atcataacta cactactcac ctccaacacc acaggaaatc cagaactcac aagtcaaatg 4320
gaaaccttcc actcaacttc ctccgaaggc aatccaagcc cttctcaagt ctctacaaca 4380
tccgagtacc catcacaacc ttcatctcca cccaacacac cacgccagta gttacttaaa 4440
aacatattat cacaaaaggc cttgaccaac ttaaacagaa tcaaaataaa ctctggggca 4500
aataacaatg gagttgctaa tcctcaaagc aaatgcaatt accacaatcc tcactgcagt 4560
cacattttgt tttgcttctg gtcaaaacat cactgaagaa ttttatcaat caacatgcag 4620
tgcagttagc aaaggctatc ttagtgctct gagaactggt tggtatacca gtgttataac 4680
tatagaatta agtaatatca agaaaaataa gtgtaatgga acagatgcta aggtaaaatt 4740
gataaaacaa gaattagata aatataaaaa tgctgtaaca gaattgcagt tgctcatgca 4800
aagcacacaa gcaacaaaca atcgagccag aagagaacta ccaaggttta tgaattatac 4860
actcaacaat gccaaaaaaa ccaatgtaac attaagcaag aaaaggaaaa gaagatttct 4920
tggtttttttg ttaggtgttg gatctgcaat cgccagtggc gttgctgtat ctaaggtcct 4980
gcacctagaa ggggaagtga acaagatcaa aagtgctcta ctatccacaa acaaggctgt 5040
agtcagctta tcaaatggag ttagtgtttt aaccagcaaa gtgttagacc tcaaaaacta 5100
tatagataaa caattgttac ctattgtgaa caagcaaagc tgcagcatat caaatataga 5160
aactgtgata gagttccaac aaaagaacaa cagactacta gagattacca gggaatttag 5220
tgttaatgca ggcgtaacta cacctgtaag cacttacatg ttaactaata gtgaattatt 5280
gtcattaatc aatgatatgc ctataacaaa tgatcagaaa aagttaatgt ccaacaatgt 5340
tcaaatagtt agacagcaaa gttactctat catgtccata ataaaagagg aagtcttagc 5400
atatgtagta caattaccac tatatggtgt tatagataca ccctgttgga aactacacac 5460
atcccctcta tgtacaacca acacaaaaga agggtccaac atctgtttaa caagaactga 5520
cagaggatgg tactgtgaca atgcaggatc agtatctttc ttcccacaag ctgaaacatg 5580
taaagttcaa tcaaatcgag tattttgtga cacaatgaac agtttaacat taccaagtga 5640
agtaaatctc tgcaatgttg acatattcaa ccccaaatat gattgtaaaa ttatgacttc 5700
aaaaacagat gtaagcagct ccgttatcac atctctagga gccattgtgt catgctatgg 5760
caaaactaaa tgtacagcat ccaataaaaa tcgtggaatc ataaagacat tttctaacgg 5820
gtgcgattat gtatcaaata aaggggtgga cactgtgtct gtaggtaaca cattatatta 5880
tgtaaataag caagaaggta aaagtctcta tgtaaaaggt gaaccaataa taaatttcta 5940
tgacccatta gtattcccct ctgatgaatt tgatgcatca atatctcaag tcaacgagaa 6000
gattaaccag agcctagcat ttattcgtaa atccgatgaa ttattacata atgtaaatgc 6060
tggtaaatcc accacaaata tcatgataac tactataatt atagtgatta tagtaatatt 6120
gttatcatta attgctgttg gactgctctt atactgtaag gccagaagca caccagtcac 6180
actaagcaaa gatcaactga gtggtataaa taatattgca tttagtaact aaataaaaat 6240
agcacctaat catgttctta caatggttta ctatctgctc atagacaacc catctgtcat 6300
tggattttct taaaatctga acttcatcga aactctcatc tataaaccat ctcacttaca 6360
ctatttaagt agattcctag tttatagtta tataaaacac aattgcatgc caggtaccat 6420
ggggcaaata agaatttgat aagtaccact taaatttaac tcccttggtt agagatgggc 6480
agcaattcat tgagtatgat aaaagttaga ttacaaaatt tgtttgacaa tgatgaagta 6540
gcattgttaa aaataacatg ctatactgat aaattaatac atttaactaa tgctttggct 6600
aaggcagtga tacatacaat caaattgaat ggcattgtgt ttgtgcatgt tattacaagt 6660
agtgatattt gccctaataa taatattgta gtaaaatcca atttcacaac aatgccagta 6720
ctacaaaatg gaggttatat atgggaaatg atggaattaa cacattgctc tcaacctaat 6780
ggtctactag atgacaattg tgaaattaaa ttctccaaaa aactaagtga ttcaacaatg 6840
accaattata tgaatcaatt atctgaatta cttggatttg atcttaatcc ataaattata 6900
attaatatca actagcaaat caatgtcact aacaccatta gttaatataa aacttaacag 6960
aagacaaaaa tggggcaaat aaatcaattc agccaaccca accatggaca caacccacaa 7020
tgataataca ccacaaagac tgatgatcac agacatgaga ccgttgtcac ttgagaccat 7080
aataacatca ctaaccagag acatcataac acacaaattt atatacttga taaatcatga 7140
atgcatagtg agaaaacttg atgaaagaca ggccacattt acattcctgg tcaactatga 7200
aatgaaacta ttacacaaag taggaagcac taaatataaa aaatatactg aatacaacac 7260
aaaatatggc actttcccta tgccaatatt catcaatcat gatgggttct tagaatgcat 7320
tggcattaag cctacaaagc atactcccat aatatacaag tatgatctca atccataaat 7380
ttcaacacaa tattcacaca atctaaaaca acaactctat gcataactat actccatagt 7440
ccagatggag cctgaaaatt atagtaattt aaaacttaag gagagatata agatagaaga 7500
tggtaccctt accatctgta aaaatgaaaa ctggggcaaa tatgtcacga aggaatcctt 7560
gcaaatttga aattcgaggt cattgcttaa atggtaagag gtgtcatttt agtcataatt 7620
attttgaatg gccaccccat gcactgcttg taagacaaaa ctttatgtta aacagaatac 7680
ttaagtctat ggataaaagt atagatacct tatcagaaat aagtggagct gcagagttgg 7740
acagaacaga agagtatgct cttggtgtag ttggagtgct agagagttat ataggatcaa 7800
taaacaatat aactaaacaa tcagcatgtg ttgccatgag caaactcctc actgaactca 7860
atagtgatga tatcaaaaag ctgagggaca atgaagagct aaattcaccc aagataagag 7920
tgtacaatac tgtcatatca tatattgaaa gcaacaggaa aaacaataaa caaactatcc 7980
atctgttaaa aagattgcca gcagacgtat tgaagaaaac catcaaaaac acattggata 8040
tccataagag cataaccatc aacaacccaa aagaatcaac tgttagtgat acaaatgacc 8100
atgccaaaaa taatgatact acctgacaaa tatccttgta gtataacttc catactaata 8160
acaagtagat gtagagttac tatgtataat caaaagaaca cactatattt caatcaaaac 8220
aacccaaata accatatgta ctcaccgaat caaacattca atgaaatcca ttggacctct 8280
caagaattga ttgacacaat tcaaaatttt ctacaacatc taggtattat tgaggatata 8340
tatacaatat atatattagt gtcataacac tcaattctaa cactcaccac atcgttacat 8400
tattaattca aacaattcaa gttgtgggac aaaatggatc ccattattaa tggaaattct 8460
gctaatgttt atctaaccga tagttattta aaaggtgtta tctctttctc agagtgtaat 8520
gctttaggaa gttacatatt caatggtcct tatctcaaaa atgattatac caacttaatt 8580
agtagacaaa atccattaat agaacacatg aatctaaaga aactaaatat aacacagtcc 8640
ttaatatcta agtatcataa aggtgaaata aaattagaag aacctactta ttttcagtca 8700
ttacttatga catacaagag tatgacctcg tcagaacaga ttgctaccac taatttactt 8760
aaaaagataa taagaagagc tatagaaata agtgatgtca aagtctatgc tatattgaat 8820
aaactagggc ttaaagaaaa ggacaagatt aaatccaaca atggacaaga tgaagacaac 8880
tcagttatta cgaccataat caaagatgat atactttcag ctgttaaaga taatcaatct 8940
catcttaaag cagacaaaaa tcactctaca aaacaaaaag acacaatcaa aacaacactc 9000
ttgaagaaat tgatgtgttc aatgcaacat cctccatcat ggttaataca ttggtttaac 9060

-continued

```
ttatacacaa aattaaacaa catattaaca cagtatcgat caaatgaggt aaaaaaccat   9120
gggtttacat tgatagataa tcaaactctt agtggatttc aatttatttt gaaccaatat   9180
ggttgtatag tttatcataa ggaactcaaa agaattactg tgacaaccta taatcaattc   9240
ttgacatgga aagatattag ccttagtaga ttaaatgttt gtttaattac atggattagt   9300
aactgcttga acacattaaa taaaagctta ggcttaagat gcggattcaa taatgttatc   9360
ttgacacaac tattccttta tggagattgt atactaaagc tatttcacaa tgaggggttc   9420
tacataataa aagaggtaga gggatttatt atgtctctaa ttttaaatat aacagaagaa   9480
gatcaattca gaaaacgatt ttataatagt atgctcaaca acatcacaga tgctgctaat   9540
aaagctcaga aaaatctgct atcaagagta tgtcatacat tattagataa gacagtgtcc   9600
gataatataa taaatggcag atggataatt ctattaagta agttccttaa attaattaag   9660
cttgcaggtg acaataacct taacaatctg agtgaactat attttttgtt cagaatattt   9720
ggacacccaa tggtagatga aagacaagcc atggatgctg ttaaaattaa ttgcaatgag   9780
accaaatttt acttgttaag cagtctgagt atgttaagag gtgcctttat atatagaatt   9840
ataaaagggt ttgtaaataa ttacaacaga tggcctactt taagaaatgc tattgtttta   9900
cccttaagat ggttaactta ctataaacta aacacttatc cttctttgtt ggaacttaca   9960
gaaagagatt tgattgtgtt atcaggacta cgtttctatc gtgagtttcg gttgcctaaa  10020
aaagtggatc ttgaaatgat tataaatgat aaagctatat cacctcctaa aaatttgata  10080
tggactagtt tccctagaaa ttacatgcca tcacacatac aaaactatat agaacatgaa  10140
aaattaaaat tttccgagag tgataaatca agaagagtat tagagtatta tttaagagat  10200
aacaaattca atgaatgtga tttatacaac tgtgtagtta atcaaagtta tctcaacaac  10260
cctaatcatg tggtatcatt gacaggcaaa gaaagagaac tcagtgtagg tagaatgttt  10320
gcaatgcaac cgggaatgtt cagacaggtt caaatattgg cagagaaaat gatagctgaa  10380
aacattttac aattctttcc tgaaagtctt acaagatatg gtgatctaga actacaaaaa  10440
atattagaac tgaaagcagg aataagtaac aaatcaaatc gctacaatga taattacaac  10500
aattacatta gtaagtgctc tatcatcaca gatctcagca aattcaatca agcatttcga  10560
tatgaaacgt catgtatttg tagtgatgtg ctggatgaac tgcatggtgt acaatctcta  10620
ttttcctggt tacatttaac tattcctcat gtcacaataa tatgcacata taggcatgca  10680
ccccccctata taggagatca tattgtagat cttaacaatg tagatgaaca aagtggatta  10740
tatagatatc acatgggtgg catcgaaggg tggtgtcaaa aactatggac catagaagct  10800
atatcactat tggatctaat atctctcaaa gggaaattct caattactgc tttaattaat  10860
ggtgacaatc aatcaataga tataagcaaa ccaatcagac tcatggaagg tcaaactcat  10920
gctcaagcag attatttgct agcattaaat agccttaaat tactgtataa agagtatgca  10980
ggcataggcc acaaattaaa aggaactgag acttatatat cacgagatat gcaatttatg  11040
agtaaaacaa ttcaacataa cggtgtatat tacccagcta gtataaagaa agtcctaaga  11100
gtgggaccgt ggataaacac tatacttgat gatttcaaag tgagtctaga atctataggt  11160
agtttgacac aagaattaga atatagaggt gaaagtctat tatgcagttt aatatttaga  11220
aatgtatggt tatataatca gattgctcta caattaaaaa atcatgcatt atgtaacaat  11280
aaactatatt tggacatatt aaaggttctg aaacacttaa aaaccttttt taatcttgat  11340
aatattgata cagcattaac attgtatatg aatttaccca tgttatttgg tggtggtgat  11400
cccaacttgt tatatcgaag tttctataga agaactcctg acttcctcac agaggctata  11460
```

-continued gttcactctg tgttcatact tagttattat acaaaccatg acttaaaaga taaacttcaa 11520
gatctgtcag atgatagatt gaataagttc ttaacatgca taatcacgtt tgacaaaaac 11580
cctaatgctg aattcgtaac attgatgaga gatcctcaag ctttagggtc tgagagacaa 11640
gctaaaatta ctagcgaaat caatagactg gcagttacag aggttttgag tacagctcca 11700
aacaaaatat tctccaaaag tgcacaacat tatactacta cagagataga tctaaatgat 11760
attatgcaaa atatagaacc tacatatcct catgggctaa gagttgttta tgaaagttta 11820
ccctttttata aagcagagaa aatagtaaat cttatatcag gtacaaaatc tataactaac 11880
atactggaaa aaacttctgc catagactta acagatattg atagagccac tgagatgatg 11940
aggaaaaaca taactttgct tataaggata cttccattgg attgtaacag agataaaaga 12000
gagatattga gtatggaaaa cctaagtatt actgaattaa gcaaatatgt tagggaaaga 12060
tcttggtctt tatccaatat agttggtgtt acatcaccca gtatcatgta tacaatggac 12120
atcaaatata ctacaagcac tatatctagt ggcataatta tagagaaata taatgttaac 12180
agtttaacac gtggtgagag aggacccact aaaccatggg ttggttcatc tacacaagag 12240
aaaaaaacaa tgccagttta taatagacaa gtcttaacca aaaaacagag agatcaaata 12300
gatctattag caaaattgga ttgggtgtat gcatctatag ataacaagga tgaattcatg 12360
gaagaactca gcataggaac ccttgggtta acatatgaaa aggccaagaa attatttcca 12420
caatatttaa gtgtcaatta tttgcatcgc cttacagtca gtagtagacc atgtgaattc 12480
cctgcatcaa taccagctta tagaacaaca aattatcact ttgacactag ccctattaat 12540
cgcatattaa cagaaaagta tggtgatgaa gatattgaca tagtattcca aaactgtata 12600
agctttggcc ttagtttaat gtcagtagta gaacaattta ctaatgtatg tcctaacaga 12660
attattctca tacctaagct taatgagata catttgatga aacctcccat attcacaggt 12720
gatgttgata ttcacaagtt aaaacaagtg atacaaaaac agcatatgtt tttaccagac 12780
aaaataagtt tgactcaata tgtggaatta ttcttaagta ataaaacact caaatctgga 12840
tctcatgtta attctaattt aatattggca cataaaatat ctgactattt tcataatact 12900
tacattttaa gtactaattt agctggacat tggattctga ttatacaact tatgaaagat 12960
tctaaaggta tttttgaaaa agattgggga gagggatata taactgatca tatgtttatt 13020
aatttgaaag ttttcttcaa tgcttataag acctatctct tgtgttttca taaaggttat 13080
ggcaaagcaa agctggagtg tgatatgaac acttcagatc ttctatgtgt attggaatta 13140
atagacagta gttattggaa gtctatgtct aaggtatttt tagaacaaaa agttatcaaa 13200
tacattctta gccaagatgc aagtttacat agagtaaaag gatgtcatag cttcaaatta 13260
tggtttctta aacgtcttaa tgtagcagaa ttcacagttt gcccttgggt tgttaacata 13320
gattatcatc caacacatat gaaagcaata ttaacttata tagatcttgt tagaatggga 13380
ttgataaata tagatagaat acacattaaa aataaacaca aattcaatga tgaattttat 13440
acttctaatc tcttctacat taattataac ttctcagata atactcatct attaactaaa 13500
catataagga ttgctaattc tgaattagaa aataattaca acaaattata tcatcctaca 13560
ccagaaaccc tagagaatat actagccaat ccgattaaaa gtaatgacaa aaagacactg 13620
aatgactatt gtataggtaa aaatgttgac tcaataatgt taccattgtt atctaataag 13680
aagcttatta aatcgtctgc aatgattaga accaattaca gcaaacaaga tttgtataat 13740
ttattcccta tggttgtgat tgatagaatt atagatcatt caggcaatac agccaaatcc 13800
aaccaacttt acactactac ttcccaccaa atatccttag tgcacaatag cacatcactt 13860
tactgcatgc ttccttggca tcatattaat agattcaatt ttgtatttag ttctacaggt 13920
tgtaaaatta gtatagagta tattttaaaa gatcttaaaa ttaaagatcc caattgtata 13980
gcattcatag gtgaaggagc agggaattta ttattgcgta cagtagtgga acttcatcct 14040
gacataagat atatttacag aagtctgaaa gattgcaatg atcatagttt acctattgag 14100
tttttaaggc tgtacaatgg acatatcaac attgattatg gtgaaaattt gaccattcct 14160
gctacagatg caaccaacaa cattcattgg tcttatttac atataaagtt tgctgaacct 14220
atcagtcttt ttgtctgtga tgccgaattg tctgtaacag tcaactggag taaaattata 14280
atagaatgga gcaagcatgt aagaaagtgc aagtactgtt cctcagttaa taaatgtatg 14340
ttaatagtaa aatatcatgc tcaagatgat attgatttca aattagacaa tataactata 14400
ttaaaaactt atgtatgctt aggcagtaag ttaaagggat cggaggttta cttagtcctt 14460
acaataggtc ctgcgaatat attcccagta tttaatgtag tacaaaatgc taaattgata 14520
ctatcaagaa ccaaaaattt catcatgcct aagaaagctg ataaagagtc tattgatgca 14580
aatattaaaa gtttgatacc ctttctttgt taccctataa caaaaaaagg aattaatact 14640
gcattgtcaa aactaaagag tgttgttagt ggagatatac tatcatattc tatagctgga 14700
cgtaatgaag ttttcagcaa taaacttata aatcataagc atatgaacat cttaaaatgg 14760
ttcaatcatg ttttaaattt cagatcaaca gaactaaact ataaccattt atatatggta 14820
gaatctacat atccttacct aagtgaattg ttaaacagct tgacaaccaa tgaacttaaa 14880
aaactgatta aaatcacagg tagtctgtta tacaactttc ataatgaata atgaataaag 14940
atcttataat aaaaattccc atagctatac actaacactg tattcaatta tagttattaa 15000
aaattaaaaa tcatataatt ttttaaataa cttttagtga actaatccta aagttatcat 15060
tttaatcttg gaggaataaa tttaaaccct aatctaattg gtttatatgt gtattaacta 15120
aattacgaga tattagtttt tgacactttt tttctcgt 15158

<210> SEQ ID NO 3
<211> LENGTH: 15918
<212> TYPE: DNA
<213> ORGANISM: Artificial Sequence
<220> FEATURE:
<223> OTHER INFORMATION: recombinant RSV sequence

<400> SEQUENCE: 3
acgggaaaaa atgcgtacaa caaacttgca taaaccaaaa aaatggggca aataagaatt 60
tgataagtac cacttaaatt taactccctt ggttagagat ggctcttagc aaagtcaagt 120
tgaatgatac actcaacaaa gatcaacttc tgtcatccag caaatacacc atccaacgga 180
gcacaggaga tagtattgat actcctaatt atgatgtgca gaaacacatc aataagttat 240
gtggcatgtt attaatcaca gaagatgcta atcataaatt cactgggtta ataggtatgt 300
tatatgcgat gtctaggtta ggaagagaag acaccataaa aatactcaga gatgcgggat 360
atcatgtaaa agcaaatgga gtagatgtaa caacacatcg tcaagacatt aatggaaaag 420
aaatgaaatt tgaagtgtta acattggcaa gcttaacaac tgaaattcaa atcaacattg 480
agatagaatc tagaaaatcc tacaaaaaaa tgctaaaaga aatgggagag gtagctccag 540
aatacaggca tgactctcct gattgtggga tgataatatt atgtatagca gcattagtaa 600
taactaaatt agcagcaggg gacagatctg gtcttacagc cgtgattagg agagctaata 660
atgtcctaaa aaatgaaatg aaacgttaca aaggcttact acccaaggac atagccaaca 720

-continued

```
gcttctatga agtgtttgaa aaacatcccc actttataga tgtttttgtt cattttggta    780
tagcacaatc ttctaccaga ggtggcagta gagttgaagg gatttttgca ggattgttta    840
tgaatgccta tggtgcaggg caagtgatgt tacggtgggg agtcttagca aaatcagtta    900
aaaatattat gttaggacat gctagtgtgc aagcagaaat ggaacaagtt gttgaggttt    960
atgaatatgc ccaaaaattg ggtggtgaag caggattcta ccatatattg aacaacccaa   1020
aagcatcatt attatctttg actcaatttc ctcacttctc cagtgtagta ttaggcaatg   1080
ctgctggcct aggcataatg ggagagtaca gaggtacacc gaggaatcaa gatctatatg   1140
atgcagcaaa ggcatatgct gaacaactca aagaaaatgg tgtgattaac tacagtgtac   1200
tagacttgac agcagaagaa ctagaggcta tcaaacatca gcttaatcca aaagataatg   1260
atgtagagct ttgagttaat aaaaaatggg gcaaataaat catcatggaa aagtttgctc   1320
ctgaattcca tggagaagat gcaaacaaca gggctactaa attcctagaa tcaataaagg   1380
gcaaattcac atcacccaaa gatcccaaga aaaaagatag tatcatatct gtcaactcaa   1440
tagatataga agtaaccaaa gaaagcccta taacatcaaa ttcaactatt atcaacccaa   1500
caaatgagac agatgatact gcagggaaca agcccaatta tcaaagaaaa cctctagtaa   1560
gtttcaaaga agaccctaca ccaagtgata atccctttc taaactatac aaagaaacca   1620
tagaaacatt tgataacaat gaagaagaat ccagctattc atacgaagaa ataaatgatc   1680
agacaaacga taatataaca gcaagattag ataggattga tgaaaaatta agtgaaatac   1740
taggaatgct tcacacatta gtagtggcaa gtgcaggacc tacatctgct cgggatggta   1800
taagagatgc catggttggt ttaagagaag aaatgataga aaaaatcaga actgaagcat   1860
taatgaccaa tgacagatta gaagctatgg caagactcag gaatgaggaa agtgaaaaga   1920
tggcaaaaga cacatcagat gaagtgtctc tcaatccaac atcagagaaa ttgaacaacc   1980
tattggaagg gaatgatagt gacaatgatc tatcacttga agatttctga ttagttacca   2040
atcttcacat caacacacaa taccaacaga agaccaacaa actaaccaac ccaatcatcc   2100
aaccaaacat ccatccgcca atcagccaaa cagccaacaa aacaaccagc caatccaaaa   2160
ctaaccaccc ggaaaaaatc tataatatag ttacaaaaaa aggaatcgat ggggcaaata   2220
caagtatggt gagcaagggc gaggagctgt tcaccggggt ggtgcccatc ctggtcgagc   2280
tggacggcga cgtaaacggc cacaagttca gcgtgtccgg cgagggcgag ggcgatgcca   2340
cctacggcaa gctgaccctg aagttcatct gcaccaccgg caagctgccc gtgccctggc   2400
ccaccctcgt gaccaccctg acctacggcg tgcagtgctt cagccgctac cccgaccaca   2460
tgaagcagca cgacttcttc aagtccgcca tgcccgaagg ctacgtccag gagcgcacca   2520
tcttcttcaa ggacgacggc aactacaaga cccgcgccga ggtgaagttc gagggcgaca   2580
ccctggtgaa ccgcatcgag ctgaagggca tcgacttcaa ggaggacggc aacatcctgg   2640
ggcacaagct ggagtacaac tacaacagcc acaacgtcta tatcatggcc gacaagcaga   2700
agaacggcat caaggtgaac ttcaagatcc gccacaacat cgaggacggc agcgtgcagc   2760
tcgccgacca ctaccagcag aacaccccca tcggcgacgg ccccgtgctg ctgcccgaca   2820
accactacct gagcacccag tccgccctga gcaaagaccc caacgagaag cgcgatcaca   2880
tggtcctgct ggagttcgtg accgccgccg ggatcactct cggcatggac gagctgtaca   2940
agtaaaagta gttacttaaa aagtcgacgg tggggcaaat atggaaacat acgtgaacaa   3000
gcttcacgaa ggctccacat acacagctgc tgttcaatac aatgtcttag aaaaagacga   3060
```

tgaccctgca tcacttacaa tatgggtgcc catgttccaa tcatctatgc cagcagattt 3120
acttataaaa gaactagcta atgtcaacat actagtgaaa caaatatcca cacccaaggg 3180
accttcacta agagtcatga taaactcaag aagtgcagtg ctagcacaaa tgcccagcaa 3240
atttaccata tgcgctaatg tgtccttgga tgaaagaagc aaactagcat atgatgtaac 3300
cacaccctgt gaaatcaagg catgtagtct aacatgccta aaatcaaaaa atatgttgac 3360
tacagttaaa gatctcacta tgaagacact caaccctaca catgatatta ttgctttatg 3420
tgaatttgaa aacatagtaa catcaaaaaa agtcataata ccaacatacc taagatccat 3480
cagtgtcaga aataaagatc tgaacacact tgaaaatata acaaccactg aattcaaaaa 3540
tgctatcaca aatgcaaaaa tcatccctta ctcaggatta ctattagtca tcacagtgac 3600
tgacaacaaa ggagcattca aatacataaa gccacaaagt caattcatag tagatcttgg 3660
agcttaccta gaaaaagaaa gtatatatta tgttaccaca aattggaagc acacagctac 3720
acgatttgca atcaaaccca tggaagatta accttttcc tctacatcag tgtgttaatt 3780
catacaaact ttctacctac attcttcact tcaccatcac aatcacaaac actctgtggt 3840
tcaaccaatc aaacaaaact tatctgaagt cccagatcat cccaagtcat tgtttatcag 3900
atctagtact caaataagtt aataaaaaat atacacatgg ggcaaataat cattggagga 3960
aatccaacta atcacaatat ctgttaacat agacaagtcc acacaccata cagaatcaac 4020
caatggaaaa tacatccata acaatagaat tctcaagcaa attctggcct tactttacac 4080
taatacacat gatcacaaca ataatctctt tgctaatcat aatctccatc atgattgcaa 4140
tactaaacaa actttgtgaa tataacgtat tccataacaa aacctttgag ttaccaagag 4200
ctcgagttaa tacttgataa agtagttaat taaaaatagt cataacaatg aactaggata 4260
tcaagactaa caataacatt ggggcaaatg caaacatgtc caaaaacaag gaccaacgca 4320
ccgctaagac attagaaagg acctgggaca ctctcaatca tttattattc atatcatcgt 4380
gcttatataa gttaaatctt aaatctgtag cacaaatcac attatccatt ctggcaatga 4440
taatctcaac ttcacttata attgcagcca tcatattcat agcctcggca aaccacaaag 4500
tcacaccaac aactgcaatc atacaagatg caacaagcca gatcaagaac acaaccccaa 4560
catacctcac ccagaatcct cagcttggaa tcagtccctc taatccgtct gaaattacat 4620
cacaaatcac caccatacta gcttcaacaa caccaggagt caagtcaacc ctgcaatcca 4680
caacagtcaa gaccaaaaac acaacaacaa ctcaaacaca acccagcaag cccaccacaa 4740
aacaacgcca aaacaaacca ccaagcaaac ccaataatga ttttcacttt gaagtgttca 4800
actttgtacc ctgcagcata tgcagcaaca atccaacctg ctgggctatc tgcaaaagaa 4860
taccaaacaa aaaaccagga aagaaaacca ctaccaagcc cacaaaaaaa ccaaccctca 4920
agacaaccaa aaaagatccc aaacctcaaa ccactaaatc aaaggaagta cccaccacca 4980
agcccacaga agagccaacc atcaacacca ccaaaacaaa catcataact acactactca 5040
cctccaacac cacaggaaat ccagaactca caagtcaaat ggaaaccttc cactcaactt 5100
cctccgaagg caatccaagc ccttctcaag tctctacaac atccgagtac ccatcacaac 5160
cttcatctcc acccaacaca ccacgccagt agttacttaa aaacatatta tcacaaaagg 5220
ccttgaccaa cttaaacaga atcaaaataa actctggggc aaataacaat ggagttgcta 5280
atcctcaaag caaatgcaat taccacaatc ctcactgcag tcacattttg ttttgcttct 5340
ggtcaaaaca tcactgaaga attttatcaa tcaacatgca gtgcagttag caaaggctat 5400
cttagtgctc tgagaactgg ttggtatacc agtgttataa ctatagaatt aagtaatatc 5460

-continued

```
aagaaaaata agtgtaatgg aacagatgct aaggtaaaat tgataaaaca agaattagat   5520
aaatataaaa atgctgtaac agaattgcag ttgctcatgc aaagcacaca agcaacaaac   5580
aatcgagcca gaagagaact accaaggttt atgaattata cactcaacaa tgccaaaaaa   5640
accaatgtaa cattaagcaa gaaaaggaaa agaagatttc ttggtttttt gttaggtgtt   5700
ggatctgcaa tcgccagtgg cgttgctgta tctaaggtcc tgcacctaga aggggaagtg   5760
aacaagatca aaagtgctct actatccaca aacaaggctg tagtcagctt atcaaatgga   5820
gttagtgttt taaccagcaa agtgttagac ctcaaaaact atatagataa acaattgtta   5880
cctattgtga acaagcaaag ctgcagcata tcaaatatag aaactgtgat agagttccaa   5940
caaaagaaca acagactact agagattacc agggaattta gtgttaatgc aggcgtaact   6000
acacctgtaa gcacttacat gttaactaat agtgaattat tgtcattaat caatgatatg   6060
cctataacaa atgatcagaa aaagttaatg tccaacaatg ttcaaatagt tagacagcaa   6120
agttactcta tcatgtccat aataaaagag gaagtcttag catatgtagt acaattacca   6180
ctatatggtg ttatagatac accctgttgg aaactacaca catcccctct atgtacaacc   6240
aacacaaaag aagggtccaa catctgttta acaagaactg acagaggatg gtactgtgac   6300
aatgcaggat cagtatcttt cttcccacaa gctgaaacat gtaaagttca atcaaatcga   6360
gtattttgtg acacaatgaa cagtttaaca ttaccaagtg aagtaaatct ctgcaatgtt   6420
gacatattca accccaaata tgattgtaaa attatgactt caaaaacaga tgtaagcagc   6480
tccgttatca catctctagg agccattgtg tcatgctatg gcaaaactaa atgtacagca   6540
tccaataaaa atcgtggaat cataaagaca ttttctaacg ggtgcgatta tgtatcaaat   6600
aaaggggtgg acactgtgtc tgtaggtaac acattatatt atgtaaataa gcaagaaggt   6660
aaaagtctct atgtaaaagg tgaaccaata ataaatttct atgacccatt agtattcccc   6720
tctgatgaat ttgatgcatc aatatctcaa gtcaacgaga agattaacca gagcctagca   6780
tttattcgta aatccgatga attattacat aatgtaaatg ctggtaaatc caccacaaat   6840
atcatgataa ctactataat tatagtgatt atagtaatat tgttatcatt aattgctgtt   6900
ggactgctct tatactgtaa ggccagaagc acaccagtca cactaagcaa agatcaactg   6960
agtggtataa ataatattgc atttagtaac taaataaaaa tagcacctaa tcatgttctt   7020
acaatggttt actatctgct catagacaac ccatctgtca ttggattttc ttaaaatctg   7080
aacttcatcg aaactctcat ctataaacca tctcacttac actatttaag tagattccta   7140
gtttatagtt atataaaaca caattgcatg ccagattaac ttaccatctg taaaaatgaa   7200
aactggggca aatatgtcac gaaggaatcc ttgcaaattt gaaattcgag gtcattgctt   7260
aaatggtaag aggtgtcatt ttagtcataa ttattttgaa tggccacccc atgcactgct   7320
tgtaagacaa aactttatgt taaacagaat acttaagtct atggataaaa gtatagatac   7380
cttatcagaa ataagtggag ctgcagagtt ggacagaaca gaagagtatg ctcttggtgt   7440
agttggagtg ctagagagtt atataggatc aataaacaat ataactaaac aatcagcatg   7500
tgttgccatg agcaaactcc tcactgaact caatagtgat gatatcaaaa agctgaggga   7560
caatgaagag ctaaattcac ccaagataag agtgtacaat actgtcatat catatattga   7620
aagcaacagg aaaaacaata aacaaactat ccatctgtta aaaagattgc cagcagacgt   7680
attgaagaaa accatcaaaa acacattgga tatccataag agcataacca tcaacaaccc   7740
aaaagaatca actgttagtg atacaaatga ccatgccaaa aataatgata ctacctgaca   7800
```

-continued

```
aatatccttg tagtataact tccatactaa taacaagtag atgtagagtt actatgtata   7860
atcaaaagaa cacactatat ttcaatcaaa acaacccaaa taaccatatg tactcaccga   7920
atcaaacatt caatgaaatc cattggacct ctcaagaatt gattgacaca attcaaaatt   7980
ttctacaaca tctaggtatt attgaggata tatatacaat atatatatta gtgtcataac   8040
actcaattct aacactcacc acatcgttac attattaatt caaacaattc aagttgtggg   8100
acaaaatgga tcccattatt aatggaaatt ctgctaatgt ttatctaacc gatagttatt   8160
taaaaggtgt tatctctttc tcagagtgta atgctttagg aagttacata ttcaatggtc   8220
cttatctcaa aaatgattat accaacttaa ttagtagaca aaatccatta atagaacaca   8280
tgaatctaaa gaaactaaat ataacacagt ccttaatatc taagtatcat aaaggtgaaa   8340
taaaattaga agaacctact tattttcagt cattacttat gacatacaag agtatgacct   8400
cgtcagaaca gattgctacc actaatttac ttaaaaagat aataagaaga gctatagaaa   8460
taagtgatgt caaagtctat gctatattga ataaactagg gcttaaagaa aaggacaaga   8520
ttaaatccaa caatggacaa gatgaagaca actcagttat tacgaccata atcaaagatg   8580
atatactttc agctgttaaa gataatcaat ctcatcttaa agcagacaaa aatcactcta   8640
caaaacaaaa agacacaatc aaaacaacac tcttgaagaa attgatgtgt tcaatgcaac   8700
atcctccatc atggttaata cattggttta acttatacac aaaattaaac aacatattaa   8760
cacagtatcg atcaaatgag gtaaaaaacc atgggtttac attgatagat aatcaaactc   8820
ttagtggatt tcaatttatt ttgaaccaat atggttgtat agtttatcat aaggaactca   8880
aaagaattac tgtgacaacc tataatcaat tcttgacatg gaaagatatt agccttagta   8940
gattaaatgt ttgtttaatt acatggatta gtaactgctt gaacacatta aataaaagct   9000
taggcttaag atgcggattc aataatgtta tcttgacaca actattcctt tatggagatt   9060
gtatactaaa gctatttcac aatgaggggt tctacataat aaaagaggta gagggattta   9120
ttatgtctct aattttaaat ataacagaag aagatcaatt cagaaaacga ttttataata   9180
gtatgctcaa caacatcaca gatgctgcta ataaagctca gaaaaatctg ctatcaagag   9240
tatgtcatac attattagat aagacagtgt ccgataatat aataaatggc agatggataa   9300
ttctattaag taagttcctt aaattaatta agcttgcagg tgacaataac cttaacaatc   9360
tgagtgaact atattttttg ttcagaatat ttggacaccc aatggtagat gaaagacaag   9420
ccatggatgc tgttaaaatt aattgcaatg agaccaaatt ttacttgtta agcagtctga   9480
gtatgttaag aggtgccttt atatatagaa ttataaaagg gtttgtaaat aattacaaca   9540
gatggcctac tttaagaaat gctattgttt taccettaag atggttaact tactataaac   9600
taaacactta tccttctttg ttggaactta cagaaagaga tttgattgtg ttatcaggac   9660
tacgtttcta tcgtgagttt cggttgccta aaaaagtgga tcttgaaatg attataaatg   9720
ataaagctat atcacctcct aaaaatttga tatggactag tttccctaga aattacatgc   9780
catcacacat acaaaactat atagaacatg aaaaattaaa attttccgag agtgataaat   9840
caagaagagt attagagtat tatttaagag ataacaaatt caatgaatgt gatttataca   9900
actgtgtagt taatcaaagt tatctcaaca accctaatca tgtggtatca ttgacaggca   9960
aagaaagaga actcagtgta ggtagaatgt ttgcaatgca accgggaatg ttcagacagg  10020
ttcaaatatt ggcagagaaa atgatagctg aaaacatttt acaattcttt cctgaaagtc  10080
ttacaagata tggtgatcta gaactacaaa aaatattaga actgaaagca ggaataagta  10140
acaaatcaaa tcgctacaat gataattaca acaattacat tagtaagtgc tctatcatca  10200
```

-continued

```
cagatctcag caaattcaat caagcatttc gatatgaaac gtcatgtatt tgtagtgatg  10260
tgctggatga actgcatggt gtacaatctc tattttcctg gttacattta actattcctc  10320
atgtcacaat aatatgcaca tataggcatg caccccccta tataggagat catattgtag  10380
atcttaacaa tgtagatgaa caaagtggat tatatagata tcacatgggt ggcatcgaag  10440
ggtggtgtca aaaactatgg accatagaag ctatatcact attggatcta atatctctca  10500
aagggaaatt ctcaattact gctttaatta atggtgacaa tcaatcaata gatataagca  10560
aaccaatcag actcatggaa ggtcaaactc atgctcaagc agattatttg ctagcattaa  10620
atagccttaa attactgtat aaagagtatg caggcatagg ccacaaatta aaaggaactg  10680
agacttatat atcacgagat atgcaattta tgagtaaaac aattcaacat aacggtgtat  10740
attacccagc tagtataaag aaagtcctaa gagtgggacc gtggataaac actatacttg  10800
atgatttcaa agtgagtcta gaatctatag gtagtttgac acaagaatta gaatatagag  10860
gtgaaagtct attatgcagt ttaatattta gaaatgtatg gttatataat cagattgctc  10920
tacaattaaa aaatcatgca ttatgtaaca ataaactata tttggacata ttaaaggttc  10980
tgaaacactt aaaaaccttt tttaatcttg ataatattga tacagcatta acattgtata  11040
tgaatttacc catgttattt ggtggtggtg atcccaactt gttatatcga agtttctata  11100
gaagaactcc tgacttcctc acagaggcta tagttcactc tgtgttcata cttagttatt  11160
atacaaacca tgacttaaaa gataaacttc aagatctgtc agatgataga ttgaataagt  11220
tcttaacatg cataatcacg tttgacaaaa accctaatgc tgaattcgta acattgatga  11280
gagatcctca agctttaggg tctgagagac aagctaaaat tactagcgaa atcaatagac  11340
tggcagttac agaggttttg agtacagctc caaacaaaat attctccaaa agtgcacaac  11400
attatactac tacagagata gatctaaatg atattatgca aaatatagaa cctacatatc  11460
ctcatgggct aagagttgtt tatgaaagtt taccctttta taaagcagag aaaatagtaa  11520
atcttatatc aggtacaaaa tctataacta acatactgga aaaaacttct gccatagact  11580
taacagatat tgatagagcc actgagatga tgaggaaaaa cataactttg cttataagga  11640
tacttccatt ggattgtaac agagataaaa gagagatatt gagtatggaa aacctaagta  11700
ttactgaatt aagcaaatat gttagggaaa gatcttggtc tttatccaat atagttggtg  11760
ttacatcacc cagtatcatg tatacaatgg acatcaaata tactacaagc actatatcta  11820
gtggcataat tatagagaaa tataatgtta acagtttaac acgtggtgag agaggaccca  11880
ctaaaccatg ggttggttca tctacacaag agaaaaaaac aatgccagtt tataatagac  11940
aagtcttaac caaaaaacag agagatcaaa tagatctatt agcaaaattg gattgggtgt  12000
atgcatctat agataacaag gatgaattca tggaagaact cagcatagga acccttgggt  12060
taacatatga aaaggccaag aaattatttc cacaatattt aagtgtcaat tatttgcatc  12120
gccttacagt cagtagtaga ccatgtgaat tccctgcatc aataccagct tatagaacaa  12180
caaattatca ctttgacact agccctatta atcgcatatt aacagaaaag tatggtgatg  12240
aagatattga catagtattc caaaactgta taagctttgg ccttagttta atgtcagtag  12300
tagaacaatt tactaatgta tgtcctaaca gaattattct catacctaag cttaatgaga  12360
tacatttgat gaaacctccc atattcacag gtgatgttga tattcacaag ttaaaacaag  12420
tgatacaaaa acagcatatg tttttaccag acaaaataag tttgactcaa tatgtggaat  12480
tattcttaag taataaaaca ctcaaatctg gatctcatgt taattctaat ttaatattgg  12540
```

-continued

```
cacataaaat atctgactat tttcataata cttacatttt aagtactaat ttagctggac  12600
attggattct gattatacaa cttatgaaag attctaaagg tatttttgaa aaagattggg  12660
gagagggata tataactgat catatgttta ttaatttgaa agttttcttc aatgcttata  12720
agacctatct cttgtgtttt cataaaggtt atggcaaagc aaagctggag tgtgatatga  12780
acacttcaga tcttctatgt gtattggaat taatagacag tagttattgg aagtctatgt  12840
ctaaggtatt tttagaacaa aaagttatca aatacattct tagccaagat gcaagtttac  12900
atagagtaaa aggatgtcat agcttcaaat tatggtttct taaacgtctt aatgtagcag  12960
aattcacagt ttgcccttgg gttgttaaca tagattatca tccaacacat atgaaagcaa  13020
tattaactta tatagatctt gttagaatgg gattgataaa tatagataga atacacatta  13080
aaaataaaca caaattcaat gatgaatttt atacttctaa tctcttctac attaattata  13140
acttctcaga taatactcat ctattaacta aacatataag gattgctaat tctgaattag  13200
aaaataatta caacaaatta tatcatccta caccagaaac cctagagaat atactagcca  13260
atccgattaa aagtaatgac aaaaagacac tgaatgacta ttgtataggt aaaaatgttg  13320
actcaataat gttaccattg ttatctaata agaagcttat taaatcgtct gcaatgatta  13380
gaaccaatta cagcaaacaa gatttgtata atttattccc tatggttgtg attgatagaa  13440
ttatagatca ttcaggcaat acagccaaat ccaaccaact ttacactact acttcccacc  13500
aaatatcctt agtgcacaat agcacatcac tttactgcat gcttccttgg catcatatta  13560
atagattcaa ttttgtattt agttctacag gttgtaaaat tagtatagag tatattttaa  13620
aagatcttaa aattaaagat cccaattgta tagcattcat aggtgaagga gcagggaatt  13680
tattattgcg tacagtagtg gaacttcatc ctgacataag atatatttac agaagtctga  13740
aagattgcaa tgatcatagt ttacctattg agtttttaag gctgtacaat ggacatatca  13800
acattgatta tggtgaaaat ttgaccattc ctgctacaga tgcaaccaac aacattcatt  13860
ggtcttattt acatataaag tttgctgaac ctatcagtct ttttgtctgt gatgccgaat  13920
tgtctgtaac agtcaactgg agtaaaatta taatagaatg gagcaagcat gtaagaaagt  13980
gcaagtactg ttcctcagtt aataaatgta tgttaatagt aaaatatcat gctcaagatg  14040
atattgattt caaattagac aatataacta tattaaaaac ttatgtatgc ttaggcagta  14100
agttaaaggg atcggaggtt tacttagtcc ttacaatagg tcctgcgaat atattcccag  14160
tatttaatgt agtacaaaat gctaaattga tactatcaag aaccaaaaat ttcatcatgc  14220
ctaagaaagc tgataaagag tctattgatg caaatattaa aagtttgata ccctttcttt  14280
gttaccctat aacaaaaaaa ggaattaata ctgcattgtc aaaactaaag agtgttgtta  14340
gtggagatat actatcatat tctatagctg gacgtaatga agttttcagc aataaactta  14400
taaatcataa gcatatgaac atcttaaaat ggttcaatca tgttttaaat ttcagatcaa  14460
cagaactaaa ctataaccat ttatatatgg tagaatctac atatccttac ctaagtgaat  14520
tgttaaacag cttgacaacc aatgaactta aaaaactgat taaaatcaca ggtagtctgt  14580
tatacaactt tcataatgaa taatgaataa agatcttata ataaaaattc ccatagctat  14640
acactaacac tgtattcaat tatagttata aaaattaaaa atggtaccat ggggcaaata  14700
agaatttgat aagtaccact taaatttaac tcccttggtt agagatgggc agcaattcat  14760
tgagtatgat aaaagttaga ttacaaaatt tgtttgacaa tgatgaagta gcattgttaa  14820
aaataacatg ctatactgat aaattaatac atttaactaa tgctttggct aaggcagtga  14880
tacatacaat caaattgaat ggcattgtgt ttgtgcatgt tattacaagt agtgatattt  14940
```

```
gccctaataa taatattgta gtaaaatcca atttcacaac aatgccagta ctacaaaatg  15000
gaggttatat atgggaaatg atggaattaa cacattgctc tcaacctaat ggtctactag  15060
atgacaattg tgaaattaaa ttctccaaaa aactaagtga ttcaacaatg accaattata  15120
tgaatcaatt atctgaatta cttggatttg atcttaatcc ataaattata attaatatca  15180
actagcaaat caatgtcact aacaccatta gttaatataa aacttaacag aagacaaaaa  15240
tggggcaaat aaatcaattc agccaaccca accatggaca caacccacaa tgataataca  15300
ccacaaagac tgatgatcac agacatgaga ccgttgtcac ttgagaccat aataacatca  15360
ctaaccagag acatcataac acacaaattt atatacttga taaatcatga atgcatagtg  15420
agaaaacttg atgaaagaca ggccacattt acattcctgg tcaactatga aatgaaacta  15480
ttacacaaag taggaagcac taaatataaa aaatatactg aatacaacac aaaatatggc  15540
actttcccta tgccaatatt catcaatcat gatgggttct tagaatgcat tggcattaag  15600
cctacaaagc atactcccat aatatacaag tatgatctca atccataaat ttcaacacaa  15660
tattcacaca atctaaaaca acaactctat gcataactat actccatagt ccagatggag  15720
cctgaaaatt atagtaattt aaaacttaag gagagatata agatagaaga tggtaccatt  15780
ttttaaataa cttttagtga actaatccta aagttatcat tttaatcttg gaggaataaa  15840
tttaaaccct aatctaattg gtttatatgt gtattaacta aattacgaga tattagtttt  15900
tgacactttt tttctcgt                                                15918

<210> SEQ ID NO 4
<211> LENGTH: 15157
<212> TYPE: DNA
<213> ORGANISM: Artificial Sequence
<220> FEATURE:
<223> OTHER INFORMATION: recombinant RSV sequence

<400> SEQUENCE: 4

acgggaaaaa atgcgtacaa caaacttgca taaaccaaaa aaatggggca aataagaatt     60
tgataagtac cacttaaatt taactccctt ggttagagat ggctcttagc aaagtcaagt    120
tgaatgatac actcaacaaa gatcaacttc tgtcatccag caaatacacc atccaacgga    180
gcacaggaga tagtattgat actcctaatt atgatgtgca gaaacacatc aataagttat    240
gtggcatgtt attaatcaca gaagatgcta atcataaatt cactgggtta ataggtatgt    300
tatatgcgat gtctaggtta ggaagagaag acaccataaa aatactcaga gatgcgggat    360
atcatgtaaa agcaaatgga gtagatgtaa caacacatcg tcaagacatt aatggaaaag    420
aaatgaaatt tgaagtgtta acattggcaa gcttaacaac tgaaattcaa atcaacattg    480
agatagaatc tagaaaatcc tacaaaaaaa tgctaaaaga aatgggagag gtagctccag    540
aatacaggca tgactctcct gattgtggga tgataatatt atgtatagca gcattagtaa    600
taactaaatt agcagcaggg gacagatctg gtcttacagc cgtgattagg agagctaata    660
atgtcctaaa aaatgaaatg aaacgttaca aaggcttact acccaaggac atagccaaca    720
gcttctatga agtgtttgaa aaacatcccc actttataga tgtttttgtt cattttggta    780
tagcacaatc ttctaccaga ggtggcagta gagttgaagg gatttttgca ggattgttta    840
tgaatgccta tggtgcaggg caagtgatgt tacggtgggg agtcttagca aaatcagtta    900
aaaatattat gttaggacat gctagtgtgc aagcagaaat ggaacaagtt gttgaggttt    960
atgaatatgc ccaaaaattg ggtggtgaag caggattcta ccatatattg aacaacccaa   1020
```

-continued

```
aagcatcatt attatctttg actcaatttc ctcacttctc cagtgtagta ttaggcaatg   1080
ctgctggcct aggcataatg ggagagtaca gaggtacacc gaggaatcaa gatctatatg   1140
atgcagcaaa ggcatatgct gaacaactca aagaaaatgg tgtgattaac tacagtgtac   1200
tagacttgac agcagaagaa ctagaggcta tcaaacatca gcttaatcca aaagataatg   1260
atgtagagct ttgagttaat aaaaaatggg gcaaataaat catcatggaa aagtttgctc   1320
ctgaattcca tggagaagat gcaaacaaca gggctactaa attcctagaa tcaataaagg   1380
gcaaattcac atcacccaaa gatcccaaga aaaaagatag tatcatatct gtcaactcaa   1440
tagatataga agtaaccaaa gaaagcccta taacatcaaa ttcaactatt atcaacccaa   1500
caaatgagac agatgatact gcagggaaca agcccaatta tcaaagaaaa cctctagtaa   1560
gtttcaaaga agaccctaca ccaagtgata atcccttttc taaactatac aaagaaacca   1620
tagaaacatt tgataacaat gaagaagaat ccagctattc atacgaagaa ataaatgatc   1680
agacaaacga taatataaca gcaagattag ataggattga tgaaaaatta agtgaaatac   1740
taggaatgct tcacacatta gtagtggcaa gtgcaggacc tacatctgct cgggatggta   1800
taagagatgc catggttggt ttaagagaag aaatgataga aaaaatcaga actgaagcat   1860
taatgaccaa tgacagatta gaagctatgg caagactcag gaatgaggaa agtgaaaaga   1920
tggcaaaaga cacatcagat gaagtgtctc tcaatccaac atcagagaaa ttgaacaacc   1980
tattggaagg gaatgatagt gacaatgatc tatcacttga agatttctga ttagttacca   2040
atcttcacat caacacacaa taccaacaga agaccaacaa actaaccaac ccaatcatcc   2100
aaccaaacat ccatccgcca atcagccaaa cagccaacaa aacaaccagc caatccaaaa   2160
ctaaccaccc ggaaaaaatc tataatatag ttacaaaaaa aggaaagggt ggggcaaata   2220
tggaaacata cgtgaacaag cttcacgaag gctccacata cacagctgct gttcaataca   2280
atgtcttaga aaaagacgat gaccctgcat cacttacaat atgggtgccc atgttccaat   2340
catctatgcc agcagattta cttataaaag aactagctaa tgtcaacata ctagtgaaac   2400
aaatatccac acccaaggga ccttcactaa gagtcatgat aaactcaaga agtgcagtgc   2460
tagcacaaat gcccagcaaa tttaccatat gcgctaatgt gtccttggat gaaagaagca   2520
aactagcata tgatgtaacc acaccctgtg aaatcaaggc atgtagtcta acatgcctaa   2580
aatcaaaaaa tatgttgact acagttaaag atctcactat gaagacactc aaccctacac   2640
atgatattat tgctttatgt gaatttgaaa acatagtaac atcaaaaaaa gtcataatac   2700
caacatacct aagatccatc agtgtcagaa ataaagatct gaacacactt gaaaatataa   2760
caaccactga attcaaaaat gctatcacaa atgcaaaaat catcccttac tcaggattac   2820
tattagtcat cacagtgact gacaacaaag gagcattcaa atacataaag ccacaaagtc   2880
aattcatagt agatcttgga gcttacctag aaaaagaaag tatatattat gttaccacaa   2940
attggaagca cacagctaca cgatttgcaa tcaaacccat ggaagattaa ccttttttcct   3000
ctacatcagt gtgttaattc atacaaactt tctacctaca ttcttcactt caccatcaca   3060
atcacaaaca ctctgtggtt caaccaatca aacaaaactt atctgaagtc ccagatcatc   3120
ccaagtcatt gtttatcaga tctagtactc aaataagtta ataaaaaata tacacatggg   3180
gcaaataatc attggaggaa atccaactaa tcacaatatc tgttaacata gacaagtcca   3240
cacaccatac agaatcaacc aatggaaaat acatccataa caatagaatt ctcaagcaaa   3300
ttctggcctt actttacact aatacacatg atcacaacaa taatctcttt gctaatcata   3360
atctccatca tgattgcaat actaaacaaa ctttgtgaat ataacgtatt ccataacaaa   3420
```

acctttgagt taccaagagc tcgagttaat acttgataaa gtagttaatt aaaaatagtc 3480
ataacaatga actaggatat caagactaac aataacattg gggcaaatgc aaacatgtcc 3540
aaaaacaagg accaacgcac cgctaagaca ttagaaagga cctgggacac tctcaatcat 3600
ttattattca tatcatcgtg cttatataag ttaaatctta aatctgtagc acaaatcaca 3660
ttatccattc tggcaatgat aatctcaact tcacttataa ttgcagccat catattcata 3720
gcctcggcaa accacaaagt cacaccaaca actgcaatca tacaagatgc aacaagccag 3780
atcaagaaca caaccccaac atacctcacc cagaatcctc agcttggaat cagtccctct 3840
aatccgtctg aaattacatc acaaatcacc accatactag cttcaacaac accaggagtc 3900
aagtcaaccc tgcaatccac aacagtcaag accaaaaaca caacaacaac tcaaacacaa 3960
cccagcaagc ccaccacaaa acaacgccaa aacaaaccac caagcaaacc caataatgat 4020
tttcactttg aagtgttcaa ctttgtaccc tgcagcatat gcagcaacaa tccaacctgc 4080
tgggctatct gcaaaagaat accaaacaaa aaaccaggaa agaaaaccac taccaagccc 4140
acaaaaaaac caaccctcaa gacaaccaaa aaagatccca aacctcaaac cactaaatca 4200
aaggaagtac ccaccaccaa gcccacagaa gagccaacca tcaacaccac caaaacaaac 4260
atcataacta cactactcac ctccaacacc acaggaaatc cagaactcac aagtcaaatg 4320
gaaaccttcc actcaacttc ctccgaaggc aatccaagcc cttctcaagt ctctacaaca 4380
tccgagtacc catcacaacc ttcatctcca cccaacacac cacgccagta gttacttaaa 4440
aacatattat cacaaaaggc cttgaccaac ttaaacagaa tcaaaataaa ctctggggca 4500
aataacaatg gagttgctaa tcctcaaagc aaatgcaatt accacaatcc tcactgcagt 4560
cacattttgt tttgcttctg gtcaaaacat cactgaagaa ttttatcaat caacatgcag 4620
tgcagttagc aaaggctatc ttagtgctct gagaactggt tggtatacca gtgttataac 4680
tatagaatta agtaatatca agaaaaataa gtgtaatgga acagatgcta aggtaaaatt 4740
gataaaacaa gaattagata aatataaaaa tgctgtaaca gaattgcagt tgctcatgca 4800
aagcacacaa gcaacaaaca atcgagccag aagagaacta ccaaggttta tgaattatac 4860
actcaacaat gccaaaaaaa ccaatgtaac attaagcaag aaaaggaaaa gaagatttct 4920 tggtttttttg ttaggtgttg gatctgcaat cgccagtggc gttgctgtat ctaaggtcct 4980
gcacctagaa ggggaagtga acaagatcaa aagtgctcta ctatccacaa acaaggctgt 5040
agtcagctta tcaaatggag ttagtgtttt aaccagcaaa gtgttagacc tcaaaaacta 5100
tatagataaa caattgttac ctattgtgaa caagcaaagc tgcagcatat caaatataga 5160
aactgtgata gagttccaac aaaagaacaa cagactacta gagattacca gggaatttag 5220
tgttaatgca ggcgtaacta cacctgtaag cacttacatg ttaactaata gtgaattatt 5280
gtcattaatc aatgatatgc ctataacaaa tgatcagaaa aagttaatgt ccaacaatgt 5340
tcaaatagtt agacagcaaa gttactctat catgtccata ataaaagagg aagtcttagc 5400
atatgtagta caattaccac tatatggtgt tatagataca ccctgttgga aactacacac 5460
atcccctcta tgtacaacca acacaaaaga agggtccaac atctgtttaa caagaactga 5520
cagaggatgg tactgtgaca atgcaggatc agtatctttc ttcccacaag ctgaaacatg 5580
taaagttcaa tcaaatcgag tattttgtga cacaatgaac agtttaacat taccaagtga 5640
agtaaatctc tgcaatgttg acatattcaa ccccaaatat gattgtaaaa ttatgacttc 5700
aaaaacagat gtaagcagct ccgttatcac atctctagga gccattgtgt catgctatgg 5760

-continued

```
caaaactaaa tgtacagcat ccaataaaaa tcgtggaatc ataaagacat tttctaacgg   5820
gtgcgattat gtatcaaata aaggggtgga cactgtgtct gtaggtaaca cattatatta   5880
tgtaaataag caagaaggta aaagtctcta tgtaaaaggt gaaccaataa taaatttcta   5940
tgacccatta gtattcccct ctgatgaatt tgatgcatca atatctcaag tcaacgagaa   6000
gattaaccag agcctagcat ttattcgtaa atccgatgaa ttattacata atgtaaatgc   6060
tggtaaatcc accacaaata tcatgataac tactataatt atagtgatta tagtaatatt   6120
gttatcatta attgctgttg gactgctctt atactgtaag gccagaagca caccagtcac   6180
actaagcaaa gatcaactga gtggtataaa taatattgca tttagtaact aaataaaaat   6240
agcacctaat catgttctta caatggttta ctatctgctc atagacaacc catctgtcat   6300
tggattttct taaaatctga acttcatcga aactctcatc tataaaccat ctcacttaca   6360
ctatttaagt agattcctag tttatagtta tataaaacac aattgcatgc cagattaact   6420
taccatctgt aaaaatgaaa actggggcaa atatgtcacg aaggaatcct tgcaaatttg   6480
aaattcgagg tcattgctta aatggtaaga ggtgtcattt tagtcataat tattttgaat   6540
ggccacccca tgcactgctt gtaagacaaa actttatgtt aaacagaata cttaagtcta   6600
tggataaaag tatagatacc ttatcagaaa taagtggagc tgcagagttg gacagaacag   6660
aagagtatgc tcttggtgta gttggagtgc tagagagtta tataggatca ataaacaata   6720
taactaaaca atcagcatgt gttgccatga gcaaactcct cactgaactc aatagtgatg   6780
atatcaaaaa gctgagggac aatgaagagc taaattcacc caagataaga gtgtacaata   6840
ctgtcatatc atatattgaa agcaacagga aaaacaataa acaaactatc catctgttaa   6900
aaagattgcc agcagacgta ttgaagaaaa ccatcaaaaa cacattggat atccataaga   6960
gcataaccat caacaaccca aaagaatcaa ctgttagtga tacaaatgac catgccaaaa   7020
ataatgatac tacctgacaa atatccttgt agtataactt ccatactaat aacaagtaga   7080
tgtagagtta ctatgtataa tcaaaagaac acactatatt tcaatcaaaa caacccaaat   7140
aaccatatgt actcaccgaa tcaaacattc aatgaaatcc attggacctc tcaagaattg   7200
attgacacaa ttcaaaattt tctacaacat ctaggtatta ttgaggatat atatacaata   7260
tatatattag tgtcataaca ctcaattcta acactcacca catcgttaca ttattaattc   7320
aaacaattca agttgtggga caaaatggat cccattatta atggaaattc tgctaatgtt   7380
tatctaaccg atagttattt aaaaggtgtt atctctttct cagagtgtaa tgctttagga   7440
agttacatat tcaatggtcc ttatctcaaa aatgattata ccaacttaat tagtagacaa   7500
aatccattaa tagaacacat gaatctaaag aaactaaata taacacagtc cttaatatct   7560
aagtatcata aaggtgaaat aaaattagaa gaacctactt attttcagtc attacttatg   7620
acatacaaga gtatgacctc gtcagaacag attgctacca ctaatttact taaaaagata   7680
ataagaagag ctatagaaat aagtgatgtc aaagtctatg ctatattgaa taaactaggg   7740
cttaaagaaa aggacaagat taaatccaac aatggacaag atgaagacaa ctcagttatt   7800
acgaccataa tcaaagatga tatactttca gctgttaaag ataatcaatc tcatcttaaa   7860
gcagacaaaa atcactctac aaaacaaaaa gacacaatca aaacaacact cttgaagaaa   7920
ttgatgtgtt caatgcaaca tcctccatca tggttaatac attggtttaa cttatacaca   7980
aaattaaaca acatattaac acagtatcga tcaaatgagg taaaaaacca tgggtttaca   8040
ttgatagata atcaaactct tagtggattt caatttattt tgaaccaata tggttgtata   8100
gtttatcata aggaactcaa aagaattact gtgacaacct ataatcaatt cttgacatgg   8160
```

aaagatatta gccttagtag attaaatgtt tgtttaatta catggattag taactgcttg 8220
aacacattaa ataaaagctt aggcttaaga tgcggattca ataatgttat cttgacacaa 8280
ctattccttt atggagattg tatactaaag ctatttcaca atgaggggtt ctacataata 8340
aaagaggtag agggatttat tatgtctcta attttaaata taacagaaga agatcaattc 8400
agaaaacgat tttataatag tatgctcaac aacatcacag atgctgctaa taaagctcag 8460
aaaaatctgc tatcaagagt atgtcataca ttattagata agacagtgtc cgataatata 8520
ataaatggca gatggataat tctattaagt aagttcctta aattaattaa gcttgcaggt 8580
gacaataacc ttaacaatct gagtgaacta tatttttgt tcagaatatt tggacaccca 8640
atggtagatg aaagacaagc catggatgct gttaaaatta attgcaatga gaccaaattt 8700
tacttgttaa gcagtctgag tatgttaaga ggtgccttta tatatagaat tataaaaggg 8760
tttgtaaata attacaacag atggcctact ttaagaaatg ctattgtttt acccttaaga 8820
tggttaactt actataaact aaacacttat ccttctttgt tggaacttac agaaagagat 8880
ttgattgtgt tatcaggact acgtttctat cgtgagtttc ggttgcctaa aaaagtggat 8940
cttgaaatga ttataaatga taaagctata tcacctccta aaaatttgat atggactagt 9000
ttccctagaa attacatgcc atcacacata caaaactata tagaacatga aaaattaaaa 9060
ttttccgaga gtgataaatc aagaagagta ttagagtatt atttaagaga taacaaattc 9120
aatgaatgtg atttatacaa ctgtgtagtt aatcaaagtt atctcaacaa ccctaatcat 9180
gtggtatcat tgacaggcaa agaaagagaa ctcagtgtag gtagaatgtt tgcaatgcaa 9240
ccgggaatgt tcagacaggt tcaaatattg gcagagaaaa tgatagctga aaacatttta 9300
caattctttc ctgaaagtct tacaagatat ggtgatctag aactacaaaa aatattagaa 9360
ctgaaagcag gaataagtaa caaatcaaat cgctacaatg ataattacaa caattacatt 9420
agtaagtgct ctatcatcac agatctcagc aaattcaatc aagcatttcg atatgaaacg 9480
tcatgtattt gtagtgatgt gctggatgaa ctgcatggtg tacaatctct attttcctgg 9540
ttacatttaa ctattcctca tgtcacaata atatgcacat ataggcatgc acccccctat 9600
ataggagatc atattgtaga tcttaacaat gtagatgaac aaagtggatt atatagatat 9660
cacatgggtg gcatcgaagg gtggtgtcaa aaactatgga ccatagaagc tatatcacta 9720
ttggatctaa tatctctcaa agggaaattc tcaattactg ctttaattaa tggtgacaat 9780
caatcaatag atataagcaa accaatcaga ctcatggaag gtcaaactca tgctcaagca 9840
gattatttgc tagcattaaa tagccttaaa ttactgtata aagagtatgc aggcataggc 9900
cacaaattaa aaggaactga gacttatata tcacgagata tgcaatttat gagtaaaaca 9960
attcaacata acggtgtata ttacccagct agtataaaga aagtcctaag agtgggaccg 10020
tggataaaca ctatacttga tgatttcaaa gtgagtctag aatctatagg tagtttgaca 10080
caagaattag aatatagagg tgaaagtcta ttatgcagtt taatatttag aaatgtatgg 10140
ttatataatc agattgctct acaattaaaa aatcatgcat tatgtaacaa taaactatat 10200
ttggacatat taaaggttct gaaacactta aaaacctttt ttaatcttga taatattgat 10260
acagcattaa cattgtatat gaatttaccc atgttatttg gtggtggtga tcccaacttg 10320
ttatatcgaa gtttctatag aagaactcct gacttcctca cagaggctat agttcactct 10380
gtgttcatac ttagttatta tacaaaccat gacttaaaag ataaacttca agatctgtca 10440
gatgatagat tgaataagtt cttaacatgc ataatcacgt ttgacaaaaa ccctaatgct 10500

```
gaattcgtaa cattgatgag agatcctcaa gctttagggt ctgagagaca agctaaaatt  10560
actagcgaaa tcaatagact ggcagttaca gaggttttga gtacagctcc aaacaaaata  10620
ttctccaaaa gtgcacaaca ttatactact acagagatag atctaaatga tattatgcaa  10680
aatatagaac ctacatatcc tcatgggcta agagttgttt atgaaagttt acccttttat  10740
aaagcagaga aaatagtaaa tcttatatca ggtacaaaat ctataactaa catactggaa  10800
aaaacttctg ccatagactt aacagatatt gatagagcca ctgagatgat gaggaaaaac  10860
ataactttgc ttataaggat acttccattg gattgtaaca gagataaaag agagatattg  10920
agtatggaaa acctaagtat tactgaatta agcaaatatg ttagggaaag atcttggtct  10980
ttatccaata tagttggtgt tacatcaccc agtatcatgt atacaatgga catcaaatat  11040
actacaagca ctatatctag tggcataatt atagagaaat ataatgttaa cagtttaaca  11100
cgtggtgaga gaggacccac taaaccatgg gttggttcat ctacacaaga gaaaaaaaca  11160
atgccagttt ataatagaca agtcttaacc aaaaaacaga gagatcaaat agatctatta  11220
gcaaaattgg attgggtgta tgcatctata gataacaagg atgaattcat ggaagaactc  11280
agcataggaa cccttgggtt aacatatgaa aaggccaaga aattatttcc acaatattta  11340
agtgtcaatt atttgcatcg ccttacagtc agtagtagac catgtgaatt ccctgcatca  11400
ataccagctt atagaacaac aaattatcac tttgacacta gccctattaa tcgcatatta  11460
acagaaaagt atggtgatga agatattgac atagtattcc aaaactgtat aagctttggc  11520
cttagtttaa tgtcagtagt agaacaattt actaatgtat gtcctaacag aattattctc  11580
atacctaagc ttaatgagat acatttgatg aaacctccca tattcacagg tgatgttgat  11640
attcacaagt taaaacaagt gatacaaaaa cagcatatgt tttaccaga caaaataagt  11700
ttgactcaat atgtggaatt attcttaagt aataaaacac tcaaatctgg atctcatgtt  11760
aattctaatt taatattggc acataaaata tctgactatt ttcataatac ttacatttta  11820
agtactaatt tagctggaca ttggattctg attatacaac ttatgaaaga ttctaaaggt  11880
atttttgaaa aagattgggg agagggatat ataactgatc atatgtttat taatttgaaa  11940
gttttcttca atgcttataa gacctatctc ttgtgttttc ataaaggtta tggcaaagca  12000
aagctggagt gtgatatgaa cacttcagat cttctatgtg tattggaatt aatagacagt  12060
agttattgga agtctatgtc taaggtattt ttagaacaaa aagttatcaa atacattctt  12120
agccaagatg caagtttaca tagagtaaaa ggatgtcata gcttcaaatt atggtttctt  12180
aaacgtctta atgtagcaga attcacagtt tgcccttggg ttgttaacat agattatcat  12240
ccaacacata tgaaagcaat attaacttat atagatcttg ttagaatggg attgataaat  12300
atagatagaa tacacattaa aaataaacac aaattcaatg atgaatttta tacttctaat  12360
ctcttctaca ttaattataa cttctcagat aatactcatc tattaactaa acatataagg  12420
attgctaatt ctgaattaga aaataattac aacaaattat atcatcctac accagaaacc  12480
ctagagaata tactagccaa tccgattaaa agtaatgaca aaaagacact gaatgactat  12540
tgtataggta aaaatgttga ctcaataatg ttaccattgt tatctaataa gaagcttatt  12600
aaatcgtctg caatgattag aaccaattac agcaaacaag atttgtataa tttattccct  12660
atggttgtga ttgatagaat tatagatcat tcaggcaata cagccaaatc caaccaactt  12720
tacactacta cttcccacca aatatcctta gtgcacaata gcacatcact ttactgcatg  12780
cttccttggc atcatattaa tagattcaat tttgtattta gttctacagg ttgtaaaatt  12840
agtatagagt atattttaaa agatcttaaa attaaagatc ccaattgtat agcattcata  12900
```

```
ggtgaaggag cagggaattt attattgcgt acagtagtgg aacttcatcc tgacataaga  12960
tatatttaca gaagtctgaa agattgcaat gatcatagtt tacctattga gtttttaagg  13020
ctgtacaatg gacatatcaa cattgattat ggtgaaaatt tgaccattcc tgctacagat  13080
gcaaccaaca acattcattg gtcttattta catataaagt ttgctgaacc tatcagtctt  13140
tttgtctgtg atgccgaatt gtctgtaaca gtcaactgga gtaaaattat aatagaatgg  13200
agcaagcatg taagaaagtg caagtactgt tcctcagtta ataaatgtat gttaatagta  13260
aaatatcatg ctcaagatga tattgatttc aaattagaca atataactat attaaaaact  13320
tatgtatgct taggcagtaa gttaaaggga tcggaggttt acttagtcct tacaataggt  13380
cctgcgaata tattcccagt atttaatgta gtacaaaatg ctaaattgat actatcaaga  13440
accaaaaatt tcatcatgcc taagaaagct gataaagagt ctattgatgc aaatattaaa  13500
agtttgatac cctttctttg ttaccctata acaaaaaaag gaattaatac tgcattgtca  13560
aaactaaaga gtgttgttag tggagatata ctatcatatt ctatagctgg acgtaatgaa  13620
gttttcagca ataaacttat aaatcataag catatgaaca tcttaaaatg gttcaatcat  13680
gttttaaatt tcagatcaac agaactaaac tataaccatt tatatatggt agaatctaca  13740
tatccttacc taagtgaatt gttaaacagc ttgacaacca atgaacttaa aaaactgatt  13800
aaaatcacag gtagtctgtt atacaacttt cataatgaat aatgaataaa gatcttataa  13860
taaaaattcc catagctata cactaacact gtattcaatt atagttataa aaattaaaaa  13920
tggtaccatg gggcaaataa gaatttgata agtaccactt aaatttaact cccttggtta  13980
gagatgggca gcaattcatt gagtatgata aaagttagat tacaaaattt gtttgacaat  14040
gatgaagtag cattgttaaa aataacatgc tatactgata aattaataca tttaactaat  14100
gctttggcta aggcagtgat acatacaatc aaattgaatg gcattgtgtt tgtgcatgtt  14160
attacaagta gtgatatttg ccctaataat aatattgtag taaaatccaa tttcacaaca  14220
atgccagtac tacaaaatgg aggttatata tgggaaatga tggaattaac acattgctct  14280
caacctaatg gtctactaga tgacaattgt gaaattaaat tctccaaaaa actaagtgat  14340
tcaacaatga ccaattatat gaatcaatta tctgaattac ttggatttga tcttaatcca  14400
taaattataa ttaatatcaa ctagcaaatc aatgtcacta acaccattag ttaatataaa  14460
acttaacaga agacaaaaat ggggcaaata aatcaattca gccaacccaa ccatggacac  14520
aacccacaat gataatacac cacaaagact gatgatcaca gacatgagac cgttgtcact  14580
tgagaccata ataacatcac taaccagaga catcataaca cacaaattta tatacttgat  14640
aaatcatgaa tgcatagtga gaaaacttga tgaaagacag gccacattta cattcctggt  14700
caactatgaa atgaaactat tacacaaagt aggaagcact aaatataaaa aatatactga  14760
atacaacaca aaatatggca ctttccctat gccaatattc atcaatcatg atgggttctt  14820
agaatgcatt ggcattaagc ctacaaagca tactcccata atatacaagt atgatctcaa  14880
tccataaatt tcaacacaat attcacacaa tctaaaacaa caactctatg cataactata  14940
ctccatagtc cagatggagc ctgaaaatta tagtaattta aaacttaagg agagatataa  15000
gatagaagat ggtaccattt tttaaataac ttttagtgaa ctaatcctaa agttatcatt  15060
ttaatcttgg aggaataaat ttaaacccta atctaattgg tttatatgtg tattaactaa  15120
attacgagat attagttttt gacacttttt ttctcgt                          15157
```

<210> SEQ ID NO 5

<211> LENGTH: 15358
<212> TYPE: DNA
<213> ORGANISM: Artificial Sequence
<220> FEATURE:
<223> OTHER INFORMATION: recombinant RSV sequence

<400> SEQUENCE: 5
acgggaaaaa atgcgtacaa caaacttgca taaaccaaaa aaatggggca aataagaatt 60
tgataagtac cacttaaatt taactccctt ggttagagat ggctcttagc aaagtcaagt 120
tgaatgatac actcaacaaa gatcaacttc tgtcatccag caaatacacc atccaacgga 180
gcacaggaga tagtattgat actcctaatt atgatgtgca gaaacacatc aataagttat 240
gtggcatgtt attaatcaca gaagatgcta atcataaatt cactgggtta ataggtatgt 300
tatatgcgat gtctaggtta ggaagagaag acaccataaa aatactcaga gatgcgggat 360
atcatgtaaa agcaaatgga gtagatgtaa caacacatcg tcaagacatt aatggaaaag 420
aaatgaaatt tgaagtgtta acattggcaa gcttaacaac tgaaattcaa atcaacattg 480
agatagaatc tagaaaatcc tacaaaaaaa tgctaaaaga aatgggagag gtagctccag 540
aatacaggca tgactctcct gattgtggga tgataatatt atgtatagca gcattagtaa 600
taactaaatt agcagcaggg gacagatctg gtcttacagc cgtgattagg agagctaata 660
atgtcctaaa aaatgaaatg aaacgttaca aaggcttact acccaaggac atagccaaca 720
gcttctatga agtgtttgaa aaacatcccc actttataga tgtttttgtt cattttggta 780
tagcacaatc ttctaccaga ggtggcagta gagttgaagg gatttttgca ggattgttta 840
tgaatgccta tggtgcaggg caagtgatgt tacggtgggg agtcttagca aaatcagtta 900
aaaatattat gttaggacat gctagtgtgc aagcagaaat ggaacaagtt gttgaggttt 960
atgaatatgc ccaaaaattg ggtggtgaag caggattcta ccatatattg aacaacccaa 1020
aagcatcatt attatctttg actcaatttc ctcacttctc cagtgtagta ttaggcaatg 1080
ctgctggcct aggcataatg ggagagtaca gaggtacacc gaggaatcaa gatctatatg 1140
atgcagcaaa ggcatatgct gaacaactca aagaaaatgg tgtgattaac tacagtgtac 1200
tagacttgac agcagaagaa ctagaggcta tcaaacatca gcttaatcca aaagataatg 1260
atgtagagct ttgagttaat aaaaaatggg gcaaataaat catcatggaa aagtttgctc 1320
ctgaattcca tggagaagat gcaaacaaca gggctactaa attcctagaa tcaataaagg 1380
gcaaattcac atcacccaaa gatcccaaga aaaaagatag tatcatatct gtcaactcaa 1440
tagatataga agtaaccaaa gaaagcccta taacatcaaa ttcaactatt atcaacccaa 1500
caaatgagac agatgatact gcagggaaca agcccaatta tcaaagaaaa cctctagtaa 1560
gtttcaaaga agaccctaca ccaagtgata atcccttttc taaactatac aaagaaacca 1620
tagaaacatt tgataacaat gaagaagaat ccagctattc atacgaagaa ataaatgatc 1680
agacaaacga taatataaca gcaagattag ataggattga tgaaaaatta agtgaaatac 1740
taggaatgct tcacacatta gtagtggcaa gtgcaggacc tacatctgct cgggatggta 1800
taagagatgc catggttggt ttaagagaag aaatgataga aaaaatcaga actgaagcat 1860
taatgaccaa tgacagatta gaagctatgg caagactcag gaatgaggaa agtgaaaaga 1920
tggcaaaaga cacatcagat gaagtgtctc tcaatccaac atcagagaaa ttgaacaacc 1980
tattggaagg gaatgatagt gacaatgatc tatcacttga agatttctga ttagttacca 2040
atcttcacat caacacacaa taccaacaga agaccaacaa actaaccaac ccaatcatcc 2100
aaccaaacat ccatccgcca atcagccaaa cagccaacaa aacaaccagc caatccaaaa 2160

```
ctaaccaccc ggaaaaaatc tataatatag ttacaaaaaa aggaatcgat ggggcaaata   2220
caagtatggt gagcaagggc gaggagctgt tcaccggggt ggtgcccatc ctggtcgagc   2280
tggacggcga cgtaaacggc cacaagttca gcgtgtccgg cgagggcgag ggcgatgcca   2340
cctacggcaa gctgaccctg aagttcatct gcaccaccgg caagctgccc gtgccctggc   2400
ccaccctcgt gaccaccctg acctacggcg tgcagtgctt cagccgctac cccgaccaca   2460
tgaagcagca cgacttcttc aagtccgcca tgcccgaagg ctacgtccag gagcgcacca   2520
tcttcttcaa ggacgacggc aactacaaga cccgcgccga ggtgaagttc gagggcgaca   2580
ccctggtgaa ccgcatcgag ctgaagggca tcgacttcaa ggaggacggc aacatcctgg   2640
ggcacaagct ggagtacaac tacaacagcc acaacgtcta tatcatggcc gacaagcaga   2700
agaacggcat caaggtgaac ttcaagatcc gccacaacat cgaggacggc agcgtgcagc   2760
tcgccgacca ctaccagcag aacaccccca tcggcgacgg ccccgtgctg ctgcccgaca   2820
accactacct gagcacccag tccgccctga gcaaagaccc caacgagaag cgcgatcaca   2880
tggtcctgct ggagttcgtg accgccgccg ggatcactct cggcatggac gagctgtaca   2940
agtaaaagta gttacttaaa aagtcgacgg tggggcaaat atggaaacat acgtgaacaa   3000
gcttcacgaa ggctccacat acacagctgc tgttcaatac aatgtcttag aaaaagacga   3060
tgaccctgca tcacttacaa tatgggtgcc catgttccaa tcatctatgc cagcagattt   3120
acttataaaa gaactagcta atgtcaacat actagtgaaa caaatatcca cacccaaggg   3180
accttcacta agagtcatga taaactcaag aagtgcagtg ctagcacaaa tgcccagcaa   3240
atttaccata tgcgctaatg tgtccttgga tgaaagaagc aaactagcat atgatgtaac   3300
cacaccctgt gaaatcaagg catgtagtct aacatgccta aaatcaaaaa atatgttgac   3360
tacagttaaa gatctcacta tgaagacact caaccctaca catgatatta ttgctttatg   3420
tgaatttgaa aacatagtaa catcaaaaaa agtcataata ccaacatacc taagatccat   3480
cagtgtcaga aataaagatc tgaacacact tgaaaatata acaaccactg aattcaaaaa   3540
tgctatcaca aatgcaaaaa tcatccctta ctcaggatta ctattagtca tcacagtgac   3600
tgacaacaaa ggagcattca aatacataaa gccacaaagt caattcatag tagatcttgg   3660
agcttaccta gaaaaagaaa gtatatatta tgttaccaca aattggaagc acacagctac   3720
acgatttgca atcaaaccca tggaagatta accttttttcc tctacatcag tgtgttaatt   3780
catacaaact ttctacctac attcttcact tcaccatcac aatcacaaac actctgtggt   3840
tcaaccaatc aaacaaaact tatctgaagt cccagatcat cccaagtcat tgtttatcag   3900
atctagtact caaataagtt aataaaaaat atacacatgg ggcaaataat cattggagga   3960
aatccaacta atcacaatat ctgttaacat agacaagtcc acacaccata cagaatcaac   4020
caatggaaaa tacatccata acaatagaat tctcaagcaa attctggcct tactttacac   4080
taatacacat gatcacaaca ataatctctt tgctaatcat aatctccatc atgattgcaa   4140
tactaaacaa actttgtgaa tataacgtat tccataacaa aacctttgag ttaccaagag   4200
ctcgagttaa tacttgataa agtagttaat taaaaatagt cataacaatg aactaggata   4260
tcaagactaa caataacatt ggggcaaatg caaacatgtc caaaaacaag gaccaacgca   4320
ccgctaagac attagaaagg acctgggaca ctctcaatca tttattattc atatcatcgt   4380
gcttatataa gttaaatctt aaatctgtag cacaaatcac attatccatt ctggcaatga   4440
taatctcaac ttcacttata attgcagcca tcatattcat agcctcggca aaccacaaag   4500
```

-continued

```
tcacaccaac aactgcaatc atacaagatg caacaagcca gatcaagaac acaaccccaa   4560
catacctcac ccagaatcct cagcttggaa tcagtccctc taatccgtct gaaattacat   4620
cacaaatcac caccatacta gcttcaacaa caccaggagt caagtcaacc ctgcaatcca   4680
caacagtcaa gaccaaaaac acaacaacaa ctcaaacaca acccagcaag cccaccacaa   4740
aacaacgcca aaacaaacca ccaagcaaac ccaataatga ttttcacttt gaagtgttca   4800
actttgtacc ctgcagcata tgcagcaaca atccaacctg ctgggctatc tgcaaaagaa   4860
taccaaacaa aaaaccagga aagaaaacca ctaccaagcc cacaaaaaaa ccaaccctca   4920
agacaaccaa aaaagatccc aaacctcaaa ccactaaatc aaaggaagta cccaccacca   4980
agcccacaga agagccaacc atcaacacca ccaaaacaaa catcataact acactactca   5040
cctccaacac cacaggaaat ccagaactca caagtcaaat ggaaaccttc cactcaactt   5100
cctccgaagg caatccaagc ccttctcaag tctctacaac atccgagtac ccatcacaac   5160
cttcatctcc acccaacaca ccacgccagt agttacttaa aaacatatta tcacaaaagg   5220
ccttgaccaa cttaaacaga atcaaaataa actctggggc aaataacaat ggagttgcta   5280
atcctcaaag caaatgcaat taccacaatc ctcactgcag tcacattttg ttttgcttct   5340
ggtcaaaaca tcactgaaga attttatcaa tcaacatgca gtgcagttag caaaggctat   5400
cttagtgctc tgagaactgg ttggtatacc agtgttataa ctatagaatt aagtaatatc   5460
aagaaaaata agtgtaatgg aacagatgct aaggtaaaat tgataaaaca agaattagat   5520
aaatataaaa atgctgtaac agaattgcag ttgctcatgc aaagcacaca agcaacaaac   5580
aatcgagcca gaagagaact accaaggttt atgaattata cactcaacaa tgccaaaaaa   5640
accaatgtaa cattaagcaa gaaaaggaaa agaagatttc ttggtttttt gttaggtgtt   5700
ggatctgcaa tcgccagtgg cgttgctgta tctaaggtcc tgcacctaga aggggaagtg   5760
aacaagatca aaagtgctct actatccaca aacaaggctg tagtcagctt atcaaatgga   5820
gttagtgttt taaccagcaa agtgttagac ctcaaaaact atatagataa acaattgtta   5880
cctattgtga acaagcaaag ctgcagcata tcaaatatag aaactgtgat agagttccaa   5940
caaaagaaca acagactact agagattacc agggaattta gtgttaatgc aggcgtaact   6000
acacctgtaa gcacttacat gttaactaat agtgaattat tgtcattaat caatgatatg   6060
cctataacaa atgatcagaa aaagttaatg tccaacaatg ttcaaatagt tagacagcaa   6120
agttactcta tcatgtccat aataaaagag gaagtcttag catatgtagt acaattacca   6180
ctatatggtg ttatagatac accctgttgg aaactacaca catcccctct atgtacaacc   6240
aacacaaaag aagggtccaa catctgttta acaagaactg acagaggatg gtactgtgac   6300
aatgcaggat cagtatcttt cttcccacaa gctgaaacat gtaaagttca atcaaatcga   6360
gtattttgtg acacaatgaa cagtttaaca ttaccaagtg aagtaaatct ctgcaatgtt   6420
gacatattca accccaaata tgattgtaaa attatgactt caaaaacaga tgtaagcagc   6480
tccgttatca catctctagg agccattgtg tcatgctatg gcaaaactaa atgtacagca   6540
tccaataaaa atcgtggaat cataaagaca ttttctaacg ggtgcgatta tgtatcaaat   6600
aaaggggtgg acactgtgtc tgtaggtaac acattatatt atgtaaataa gcaagaaggt   6660
aaaagtctct atgtaaaagg tgaaccaata ataaatttct atgacccatt agtattcccc   6720
tctgatgaat ttgatgcatc aatatctcaa gtcaacgaga agattaacca gagcctagca   6780
tttattcgta aatccgatga attattacat aatgtaaatg ctggtaaatc caccacaaat   6840
atcatgataa ctactataat tatagtgatt atagtaatat tgttatcatt aattgctgtt   6900
```

-continued

```
ggactgctct tatactgtaa ggccagaagc acaccagtca cactaagcaa agatcaactg   6960
agtggtataa ataatattgc atttagtaac taaataaaaa tagcacctaa tcatgttctt   7020
acaatggttt actatctgct catagacaac ccatctgtca ttggattttc ttaaaatctg   7080
aacttcatcg aaactctcat ctataaacca tctcacttac actatttaag tagattccta   7140
gtttatagtt atataaaaca caattgcatg ccaggtacca tggggcaaat aagaatttga   7200
taagtaccac ttaaatttaa ctcccttggt tagagatggg cagcaattca ttgagtatga   7260
taaaagttag attacaaaat ttgtttgaca atgatgaagt agcattgtta aaaataacat   7320
gctatactga taaattaata catttaacta atgctttggc taaggcagtg atacatacaa   7380
tcaaattgaa tggcattgtg tttgtgcatg ttattacaag tagtgatatt tgccctaata   7440
ataatattgt agtaaaatcc aatttcacaa caatgccagt actacaaaat ggaggttata   7500
tatgggaaat gatggaatta acacattgct ctcaacctaa tggtctacta gatgacaatt   7560
gtgaaattaa attctccaaa aaactaagtg attcaacaat gaccaattat atgaatcaat   7620
tatctgaatt acttggattt gatcttaatc cataaattat aattaatatc aactagcaaa   7680
tcaatgtcac taacaccatt agttaatata aaacttaaca gaagacaaaa atggggcaaa   7740
tatgtcacga aggaatcctt gcaaatttga aattcgaggt cattgcttaa atggtaagag   7800
gtgtcatttt agtcataatt attttgaatg gccacccccat gcactgcttg taagacaaaa   7860
ctttatgtta aacagaatac ttaagtctat ggataaaagt atagatacct tatcagaaat   7920
aagtggagct gcagagttgg acagaacaga agagtatgct cttggtgtag ttggagtgct   7980
agagagttat ataggatcaa taaacaatat aactaaacaa tcagcatgtg ttgccatgag   8040
caaactcctc actgaactca atagtgatga tatcaaaaag ctgagggaca atgaagagct   8100
aaattcaccc aagataagag tgtacaatac tgtcatatca tatattgaaa gcaacaggaa   8160
aaacaataaa caaactatcc atctgttaaa aagattgcca gcagacgtat tgaagaaaac   8220
catcaaaaac acattggata tccataagag cataaccatc aacaacccaa aagaatcaac   8280
tgttagtgat acaaatgacc atgccaaaaa taatgatact acctgacaaa tatccttgta   8340
gtataacttc catactaata acaagtagat gtagagttac tatgtataat caaaagaaca   8400
cactatattt caatcaaaac aacccaaata accatatgta ctcaccgaat caaacattca   8460
atgaaatcca ttggacctct caagaattga ttgacacaat tcaaaatttt ctacaacatc   8520
taggtattat tgaggatata tatacaatat atatattagt gtcataacac tcaattctaa   8580
cactcaccac atcgttacat tattaattca aacaattcaa gttgtgggac aaaatggatc   8640
ccattattaa tggaaattct gctaatgttt atctaaccga tagttattta aaaggtgtta   8700
tctctttctc agagtgtaat gctttaggaa gttacatatt caatggtcct tatctcaaaa   8760
atgattatac caacttaatt agtagacaaa atccattaat agaacacatg aatctaaaga   8820
aactaaatat aacacagtcc ttaatatcta agtatcataa aggtgaaata aaattagaag   8880
aacctactta ttttcagtca ttacttatga catacaagag tatgacctcg tcagaacaga   8940
ttgctaccac taatttactt aaaaagataa taagaagagc tatagaaata agtgatgtca   9000
aagtctatgc tatattgaat aaactagggc ttaaagaaaa ggacaagatt aaatccaaca   9060
atggacaaga tgaagacaac tcagttatta cgaccataat caaagatgat atactttcag   9120
ctgttaaaga taatcaatct catcttaaag cagacaaaaa tcactctaca aaacaaaaag   9180
acacaatcaa aacaacactc ttgaagaaat tgatgtgttc aatgcaacat cctccatcat   9240
```

-continued

```
ggttaataca ttggtttaac ttatacacaa aattaaacaa catattaaca cagtatcgat   9300
caaatgaggt aaaaaaccat gggtttacat tgatagataa tcaaactctt agtggatttc   9360
aatttatttt gaaccaatat ggttgtatag tttatcataa ggaactcaaa agaattactg   9420
tgacaaccta taatcaattc ttgacatgga aagatattag ccttagtaga ttaaatgttt   9480
gtttaattac atggattagt aactgcttga acacattaaa taaaagctta ggcttaagat   9540
gcggattcaa taatgttatc ttgacacaac tattccttta tggagattgt atactaaagc   9600
tatttcacaa tgaggggttc tacataataa aagaggtaga gggatttatt atgtctctaa   9660
ttttaaatat aacagaagaa gatcaattca gaaaacgatt ttataatagt atgctcaaca   9720
acatcacaga tgctgctaat aaagctcaga aaaatctgct atcaagagta tgtcatacat   9780
tattagataa gacagtgtcc gataatataa taaatggcag atggataatt ctattaagta   9840
agttccttaa attaattaag cttgcaggtg acaataacct taacaatctg agtgaactat   9900
atttttgtt cagaatattt ggacacccaa tggtagatga aagacaagcc atggatgctg   9960
ttaaaattaa ttgcaatgag accaaatttt acttgttaag cagtctgagt atgttaagag  10020
gtgcctttat atatagaatt ataaaagggt ttgtaaataa ttacaacaga tggcctactt  10080
taagaaatgc tattgtttta cccttaagat ggttaactta ctataaacta aacacttatc  10140
cttctttgtt ggaacttaca gaaagagatt tgattgtgtt atcaggacta cgtttctatc  10200
gtgagtttcg gttgcctaaa aaagtggatc ttgaaatgat tataaatgat aaagctatat  10260
cacctcctaa aaatttgata tggactagtt tccctagaaa ttacatgcca tcacacatac  10320
aaaactatat agaacatgaa aaattaaaat tttccgagag tgataaatca agaagagtat  10380
tagagtatta tttaagagat aacaaattca atgaatgtga tttatacaac tgtgtagtta  10440
atcaaagtta tctcaacaac cctaatcatg tggtatcatt gacaggcaaa gaaagagaac  10500
tcagtgtagg tagaatgttt gcaatgcaac cgggaatgtt cagacaggtt caaatattgg  10560
cagagaaaat gatagctgaa aacattttac aattctttcc tgaaagtctt acaagatatg  10620
gtgatctaga actacaaaaa atattagaac tgaaagcagg aataagtaac aaatcaaatc  10680
gctacaatga taattacaac aattacatta gtaagtgctc tatcatcaca gatctcagca  10740
aattcaatca agcatttcga tatgaaacgt catgtatttg tagtgatgtg ctggatgaac  10800
tgcatggtgt acaatctcta ttttcctggt tacatttaac tattcctcat gtcacaataa  10860
tatgcacata taggcatgca ccccctata taggagatca tattgtagat cttaacaatg  10920
tagatgaaca aagtggatta tatagatatc acatgggtgg catcgaaggg tggtgtcaaa  10980
aactatggac catagaagct atatcactat tggatctaat atctctcaaa gggaaattct  11040
caattactgc tttaattaat ggtgacaatc aatcaataga tataagcaaa ccaatcagac  11100
tcatggaagg tcaaactcat gctcaagcag attatttgct agcattaaat agccttaaat  11160
tactgtataa agagtatgca ggcataggcc acaaattaaa aggaactgag acttatatat  11220
cacgagatat gcaatttatg agtaaaacaa ttcaacataa cggtgtatat tacccagcta  11280
gtataaagaa agtcctaaga gtgggaccgt ggataaacac tatacttgat gatttcaaag  11340
tgagtctaga atctataggt agtttgacac aagaattaga atatagaggt gaaagtctat  11400
tatgcagttt aatatttaga aatgtatggt tatataatca gattgctcta caattaaaaa  11460
atcatgcatt atgtaacaat aaactatatt tggacatatt aaaggttctg aaacacttaa  11520
aaaccttttt taatcttgat aatattgata cagcattaac attgtatatg aatttaccca  11580
tgttatttgg tggtggtgat cccaacttgt tatatcgaag tttctataga agaactcctg  11640
```

-continued

```
acttcctcac agaggctata gttcactctg tgttcatact tagttattat acaaaccatg  11700
acttaaaaga taaacttcaa gatctgtcag atgatagatt gaataagttc ttaacatgca  11760
taatcacgtt tgacaaaaac cctaatgctg aattcgtaac attgatgaga gatcctcaag  11820
ctttagggtc tgagagacaa gctaaaatta ctagcgaaat caatagactg gcagttacag  11880
aggttttgag tacagctcca aacaaaatat tctccaaaag tgcacaacat tatactacta  11940
cagagataga tctaaatgat attatgcaaa atatagaacc tacatatcct catgggctaa  12000
gagttgttta tgaaagttta ccctttttata aagcagagaa aatagtaaat cttatatcag  12060
gtacaaaatc tataactaac atactggaaa aaacttctgc catagactta acagatattg  12120
atagagccac tgagatgatg aggaaaaaca taactttgct tataaggata cttccattgg  12180
attgtaacag agataaaaga gagatattga gtatggaaaa cctaagtatt actgaattaa  12240
gcaaatatgt tagggaaaga tcttggtctt tatccaatat agttggtgtt acatcaccca  12300
gtatcatgta tacaatggac atcaaatata ctacaagcac tatatctagt ggcataatta  12360
tagagaaata taatgttaac agtttaacac gtggtgagag aggacccact aaaccatggg  12420
ttggttcatc tacacaagag aaaaaaaacaa tgccagttta taatagacaa gtcttaacca  12480
aaaaacagag agatcaaata gatctattag caaaattgga ttgggtgtat gcatctatag  12540
ataacaagga tgaattcatg gaagaactca gcataggaac ccttgggtta acatatgaaa  12600
aggccaagaa attatttcca caatatttaa gtgtcaatta tttgcatcgc cttacagtca  12660
gtagtagacc atgtgaattc cctgcatcaa taccagctta tagaacaaca aattatcact  12720
ttgacactag ccctattaat cgcatattaa cagaaaagta tggtgatgaa gatattgaca  12780
tagtattcca aaactgtata agctttggcc ttagtttaat gtcagtagta gaacaattta  12840
ctaatgtatg tcctaacaga attattctca tacctaagct taatgagata catttgatga  12900
aacctcccat attcacaggt gatgttgata ttcacaagtt aaaacaagtg atacaaaaac  12960
agcatatgtt tttaccagac aaaataagtt tgactcaata tgtggaatta ttcttaagta  13020
ataaaacact caaatctgga tctcatgtta attctaattt aatattggca cataaaatat  13080
ctgactattt tcataatact tacattttaa gtactaattt agctggacat tggattctga  13140
ttatacaact tatgaaagat tctaaaggta tttttgaaaa agattgggga gagggatata  13200
taactgatca tatgtttatt aatttgaaag ttttcttcaa tgcttataag acctatctct  13260
tgtgttttca taaaggttat ggcaaagcaa agctggagtg tgatatgaac acttcagatc  13320
ttctatgtgt attggaatta atagacagta gttattggaa gtctatgtct aaggtatttt  13380
tagaacaaaa agttatcaaa tacattctta gccaagatgc aagtttacat agagtaaaag  13440
gatgtcatag cttcaaatta tggtttctta aacgtcttaa tgtagcagaa ttcacagttt  13500
gcccttgggt tgttaacata gattatcatc caacacatat gaaagcaata ttaacttata  13560
tagatcttgt tagaatggga ttgataaata tagatagaat acacattaaa aataaacaca  13620
aattcaatga tgaattttat acttctaatc tcttctacat taattataac ttctcagata  13680
atactcatct attaactaaa catataagga ttgctaattc tgaattagaa aataattaca  13740
acaaattata tcatcctaca ccagaaaccc tagagaatat actagccaat ccgattaaaa  13800
gtaatgacaa aaagacactg aatgactatt gtataggtaa aaatgttgac tcaataatgt  13860
taccattgtt atctaataag aagcttatta aatcgtctgc aatgattaga accaattaca  13920
gcaaacaaga tttgtataat ttattcccta tggttgtgat tgatagaatt atagatcatt  13980
```

caggcaatac agccaaatcc aaccaacttt acactactac ttcccaccaa atatccttag 14040
tgcacaatag cacatcactt tactgcatgc ttccttggca tcatattaat agattcaatt 14100
ttgtatttag ttctacaggt tgtaaaatta gtatagagta tattttaaaa gatcttaaaa 14160
ttaaagatcc caattgtata gcattcatag gtgaaggagc agggaattta ttattgcgta 14220
cagtagtgga acttcatcct gacataagat atatttacag aagtctgaaa gattgcaatg 14280
atcatagttt acctattgag tttttaaggc tgtacaatgg acatatcaac attgattatg 14340
gtgaaaattt gaccattcct gctacagatg caaccaacaa cattcattgg tcttatttac 14400
atataaagtt tgctgaacct atcagtcttt ttgtctgtga tgccgaattg tctgtaacag 14460
tcaactggag taaaattata atagaatgga gcaagcatgt aagaaagtgc aagtactgtt 14520
cctcagttaa taaatgtatg ttaatagtaa aatatcatgc tcaagatgat attgatttca 14580
aattagacaa tataactata ttaaaaactt atgtatgctt aggcagtaag ttaaagggat 14640
cggaggttta cttagtcctt acaataggtc ctgcgaatat attcccagta tttaatgtag 14700
tacaaaatgc taaattgata ctatcaagaa ccaaaaattt catcatgcct aagaaagctg 14760
ataaagagtc tattgatgca aatattaaaa gtttgatacc ctttctttgt taccctataa 14820
caaaaaaagg aattaatact gcattgtcaa aactaaagag tgttgttagt ggagatatac 14880
tatcatattc tatagctgga cgtaatgaag ttttcagcaa taaacttata aatcataagc 14940
atatgaacat cttaaaatgg ttcaatcatg ttttaaattt cagatcaaca gaactaaact 15000
ataaccattt atatatggta gaatctacat atccttacct aagtgaattg ttaaacagct 15060
tgacaaccaa tgaacttaaa aaactgatta aaatcacagg tagtctgtta tacaactttc 15120
ataatgaata atgaataaag atcttataat aaaaattccc atagctatac actaacactg 15180
tattcaatta tagttattaa aaattaaaaa tcatataatt ttttaaataa cttttagtga 15240
actaatccta aagttatcat tttaatcttg gaggaataaa tttaaaccct aatctaattg 15300
gtttatatgt gtattaacta aattacgaga tattagtttt tgacactttt tttctcgt 15358

<210> SEQ ID NO 6
<211> LENGTH: 14597
<212> TYPE: DNA
<213> ORGANISM: Artificial Sequence
<220> FEATURE:
<223> OTHER INFORMATION: recombinant RSV sequence

<400> SEQUENCE: 6
acgggaaaaa atgcgtacaa caaacttgca taaaccaaaa aaatggggca aataagaatt 60
tgataagtac cacttaaatt taactccctt ggttagagat ggctcttagc aaagtcaagt 120
tgaatgatac actcaacaaa gatcaacttc tgtcatccag caaatacacc atccaacgga 180
gcacaggaga tagtattgat actcctaatt atgatgtgca gaaacacatc aataagttat 240
gtggcatgtt attaatcaca gaagatgcta atcataaatt cactgggtta ataggtatgt 300
tatatgcgat gtctaggtta ggaagagaag acaccataaa aatactcaga gatgcgggat 360
atcatgtaaa agcaaatgga gtagatgtaa caacacatcg tcaagacatt aatggaaaag 420
aaatgaaatt tgaagtgtta acattggcaa gcttaacaac tgaaattcaa atcaacattg 480
agatagaatc tagaaaatcc tacaaaaaaa tgctaaaaga aatgggagag gtagctccag 540
aatacaggca tgactctcct gattgtggga tgataatatt atgtatagca gcattagtaa 600
taactaaatt agcagcaggg gacagatctg gtcttacagc cgtgattagg agagctaata 660
atgtcctaaa aaatgaaatg aaacgttaca aaggcttact acccaaggac atagccaaca 720

```
gcttctatga agtgtttgaa aaacatcccc actttataga tgtttttgtt cattttggta    780
tagcacaatc ttctaccaga ggtggcagta gagttgaagg gatttttgca ggattgttta    840
tgaatgccta tggtgcaggg caagtgatgt tacggtgggg agtcttagca aaatcagtta    900
aaaatattat gttaggacat gctagtgtgc aagcagaaat ggaacaagtt gttgaggttt    960
atgaatatgc ccaaaaattg ggtggtgaag caggattcta ccatatattg aacaacccaa   1020
aagcatcatt attatctttg actcaatttc ctcacttctc cagtgtagta ttaggcaatg   1080
ctgctggcct aggcataatg ggagagtaca gaggtacacc gaggaatcaa gatctatatg   1140
atgcagcaaa ggcatatgct gaacaactca aagaaaatgg tgtgattaac tacagtgtac   1200
tagacttgac agcagaagaa ctagaggcta tcaaacatca gcttaatcca aaagataatg   1260
atgtagagct ttgagttaat aaaaaatggg gcaaataaat catcatggaa aagtttgctc   1320
ctgaattcca tggagaagat gcaaacaaca gggctactaa attcctagaa tcaataaagg   1380
gcaaattcac atcacccaaa gatcccaaga aaaaagatag tatcatatct gtcaactcaa   1440
tagatataga agtaaccaaa gaaagcccta taacatcaaa ttcaactatt atcaacccaa   1500
caaatgagac agatgatact gcagggaaca agcccaatta tcaaagaaaa cctctagtaa   1560
gtttcaaaga agaccctaca ccaagtgata atcccttttc taaactatac aaagaaacca   1620
tagaaacatt tgataacaat gaagaagaat ccagctattc atacgaagaa ataaatgatc   1680
agacaaacga taatataaca gcaagattag ataggattga tgaaaaatta agtgaaatac   1740
taggaatgct tcacacatta gtagtggcaa gtgcaggacc tacatctgct cgggatggta   1800
taagagatgc catggttggt ttaagagaag aaatgataga aaaaatcaga actgaagcat   1860
taatgaccaa tgacagatta gaagctatgg caagactcag gaatgaggaa agtgaaaaga   1920
tggcaaaaga cacatcagat gaagtgtctc tcaatccaac atcagagaaa ttgaacaacc   1980
tattggaagg gaatgatagt gacaatgatc tatcacttga agatttctga ttagttacca   2040
atcttcacat caacacacaa taccaacaga agaccaacaa actaaccaac ccaatcatcc   2100
aaccaaacat ccatccgcca atcagccaaa cagccaacaa aacaaccagc caatccaaaa   2160
ctaaccaccc ggaaaaaatc tataatatag ttacaaaaaa aggaaagggt ggggcaaata   2220
tggaaacata cgtgaacaag cttcacgaag gctccacata cacagctgct gttcaataca   2280
atgtcttaga aaaagacgat gaccctgcat cacttacaat atgggtgccc atgttccaat   2340
catctatgcc agcagattta cttataaaag aactagctaa tgtcaacata ctagtgaaac   2400
aaatatccac acccaaggga ccttcactaa gagtcatgat aaactcaaga agtgcagtgc   2460
tagcacaaat gcccagcaaa tttaccatat gcgctaatgt gtccttggat gaaagaagca   2520
aactagcata tgatgtaacc acaccctgtg aaatcaaggc atgtagtcta acatgcctaa   2580
aatcaaaaaa tatgttgact acagttaaag atctcactat gaagacactc aaccctacac   2640
atgatattat tgctttatgt gaatttgaaa acatagtaac atcaaaaaaa gtcataatac   2700
caacatacct aagatccatc agtgtcagaa ataaagatct gaacacactt gaaaatataa   2760
caaccactga attcaaaaat gctatcacaa atgcaaaaat catcccttac tcaggattac   2820
tattagtcat cacagtgact gacaacaaag gagcattcaa atacataaag ccacaaagtc   2880
aattcatagt agatcttgga gcttacctag aaaaagaaag tatatattat gttaccacaa   2940
attggaagca cacagctaca cgatttgcaa tcaaacccat ggaagattaa cctttttcct   3000
ctacatcagt gtgttaattc atacaaactt tctacctaca ttcttcactt caccatcaca   3060
```

-continued

```
atcacaaaca ctctgtggtt caaccaatca aacaaaactt atctgaagtc ccagatcatc   3120
ccaagtcatt gtttatcaga tctagtactc aaataagtta ataaaaaata tacacatggg   3180
gcaaataatc attggaggaa atccaactaa tcacaatatc tgttaacata gacaagtcca   3240
cacaccatac agaatcaacc aatggaaaat acatccataa caatagaatt ctcaagcaaa   3300
ttctggcctt actttacact aatacacatg atcacaacaa taatctcttt gctaatcata   3360
atctccatca tgattgcaat actaaacaaa ctttgtgaat ataacgtatt ccataacaaa   3420
acctttgagt taccaagagc tcgagttaat acttgataaa gtagttaatt aaaaatagtc   3480
ataacaatga actaggatat caagactaac aataacattg gggcaaatgc aaacatgtcc   3540
aaaaacaagg accaacgcac cgctaagaca ttagaaagga cctgggacac tctcaatcat   3600
ttattattca tatcatcgtg cttatataag ttaaatctta aatctgtagc acaaatcaca   3660
ttatccattc tggcaatgat aatctcaact tcacttataa ttgcagccat catattcata   3720
gcctcggcaa accacaaagt cacaccaaca actgcaatca tacaagatgc aacaagccag   3780
atcaagaaca caaccccaac atacctcacc cagaatcctc agcttggaat cagtccctct   3840
aatccgtctg aaattacatc acaaatcacc accatactag cttcaacaac accaggagtc   3900
aagtcaaccc tgcaatccac aacagtcaag accaaaaaca caacaacaac tcaaacacaa   3960
cccagcaagc ccaccacaaa acaacgccaa aacaaaccac caagcaaacc caataatgat   4020
tttcactttg aagtgttcaa ctttgtaccc tgcagcatat gcagcaacaa tccaacctgc   4080
tgggctatct gcaaaagaat accaaacaaa aaaccaggaa agaaaaccac taccaagccc   4140
acaaaaaaac caaccctcaa gacaaccaaa aaagatccca aacctcaaac cactaaatca   4200
aaggaagtac ccaccaccaa gcccacagaa gagccaacca tcaacaccac caaaacaaac   4260
atcataacta cactactcac ctccaacacc acaggaaatc cagaactcac aagtcaaatg   4320
gaaaccttcc actcaacttc ctccgaaggc aatccaagcc cttctcaagt ctctacaaca   4380
tccgagtacc catcacaacc ttcatctcca cccaacacac cacgccagta gttacttaaa   4440
aacatattat cacaaaaggc cttgaccaac ttaaacagaa tcaaaataaa ctctggggca   4500
aataacaatg gagttgctaa tcctcaaagc aaatgcaatt accacaatcc tcactgcagt   4560
cacattttgt tttgcttctg gtcaaaacat cactgaagaa ttttatcaat caacatgcag   4620
tgcagttagc aaaggctatc ttagtgctct gagaactggt tggtatacca gtgttataac   4680
tatagaatta agtaatatca agaaaaataa gtgtaatgga acagatgcta aggtaaaatt   4740
gataaaacaa gaattagata aatataaaaa tgctgtaaca gaattgcagt tgctcatgca   4800
aagcacacaa gcaacaaaca atcgagccag aagagaacta ccaaggttta tgaattatac   4860
actcaacaat gccaaaaaaa ccaatgtaac attaagcaag aaaaggaaaa gaagatttct   4920
tggtttttttg ttaggtgttg gatctgcaat cgccagtggc gttgctgtat ctaaggtcct   4980
gcacctagaa ggggaagtga acaagatcaa aagtgctcta ctatccacaa acaaggctgt   5040
agtcagctta tcaaatggag ttagtgtttt aaccagcaaa gtgttagacc tcaaaaacta   5100
tatagataaa caattgttac ctattgtgaa caagcaaagc tgcagcatat caaatataga   5160
aactgtgata gagttccaac aaaagaacaa cagactacta gagattacca gggaatttag   5220
tgttaatgca ggcgtaacta cacctgtaag cacttacatg ttaactaata gtgaattatt   5280
gtcattaatc aatgatatgc ctataacaaa tgatcagaaa aagttaatgt ccaacaatgt   5340
tcaaatagtt agacagcaaa gttactctat catgtccata ataaaagagg aagtcttagc   5400
atatgtagta caattaccac tatatggtgt tatagataca ccctgttgga aactacacac   5460
```

```
atcccctcta tgtacaacca acacaaaaga agggtccaac atctgtttaa caagaactga   5520
cagaggatgg tactgtgaca atgcaggatc agtatctttc ttcccacaag ctgaaacatg   5580
taaagttcaa tcaaatcgag tattttgtga cacaatgaac agtttaacat taccaagtga   5640
agtaaatctc tgcaatgttg acatattcaa ccccaaatat gattgtaaaa ttatgacttc   5700
aaaaacagat gtaagcagct ccgttatcac atctctagga gccattgtgt catgctatgg   5760
caaaactaaa tgtacagcat ccaataaaaa tcgtggaatc ataaagacat tttctaacgg   5820
gtgcgattat gtatcaaata aaggggtgga cactgtgtct gtaggtaaca cattatatta   5880
tgtaaataag caagaaggta aaagtctcta tgtaaaaggt gaaccaataa taaatttcta   5940
tgacccatta gtattcccct ctgatgaatt tgatgcatca atatctcaag tcaacgagaa   6000
gattaaccag agcctagcat ttattcgtaa atccgatgaa ttattacata atgtaaatgc   6060
tggtaaatcc accacaaata tcatgataac tactataatt atagtgatta tagtaatatt   6120
gttatcatta attgctgttg gactgctctt atactgtaag gccagaagca caccagtcac   6180
actaagcaaa gatcaactga gtggtataaa taatattgca tttagtaact aaataaaaat   6240
agcacctaat catgttctta caatggttta ctatctgctc atagacaacc catctgtcat   6300
tggattttct taaaatctga acttcatcga aactctcatc tataaaccat ctcacttaca   6360
ctatttaagt agattcctag tttatagtta tataaaacac aattgcatgc caggtaccat   6420
ggggcaaata agaatttgat aagtaccact taaatttaac tcccttggtt agagatgggc   6480
agcaattcat tgagtatgat aaaagttaga ttacaaaatt tgtttgacaa tgatgaagta   6540
gcattgttaa aaataacatg ctatactgat aaattaatac atttaactaa tgctttggct   6600
aaggcagtga tacatacaat caaattgaat ggcattgtgt ttgtgcatgt tattacaagt   6660
agtgatattt gccctaataa taatattgta gtaaaatcca atttcacaac aatgccagta   6720
ctacaaaatg gaggttatat atgggaaatg atggaattaa cacattgctc tcaacctaat   6780
ggtctactag atgacaattg tgaaattaaa ttctccaaaa aactaagtga ttcaacaatg   6840
accaattata tgaatcaatt atctgaatta cttggatttg atcttaatcc ataaattata   6900
attaatatca actagcaaat caatgtcact aacaccatta gttaatataa aacttaacag   6960
aagacaaaaa tggggcaaat atgtcacgaa ggaatccttg caaatttgaa attcgaggtc   7020
attgcttaaa tggtaagagg tgtcatttta gtcataatta ttttgaatgg ccaccccatg   7080
cactgcttgt aagacaaaac tttatgttaa acagaatact taagtctatg gataaaagta   7140
tagatacctt atcagaaata agtggagctg cagagttgga cagaacagaa gagtatgctc   7200
ttggtgtagt tggagtgcta gagagttata taggatcaat aaacaatata actaaacaat   7260
cagcatgtgt tgccatgagc aaactcctca ctgaactcaa tagtgatgat atcaaaaagc   7320
tgagggacaa tgaagagcta aattcaccca agataagagt gtacaatact gtcatatcat   7380
atattgaaag caacaggaaa aacaataaac aaactatcca tctgttaaaa agattgccag   7440
cagacgtatt gaagaaaacc atcaaaaaca cattggatat ccataagagc ataaccatca   7500
acaacccaaa agaatcaact gttagtgata caaatgacca tgccaaaaat aatgatacta   7560
cctgacaaat atccttgtag tataacttcc atactaataa caagtagatg tagagttact   7620
atgtataatc aaaagaacac actatatttc aatcaaaaca acccaaataa ccatatgtac   7680
tcaccgaatc aaacattcaa tgaaatccat tggacctctc aagaattgat tgacacaatt   7740
caaaatttc tacaacatct aggtattatt gaggatatat atacaatata tatattagtg   7800
```

-continued

```
tcataacact caattctaac actcaccaca tcgttacatt attaattcaa acaattcaag   7860
ttgtgggaca aaatggatcc cattattaat ggaaattctg ctaatgttta tctaaccgat   7920
agttatttaa aggtgttat ctctttctca gagtgtaatg ctttaggaag ttacatattc   7980
aatggtcctt atctcaaaaa tgattatacc aacttaatta gtagacaaaa tccattaata   8040
gaacacatga atctaaagaa actaaatata acacagtcct taatatctaa gtatcataaa   8100
ggtgaaataa aattagaaga acctacttat tttcagtcat tacttatgac atacaagagt   8160
atgacctcgt cagaacagat tgctaccact aatttactta aaaagataat aagaagagct   8220
atagaaataa gtgatgtcaa agtctatgct atattgaata aactagggct taaagaaaag   8280
gacaagatta aatccaacaa tggacaagat gaagacaact cagttattac gaccataatc   8340
aaagatgata tactttcagc tgttaaagat aatcaatctc atcttaaagc agacaaaaat   8400
cactctacaa aacaaaaaga cacaatcaaa acaacactct tgaagaaatt gatgtgttca   8460
atgcaacatc ctccatcatg gttaatacat tggtttaact tatacacaaa attaaacaac   8520
atattaacac agtatcgatc aaatgaggta aaaaaccatg ggtttacatt gatagataat   8580
caaactctta gtggatttca atttattttg aaccaatatg gttgtatagt ttatcataag   8640
gaactcaaaa gaattactgt gacaacctat aatcaattct tgacatggaa agatattagc   8700
cttagtagat taaatgtttg tttaattaca tggattagta actgcttgaa cacattaaat   8760
aaaagcttag gcttaagatg cggattcaat aatgttatct tgacacaact attcctttat   8820
ggagattgta tactaaagct atttcacaat gaggggttct acataataaa agaggtagag   8880
ggatttatta tgtctctaat tttaaatata acagaagaag atcaattcag aaaacgattt   8940
tataatagta tgctcaacaa catcacagat gctgctaata aagctcagaa aaatctgcta   9000
tcaagagtat gtcatacatt attagataag acagtgtccg ataatataat aaatggcaga   9060
tggataattc tattaagtaa gttccttaaa ttaattaagc ttgcaggtga caataacctt   9120
aacaatctga gtgaactata ttttttgttc agaatatttg gacacccaat ggtagatgaa   9180
agacaagcca tggatgctgt taaaattaat tgcaatgaga ccaaatttta cttgttaagc   9240
agtctgagta tgttaagagg tgcctttata tatagaatta taaaagggtt tgtaaataat   9300
tacaacagat ggcctacttt aagaaatgct attgttttac ccttaagatg gttaacttac   9360
tataaactaa acacttatcc ttctttgttg gaacttacag aaagagattt gattgtgtta   9420
tcaggactac gtttctatcg tgagtttcgg ttgcctaaaa aagtggatct tgaaatgatt   9480
ataaatgata aagctatatc acctcctaaa aatttgatat ggactagttt ccctagaaat   9540
tacatgccat cacacataca aaactatata gaacatgaaa aattaaaatt ttccgagagt   9600
gataaatcaa gaagagtatt agagtattat ttaagagata acaaattcaa tgaatgtgat   9660
ttatacaact gtgtagttaa tcaaagttat ctcaacaacc ctaatcatgt ggtatcattg   9720
acaggcaaag aaagagaact cagtgtaggt agaatgtttg caatgcaacc gggaatgttc   9780
agacaggttc aaatattggc agagaaaatg atagctgaaa acattttaca attctttcct   9840
gaaagtctta caagatatgg tgatctagaa ctacaaaaaa tattagaact gaaagcagga   9900
ataagtaaca aatcaaatcg ctacaatgat aattacaaca attacattag taagtgctct   9960
atcatcacag atctcagcaa attcaatcaa gcatttcgat atgaaacgtc atgtatttgt  10020
agtgatgtgc tggatgaact gcatggtgta caatctctat tttcctggtt acatttaact  10080
attcctcatg tcacaataat atgcacatat aggcatgcac ccccctatat aggagatcat  10140
attgtagatc ttaacaatgt agatgaacaa agtggattat atagatatca catgggtggc  10200
```

atcgaagggt ggtgtcaaaa actatggacc atagaagcta tatcactatt ggatctaata 10260
tctctcaaag ggaaattctc aattactgct ttaattaatg gtgacaatca atcaatagat 10320
ataagcaaac caatcagact catggaaggt caaactcatg ctcaagcaga ttatttgcta 10380
gcattaaata gccttaaatt actgtataaa gagtatgcag gcataggcca caaattaaaa 10440
ggaactgaga cttatatatc acgagatatg caatttatga gtaaaacaat tcaacataac 10500
ggtgtatatt acccagctag tataaagaaa gtcctaagag tgggaccgtg gataaacact 10560
atacttgatg atttcaaagt gagtctagaa tctataggta gtttgacaca agaattagaa 10620
tatagaggtg aaagtctatt atgcagttta atatttagaa atgtatggtt atataatcag 10680
attgctctac aattaaaaaa tcatgcatta tgtaacaata aactatattt ggacatatta 10740
aaggttctga aacacttaaa aaccttttt aatcttgata atattgatac agcattaaca 10800
ttgtatatga atttacccat gttatttggt ggtggtgatc ccaacttgtt atatcgaagt 10860
ttctatagaa gaactcctga cttcctcaca gaggctatag ttcactctgt gttcatactt 10920
agttattata caaaccatga cttaaaagat aaacttcaag atctgtcaga tgatagattg 10980
aataagttct taacatgcat aatcacgttt gacaaaaacc ctaatgctga attcgtaaca 11040
ttgatgagag atcctcaagc tttagggtct gagagacaag ctaaaattac tagcgaaatc 11100
aatagactgg cagttacaga ggttttgagt acagctccaa acaaaatatt ctccaaaagt 11160
gcacaacatt atactactac agagatagat ctaaatgata ttatgcaaaa tatagaacct 11220
acatatcctc atgggctaag agttgtttat gaaagtttac ccttttataa agcagagaaa 11280
atagtaaatc ttatatcagg tacaaaatct ataactaaca tactggaaaa aacttctgcc 11340
atagacttaa cagatattga tagagccact gagatgatga ggaaaaacat aactttgctt 11400
ataaggatac ttccattgga ttgtaacaga gataaaagag agatattgag tatggaaaac 11460
ctaagtatta ctgaattaag caaatatgtt agggaaagat cttggtcttt atccaatata 11520
gttggtgtta catcacccag tatcatgtat acaatggaca tcaaatatac tacaagcact 11580
atatctagtg gcataattat agagaaatat aatgttaaca gtttaacacg tggtgagaga 11640
ggacccacta aaccatgggt tggttcatct acacaagaga aaaaaacaat gccagtttat 11700
aatagacaag tcttaaccaa aaaacagaga gatcaaatag atctattagc aaaattggat 11760
tgggtgtatg catctataga taacaaggat gaattcatgg aagaactcag cataggaacc 11820
cttgggttaa catatgaaaa ggccaagaaa ttatttccac aatatttaag tgtcaattat 11880
ttgcatcgcc ttacagtcag tagtagacca tgtgaattcc ctgcatcaat accagcttat 11940
agaacaacaa attatcactt tgacactagc cctattaatc gcatattaac agaaaagtat 12000
ggtgatgaag atattgacat agtattccaa aactgtataa gctttggcct tagtttaatg 12060
tcagtagtag aacaatttac taatgtatgt cctaacagaa ttattctcat acctaagctt 12120
aatgagatac atttgatgaa acctcccata ttcacaggtg atgttgatat tcacaagtta 12180
aaacaagtga tacaaaaaca gcatatgttt ttaccagaca aaataagttt gactcaatat 12240
gtggaattat tcttaagtaa taaaacactc aaatctggat ctcatgttaa ttctaattta 12300
atattggcac ataaaatatc tgactatttt cataatactt acattttaag tactaattta 12360
gctggacatt ggattctgat tatacaactt atgaaagatt ctaaaggtat ttttgaaaaa 12420
gattggggag agggatatat aactgatcat atgtttatta atttgaaagt tttcttcaat 12480
gcttataaga cctatctctt gtgttttcat aaaggttatg gcaaagcaaa gctggagtgt 12540

-continued

```
gatatgaaca cttcagatct tctatgtgta ttggaattaa tagacagtag ttattggaag  12600
tctatgtcta aggtattttt agaacaaaaa gttatcaaat acattcttag ccaagatgca  12660
agtttacata gagtaaaagg atgtcatagc ttcaaattat ggtttcttaa acgtcttaat  12720
gtagcagaat tcacagtttg cccttgggtt gttaacatag attatcatcc aacacatatg  12780
aaagcaatat taacttatat agatcttgtt agaatgggat tgataaatat agatagaata  12840
cacattaaaa ataaacacaa attcaatgat gaattttata cttctaatct cttctacatt  12900
aattataact tctcagataa tactcatcta ttaactaaac atataaggat tgctaattct  12960
gaattagaaa ataattacaa caaattatat catcctacac cagaaaccct agagaatata  13020
ctagccaatc cgattaaaag taatgacaaa aagacactga atgactattg tataggtaaa  13080
aatgttgact caataatgtt accattgtta tctaataaga agcttattaa atcgtctgca  13140
atgattagaa ccaattacag caaacaagat ttgtataatt tattccctat ggttgtgatt  13200
gatagaatta tagatcattc aggcaataca gccaaatcca accaacttta cactactact  13260
tcccaccaaa tatccttagt gcacaatagc acatcacttt actgcatgct tccttggcat  13320
catattaata gattcaattt tgtatttagt tctacaggtt gtaaaattag tatagagtat  13380
attttaaaag atcttaaaat taaagatccc aattgtatag cattcatagg tgaaggagca  13440
gggaatttat tattgcgtac agtagtggaa cttcatcctg acataagata tatttacaga  13500
agtctgaaag attgcaatga tcatagttta cctattgagt ttttaaggct gtacaatgga  13560
catatcaaca ttgattatgg tgaaaatttg accattcctg ctacagatgc aaccaacaac  13620
attcattggt cttatttaca tataaagttt gctgaaccta tcagtctttt tgtctgtgat  13680
gccgaattgt ctgtaacagt caactggagt aaaattataa tagaatggag caagcatgta  13740
agaaagtgca agtactgttc ctcagttaat aaatgtatgt taatagtaaa atatcatgct  13800
caagatgata ttgatttcaa attagacaat ataactatat taaaaactta tgtatgctta  13860
ggcagtaagt taaagggatc ggaggtttac ttagtcctta caataggtcc tgcgaatata  13920
ttcccagtat ttaatgtagt acaaaatgct aaattgatac tatcaagaac caaaaatttc  13980
atcatgccta agaaagctga taaagagtct attgatgcaa atattaaaag tttgataccc  14040
tttctttgtt accctataac aaaaaaagga attaatactg cattgtcaaa actaaagagt  14100
gttgttagtg gagatatact atcatattct atagctggac gtaatgaagt tttcagcaat  14160
aaacttataa atcataagca tatgaacatc ttaaaatggt tcaatcatgt tttaaatttc  14220
agatcaacag aactaaacta taaccattta tatatggtag aatctacata tccttaccta  14280
agtgaattgt taaacagctt gacaaccaat gaacttaaaa aactgattaa aatcacaggt  14340
agtctgttat acaactttca taatgaataa tgaataaaga tcttataata aaaattccca  14400
tagctataca ctaacactgt attcaattat agttattaaa aattaaaaat catataattt  14460
tttaaataac ttttagtgaa ctaatcctaa agttatcatt ttaatcttgg aggaataaat  14520
ttaaacccta atctaattgg tttatatgtg tattaactaa attacgagat attagttttt  14580
gacacttttt ttctcgt                                                 14597
```

<210> SEQ ID NO 7
<211> LENGTH: 15415
<212> TYPE: DNA
<213> ORGANISM: Artificial Sequence
<220> FEATURE:
<223> OTHER INFORMATION: recombinant RSV sequence

<400> SEQUENCE: 7

-continued

```
acgggaaaaa atgcgtacaa caaacttgca taaaccaaaa aaatggggca aataagaatt     60
tgataagtac cacttaaatt taactccctt ggttagagat ggctcttagc aaagtcaagt    120
tgaatgatac actcaacaaa gatcaacttc tgtcatccag caaatacacc atccaacgga    180
gcacaggaga tagtattgat actcctaatt atgatgtgca gaaacacatc aataagttat    240
gtggcatgtt attaatcaca gaagatgcta atcataaatt cactgggtta ataggtatgt    300
tatatgcgat gtctaggtta ggaagagaag acaccataaa aatactcaga gatgcgggat    360
atcatgtaaa agcaaatgga gtagatgtaa caacacatcg tcaagacatt aatggaaaag    420
aaatgaaatt tgaagtgtta acattggcaa gcttaacaac tgaaattcaa atcaacattg    480
agatagaatc tagaaaatcc tacaaaaaaa tgctaaaaga aatgggagag gtagctccag    540
aatacaggca tgactctcct gattgtggga tgataatatt atgtatagca gcattagtaa    600
taactaaatt agcagcaggg gacagatctg gtcttacagc cgtgattagg agagctaata    660
atgtcctaaa aaatgaaatg aaacgttaca aaggcttact acccaaggac atagccaaca    720
gcttctatga agtgtttgaa aaacatcccc actttataga tgtttttgtt cattttggta    780
tagcacaatc ttctaccaga ggtggcagta gagttgaagg gatttttgca ggattgttta    840
tgaatgccta tggtgcaggg caagtgatgt tacggtgggg agtcttagca aaatcagtta    900
aaaatattat gttaggacat gctagtgtgc aagcagaaat ggaacaagtt gttgaggttt    960
atgaatatgc ccaaaaattg ggtggtgaag caggattcta ccatatattg aacaacccaa   1020
aagcatcatt attatctttg actcaatttc ctcacttctc cagtgtagta ttaggcaatg   1080
ctgctggcct aggcataatg ggagagtaca gaggtacacc gaggaatcaa gatctatatg   1140
atgcagcaaa ggcatatgct gaacaactca aagaaaatgg tgtgattaac tacagtgtac   1200
tagacttgac agcagaagaa ctagaggcta tcaaacatca gcttaatcca aaagataatg   1260
atgtagagct ttgagttaat aaaaaatggg gcaaataaat catcatggaa aagtttgctc   1320
ctgaattcca tggagaagat gcaaacaaca gggctactaa attcctagaa tcaataaagg   1380
gcaaattcac atcacccaaa gatcccaaga aaaaagatag tatcatatct gtcaactcaa   1440
tagatataga agtaaccaaa gaaagcccta taacatcaaa ttcaactatt atcaacccaa   1500
caaatgagac agatgatact gcagggaaca agcccaatta tcaaagaaaa cctctagtaa   1560
gtttcaaaga agaccctaca ccaagtgata atcccttttc taaactatac aaagaaacca   1620
tagaaacatt tgataacaat gaagaagaat ccagctattc atacgaagaa ataaatgatc   1680
agacaaacga taatataaca gcaagattag ataggattga tgaaaaatta agtgaaatac   1740
taggaatgct tcacacatta gtagtggcaa gtgcaggacc tacatctgct cgggatggta   1800
taagagatgc catggttggt ttaagagaag aaatgataga aaaaatcaga actgaagcat   1860
taatgaccaa tgacagatta gaagctatgg caagactcag gaatgaggaa agtgaaaaga   1920
tggcaaaaga cacatcagat gaagtgtctc tcaatccaac atcagagaaa ttgaacaacc   1980
tattggaagg gaatgatagt gacaatgatc tatcacttga agatttctga ttagttacca   2040
atcttcacat caacacacaa taccaacaga agaccaacaa actaaccaac ccaatcatcc   2100
aaccaaacat ccatccgcca atcagccaaa cagccaacaa aacaaccagc caatccaaaa   2160
ctaaccaccc ggaaaaaatc tataatatag ttacaaaaaa aggaatcgat ggggcaaata   2220
caagtatggt gagcaagggc gaggagctgt tcaccggggt ggtgcccatc ctggtcgagc   2280
tggacggcga cgtaaacggc cacaagttca gcgtgtccgg cgagggcgag ggcgatgcca   2340
```

```
cctacggcaa gctgaccctg aagttcatct gcaccaccgg caagctgccc gtgccctggc   2400
ccaccctcgt gaccaccctg acctacggcg tgcagtgctt cagccgctac cccgaccaca   2460
tgaagcagca cgacttcttc aagtccgcca tgcccgaagg ctacgtccag gagcgcacca   2520
tcttcttcaa ggacgacggc aactacaaga cccgcgccga ggtgaagttc gagggcgaca   2580
ccctggtgaa ccgcatcgag ctgaagggca tcgacttcaa ggaggacggc aacatcctgg   2640
ggcacaagct ggagtacaac tacaacagcc acaacgtcta tatcatggcc gacaagcaga   2700
agaacggcat caaggtgaac ttcaagatcc gccacaacat cgaggacggc agcgtgcagc   2760
tcgccgacca ctaccagcag aacaccccca tcggcgacgg ccccgtgctg ctgcccgaca   2820
accactacct gagcacccag tccgccctga gcaaagaccc caacgagaag cgcgatcaca   2880
tggtcctgct ggagttcgtg accgccgccg ggatcactct cggcatggac gagctgtaca   2940
agtaaaagta gttacttaaa aagtcgacgg tggggcaaat atggaaacat acgtgaacaa   3000
gcttcacgaa ggctccacat acacagctgc tgttcaatac aatgtcttag aaaaagacga   3060
tgaccctgca tcacttacaa tatgggtgcc catgttccaa tcatctatgc cagcagattt   3120
acttataaaa gaactagcta atgtcaacat actagtgaaa caaatatcca cacccaaggg   3180
accttcacta agagtcatga taaactcaag aagtgcagtg ctagcacaaa tgcccagcaa   3240
atttaccata tgcgctaatg tgtccttgga tgaaagaagc aaactagcat atgatgtaac   3300
cacaccctgt gaaatcaagg catgtagtct aacatgccta aaatcaaaaa atatgttgac   3360
tacagttaaa gatctcacta tgaagacact caaccctaca catgatatta ttgctttatg   3420
tgaatttgaa aacatagtaa catcaaaaaa agtcataata ccaacatacc taagatccat   3480
cagtgtcaga aataaagatc tgaacacact tgaaaatata acaaccactg aattcaaaaa   3540
tgctatcaca aatgcaaaaa tcatccctta ctcaggatta ctattagtca tcacagtgac   3600
tgacaacaaa ggagcattca aatacataaa gccacaaagt caattcatag tagatcttgg   3660
agcttaccta gaaaaagaaa gtatatatta tgttaccaca aattggaagc acacagctac   3720
acgatttgca atcaaaccca tggaagatta accttttttcc tctacatcag tgtgttaatt   3780
catacaaact ttctacctac attcttcact tcaccatcac aatcacaaac actctgtggt   3840
tcaaccaatc aaacaaaact tatctgaagt cccagatcat cccaagtcat tgtttatcag   3900
atctagtact caaataagtt aataaaaaat atacacatgg ggcaaataat cattggagga   3960
aatccaacta atcacaatat ctgttaacat agacaagtcc acacaccata cagaatcaac   4020
caatggaaaa tacatccata acaatagaat tctcaagcaa attctggcct tactttacac   4080
taatacacat gatcacaaca ataatctctt tgctaatcat aatctccatc atgattgcaa   4140
tactaaacaa actttgtgaa tataacgtat tccataacaa aacctttgag ttaccaagag   4200
ctcgagttaa tacttgataa agtagttaat taaaaatagt cataacaatg aactaggata   4260
tcaagactaa caataacatt ggggcaaatg caaacatgtc caaaaacaag gaccaacgca   4320
ccgctaagac attagaaagg acctgggaca ctctcaatca tttattattc atatcatcgt   4380
gcttatataa gttaaatctt aaatctgtag cacaaatcac attatccatt ctggcaatga   4440
taatctcaac ttcacttata attgcagcca tcatattcat agcctcggca aaccacaaag   4500
tcacaccaac aactgcaatc atacaagatg caacaagcca gatcaagaac acaaccccaa   4560
catacctcac ccagaatcct cagcttggaa tcagtccctc taatccgtct gaaattacat   4620
cacaaatcac caccatacta gcttcaacaa caccaggagt caagtcaacc ctgcaatcca   4680
caacagtcaa gaccaaaaac acaacaacaa ctcaaacaca acccagcaag cccaccacaa   4740
```

```
aacaacgcca aaacaaacca ccaagcaaac ccaataatga ttttcacttt gaagtgttca   4800
actttgtacc ctgcagcata tgcagcaaca atccaacctg ctgggctatc tgcaaaagaa   4860
taccaaacaa aaaaccagga aagaaaacca ctaccaagcc cacaaaaaaa ccaaccctca   4920
agacaaccaa aaaagatccc aaacctcaaa ccactaaatc aaaggaagta cccaccacca   4980
agcccacaga agagccaacc atcaacacca ccaaaacaaa catcataact acactactca   5040
cctccaacac cacaggaaat ccagaactca caagtcaaat ggaaaccttc cactcaactt   5100
cctccgaagg caatccaagc ccttctcaag tctctacaac atccgagtac ccatcacaac   5160
cttcatctcc acccaacaca ccacgccagt agttacttaa aaacatatta tcacaaaagg   5220
ccttgaccaa cttaaacaga atcaaaataa actctggggc aaataacaat ggagttgcta   5280
atcctcaaag caaatgcaat taccacaatc ctcactgcag tcacattttg ttttgcttct   5340
ggtcaaaaca tcactgaaga attttatcaa tcaacatgca gtgcagttag caaaggctat   5400
cttagtgctc tgagaactgg ttggtatacc agtgttataa ctatagaatt aagtaatatc   5460
aagaaaaata agtgtaatgg aacagatgct aaggtaaaat tgataaaaca agaattagat   5520
aaatataaaa atgctgtaac agaattgcag ttgctcatgc aaagcacaca agcaacaaac   5580
aatcgagcca gaagagaact accaaggttt atgaattata cactcaacaa tgccaaaaaa   5640
accaatgtaa cattaagcaa gaaaaggaaa agaagatttc ttggtttttt gttaggtgtt   5700
ggatctgcaa tcgccagtgg cgttgctgta tctaaggtcc tgcacctaga aggggaagtg   5760
aacaagatca aaagtgctct actatccaca aacaaggctg tagtcagctt atcaaatgga   5820
gttagtgttt taaccagcaa agtgttagac ctcaaaaact atatagataa acaattgtta   5880
cctattgtga acaagcaaag ctgcagcata tcaaatatag aaactgtgat agagttccaa   5940
caaaagaaca acagactact agagattacc agggaattta gtgttaatgc aggcgtaact   6000
acacctgtaa gcacttacat gttaactaat agtgaattat tgtcattaat caatgatatg   6060
cctataacaa atgatcagaa aaagttaatg tccaacaatg ttcaaatagt tagacagcaa   6120
agttactcta tcatgtccat aataaaagag gaagtcttag catatgtagt acaattacca   6180
ctatatggtg ttatagatac accctgttgg aaactacaca catcccctct atgtacaacc   6240
aacacaaaag aagggtccaa catctgttta acaagaactg acagaggatg gtactgtgac   6300
aatgcaggat cagtatcttt cttcccacaa gctgaaacat gtaaagttca atcaaatcga   6360
gtattttgtg acacaatgaa cagtttaaca ttaccaagtg aagtaaatct ctgcaatgtt   6420
gacatattca accccaaata tgattgtaaa attatgactt caaaaacaga tgtaagcagc   6480
tccgttatca catctctagg agccattgtg tcatgctatg gcaaaactaa atgtacagca   6540
tccaataaaa atcgtggaat cataaagaca ttttctaacg ggtgcgatta tgtatcaaat   6600
aaaggggtgg acactgtgtc tgtaggtaac acattatatt atgtaaataa gcaagaaggt   6660
aaaagtctct atgtaaaagg tgaaccaata ataaatttct atgacccatt agtattcccc   6720
tctgatgaat ttgatgcatc aatatctcaa gtcaacgaga agattaacca gagcctagca   6780
tttattcgta aatccgatga attattacat aatgtaaatg ctggtaaatc caccacaaat   6840
atcatgataa ctactataat tatagtgatt atagtaatat tgttatcatt aattgctgtt   6900
ggactgctct tatactgtaa ggccagaagc acaccagtca cactaagcaa agatcaactg   6960
agtggtataa ataatattgc atttagtaac taaataaaaa tagcacctaa tcatgttctt   7020
acaatggttt actatctgct catagacaac ccatctgtca ttggattttc ttaaaatctg   7080
```

-continued

```
aacttcatcg aaactctcat ctataaacca tctcacttac actatttaag tagattccta   7140
gtttatagtt atataaaaca caattgcatg ccagattaac ttaccatctg taaaaatgaa   7200
aactggggca aatatgtcac gaaggaatcc ttgcaaattt gaaattcgag gtcattgctt   7260
aaatggtaag aggtgtcatt ttagtcataa ttattttgaa tggccacccc atgcactgct   7320
tgtaagacaa aactttatgt taaacagaat acttaagtct atggataaaa gtatagatac   7380
cttatcagaa ataagtggag ctgcagagtt ggacagaaca gaagagtatg ctcttggtgt   7440
agttggagtg ctagagagtt atataggatc aataaacaat ataactaaac aatcagcatg   7500
tgttgccatg agcaaactcc tcactgaact caatagtgat gatatcaaaa agctgaggga   7560
caatgaagag ctaaattcac ccaagataag agtgtacaat actgtcatat catatattga   7620
aagcaacagg aaaaacaata aacaaactat ccatctgtta aaaagattgc cagcagacgt   7680
attgaagaaa accatcaaaa acacattgga tatccataag agcataacca tcaacaaccc   7740
aaaagaatca actgttagtg atacaaatga ccatgccaaa aataatgata ctacctgaca   7800
aatatccttg tagtataact tccatactaa taacaagtag atgtagagtt actatgtata   7860
atcaaaagaa cacactatat ttcaatcaaa acaacccaaa taaccatatg tactcaccga   7920
atcaaacatt caatgaaatc cattggacct ctcaagaatt gattgacaca attcaaaatt   7980
ttctacaaca tctaggtatt attgaggata tatatacaat atatatatta gtgtcataac   8040
actcaattct aacactcacc acatcgttac attattaatt caaacaattc aagttgtggg   8100
acaaaatgga tcccattatt aatggaaatt ctgctaatgt ttatctaacc gatagttatt   8160
taaaaggtgt tatctctttc tcagagtgta atgctttagg aagttacata ttcaatggtc   8220
cttatctcaa aaatgattat accaacttaa ttagtagaca aaatccatta atagaacaca   8280
tgaatctaaa gaaactaaat ataacacagt ccttaatatc taagtatcat aaaggtgaaa   8340
taaaattaga agaacctact tattttcagt cattacttat gacatacaag agtatgacct   8400
cgtcagaaca gattgctacc actaatttac ttaaaaagat aataagaaga gctatagaaa   8460
taagtgatgt caaagtctat gctatattga ataaactagg gcttaaagaa aaggacaaga   8520
ttaaatccaa caatggacaa gatgaagaca actcagttat tacgaccata atcaaagatg   8580
atatactttc agctgttaaa gataatcaat ctcatcttaa agcagacaaa aatcactcta   8640
caaaacaaaa agacacaatc aaaacaacac tcttgaagaa attgatgtgt tcaatgcaac   8700
atcctccatc atggttaata cattggttta acttatacac aaaattaaac aacatattaa   8760
cacagtatcg atcaaatgag gtaaaaaacc atgggtttac attgatagat aatcaaactc   8820
ttagtggatt tcaatttatt ttgaaccaat atggttgtat agtttatcat aaggaactca   8880
aaagaattac tgtgacaacc tataatcaat tcttgacatg gaaagatatt agccttagta   8940
gattaaatgt ttgtttaatt acatggatta gtaactgctt gaacacatta aataaaagct   9000
taggcttaag atgcggattc aataatgtta tcttgacaca actattcctt tatggagatt   9060
gtatactaaa gctatttcac aatgaggggt tctacataat aaaagaggta gagggattta   9120
ttatgtctct aattttaaat ataacagaag aagatcaatt cagaaaacga ttttataata   9180
gtatgctcaa caacatcaca gatgctgcta ataaagctca gaaaaatctg ctatcaagag   9240
tatgtcatac attattagat aagacagtgt ccgataatat aataaatggc agatggataa   9300
ttctattaag taagttcctt aaattaatta agcttgcagg tgacaataac cttaacaatc   9360
tgagtgaact atatttttg ttcagaatat ttggacaccc aatggtagat gaaagacaag   9420
ccatggatgc tgttaaaatt aattgcaatg agaccaaatt ttacttgtta agcagtctga   9480
```

```
gtatgttaag aggtgccttt atatatagaa ttataaaagg gtttgtaaat aattacaaca   9540
gatggcctac tttaagaaat gctattgttt tacccttaag atggttaact tactataaac   9600
taaacactta tccttctttg ttggaactta cagaaagaga tttgattgtg ttatcaggac   9660
tacgtttcta tcgtgagttt cggttgccta aaaaagtgga tcttgaaatg attataaatg   9720
ataaagctat atcacctcct aaaaatttga tatggactag tttccctaga aattacatgc   9780
catcacacat acaaaactat atagaacatg aaaaattaaa attttccgag agtgataaat   9840
caagaagagt attagagtat tatttaagag ataacaaatt caatgaatgt gatttataca   9900
actgtgtagt taatcaaagt tatctcaaca accctaatca tgtggtatca ttgacaggca   9960
aagaaagaga actcagtgta ggtagaatgt ttgcaatgca accgggaatg ttcagacagg  10020
ttcaaatatt ggcagagaaa atgatagctg aaaacatttt acaattcttt cctgaaagtc  10080
ttacaagata tggtgatcta gaactacaaa aaatattaga actgaaagca ggaataagta  10140
acaaatcaaa tcgctacaat gataattaca acaattacat tagtaagtgc tctatcatca  10200
cagatctcag caaattcaat caagcatttc gatatgaaac gtcatgtatt tgtagtgatg  10260
tgctggatga actgcatggt gtacaatctc tattttcctg gttacattta actattcctc  10320
atgtcacaat aatatgcaca tataggcatg caccccccta tataggagat catattgtag  10380
atcttaacaa tgtagatgaa caaagtggat tatatagata tcacatgggt ggcatcgaag  10440
ggtggtgtca aaaactatgg accatagaag ctatatcact attggatcta atatctctca  10500
aagggaaatt ctcaattact gctttaatta atggtgacaa tcaatcaata gatataagca  10560
aaccaatcag actcatggaa ggtcaaactc atgctcaagc agattatttg ctagcattaa  10620
atagccttaa attactgtat aaagagtatg caggcatagg ccacaaatta aaaggaactg  10680
agacttatat atcacgagat atgcaattta tgagtaaaac aattcaacat aacggtgtat  10740
attacccagc tagtataaag aaagtcctaa gagtgggacc gtggataaac actatacttg  10800
atgatttcaa agtgagtcta gaatctatag gtagtttgac acaagaatta gaatatagag  10860
gtgaaagtct attatgcagt ttaatattta gaaatgtatg gttatataat cagattgctc  10920
tacaattaaa aaatcatgca ttatgtaaca ataaactata tttggacata ttaaaggttc  10980
tgaaacactt aaaaaccttt tttaatcttg ataatattga tacagcatta acattgtata  11040
tgaatttacc catgttattt ggtggtggtg atcccaactt gttatatcga agtttctata  11100
gaagaactcc tgacttcctc acagaggcta tagttcactc tgtgttcata cttagttatt  11160
atacaaacca tgacttaaaa gataaacttc aagatctgtc agatgataga ttgaataagt  11220
tcttaacatg cataatcacg tttgacaaaa accctaatgc tgaattcgta acattgatga  11280
gagatcctca agctttaggg tctgagagac aagctaaaat tactagcgaa atcaatagac  11340
tggcagttac agaggttttg agtacagctc caaacaaaat attctccaaa agtgcacaac  11400
attatactac tacagagata gatctaaatg atattatgca aaatatagaa cctacatatc  11460
ctcatgggct aagagttgtt tatgaaagtt taccctttta taaagcagag aaaatagtaa  11520
atcttatatc aggtacaaaa tctataacta acatactgga aaaaacttct gccatagact  11580
taacagatat tgatagagcc actgagatga tgaggaaaaa cataactttg cttataagga  11640
tacttccatt ggattgtaac agagataaaa gagagatatt gagtatggaa aacctaagta  11700
ttactgaatt aagcaaatat gttagggaaa gatcttggtc tttatccaat atagttggtg  11760
ttacatcacc cagtatcatg tatacaatgg acatcaaata tactacaagc actatatcta  11820
```

```
gtggcataat tatagagaaa tataatgtta acagtttaac acgtggtgag agaggaccca  11880
ctaaaccatg ggttggttca tctacacaag agaaaaaaac aatgccagtt tataatagac  11940
aagtcttaac caaaaaacag agagatcaaa tagatctatt agcaaaattg gattgggtgt  12000
atgcatctat agataacaag gatgaattca tggaagaact cagcatagga acccttgggt  12060
taacatatga aaaggccaag aaattatttc cacaatattt aagtgtcaat tatttgcatc  12120
gccttacagt cagtagtaga ccatgtgaat tccctgcatc aataccagct tatagaacaa  12180
caaattatca ctttgacact agccctatta atcgcatatt aacagaaaag tatggtgatg  12240
aagatattga catagtattc caaaactgta taagctttgg ccttagttta atgtcagtag  12300
tagaacaatt tactaatgta tgtcctaaca gaattattct catacctaag cttaatgaga  12360
tacatttgat gaaacctccc atattcacag gtgatgttga tattcacaag ttaaaacaag  12420
tgatacaaaa acagcatatg tttttaccag acaaaataag tttgactcaa tatgtggaat  12480
tattcttaag taataaaaca ctcaaatctg gatctcatgt taattctaat ttaatattgg  12540
cacataaaat atctgactat tttcataata cttacatttt aagtactaat ttagctggac  12600
attggattct gattatacaa cttatgaaag attctaaagg tatttttgaa aaagattggg  12660
gagagggata tataactgat catatgttta ttaatttgaa agttttcttc aatgcttata  12720
agacctatct cttgtgtttt cataaaggtt atggcaaagc aaagctggag tgtgatatga  12780
acacttcaga tcttctatgt gtattggaat taatagacag tagttattgg aagtctatgt  12840
ctaaggtatt tttagaacaa aaagttatca aatacattct tagccaagat gcaagtttac  12900
atagagtaaa aggatgtcat agcttcaaat tatggtttct taaacgtctt aatgtagcag  12960
aattcacagt ttgcccttgg gttgttaaca tagattatca tccaacacat atgaaagcaa  13020
tattaactta tatagatctt gttagaatgg gattgataaa tatagataga atacacatta  13080
aaaataaaca caaattcaat gatgaatttt atacttctaa tctcttctac attaattata  13140
acttctcaga taatactcat ctattaacta aacatataag gattgctaat tctgaattag  13200
aaaataatta caacaaatta tatcatccta caccagaaac cctagagaat atactagcca  13260
atccgattaa aagtaatgac aaaaagacac tgaatgacta ttgtataggt aaaaatgttg  13320
actcaataat gttaccattg ttatctaata agaagcttat taaatcgtct gcaatgatta  13380
gaaccaatta cagcaaacaa gatttgtata atttattccc tatggttgtg attgatagaa  13440
ttatagatca ttcaggcaat acagccaaat ccaaccaact ttacactact acttcccacc  13500
aaatatcctt agtgcacaat agcacatcac tttactgcat gcttccttgg catcatatta  13560
atagattcaa ttttgtattt agttctacag gttgtaaaat tagtatagag tatattttaa  13620
aagatcttaa aattaaagat cccaattgta tagcattcat aggtgaagga gcagggaatt  13680
tattattgcg tacagtagtg gaacttcatc ctgacataag atatatttac agaagtctga  13740
aagattgcaa tgatcatagt ttacctattg agtttttaag gctgtacaat ggacatatca  13800
acattgatta tggtgaaaat ttgaccattc ctgctacaga tgcaaccaac aacattcatt  13860
ggtcttattt acatataaag tttgctgaac ctatcagtct tttgtctgt gatgccgaat  13920
tgtctgtaac agtcaactgg agtaaaatta taatagaatg gagcaagcat gtaagaaagt  13980
gcaagtactg ttcctcagtt aataaatgta tgttaatagt aaaatatcat gctcaagatg  14040
atattgattt caaattagac aatataacta tattaaaaac ttatgtatgc ttaggcagta  14100
agttaaaggg atcggaggtt tacttagtcc ttacaatagg tcctgcgaat atattcccag  14160
tatttaatgt agtacaaaat gctaaattga tactatcaag aaccaaaaat ttcatcatgc  14220
```

-continued

```
ctaagaaagc tgataaagag tctattgatg caaatattaa aagtttgata ccctttcttt  14280

gttaccctat aacaaaaaaa ggaattaata ctgcattgtc aaaactaaag agtgttgtta  14340

gtggagatat actatcatat tctatagctg gacgtaatga agttttcagc aataaactta  14400

taaatcataa gcatatgaac atcttaaaat ggttcaatca tgttttaaat ttcagatcaa  14460

cagaactaaa ctataaccat ttatatatgg tagaatctac atatccttac ctaagtgaat  14520

tgttaaacag cttgacaacc aatgaactta aaaaactgat taaaatcaca ggtagtctgt  14580

tatacaactt tcataatgaa taatgaataa agatcttata ataaaaattc ccatagctat  14640

acactaacac tgtattcaat tatagttata aaaattaaaa atggtaccat ggggcaaata  14700

agaatttgat aagtaccact taaatttaac tcccttggtt agagatgggc agcaattcat  14760

tgagtatgat aaaagttaga ttacaaaatt tgtttgacaa tgatgaagta gcattgttaa  14820

aaataacatg ctatactgat aaattaatac atttaactaa tgctttggct aaggcagtga  14880

tacatacaat caaattgaat ggcattgtgt ttgtgcatgt tattacaagt agtgatattt  14940

gccctaataa taatattgta gtaaaatcca atttcacaac aatgccagta ctacaaaatg  15000

gaggttatat atgggaaatg atggaattaa cacattgctc tcaacctaat ggtctactag  15060

atgacaattg tgaaattaaa ttctccaaaa aactaagtga ttcaacaatg accaattata  15120

tgaatcaatt atctgaatta cttggatttg atcttaatcc ataaattata attaatatca  15180

actagcaaat caatgtcact aacaccatta gttaatataa aacttaacag aagacaaaaa  15240

tcttaaggag agatataaga tagaagatgg taccattttt taaataactt ttagtgaact  15300

aatcctaaag ttatcatttt aatcttggag gaataaattt aaaccctaat ctaattggtt  15360

tatatgtgta ttaactaaat tacgagatat tagtttttga cacttttttt ctcgt       15415
```

<210> SEQ ID NO 8
<211> LENGTH: 14654
<212> TYPE: DNA
<213> ORGANISM: Artificial Sequence
<220> FEATURE:
<223> OTHER INFORMATION: recombinant RSV sequence

<400> SEQUENCE: 8

```
acgggaaaaa atgcgtacaa caaacttgca taaaccaaaa aaatggggca aataagaatt     60

tgataagtac cacttaaatt taactccctt ggttagagat ggctcttagc aaagtcaagt    120

tgaatgatac actcaacaaa gatcaacttc tgtcatccag caaatacacc atccaacgga    180

gcacaggaga tagtattgat actcctaatt atgatgtgca gaaacacatc aataagttat    240

gtggcatgtt attaatcaca gaagatgcta atcataaatt cactgggtta ataggtatgt    300

tatatgcgat gtctaggtta ggaagagaag acaccataaa aatactcaga gatgcgggat    360

atcatgtaaa agcaaatgga gtagatgtaa caacacatcg tcaagacatt aatggaaaag    420

aaatgaaatt tgaagtgtta acattggcaa gcttaacaac tgaaattcaa atcaacattg    480

agatagaatc tagaaaatcc tacaaaaaaa tgctaaaaga aatgggagag gtagctccag    540

aatacaggca tgactctcct gattgtggga tgataatatt atgtatagca gcattagtaa    600

taactaaatt agcagcaggg gacagatctg gtcttacagc cgtgattagg agagctaata    660

atgtcctaaa aaatgaaatg aaacgttaca aaggcttact acccaaggac atagccaaca    720

gcttctatga agtgtttgaa aaacatcccc actttataga tgtttttgtt cattttggta    780

tagcacaatc ttctaccaga ggtggcagta gagttgaagg gatttttgca ggattgttta    840
```

-continued

```
tgaatgccta tggtgcaggg caagtgatgt tacggtgggg agtcttagca aaatcagtta     900
aaaatattat gttaggacat gctagtgtgc aagcagaaat ggaacaagtt gttgaggttt     960
atgaatatgc ccaaaaattg ggtggtgaag caggattcta ccatatattg aacaacccaa    1020
aagcatcatt attatctttg actcaatttc ctcacttctc cagtgtagta ttaggcaatg    1080
ctgctggcct aggcataatg ggagagtaca gaggtacacc gaggaatcaa gatctatatg    1140
atgcagcaaa ggcatatgct gaacaactca aagaaaatgg tgtgattaac tacagtgtac    1200
tagacttgac agcagaagaa ctagaggcta tcaaacatca gcttaatcca aaagataatg    1260
atgtagagct ttgagttaat aaaaaatggg gcaaataaat catcatggaa aagtttgctc    1320
ctgaattcca tggagaagat gcaaacaaca gggctactaa attcctagaa tcaataaagg    1380
gcaaattcac atcacccaaa gatcccaaga aaaaagatag tatcatatct gtcaactcaa    1440
tagatataga agtaaccaaa gaaagcccta taacatcaaa ttcaactatt atcaacccaa    1500
caaatgagac agatgatact gcagggaaca agcccaatta tcaaagaaaa cctctagtaa    1560
gtttcaaaga agaccctaca ccaagtgata atccctttc taaactatac aaagaaacca    1620
tagaaacatt tgataacaat gaagaagaat ccagctattc atacgaagaa ataaatgatc    1680
agacaaacga taatataaca gcaagattag ataggattga tgaaaaatta agtgaaatac    1740
taggaatgct tcacacatta gtagtggcaa gtgcaggacc tacatctgct cgggatggta    1800
taagagatgc catggttggt ttaagagaag aaatgataga aaaaatcaga actgaagcat    1860
taatgaccaa tgacagatta gaagctatgg caagactcag gaatgaggaa agtgaaaaga    1920
tggcaaaaga cacatcagat gaagtgtctc tcaatccaac atcagagaaa ttgaacaacc    1980
tattggaagg gaatgatagt gacaatgatc tatcacttga agatttctga ttagttacca    2040
atcttcacat caacacacaa taccaacaga agaccaacaa actaaccaac ccaatcatcc    2100
aaccaaacat ccatccgcca atcagccaaa cagccaacaa aacaaccagc caatccaaaa    2160
ctaaccaccc ggaaaaaatc tataatatag ttacaaaaaa aggaaagggt ggggcaaata    2220
tggaaacata cgtgaacaag cttcacgaag gctccacata cacagctgct gttcaataca    2280
atgtcttaga aaaagacgat gaccctgcat cacttacaat atgggtgccc atgttccaat    2340
catctatgcc agcagattta cttataaaag aactagctaa tgtcaacata ctagtgaaac    2400
aaatatccac acccaaggga ccttcactaa gagtcatgat aaactcaaga agtgcagtgc    2460
tagcacaaat gcccagcaaa tttaccatat gcgctaatgt gtccttggat gaaagaagca    2520
aactagcata tgatgtaacc acaccctgtg aaatcaaggc atgtagtcta acatgcctaa    2580
aatcaaaaaa tatgttgact acagttaaag atctcactat gaagacactc aaccctacac    2640
atgatattat tgctttatgt gaatttgaaa acatagtaac atcaaaaaaa gtcataatac    2700
caacatacct aagatccatc agtgtcagaa ataaagatct gaacacactt gaaaatataa    2760
caaccactga attcaaaaat gctatcacaa atgcaaaaat catcccttac tcaggattac    2820
tattagtcat cacagtgact gacaacaaag gagcattcaa atacataaag ccacaaagtc    2880
aattcatagt agatcttgga gcttacctag aaaaagaaag tatatattat gttaccacaa    2940
attggaagca cacagctaca cgatttgcaa tcaaacccat ggaagattaa cctttttcct    3000
ctacatcagt gtgttaattc atacaaactt tctacctaca ttcttcactt caccatcaca    3060
atcacaaaca ctctgtggtt caaccaatca aacaaaactt atctgaagtc ccagatcatc    3120
ccaagtcatt gtttatcaga tctagtactc aaataagtta ataaaaaata tacacatggg    3180
gcaaataatc attggaggaa atccaactaa tcacaatatc tgttaacata gacaagtcca    3240
```

-continued

```
cacaccatac agaatcaacc aatggaaaat acatccataa caatagaatt ctcaagcaaa   3300
ttctggcctt actttacact aatacacatg atcacaacaa taatctcttt gctaatcata   3360
atctccatca tgattgcaat actaaacaaa ctttgtgaat ataacgtatt ccataacaaa   3420
acctttgagt taccaagagc tcgagttaat acttgataaa gtagttaatt aaaaatagtc   3480
ataacaatga actaggatat caagactaac aataacattg gggcaaatgc aaacatgtcc   3540
aaaaacaagg accaacgcac cgctaagaca ttagaaagga cctgggacac tctcaatcat   3600
ttattattca tatcatcgtg cttatataag ttaaatctta aatctgtagc acaaatcaca   3660
ttatccattc tggcaatgat aatctcaact tcacttataa ttgcagccat catattcata   3720
gcctcggcaa accacaaagt cacaccaaca actgcaatca tacaagatgc aacaagccag   3780
atcaagaaca caaccccaac atacctcacc cagaatcctc agcttggaat cagtccctct   3840
aatccgtctg aaattacatc acaaatcacc accatactag cttcaacaac accaggagtc   3900
aagtcaaccc tgcaatccac aacagtcaag accaaaaaca caacaacaac tcaaacacaa   3960
cccagcaagc ccaccacaaa acaacgccaa aacaaaccac caagcaaacc caataatgat   4020
tttcactttg aagtgttcaa ctttgtaccc tgcagcatat gcagcaacaa tccaacctgc   4080
tgggctatct gcaaaagaat accaaacaaa aaaccaggaa agaaaaccac taccaagccc   4140
acaaaaaaac caaccctcaa gacaaccaaa aaagatccca aacctcaaac cactaaatca   4200
aaggaagtac ccaccaccaa gcccacagaa gagccaacca tcaacaccac caaaacaaac   4260
atcataacta cactactcac ctccaacacc acaggaaatc cagaactcac aagtcaaatg   4320
gaaaccttcc actcaacttc ctccgaaggc aatccaagcc cttctcaagt ctctacaaca   4380
tccgagtacc catcacaacc ttcatctcca cccaacacac cacgccagta gttacttaaa   4440
aacatattat cacaaaaggc cttgaccaac ttaaacagaa tcaaaataaa ctctggggca   4500
aataacaatg gagttgctaa tcctcaaagc aaatgcaatt accacaatcc tcactgcagt   4560
cacattttgt tttgcttctg gtcaaaacat cactgaagaa ttttatcaat caacatgcag   4620
tgcagttagc aaaggctatc ttagtgctct gagaactggt tggtatacca gtgttataac   4680
tatagaatta agtaatatca agaaaaataa gtgtaatgga acagatgcta aggtaaaatt   4740
gataaaacaa gaattagata aatataaaaa tgctgtaaca gaattgcagt tgctcatgca   4800
aagcacacaa gcaacaaaca atcgagccag aagagaacta ccaaggttta tgaattatac   4860
actcaacaat gccaaaaaaa ccaatgtaac attaagcaag aaaaggaaaa gaagatttct   4920
tggtttttttg ttaggtgttg gatctgcaat cgccagtggc gttgctgtat ctaaggtcct   4980
gcacctagaa ggggaagtga acaagatcaa aagtgctcta ctatccacaa acaaggctgt   5040
agtcagctta tcaaatggag ttagtgtttt aaccagcaaa gtgttagacc tcaaaaacta   5100
tatagataaa caattgttac ctattgtgaa caagcaaagc tgcagcatat caaatataga   5160
aactgtgata gagttccaac aaaagaacaa cagactacta gagattacca gggaatttag   5220
tgttaatgca ggcgtaacta cacctgtaag cacttacatg ttaactaata gtgaattatt   5280
gtcattaatc aatgatatgc ctataacaaa tgatcagaaa aagttaatgt ccaacaatgt   5340
tcaaatagtt agacagcaaa gttactctat catgtccata ataaaagagg aagtcttagc   5400
atatgtagta caattaccac tatatggtgt tatagataca ccctgttgga aactacacac   5460
atcccctcta tgtacaacca acacaaaaga agggtccaac atctgtttaa caagaactga   5520
cagaggatgg tactgtgaca atgcaggatc agtatctttc ttcccacaag ctgaaacatg   5580
```

-continued

```
taaagttcaa tcaaatcgag tattttgtga cacaatgaac agtttaacat taccaagtga   5640
agtaaatctc tgcaatgttg acatattcaa ccccaaatat gattgtaaaa ttatgacttc   5700
aaaaacagat gtaagcagct ccgttatcac atctctagga gccattgtgt catgctatgg   5760
caaaactaaa tgtacagcat ccaataaaaa tcgtggaatc ataaagacat tttctaacgg   5820
gtgcgattat gtatcaaata aaggggtgga cactgtgtct gtaggtaaca cattatatta   5880
tgtaaataag caagaaggta aaagtctcta tgtaaaaggt gaaccaataa taaatttcta   5940
tgacccatta gtattcccct ctgatgaatt tgatgcatca atatctcaag tcaacgagaa   6000
gattaaccag agcctagcat ttattcgtaa atccgatgaa ttattacata atgtaaatgc   6060
tggtaaatcc accacaaata tcatgataac tactataatt atagtgatta tagtaatatt   6120
gttatcatta attgctgttg gactgctctt atactgtaag gccagaagca caccagtcac   6180
actaagcaaa gatcaactga gtggtataaa taatattgca tttagtaact aaataaaaat   6240
agcacctaat catgttctta caatggttta ctatctgctc atagacaacc catctgtcat   6300
tggattttct taaaatctga acttcatcga aactctcatc tataaaccat ctcacttaca   6360
ctatttaagt agattcctag tttatagtta tataaaacac aattgcatgc cagattaact   6420
taccatctgt aaaaatgaaa actggggcaa atatgtcacg aaggaatcct tgcaaatttg   6480
aaattcgagg tcattgctta aatggtaaga ggtgtcattt tagtcataat tattttgaat   6540
ggccacccca tgcactgctt gtaagacaaa actttatgtt aaacagaata cttaagtcta   6600
tggataaaag tatagatacc ttatcagaaa taagtggagc tgcagagttg gacagaacag   6660
aagagtatgc tcttggtgta gttggagtgc tagagagtta tataggatca ataaacaata   6720
taactaaaca atcagcatgt gttgccatga gcaaactcct cactgaactc aatagtgatg   6780
atatcaaaaa gctgagggac aatgaagagc taaattcacc caagataaga gtgtacaata   6840
ctgtcatatc atatattgaa agcaacagga aaaacaataa acaaactatc catctgttaa   6900
aaagattgcc agcagacgta ttgaagaaaa ccatcaaaaa cacattggat atccataaga   6960
gcataaccat caacaaccca aaagaatcaa ctgttagtga tacaaatgac catgccaaaa   7020
ataatgatac tacctgacaa atatccttgt agtataactt ccatactaat aacaagtaga   7080
tgtagagtta ctatgtataa tcaaaagaac acactatatt tcaatcaaaa caacccaaat   7140
aaccatatgt actcaccgaa tcaaacattc aatgaaatcc attggacctc tcaagaattg   7200
attgacacaa ttcaaaattt tctacaacat ctaggtatta ttgaggatat atatacaata   7260
tatatattag tgtcataaca ctcaattcta acactcacca catcgttaca ttattaattc   7320
aaacaattca agttgtggga caaaatggat cccattatta atggaaattc tgctaatgtt   7380
tatctaaccg atagttattt aaaaggtgtt atctctttct cagagtgtaa tgctttagga   7440
agttacatat tcaatggtcc ttatctcaaa aatgattata ccaacttaat tagtagacaa   7500
aatccattaa tagaacacat gaatctaaag aaactaaata taacacagtc cttaatatct   7560
aagtatcata aaggtgaaat aaaattagaa gaacctactt attttcagtc attacttatg   7620
acatacaaga gtatgacctc gtcagaacag attgctacca ctaatttact taaaaagata   7680
ataagaagag ctatagaaat aagtgatgtc aaagtctatg ctatattgaa taaactaggg   7740
cttaaagaaa aggacaagat taaatccaac aatggacaag atgaagacaa ctcagttatt   7800
acgaccataa tcaaagatga tatactttca gctgttaaag ataatcaatc tcatcttaaa   7860
gcagacaaaa atcactctac aaaacaaaaa gacacaatca aaacaacact cttgaagaaa   7920
ttgatgtgtt caatgcaaca tcctccatca tggttaatac attggtttaa cttatacaca   7980
```

-continued

```
aaattaaaca acatattaac acagtatcga tcaaatgagg taaaaaacca tgggtttaca   8040
ttgatagata atcaaactct tagtggattt caatttattt tgaaccaata tggttgtata   8100
gtttatcata aggaactcaa aagaattact gtgacaacct ataatcaatt cttgacatgg   8160
aaagatatta gccttagtag attaaatgtt tgtttaatta catggattag taactgcttg   8220
aacacattaa ataaaagctt aggcttaaga tgcggattca ataatgttat cttgacacaa   8280
ctattccttt atggagattg tatactaaag ctatttcaca atgaggggtt ctacataata   8340
aaagaggtag agggatttat tatgtctcta attttaaata taacagaaga agatcaattc   8400
agaaaacgat tttataatag tatgctcaac aacatcacag atgctgctaa taaagctcag   8460
aaaaatctgc tatcaagagt atgtcataca ttattagata agacagtgtc cgataatata   8520
ataaatggca gatggataat tctattaagt aagttcctta aattaattaa gcttgcaggt   8580
gacaataacc ttaacaatct gagtgaacta tattttttgt tcagaatatt tggacaccca   8640
atggtagatg aaagacaagc catggatgct gttaaaatta attgcaatga gaccaaattt   8700
tacttgttaa gcagtctgag tatgttaaga ggtgccttta tatatagaat tataaaaggg   8760
tttgtaaata attacaacag atggcctact ttaagaaatg ctattgtttt acccttaaga   8820
tggttaactt actataaact aaacacttat ccttctttgt tggaacttac agaaagagat   8880
ttgattgtgt tatcaggact acgtttctat cgtgagtttc ggttgcctaa aaaagtggat   8940
cttgaaatga ttataaatga taaagctata tcacctccta aaaatttgat atggactagt   9000
ttccctagaa attacatgcc atcacacata caaaactata tagaacatga aaaattaaaa   9060
ttttccgaga gtgataaatc aagaagagta ttagagtatt atttaagaga taacaaattc   9120
aatgaatgtg atttatacaa ctgtgtagtt aatcaaagtt atctcaacaa ccctaatcat   9180
gtggtatcat tgacaggcaa agaaagagaa ctcagtgtag gtagaatgtt tgcaatgcaa   9240
ccgggaatgt tcagacaggt tcaaatattg gcagagaaaa tgatagctga aaacatttta   9300
caattctttc ctgaaagtct tacaagatat ggtgatctag aactacaaaa aatattagaa   9360
ctgaaagcag gaataagtaa caaatcaaat cgctacaatg ataattacaa caattacatt   9420
agtaagtgct ctatcatcac agatctcagc aaattcaatc aagcatttcg atatgaaacg   9480
tcatgtattt gtagtgatgt gctggatgaa ctgcatggtg tacaatctct attttcctgg   9540
ttacatttaa ctattcctca tgtcacaata atatgcacat ataggcatgc accccccctat   9600
ataggagatc atattgtaga tcttaacaat gtagatgaac aaagtggatt atatagatat   9660
cacatgggtg gcatcgaagg gtggtgtcaa aaactatgga ccatagaagc tatatcacta   9720
ttggatctaa tatctctcaa agggaaattc tcaattactg ctttaattaa tggtgacaat   9780
caatcaatag atataagcaa accaatcaga ctcatggaag gtcaaactca tgctcaagca   9840
gattatttgc tagcattaaa tagccttaaa ttactgtata aagagtatgc aggcataggc   9900
cacaaattaa aaggaactga gacttatata tcacgagata tgcaatttat gagtaaaaca   9960
attcaacata acggtgtata ttacccagct agtataaaga aagtcctaag agtgggaccg  10020
tggataaaca ctatacttga tgatttcaaa gtgagtctag aatctatagg tagtttgaca  10080
caagaattag aatatagagg tgaaagtcta ttatgcagtt taatatttag aaatgtatgg  10140
ttatataatc agattgctct acaattaaaa aatcatgcat tatgtaacaa taaactatat  10200
ttggacatat taaaggttct gaaacactta aaaacctttt ttaatcttga taatattgat  10260
acagcattaa cattgtatat gaatttaccc atgttatttg gtggtggtga tcccaacttg  10320
```

```
ttatatcgaa gtttctatag aagaactcct gacttcctca cagaggctat agttcactct  10380
gtgttcatac ttagttatta tacaaaccat gacttaaaag ataaacttca agatctgtca  10440
gatgatagat tgaataagtt cttaacatgc ataatcacgt ttgacaaaaa ccctaatgct  10500
gaattcgtaa cattgatgag agatcctcaa gctttagggt ctgagagaca agctaaaatt  10560
actagcgaaa tcaatagact ggcagttaca gaggttttga gtacagctcc aaacaaaata  10620
ttctccaaaa gtgcacaaca ttatactact acagagatag atctaaatga tattatgcaa  10680
aatatagaac ctacatatcc tcatgggcta agagttgttt atgaaagttt acccttttat  10740
aaagcagaga aaatagtaaa tcttatatca ggtacaaaat ctataactaa catactggaa  10800
aaaacttctg ccatagactt aacagatatt gatagagcca ctgagatgat gaggaaaaac  10860
ataactttgc ttataaggat acttccattg gattgtaaca gagataaaag agagatattg  10920
agtatggaaa acctaagtat tactgaatta agcaaatatg ttagggaaag atcttggtct  10980
ttatccaata tagttggtgt tacatcaccc agtatcatgt atacaatgga catcaaatat  11040
actacaagca ctatatctag tggcataatt atagagaaat ataatgttaa cagtttaaca  11100
cgtggtgaga gaggacccac taaaccatgg gttggttcat ctacacaaga gaaaaaaaca  11160
atgccagttt ataatagaca agtcttaacc aaaaaacaga gagatcaaat agatctatta  11220
gcaaaattgg attgggtgta tgcatctata gataacaagg atgaattcat ggaagaactc  11280
agcataggaa cccttgggtt aacatatgaa aaggccaaga aattatttcc acaatattta  11340
agtgtcaatt atttgcatcg ccttacagtc agtagtagac catgtgaatt ccctgcatca  11400
ataccagctt atagaacaac aaattatcac tttgacacta gccctattaa tcgcatatta  11460
acagaaaagt atggtgatga agatattgac atagtattcc aaaactgtat aagctttggc  11520
cttagtttaa tgtcagtagt agaacaattt actaatgtat gtcctaacag aattattctc  11580
atacctaagc ttaatgagat acatttgatg aaacctccca tattcacagg tgatgttgat  11640
attcacaagt taaaacaagt gatacaaaaa cagcatatgt tttaccaga caaaataagt  11700
ttgactcaat atgtggaatt attcttaagt aataaaacac tcaaatctgg atctcatgtt  11760
aattctaatt taatattggc acataaaata tctgactatt ttcataatac ttacatttta  11820
agtactaatt tagctggaca ttggattctg attatacaac ttatgaaaga ttctaaaggt  11880
atttttgaaa aagattgggg agagggatat ataactgatc atatgtttat taatttgaaa  11940
gttttcttca atgcttataa gacctatctc ttgtgttttc ataaaggtta tggcaaagca  12000
aagctggagt gtgatatgaa cacttcagat cttctatgtg tattggaatt aatagacagt  12060
agttattgga agtctatgtc taaggtattt ttagaacaaa aagttatcaa atacattctt  12120
agccaagatg caagtttaca tagagtaaaa ggatgtcata gcttcaaatt atggtttctt  12180
aaacgtctta atgtagcaga attcacagtt tgcccttggg ttgttaacat agattatcat  12240
ccaacacata tgaaagcaat attaacttat atagatcttg ttagaatggg attgataaat  12300
atagatagaa tacacattaa aaataaacac aaattcaatg atgaatttta tacttctaat  12360
ctcttctaca ttaattataa cttctcagat aatactcatc tattaactaa acatataagg  12420
attgctaatt ctgaattaga aaataattac aacaaattat atcatcctac accagaaacc  12480
ctagagaata tactagccaa tccgattaaa agtaatgaca aaaagacact gaatgactat  12540
tgtataggta aaaatgttga ctcaataatg ttaccattgt tatctaataa gaagcttatt  12600
aaatcgtctg caatgattag aaccaattac agcaaacaag atttgtataa tttattccct  12660
atggttgtga ttgatagaat tatagatcat tcaggcaata cagccaaatc caaccaactt  12720
```

```
tacactacta cttcccacca aatatcctta gtgcacaata gcacatcact ttactgcatg  12780

cttccttggc atcatattaa tagattcaat tttgtattta gttctacagg ttgtaaaatt  12840

agtatagagt atattttaaa agatcttaaa attaaagatc ccaattgtat agcattcata  12900

ggtgaaggag cagggaattt attattgcgt acagtagtgg aacttcatcc tgacataaga  12960

tatatttaca gaagtctgaa agattgcaat gatcatagtt tacctattga gtttttaagg  13020

ctgtacaatg gacatatcaa cattgattat ggtgaaaatt tgaccattcc tgctacagat  13080

gcaaccaaca acattcattg gtcttattta catataaagt ttgctgaacc tatcagtctt  13140

tttgtctgtg atgccgaatt gtctgtaaca gtcaactgga gtaaaattat aatagaatgg  13200

agcaagcatg taagaaagtg caagtactgt tcctcagtta ataaatgtat gttaatagta  13260

aaatatcatg ctcaagatga tattgatttc aaattagaca atataactat attaaaaact  13320

tatgtatgct taggcagtaa gttaaaggga tcggaggttt acttagtcct tacaataggt  13380

cctgcgaata tattcccagt atttaatgta gtacaaaatg ctaaattgat actatcaaga  13440

accaaaaatt tcatcatgcc taagaaagct gataaagagt ctattgatgc aaatattaaa  13500

agtttgatac cctttctttg ttaccctata acaaaaaaag gaattaatac tgcattgtca  13560

aaactaaaga gtgttgttag tggagatata ctatcatatt ctatagctgg acgtaatgaa  13620

gttttcagca ataaacttat aaatcataag catatgaaca tcttaaaatg gttcaatcat  13680

gttttaaatt tcagatcaac agaactaaac tataaccatt tatatatggt agaatctaca  13740

tatccttacc taagtgaatt gttaaacagc ttgacaacca atgaacttaa aaaactgatt  13800

aaaatcacag gtagtctgtt atacaacttt cataatgaat aatgaataaa gatcttataa  13860

taaaaattcc catagctata cactaacact gtattcaatt atagttataa aaattaaaaa  13920

tggtaccatg gggcaaataa gaatttgata agtaccactt aaatttaact cccttggtta  13980

gagatgggca gcaattcatt gagtatgata aaagttagat tacaaaattt gtttgacaat  14040

gatgaagtag cattgttaaa aataacatgc tatactgata aattaataca tttaactaat  14100

gctttggcta aggcagtgat acatacaatc aaattgaatg gcattgtgtt tgtgcatgtt  14160

attacaagta gtgatatttg ccctaataat aatattgtag taaaatccaa tttcacaaca  14220

atgccagtac tacaaaatgg aggttatata tgggaaatga tggaattaac acattgctct  14280

caacctaatg gtctactaga tgacaattgt gaaattaaat tctccaaaaa actaagtgat  14340

tcaacaatga ccaattatat gaatcaatta tctgaattac ttggatttga tcttaatcca  14400

taaattataa ttaatatcaa ctagcaaatc aatgtcacta acaccattag ttaatataaa  14460

acttaacaga agacaaaaat cttaaggaga gatataagat agaagatggt accatttttt  14520

aaataacttt tagtgaacta atcctaaagt tatcatttta atcttggagg aataaattta  14580

aaccctaatc taattggttt atatgtgtat taactaaatt acgagatatt agtttttgac  14640

acttttttc tcgt                                                     14654
```

<210> SEQ ID NO 9
<211> LENGTH: 75
<212> TYPE: DNA
<213> ORGANISM: Artificial Sequence
<220> FEATURE:
<223> OTHER INFORMATION: recombinant RSV sequence

<400> SEQUENCE: 9

```
ggggcaaata agaatttgat aagtaccact taaatttaac tcccttggtt agagatggct     60
```

cttagcaaag tcaag 75

<210> SEQ ID NO 10
<211> LENGTH: 66
<212> TYPE: DNA
<213> ORGANISM: Respiratory Syncytial Virus

<400> SEQUENCE: 10
ggggcaaata agaatttgat aagtaccact taaatttaac tcccttggtt agagatgggc 60
agcaat 66

<210> SEQ ID NO 11
<211> LENGTH: 29
<212> TYPE: DNA
<213> ORGANISM: Respiratory Syncytial Virus

<400> SEQUENCE: 11
atacaaccat ggctcttagc aaagtcaag 29

<210> SEQ ID NO 12
<211> LENGTH: 68
<212> TYPE: DNA
<213> ORGANISM: Respiratory Syncytial Virus

<400> SEQUENCE: 12
agttatataa aacacaattg aatgccagat taacttacca tctgtaaaaa tgaaaactgg 60
ggcaaata 68

<210> SEQ ID NO 13
<211> LENGTH: 45
<212> TYPE: DNA
<213> ORGANISM: Artificial Sequence
<220> FEATURE:
<223> OTHER INFORMATION: recombinant RSV sequence

<400> SEQUENCE: 13
agttatataa aacacaattg catgccaggt accatggggc aaata 45

<210> SEQ ID NO 14
<211> LENGTH: 73
<212> TYPE: DNA
<213> ORGANISM: Artificial Sequence
<220> FEATURE:
<223> OTHER INFORMATION: recombinant RSV sequence

<400> SEQUENCE: 14
agtaatttaa aacttaagga gagatataag atagaagatg gtacccttac catctgtaaa 60
aatgaaaact ggg 73

<210> SEQ ID NO 15
<211> LENGTH: 41
<212> TYPE: DNA
<213> ORGANISM: Respiratory Syncytial Virus

<400> SEQUENCE: 15
agttattaaa aattaaaaat catataattt tttaaataac t 41

<210> SEQ ID NO 16
<211> LENGTH: 37
<212> TYPE: DNA
<213> ORGANISM: Artificial Sequence
<220> FEATURE:
<223> OTHER INFORMATION: recombinant RSV sequence

<400> SEQUENCE: 16
agttataaaa attaaaaatg gtaccatggg gcaaata 37

<210> SEQ ID NO 17
<211> LENGTH: 71
<212> TYPE: DNA
<213> ORGANISM: Artificial Sequence
<220> FEATURE:
<223> OTHER INFORMATION: recombinant RSV sequence

<400> SEQUENCE: 17
agtaatttaa aacttaagga gagatataag atagaagatg gtaccatttt ttaaataact 60
tttagtgaac t 71

<210> SEQ ID NO 18
<211> LENGTH: 42
<212> TYPE: DNA
<213> ORGANISM: Respiratory Syncytial Virus

<400> SEQUENCE: 18
agttaatata aaacttaaca gaagacaaaa atggggcaaa ta 42

<210> SEQ ID NO 19
<211> LENGTH: 80
<212> TYPE: DNA
<213> ORGANISM: Artificial Sequence
<220> FEATURE:
<223> OTHER INFORMATION: recombinant RSV sequence

<400> SEQUENCE: 19
agtaatttaa aacttaagga gagatataag atagaagatg gtacccttac catctgtaaa 60
aatgaaaact ggggcaaata 80

<210> SEQ ID NO 20
<211> LENGTH: 45
<212> TYPE: DNA
<213> ORGANISM: Artificial Sequence
<220> FEATURE:
<223> OTHER INFORMATION: recombinant RSV sequence

<400> SEQUENCE: 20
agttatataa aacacaattg catgccaggt accatggggc aaata 45

<210> SEQ ID NO 21
<211> LENGTH: 42
<212> TYPE: DNA
<213> ORGANISM: Artificial Sequence
<220> FEATURE:
<223> OTHER INFORMATION: recombinant RSV sequence

<400> SEQUENCE: 21
agttaatata aaacttaaca gaagacaaaa atggggcaaa ta 42

<210> SEQ ID NO 22
<211> LENGTH: 74
<212> TYPE: DNA
<213> ORGANISM: Artificial Sequence
<220> FEATURE:

-continued

```
<223> OTHER INFORMATION: recombinant RSV sequence

<400> SEQUENCE: 22

agtaatttaa aacttaagga gagatataag atagaagatg gtaccttttt taaataactt    60

tctttttttc tcgt                                                     74

<210> SEQ ID NO 23
<211> LENGTH: 37
<212> TYPE: DNA
<213> ORGANISM: Artificial Sequence
<220> FEATURE:
<223> OTHER INFORMATION: recombinant RSV sequence

<400> SEQUENCE: 23

agttataaaa attaaaaatg gtaccatggg gcaaata                            37

<210> SEQ ID NO 24
<211> LENGTH: 103
<212> TYPE: DNA
<213> ORGANISM: Artificial Sequence
<220> FEATURE:
<223> OTHER INFORMATION: recombinant RSV sequence

<400> SEQUENCE: 24

agttaatata aaacttaaca gaagacaaaa atggggcaaa tcttaaggag agatataaga   60

tagaagatgg tacctttttt aaataacttt ctttttttct cgt                    103

<210> SEQ ID NO 25
<211> LENGTH: 10
<212> TYPE: DNA
<213> ORGANISM: Artificial Sequence
<220> FEATURE:
<223> OTHER INFORMATION: recombinant RSV sequence

<400> SEQUENCE: 25

ggggcaaata                                                          10

<210> SEQ ID NO 26
<211> LENGTH: 10
<212> TYPE: DNA
<213> ORGANISM: Artificial Sequence
<220> FEATURE:
<223> OTHER INFORMATION: recombinant RSV sequence

<400> SEQUENCE: 26

ggggcaaaca                                                          10
```